US009839890B2

(12) United States Patent
Griffiths et al.

(10) Patent No.: US 9,839,890 B2
(45) Date of Patent: Dec. 12, 2017

(54) COMPARTMENTALISED COMBINATORIAL CHEMISTRY BY MICROFLUIDIC CONTROL

(75) Inventors: Andrew Griffiths, Strasbourg (FR); David Weitz, Cambridge, MA (US); Darren Link, Lexington, MA (US); Keunho Ahn, Lafayette, CA (US); Jerome Bibette, Paris (FR)

(73) Assignees: National Science Foundation, Arlington, VA (US); Medical Research Council, London (GB); President and Fellows of Harvard College, Cambridge, MA (US)

( * ) Notice: Subject to any disclaimer, the term of this patent is extended or adjusted under 35 U.S.C. 154(b) by 1034 days.

(21) Appl. No.: 11/665,099

(22) PCT Filed: Oct. 12, 2005

(86) PCT No.: PCT/GB2005/003927
§ 371 (c)(1),
(2), (4) Date: Dec. 15, 2008

(87) PCT Pub. No.: WO2006/040554
PCT Pub. Date: Apr. 20, 2006

(65) Prior Publication Data
US 2009/0197772 A1    Aug. 6, 2009

Related U.S. Application Data

(63) Continuation of application No. 10/962,952, filed on Oct. 12, 2004, now abandoned, which is a continuation of application No. PCT/GB2004/001352, filed on Mar. 31, 2004.

(51) Int. Cl.
| | | |
|---|---|---|
| *C40B 30/00* | (2006.01) | |
| *C40B 50/00* | (2006.01) | |
| *B01F 13/00* | (2006.01) | |
| *B01F 5/06* | (2006.01) | |
| *B01J 19/00* | (2006.01) | |
| *B01L 3/00* | (2006.01) | |
| *B82Y 10/00* | (2011.01) | |
| *B82Y 30/00* | (2011.01) | |
| *C07K 1/04* | (2006.01) | |
| *C40B 30/04* | (2006.01) | |
| *B01F 3/08* | (2006.01) | |
| *C40B 40/06* | (2006.01) | |
| *C40B 40/10* | (2006.01) | |

(Continued)

(52) U.S. Cl.
CPC ........ *B01F 13/0071* (2013.01); *B01F 5/0646* (2013.01); *B01F 5/0647* (2013.01); *B01F 5/0655* (2013.01); *B01F 13/0076* (2013.01); *B01J 19/0046* (2013.01); *B01L 3/5025* (2013.01); *B01L 3/502761* (2013.01); *B01L 3/502784* (2013.01); *B82Y 10/00* (2013.01); *B82Y 30/00* (2013.01); *C07K 1/047* (2013.01); *B01F 3/0807* (2013.01); *B01J 2219/005* (2013.01); *B01J 2219/0086* (2013.01); *B01J 2219/00497* (2013.01); *B01J 2219/00576* (2013.01); *B01J 2219/00585* (2013.01); *B01J 2219/00596* (2013.01); *B01J 2219/00599* (2013.01); *B01J 2219/00707* (2013.01); *B01J 2219/00722* (2013.01); *B01J 2219/00725* (2013.01); *B01J 2219/00743* (2013.01); *B01J 2219/00853* (2013.01); *B01J 2219/00889* (2013.01); *B01L 3/50273* (2013.01); *B01L 3/502746* (2013.01); *B01L 2200/0605* (2013.01); *B01L 2200/0673* (2013.01); *B01L 2300/0864* (2013.01); *B01L 2300/0867* (2013.01); *B01L 2400/0406* (2013.01); *B01L 2400/0415* (2013.01); *B01L 2400/0487* (2013.01); *B01L 2400/084* (2013.01); *C40B 40/06* (2013.01); *C40B 40/10* (2013.01); *C40B 50/08* (2013.01); *G01N 2035/1034* (2013.01)

(58) Field of Classification Search
CPC ......... C40B 30/04; C40B 50/00; C40B 30/00; C12Q 1/68
USPC ....................................... 506/9, 23, 7; 435/6
See application file for complete search history.

(56) References Cited

U.S. PATENT DOCUMENTS

| 2,097,692 A | 11/1937 | Fiegel |
|---|---|---|
| 2,164,172 A | 6/1939 | Dalton |

(Continued)

FOREIGN PATENT DOCUMENTS

| AU | 2004225691 B2 | 6/2010 |
|---|---|---|
| CA | 2520548 A1 | 10/2004 |

(Continued)

OTHER PUBLICATIONS

Shendure et al., Advanced Sequencing Technologies: Methods and Goals, Nature Review, Genetics, 5, 335-345.*

(Continued)

*Primary Examiner* — Amy M Bunker
(74) *Attorney, Agent, or Firm* — Rudnick LLP; Thomas C. Meyers

(57) ABSTRACT

The invention describes a method for the synthesis of compounds comprising the steps of: (a) compartmentalising two or more sets of primary compounds into microcapsules; such that a proportion of the microcapsules contains two or more compounds; and (b) forming secondary compounds in the microcapsules by chemical reactions between primary compounds from different sets; wherein one or both of steps (a) and (b) is performed under microfluidic control; preferably electronic microfluidic control, The invention further allows for the identification of compounds which bind to a target component of a biochemical system or modulate the activity of the target, and which is co-compartmentalised into the microcapsules.

10 Claims, 30 Drawing Sheets

(51) Int. Cl.
  *C40B 50/08* (2006.01)
  *G01N 35/10* (2006.01)

(56) References Cited

U.S. PATENT DOCUMENTS

| | | |
|---|---|---|
| 2,656,508 A | 10/1953 | Coulter |
| 2,692,800 A | 10/1954 | Nichols et al. |
| 2,797,149 A | 6/1957 | Skeggs |
| 2,879,141 A | 3/1959 | Skeggs |
| 2,971,700 A | 2/1961 | Peeps |
| 3,479,141 A | 11/1969 | Smythe et al. |
| 3,608,821 A | 9/1971 | Simm et al. |
| 3,698,635 A | 10/1972 | Sickles |
| 3,816,331 A | 6/1974 | Brown, Jr. et al. |
| 3,930,061 A | 12/1975 | Scharfenberger |
| 3,960,187 A | 6/1976 | Stock et al. |
| 3,980,541 A | 9/1976 | Aine |
| 3,982,541 A | 9/1976 | L'Esperance, Jr. |
| 4,014,469 A | 3/1977 | Sato |
| 4,022,575 A | 5/1977 | Hansen et al. |
| 4,034,966 A | 7/1977 | Suh et al. |
| 4,059,552 A | 11/1977 | Zweigle et al. |
| 4,091,042 A | 5/1978 | Alexanderson et al. |
| 4,117,550 A | 9/1978 | Folland et al. |
| 4,130,394 A | 12/1978 | Negersmith |
| 4,210,809 A | 7/1980 | Pelavin |
| 4,253,846 A | 3/1981 | Smythe et al. |
| 4,266,721 A | 5/1981 | Sickles |
| 4,279,345 A | 7/1981 | Allred |
| 4,297,345 A | 10/1981 | Howarth |
| 4,315,754 A | 2/1982 | Ruzicka et al. |
| 4,378,957 A | 4/1983 | Malkin et al. |
| 4,383,767 A | 5/1983 | Jido |
| 4,439,980 A | 4/1984 | Biblarz et al. |
| 4,508,265 A | 4/1985 | Jido |
| 4,533,634 A | 8/1985 | Maldonado et al. |
| 4,585,209 A | 4/1986 | Aine et al. |
| 4,618,476 A | 10/1986 | Columbus |
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,091,652 A | 2/1992 | Mathies et al. |
| 5,096,615 A | 3/1992 | Prescott et al. |
| 5,122,360 A | 6/1992 | Harris et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,344,594 A | 9/1994 | Sheridon |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,475,096 A | 12/1995 | Gold et al. |
| 5,480,614 A | 1/1996 | Kamahori |
| 5,486,335 A | 1/1996 | Wilding et al. |
| 5,498,392 A | 3/1996 | Wilding et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,604,097 A | 2/1997 | Brenner |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A * | 3/1998 | Trevino et al. ............... 424/9.52 |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli et al. |
| 5,779,868 A | 7/1998 | Parce et al. |
| 5,783,431 A | 7/1998 | Peterson et al. |
| 5,840,506 A | 11/1998 | Giordano |
| 5,846,719 A | 12/1998 | Brenner et al. |
| 5,849,491 A | 12/1998 | Radomski et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks, Jr. et al. |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,884,846 A | 3/1999 | Tan |
| 5,887,755 A | 3/1999 | Hood, III |
| 5,888,746 A | 3/1999 | Tabiti et al. |
| 5,888,778 A | 3/1999 | Shuber |
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |

(56) References Cited

U.S. PATENT DOCUMENTS

| | | | |
|---|---|---|---|
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,068,199 A | 5/2000 | Coffee |
| 6,080,295 A | 6/2000 | Parce et al. |
| 6,086,740 A | 7/2000 | Kennedy |
| 6,096,495 A | 8/2000 | Kasai et al. |
| 6,103,537 A | 8/2000 | Ullman et al. |
| 6,105,571 A | 8/2000 | Coffee |
| 6,105,877 A | 8/2000 | Coffee |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,149,789 A | 11/2000 | Benecke et al. |
| 6,150,180 A | 11/2000 | Parce et al. |
| 6,150,516 A | 11/2000 | Brenner et al. |
| 6,165,778 A | 12/2000 | Kedar |
| 6,171,796 B1 | 1/2001 | An et al. |
| 6,171,850 B1 | 1/2001 | Nagle et al. |
| 6,172,214 B1 | 1/2001 | Brenner |
| 6,172,218 B1 | 1/2001 | Brenner |
| 6,174,160 B1 | 1/2001 | Lee et al. |
| 6,174,469 B1 | 1/2001 | Ganan-Calvo |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,294,344 B1 | 9/2001 | O'Brien |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,475,441 B1 | 11/2002 | Parce et al. |
| 6,481,648 B1 | 11/2002 | Zimmermann |
| 6,489,103 B1 * | 12/2002 | Griffiths et al. ............ 435/6.16 |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,520,425 B1 | 2/2003 | Reneker |
| 6,524,456 B1 | 2/2003 | Ramsey et al. |
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,565,010 B2 | 5/2003 | Anderson et al. |
| 6,569,631 B1 | 5/2003 | Pantoliano et al. |
| 6,576,420 B1 | 6/2003 | Carson et al. |
| 6,591,852 B1 | 7/2003 | McNeely et al. |
| 6,592,321 B2 | 7/2003 | Bonker et al. |
| 6,592,821 B1 | 7/2003 | Wada et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B2 | 1/2004 | Harris et al. .................... 435/23 |
| 6,682,890 B2 | 1/2004 | Mack et al. |
| 6,717,136 B2 | 4/2004 | Andersson et al. |
| 6,729,561 B2 | 5/2004 | Hirae et al. |
| 6,739,036 B2 | 5/2004 | Koike et al. |
| 6,744,046 B2 | 6/2004 | Valaskovic et al. |

(56) References Cited

U.S. PATENT DOCUMENTS

| | | | |
|---|---|---|---|
| 6,752,922 B2 | 6/2004 | Huang et al. | |
| 6,753,147 B2 | 6/2004 | Vogelstein et al. | |
| 6,766,817 B2 | 7/2004 | Da Silva | 137/1 |
| 6,767,194 B2 | 7/2004 | Jeon et al. | |
| 6,767,704 B2 | 7/2004 | Waldman et al. | |
| 6,790,328 B2 | 9/2004 | Jacobson et al. | |
| 6,793,753 B2 | 9/2004 | Unger et al. | |
| 6,797,056 B2 | 9/2004 | David | |
| 6,800,849 B2 | 10/2004 | Staats | |
| 6,806,058 B2 | 10/2004 | Jesperson et al. | |
| 6,808,382 B2 | 10/2004 | Lanfranchi | |
| 6,808,882 B2 * | 10/2004 | Griffiths et al. | 506/1 |
| 6,814,980 B2 | 11/2004 | Levy et al. | |
| 6,818,395 B1 | 11/2004 | Quake et al. | |
| 6,832,787 B1 | 12/2004 | Renzi | |
| 6,833,242 B2 | 12/2004 | Quake et al. | |
| 6,841,350 B2 | 1/2005 | Ogden et al. | |
| 6,872,250 B2 | 3/2005 | David et al. | |
| 6,890,487 B1 | 5/2005 | Sklar et al. | |
| 6,897,018 B1 | 5/2005 | Yuan et al. | |
| 6,905,844 B2 | 6/2005 | Kim | |
| 6,918,404 B2 | 7/2005 | Dias da Silva | |
| 6,926,313 B1 | 8/2005 | Renzi | |
| 6,935,768 B2 | 8/2005 | Lowe et al. | |
| 6,936,417 B2 | 8/2005 | Orntoft | |
| 6,942,978 B1 | 9/2005 | O'Brien | |
| 6,949,342 B2 | 9/2005 | Golub et al. | |
| 6,960,437 B2 | 11/2005 | Enzelberger et al. | |
| 6,974,667 B2 | 12/2005 | Horne et al. | |
| 6,998,232 B1 | 2/2006 | Feinstein et al. | |
| 7,022,472 B2 | 4/2006 | Robbins et al. | |
| 7,041,481 B2 | 5/2006 | Anderson et al. | |
| 7,049,072 B2 | 5/2006 | Seshi | |
| 7,056,674 B2 | 6/2006 | Baker et al. | |
| 7,057,026 B2 | 6/2006 | Barnes et al. | |
| 7,066,586 B2 | 6/2006 | Da Silva | 347/85 |
| 7,068,874 B2 | 6/2006 | Wang et al. | |
| 7,078,180 B2 | 7/2006 | Genetta | |
| 7,081,192 B1 | 7/2006 | Wang et al. | 204/547 |
| 7,081,340 B2 | 7/2006 | Baker et al. | |
| 7,090,983 B1 | 8/2006 | Muramatsu et al. | |
| 7,115,230 B2 | 10/2006 | Sundararajan et al. | |
| 7,118,910 B2 | 10/2006 | Unger et al. | |
| 7,129,091 B2 | 10/2006 | Ismagilov et al. | |
| 7,138,233 B2 | 11/2006 | Griffiths et al. | |
| 7,153,700 B1 | 12/2006 | Pardee et al. | |
| 7,156,917 B2 | 1/2007 | Moriyama et al. | |
| 7,163,801 B2 | 1/2007 | Reed | |
| 7,169,560 B2 | 1/2007 | Lapidus et al. | |
| 7,171,311 B2 | 1/2007 | Dai et al. | |
| 7,198,899 B2 | 4/2007 | Schleyer et al. | |
| 7,204,431 B2 | 4/2007 | Li et al. | |
| 7,229,770 B1 | 6/2007 | Price et al. | |
| 7,252,943 B2 | 8/2007 | Griffiths et al. | |
| 7,268,167 B2 | 9/2007 | Higuchi et al. | |
| 7,282,337 B1 | 10/2007 | Harris | |
| 7,291,462 B2 | 11/2007 | O'Brien et al. | |
| 7,294,503 B2 * | 11/2007 | Quake et al. | 435/288.5 |
| 7,300,765 B2 | 11/2007 | Patel | |
| 7,308,364 B2 | 12/2007 | Shaughnessy et al. | |
| 7,314,721 B2 | 1/2008 | Gure et al. | |
| 7,316,906 B2 | 1/2008 | Chiorazzi et al. | |
| 7,326,529 B2 | 2/2008 | Ali et al. | |
| 7,332,280 B2 | 2/2008 | Levy et al. | |
| 7,332,590 B2 | 2/2008 | Nacht et al. | |
| 7,341,211 B2 | 3/2008 | Ganan Calvo et al. | |
| 7,348,142 B2 | 3/2008 | Wang | |
| 7,358,231 B1 | 4/2008 | McCaffey et al. | |
| 7,361,474 B2 | 4/2008 | Siegler | |
| 7,364,862 B2 | 4/2008 | Ali et al. | |
| 7,368,255 B2 | 5/2008 | Bae et al. | |
| 7,378,233 B2 | 5/2008 | Sidransky et al. | |
| 7,378,280 B2 | 5/2008 | Quake et al. | 436/63 |
| 7,390,463 B2 | 6/2008 | He et al. | |
| 7,393,665 B2 | 7/2008 | Brenner | |
| 7,416,851 B2 | 8/2008 | Davi et al. | |
| 7,432,064 B2 | 10/2008 | Salceda et al. | |
| 7,442,507 B2 | 10/2008 | Polsky et al. | |
| 7,449,303 B2 | 11/2008 | Coignet | |
| 7,473,530 B2 | 1/2009 | Huttemann | |
| 7,473,531 B1 | 1/2009 | Domon et al. | |
| 7,476,506 B2 | 1/2009 | Schleyer et al. | |
| 7,479,370 B2 | 1/2009 | Coignet | |
| 7,479,371 B2 | 1/2009 | Ando et al. | |
| 7,479,376 B2 | 1/2009 | Waldman et al. | |
| 7,482,129 B2 | 1/2009 | Soyupak et al. | |
| 7,501,244 B2 | 3/2009 | Reinhard et al. | |
| 7,504,214 B2 | 3/2009 | Erlander et al. | |
| 7,507,532 B2 | 3/2009 | Chang et al. | |
| 7,507,541 B2 | 3/2009 | Raitano et al. | |
| 7,510,707 B2 | 3/2009 | Platica et al. | |
| 7,510,842 B2 | 3/2009 | Podust et al. | |
| 7,514,209 B2 | 4/2009 | Dai et al. | |
| 7,514,210 B2 | 4/2009 | Holliger et al. | |
| 7,524,633 B2 | 4/2009 | Sidransky | |
| 7,527,933 B2 | 5/2009 | Sahin et al. | |
| 7,537,897 B2 | 5/2009 | Brenner et al. | |
| 7,541,383 B2 | 6/2009 | Fu et al. | 514/602 |
| 7,544,473 B2 | 6/2009 | Brenner | |
| 7,622,081 B2 | 11/2009 | Chou et al. | |
| 7,632,562 B2 | 12/2009 | Nair et al. | |
| 7,635,562 B2 | 12/2009 | Harris et al. | |
| 7,655,470 B2 | 2/2010 | Ismagilov et al. | |
| 7,666,593 B2 | 2/2010 | Lapidus | |
| 7,698,287 B2 | 4/2010 | Becker et al. | |
| 7,708,949 B2 | 5/2010 | Stone et al. | |
| 7,814,175 B1 | 10/2010 | Chang et al. | |
| 7,824,889 B2 | 11/2010 | Vogelstein et al. | |
| 7,888,017 B2 | 2/2011 | Quake et al. | |
| 7,897,044 B2 | 3/2011 | Hoyos et al. | |
| 7,901,939 B2 | 3/2011 | Ismagilov et al. | |
| 8,012,382 B2 | 9/2011 | Kim et al. | |
| 8,153,402 B2 | 4/2012 | Holliger et al. | |
| 2001/0010338 A1 | 8/2001 | Ganan-Calvo | |
| 2001/0020011 A1 | 9/2001 | Mathiowitz et al. | |
| 2001/0023078 A1 | 9/2001 | Bawendi et al. | |
| 2001/0029983 A1 | 10/2001 | Unger et al. | |
| 2001/0034031 A1 | 10/2001 | Short et al. | |
| 2001/0041343 A1 | 11/2001 | Pankowsky | |
| 2001/0041344 A1 | 11/2001 | Sepetov et al. | |
| 2001/0042793 A1 | 11/2001 | Ganan-Calvo | |
| 2001/0048900 A1 | 12/2001 | Bardell et al. | |
| 2001/0050881 A1 | 12/2001 | Depaoli et al. | |
| 2002/0004532 A1 | 1/2002 | Matathia et al. | |
| 2002/0005354 A1 | 1/2002 | Spence et al. | |
| 2002/0008028 A1 | 1/2002 | Jacobson et al. | |
| 2002/0012971 A1 | 1/2002 | Mehta | |
| 2002/0022038 A1 | 2/2002 | Biatry et al. | |
| 2002/0022261 A1 | 2/2002 | Anderson et al. | |
| 2002/0033422 A1 | 3/2002 | Ganan-Calvo | |
| 2002/0036139 A1 | 3/2002 | Becker et al. | |
| 2002/0058332 A1 | 5/2002 | Quake et al. | |
| 2002/0067800 A1 | 6/2002 | Newman et al. | |
| 2002/0119459 A1 * | 8/2002 | Griffiths | 435/6 |
| 2002/0143437 A1 | 10/2002 | Handique et al. | |
| 2002/0155080 A1 | 10/2002 | Glenn et al. | |
| 2002/0158027 A1 | 10/2002 | Moon et al. | |
| 2002/0164271 A1 | 11/2002 | Ho | |
| 2002/0164629 A1 | 11/2002 | Quake et al. | |
| 2003/0012586 A1 | 1/2003 | Iwata et al. | |
| 2003/0015425 A1 | 1/2003 | Bohm et al. | |
| 2003/0017579 A1 | 1/2003 | Corn et al. | |
| 2003/0039169 A1 | 2/2003 | Ehrfeld et al. | |
| 2003/0059764 A1 | 3/2003 | Ravkin et al. | |
| 2003/0061687 A1 | 4/2003 | Hansen et al. | |
| 2003/0064414 A1 | 4/2003 | Benecky et al. | |
| 2003/0082795 A1 | 5/2003 | Shuler et al. | |
| 2003/0124586 A1 | 7/2003 | Griffiths et al. | |
| 2003/0144260 A1 | 7/2003 | Gilon | |
| 2003/0148544 A1 | 8/2003 | Nie et al. | |
| 2003/0183525 A1 | 10/2003 | Elrod et al. | |
| 2003/0224509 A1 | 12/2003 | Moon et al. | |
| 2003/0229376 A1 | 12/2003 | Sandhu | |
| 2003/0230486 A1 | 12/2003 | Chien et al. | |

(56) References Cited

U.S. PATENT DOCUMENTS

| | | |
|---|---|---|
| 2003/0232356 A1 | 12/2003 | Dooley et al. |
| 2004/0005582 A1 | 1/2004 | Shipwash |
| 2004/0005594 A1 | 1/2004 | Holliger et al. |
| 2004/0018525 A1 | 1/2004 | Wirtz et al. |
| 2004/0027915 A1 | 2/2004 | Lowe et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |
| 2004/0068019 A1 | 4/2004 | Higuchi et al. |
| 2004/0071781 A1 | 4/2004 | Chattopadhyay et al. |
| 2004/0079881 A1 | 4/2004 | Fischer et al. |
| 2004/0096515 A1 | 5/2004 | Bausch et al. |
| 2004/0134854 A1 | 7/2004 | Higuchi et al. |
| 2004/0136497 A1 | 7/2004 | Meldrum et al. |
| 2004/0146921 A1 | 7/2004 | Eveleigh et al. |
| 2004/0159633 A1 | 8/2004 | Whitesides et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0188254 A1 | 9/2004 | Spaid |
| 2004/0224419 A1 | 11/2004 | Zheng et al. |
| 2004/0253731 A1 | 12/2004 | Holliger et al. |
| 2004/0258203 A1 | 12/2004 | Yamano et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0129582 A1 | 6/2005 | Breidford et al. |
| 2005/0152908 A1 | 7/2005 | Liew et al. |
| 2005/0164239 A1 | 7/2005 | Griffiths et al. |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0207940 A1 | 9/2005 | Butler et al. |
| 2005/0221339 A1 | 10/2005 | Griffiths et al. |
| 2005/0226742 A1 | 10/2005 | Unger et al. |
| 2005/0227264 A1 | 10/2005 | Nobile et al. |
| 2005/0260566 A1 | 11/2005 | Fischer et al. |
| 2005/0272159 A1 | 12/2005 | Ismagilov et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0036348 A1 | 2/2006 | Handique et al. |
| 2006/0046257 A1 | 3/2006 | Pollock et al. |
| 2006/0051329 A1 | 3/2006 | Lee et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0252057 A1 | 11/2006 | Raponi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269971 A1 | 11/2006 | Diamandis |
| 2006/0281089 A1 | 12/2006 | Gibson et al. |
| 2007/0026439 A1 | 2/2007 | Faulstich et al. |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0077572 A1 | 4/2007 | Tawfik et al. |
| 2007/0077579 A1 | 4/2007 | Griffiths et al. |
| 2007/0154889 A1 | 7/2007 | Wang |
| 2007/0166705 A1 | 7/2007 | Milton et al. |
| 2007/0184439 A1 | 8/2007 | Guilford et al. |
| 2007/0184489 A1 | 8/2007 | Griffiths et al. |
| 2007/0259351 A1 | 11/2007 | Chinitz et al. |
| 2007/0259368 A1 | 11/2007 | An et al. |
| 2007/0292869 A1 | 12/2007 | Becker et al. |
| 2008/0003142 A1 | 1/2008 | Link et al. |
| 2008/0009005 A1 | 1/2008 | Kruk |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0138806 A1 | 6/2008 | Chow et al. |
| 2008/0166772 A1 | 7/2008 | Hollinger et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0268473 A1 | 10/2008 | Moses et al. |
| 2008/0269157 A1 | 10/2008 | Srivastava et al. |
| 2008/0274908 A1 | 11/2008 | Chang |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0118128 A1 | 5/2009 | Liu et al. |
| 2009/0124569 A1 | 5/2009 | Bergan et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |

(56) References Cited

U.S. PATENT DOCUMENTS

| | | | |
|---|---|---|---|
| 2009/0191565 A1 | 7/2009 | Lapidus et al. |
| 2009/0197772 A1 | 8/2009 | Griffiths et al. |
| 2009/0246788 A1 | 10/2009 | Albert et al. |
| 2010/0003687 A1 | 1/2010 | Simen et al. |
| 2010/0009353 A1 | 1/2010 | Barnes et al. |
| 2010/0035252 A1 | 2/2010 | Rothberg et al. |
| 2010/0075436 A1 | 3/2010 | Urdea et al. |
| 2010/0105112 A1 | 4/2010 | Holtze et al. |
| 2010/0111768 A1 | 5/2010 | Banerjee et al. |
| 2010/0137143 A1 | 6/2010 | Rothberg et al. |
| 2010/0159592 A1 | 6/2010 | Holliger et al. |
| 2010/0172803 A1 | 7/2010 | Stone et al. |
| 2010/0188073 A1 | 7/2010 | Rothberg et al. |
| 2010/0197507 A1 | 8/2010 | Rothberg et al. |
| 2010/0233026 A1 | 9/2010 | Ismagliov et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0142734 A1 | 6/2011 | Ismagliov et al. |
| 2011/0174622 A1 | 7/2011 | Ismagilov et al. |
| 2011/0176966 A1 | 7/2011 | Ismagilov et al. |
| 2011/0177494 A1 | 7/2011 | Ismagilov et al. |
| 2011/0177586 A1 | 7/2011 | Ismagilov et al. |
| 2011/0177609 A1 | 7/2011 | Ismagilov et al. |

FOREIGN PATENT DOCUMENTS

| | | | | | |
|---|---|---|---|---|---|
| CH | 563807 A5 | 7/1975 | | | |
| EP | 0047130 B1 | 2/1985 | | | |
| EP | 0249007 A3 | 3/1991 | | | |
| EP | 0476178 A1 | 3/1992 | | | |
| EP | 0540281 B1 | 7/1996 | | | |
| EP | 0528580 B1 | 12/1996 | | | |
| EP | 0895120 | 2/1999 | | | |
| EP | 1447127 A1 | 8/2004 | | | |
| EP | 1741482 | 1/2007 | | | |
| EP | 1447127 B1 | 4/2007 | | | |
| EP | 2127736 | 12/2009 | | | |
| GB | 0114854.3 | 4/1969 | | | |
| GB | 1446998 | 8/1976 | | | |
| GB | 2005224 | 4/1979 | | | |
| GB | 2047880 | 12/1980 | | | |
| GB | 2062225 | 5/1981 | | | |
| GB | 2064114 | 6/1981 | | | |
| GB | 2097692 A | 11/1982 | | | |
| GB | 0221053.2 | 6/1989 | | | |
| WO | WO 84/02000 | * | 5/1984 | ............ | G01N 1/00 |
| WO | WO-91/05058 A1 | 4/1991 | | | |
| WO | WO-91/07772 | 5/1991 | | | |
| WO | WO-92/03734 | 3/1992 | | | |
| WO | WO-92/21746 | 12/1992 | | | |
| WO | WO-93/03151 | 2/1993 | | | |
| WO | WO-93/08278 | 4/1993 | | | |
| WO | WO-93/22053 | 11/1993 | | | |
| WO | WO-93/22054 | 11/1993 | | | |
| WO | WO-93/22055 | 11/1993 | | | |
| WO | WO-93/22058 | 11/1993 | | | |
| WO | WO-93/22421 | 11/1993 | | | |
| WO | WO-94/16332 | 7/1994 | | | |
| WO | WO-94/23738 | 10/1994 | | | |
| WO | WO-94/24314 | 10/1994 | | | |
| WO | WO-94/26766 | 11/1994 | | | |
| WO | WO-98/00705 | 1/1995 | | | |
| WO | WO-95/11922 | 5/1995 | | | |
| WO | WO-95/19922 | 7/1995 | | | |
| WO | WO-95/24929 | 9/1995 | | | |
| WO | WO-95/33447 | 12/1995 | | | |
| WO | WO 96/29629 | 9/1996 | | | |
| WO | WO-96/34112 | 10/1996 | | | |
| WO | WO-96/38730 | 12/1996 | | | |
| WO | WO-96/40062 | 12/1996 | | | |
| WO | WO-96/40723 | 12/1996 | | | |
| WO | WO-97/00125 | 1/1997 | | | |
| WO | WO-97/00442 | 1/1997 | | | |
| WO | WO-97/04297 | 2/1997 | | | |
| WO | WO-97/04748 | 2/1997 | | | |
| WO | WO-97/23140 | 7/1997 | | | |
| WO | WO-97/28556 | 8/1997 | | | |
| WO | WO-97/39814 | 10/1997 | | | |
| WO | WO-97/40141 | 10/1997 | | | |
| WO | WO-97/45644 | 12/1997 | | | |
| WO | WO-97/47763 | 12/1997 | | | |
| WO | WO-98/00231 | 1/1998 | | | |
| WO | WO-98/02237 | 1/1998 | | | |
| WO | WO 98/10267 | 3/1998 | | | |
| WO | WO-98/13502 | 4/1998 | | | |
| WO | WO-98/23733 | 6/1998 | | | |
| WO | WO-98/31700 | 7/1998 | | | |
| WO | WO-98/33001 | 7/1998 | | | |
| WO | WO-98/34120 | 8/1998 | | | |
| WO | WO-98/37186 | 8/1998 | | | |
| WO | WO-98/41869 | 9/1998 | | | |
| WO | WO-98/52691 | 11/1998 | | | |
| WO | WO-98/58085 | 12/1998 | | | |
| WO | WO 99/02671 | * | 1/1999 | ............ | C12N 15/10 |
| WO | WO-99/22858 | 5/1999 | | | |
| WO | WO-99/28020 | 6/1999 | | | |
| WO | WO-99/31019 | 6/1999 | | | |
| WO | WO-99/54730 | 10/1999 | | | |
| WO | WO-99/61888 | 12/1999 | | | |
| WO | WO-00/04139 A1 | 1/2000 | | | |
| WO | WO-00/47322 | 2/2000 | | | |
| WO | WO-00/52455 | 2/2000 | | | |
| WO | WO 00/40712 | * | 7/2000 | ............ | C12N 15/10 |
| WO | WO-00/61275 | 10/2000 | | | |
| WO | WO-00/70080 | 11/2000 | | | |
| WO | WO-00/76673 | 12/2000 | | | |
| WO | WO-01/12327 | 2/2001 | | | |
| WO | WO 01/14589 | 3/2001 | | | |
| WO | WO-01/18244 | 3/2001 | | | |
| WO | WO-01/64332 | 9/2001 | | | |
| WO | WO-01/68257 | 9/2001 | | | |
| WO | WO-01/69289 | 9/2001 | | | |
| WO | WO-01/72431 | 10/2001 | | | |
| WO | WO-01/80283 | 10/2001 | | | |
| WO | WO 01/89787 | 11/2001 | | | |
| WO | WO-02/18949 | 3/2002 | | | |
| WO | WO 02/22869 | 3/2002 | | | |
| WO | WO 02/23163 | 3/2002 | | | |
| WO | WO-02/31203 | 4/2002 | | | |
| WO | WO-02/47665 | 6/2002 | | | |
| WO | WO 02/68104 | 6/2002 | | | |
| WO | WO-02/047665 | 8/2002 | | | |
| WO | WO-02/060275 | 8/2002 | | | |
| WO | WO-02/068104 A1 | 9/2002 | | | |
| WO | WO-02/078845 | 10/2002 | | | |
| WO | WO 02/103011 | 12/2002 | | | |
| WO | WO-02/103363 | 12/2002 | | | |
| WO | WO-03/011443 | 2/2003 | | | |
| WO | WO 03/037302 | 5/2003 | | | |
| WO | WO-03/044187 | 5/2003 | | | |
| WO | WO 03/078659 | 9/2003 | | | |
| WO | WO-03/099843 | 12/2003 | | | |
| WO | WO 2004/002627 | 1/2004 | | | |
| WO | WO-2004/002627 | 1/2004 | | | |
| WO | WO-2004/018497 | 3/2004 | | | |
| WO | WO 2004/024917 | 3/2004 | | | |
| WO | WO-2004/038363 | 5/2004 | | | |
| WO | WO-2004/069849 | 8/2004 | | | |
| WO | WO-2004/074504 | 9/2004 | | | |
| WO | WO-2004/083443 | 9/2004 | | | |
| WO | WO 2004/087308 | 10/2004 | | | |
| WO | WO 2004/088314 | 10/2004 | | | |
| WO | WO 2004/091763 | 10/2004 | | | |
| WO | WO-2004/102204 | 11/2004 | | | |
| WO | WO-2004/103565 | 12/2004 | | | |
| WO | WO-2005/000970 | 1/2005 | | | |
| WO | WO-2005/002730 | 1/2005 | | | |
| WO | WO 2005/021151 | 3/2005 | | | |
| WO | WO 2005021151 A1 | * | 3/2005 | | |
| WO | WO-2005/103106 | 11/2005 | | | |
| WO | WO-2005/118138 | 12/2005 | | | |

(56) References Cited

FOREIGN PATENT DOCUMENTS

| WO | WO-2006/002641 | 1/2006 |
|---|---|---|
| WO | WO-2006/009657 | 1/2006 |
| WO | WO-2006/027757 | 3/2006 |
| WO | WO 2006/038035 | 4/2006 |
| WO | WO 2006/040551 | 4/2006 |
| WO | WO-2006/040554 | 4/2006 |
| WO | WO-2006/078841 | 7/2006 |
| WO | WO 2006/096571 | 9/2006 |
| WO | WO-2006/101851 | 9/2006 |
| WO | WO-2007/021343 | 2/2007 |
| WO | WO-2007/030501 | 3/2007 |
| WO | WO-2007/081385 | 7/2007 |
| WO | WO-2007/081387 | 7/2007 |
| WO | WO 2007/089541 | 8/2007 |
| WO | WO-2007/114794 | 10/2007 |
| WO | WO-2007/123744 | 11/2007 |
| WO | WO-2007/133710 | 11/2007 |
| WO | WO-2007/138178 | 12/2007 |
| WO | WO-2008/021123 | 2/2008 |
| WO | WO-2008/063227 | 5/2008 |
| WO | WO-2008/097559 | 8/2008 |
| WO | WO-2008/121342 | 10/2008 |
| WO | WO-2008/130623 | 10/2008 |
| WO | WO-2009/029229 | 3/2009 |
| WO | WO-2010/056728 | 5/2010 |
| WO | WO-2010/040006 | 8/2010 |
| WO | WO-2010/151776 | 12/2010 |
| WO | WO-2011/042564 | 4/2011 |
| WO | WO-2011/079176 | 6/2011 |

OTHER PUBLICATIONS

Song et al., A Microfluidic System for Controlling Reaction Networks in Time, Angew. Chem. Int. Ed., 2003, 42, 767-772.*
Manafi, M., New Developments in Chromogenic and Fluorogenic Culture Media, International Journal of Food Microbiology, 2000, 60, 205-218.*
Sadtler et al., Reverse Water-In-Fluorocarbon Emulsions as a Drug Delivery System: An In Vitro Study, Colloids and Surfaces A: Physicochemical and Engineering Aspects, 1999, 147, 309-315.*
Janda, et al., "Chemical Selection for Catalysis in Combinatorial Antibody Libraries", Science, 275:945-948 (1997).
Yonezawa et al., "DNA display for in vitro selection of diverse peptide libraries", Nucleic Acids Research 31(19):e118 (2003).
Grasland-Morgrain, et al., "Droplet Coalescence in Microfluidic Devices," pp. 1-30, Jan.-Jul. 2003.
Adang et al., "The Contribution of Combinatorial Chemistry to Lead Generation: An Interim Analysis",Curr. Med. Chem., 8: 985-998 (2001).
Atwell, S. & Wells, J.A., "Selection for Improved Subtiligases by Phage Display", Proc. Natl. Acad. Sci. USA, 96: 9497-9502 (1999).
Bass, et al., "Hormone Phage: An Enrichment Method for Variant Proteins With Altered Binding Properties", Proteins, 8: 309-314 (1990).
Beebe et al., "Functional hydrogel structures for autonomous flow control inside microfluidic channels", Nature, 404: 588-590 (2000).
Bernath et al., "In Vitro Compartmentalization by Double Emulsions: Sorting and Gene Enrichment by Fluorescence Activated Cell Sorting", Anal. Biochem., 325: 151-157 (2004).
Burbaum, J.J., "Miniaturization Technologies in HTS: How Fast, How Small, How Soon? Drug Discovery",Drug Discovery Today, 3(7): 313-322 (1998).
Calvert, P., "Inkjet printing for materials and devices", Chem. Mater., 13: 3299-3305 (2001).
Chiu et al., "Chemical transformations in individual ultrasmall biomimetic containers", Science, 283: 1892-1895 (1999).
Chapman, K.B. and Szostak, J.W., "In Vitro Selection of Catalytic RNAs", Curr. Op. in Struct. Biol., 4: 618-622 (1994).
Cull, et al., "Screening for Receptor Ligands Using Large Libraries of Peptides Linked to the C Terminus of the Lac Repressor", Proc Natl Acad Sci USA, 89: 1865-9 (1992).

Curran, D.P., "Strategy-Level Separations in Organic Synthesis: From Planning to Practice", Angew. Chem. Int. Ed., 37: 1174-1196 (1998).
Czamik, A.W., "Encoding Methods for Combinatorial Chemistry", Curr. Opin. Chem. Biol., 1: 60-66 (1997).
Davis et al., "Multiple Emulsions as Targetable Delivery Systems", Meth. Enzymol., 149: 51-64 (1987).
de Gans, et al., "Inkjet printing of polymers: state of the art and future developments",Advanced Materials, 16: 203-213 (2004).
Demartis, et al., "A Strategy for the Isolation of Catalytic Activities from Repertoires of Enzymes Displayed on Phage", J. Mol. Biol., 286: 617-633 (1999).
Dickinson, E., "Emulsions and Droplet Size Control", in Wedlock, D.J. (ed.), Controlled Particle, Droplet and Bubble Formulation, Butterworth-Heinemann, Oxford, Chapter 7, pp. 191-216 (1994).
Doi, N. and Yanagawa, "H. STABLE: protein-DNA fusion system for screening of combinatorial protein libraries in vitro", FEBS Lett., 457: 227-230 (1999).
Dömling A., "Recent advances in isocyanide-based multicomponent chemistry", Curr Opin Chem Biol., 6(3): 306-13 (2002).
Dömling A. and Ugi I.I., "Multicomponent Reactions with Isocyanides",Angew Chem Int Ed Engl., 39(18): 3168-3210 (2000).
Dubertret et al., "In Vivo Imaging of Quantum Dots Encapsulated in Phospholipid Micelles", Science, 298: 1759-1762 (2002).
Duffy et al., "Rapid Prototyping of Microfluidic Systems and Polydimethylsiloxane",Anal. Chem., 70: 474-480 (1998).
Ellington, A.D. and Szostak, J.W., "In Vitro Selection of RNA Molecules that Bind Specific Ligands", Nature, 346: 818-822 (1990).
Finch, C.A., "Industrial Microencapsulation: Polymers for Microcapsule Walls", Encapsulation and Controlled Release, Spec. Publ.-R. Soc. Chem., pp. 1-12 (1993).
Fu et al., "An Integrated Microfabricated Cell Sorter", Anal. Chem., 74: 2451-2457 (2002).
Fulton. et al., "Advanced Multiplexed Analysis with the FlowMetrix™ System", Clin. Chem., 43: 1749-1756 (1997).
Ganan-Calvo, A.M., "Generation of Steady Liquid Microthreads and Micron-Sized Monodisperse Sprays and Gas Streams", Phys. Rev. Lett., 80(2): 285-288 (1998).
Ghadessy et al, "Directed Evolution of Polymerase Function by Compartmentalized SelfReplication", Proc. Natl. Acad. Sci USA, 98(8): 4552-4557 (2001).
Gold, et al., "Diversity of Oligonucleotide Functions" Annu Rev Biochem, 64: 763-97 (1995).
Gordon et al., "Solid Phase Synthesis—Designer Linkers for Combinatorial Chemistry: A Review",J. Chem. Technol. Biotechnol., 74: 835-851 (1999).
Griffiths et al., "Isolation of High Affinity Human AntibodiesDirectly from Large Synthetic Repertoires", EMBO. J., 13(14): 3245-3260 (1994).
Griffiths et al., "Directed Evolution of an Extremely Fast Phosphotriesterase by In Vitro Compartmentalization", EMBO. J., 22(1) :24-35 (2003).
Guixe et al., "Ligand-Induced Conformational Transitions in Escherichia coli Phosphofructokinase 2: Evidence for an Allosteric Site for MgATP$^{2-}$", Biochem., 37: 13269-12375 (1998).
Han et al., "Quantum-dot-tagged Microbeads for Multiplexed Optical Coding of Biomolecules", Nat. Biotechnol., 19(7): 631-635 (2001).
Handen, J. S., "High-Throughput Screening-Challenges for the Future", Drug Discov. World, pp. 47-50 (2002).
Hanes, J. & Pluckthun, A., "In vitro selection and evolution of functional proteins by using ribosome display", Proc. Natl. Acad. Sci. USA, 94: 4937-4942 (1997).
Heim et al., "Engineering Green Fluorescent Protein for Improved Brightness, Longer Wavelengths and Fluorescence Response Energy Transfer", Curr. Biol., 6(2): 178-182 (1996).
Hergenrother et al., "Small-Molecule Microarrays: Covalent Attachment and Screening of Alcohol-Containing Small Molecules on Glass Slides", J. Am. Chem. Soc., 122: 7849-7850 (2000).

(56) References Cited

OTHER PUBLICATIONS

Hildebrand et al., "Liquid-Liquid Solubility of Perfluoromethylcyclohexane with Benzene, Carbon Tetrachloride, Chlorobenzene, Chloroform and Toluene", *J. Am. Chem. Soc.*, 71: 22-25 (1949).
Holmes et al., "Reagents for Combinatorial Organic Synthesis: Development of a New O-Nitrobenzyl Photolabile Linder for Solid Phase Synthesis", *J. Org Chem.*, 60: 2318-2319 (1995).
Janda, et al., "In Vitro Selection and Evolution of Functional Proteins by Using Ribosome Display", *Science*, 275: 945-948 (1997).
Jestin, et al., "A Method for the Selection of Catalytic Activity Using Phage Display and Proximity Coupling", *Agnew. Chem. Int. Ed. Engl.* 38: 1124-1127 (1999).
Johannsson, A., "Heterogeneous Enzyme Immunoassays",In *Principles and Practice of Immunoassay*, pp. 295-325 (1991).
Johannsson et al., "Amplification by Second Enzymes", In *ELISA and Other Solid Phase Immunoassays*, Kemeny et al (ed.), Chapter 4, pp. 85-106 (1988).
Joyce, G.F., "In vitro Evolution of Nucleic Acids", *Curr. Opp. Structural Biol.*, 4: 331-336 (1994).
Keij et al., "High-Speed Photodamage Cell Selection Using a Frequency-Doubled Argon Ion Laser", *Cytometry*, 19(3): 209-216 (1995).
Kerker, M., "Elastic and Inelastic Light Scattering in Flow Cytometry [1,2]", *Cytometry*, 4(1): 1-10 (1983).
Krafft et al., "Emulsions and Microemulsions with a Fluorocarbon Phase", *Curr. Op. Colloid Interface Sci.*, 8: 251-258 (2003).
Lee et al., "Investigating the target recognition of DNA cytosine-5 methyltransferase HhaI by library selection using in vitro compartmentalisation (IVC)", *Nucleic Acids Res.*, 30: 4937-4944 (2002).
Lim et al., "Microencapsulated islets as bioartificial endocrine pancreas." *Science, New Series*, 210(4472): 908-910 (1980).
Link et al., "Geometrically Mediated Breakup of Drops in Microfluidic Devices", *Phys. Rev. Lett.*, 92(5): 054503-1 thru 054503-4 (2004).
Link et al., "Electric control droplets in microfluidic devices." *Angew. Chem. Int. Ed.*, 45: 2556-2560 (2006).
Lipinski et al., "Experimental and Computational Approaches to Estimate Solubility and Permeability in Drug Discovery and Development Settings", *Adv. Drug Deily. Rev.*, 46: 3-26 (2001).
Lowe, K. C., "Perfluorochemical Respiratory Gas Carriers: Benefits to Cell Culture Systems",*J. Fluorine Chem.*, 118: 19-26 (2002).
Luisi et al., "Activity and Conformation of Enzymes in Reverse Micellar Solutions", *Meth. Enzymol.*, 136: 188-216 (1987).
Lyne, P.D., "Structure-Based Virtual Screening: An Overview", *Drug Discov. Today*, 7(20): 1047-1055 (2002).
Mackenzie et al., "The Application of Flow Microfluorimetry to Biomedical Research and Diagnosis: A Review", *Dev. Biol. Stand.*, 64: 181-193 (1986).
Mahajan et al., "Bcl-2 and Bax Interactions in Mitochondria Probed with Green Florescent Protein and Fluorescence Resonance Energy Transfer", *Nat. Biotechnol.* 16(6): 547-552 (1998).
Masui et al., "Probing of DNA-Binding Sites of *Escherichia coli* RecA Protein Utilizing 1-anilinonaphthalene-8-Sulfonic Acid", *Biochem.*, 37(35): 12133-12143 (1998).
Mattheakis, et al., "An in vitro polysome display system for identifying ligands from very large peptide libraries", *Proc Natl Acad Sci USA*, 91: 9022-6 (1994).
McCafferty, et al., "Phage antibodies: filamentous phage displaying antibody variable domains",*Nature*, 348: 552-4 (1990).
McDonald, J. C. and Whitesides, G. M. "Poly(dimethylsiloxane) as a material for fabricating microfluidic devices", *Acc. Chem. Res.*, 35: 491-499 (2002).
Miyawaki et al., "Fluorescent Indicators for Ca2+ Based on Green Fluorescent Proteins and Calmodulin", *Nature*, 388: 882-887 (1997).
Nemoto, et al., "In vitro virus: Bonding of mRNA bearing puromycin at the 3'-terminal end to the C-terminal end of its encoded protein on the ribosome in vitro." *FEBS Letters* 414: 405-408 (1997).
Norman, A., "Flow Cytometry", *Med. Phys.*, 7(6): 609-615 (1980).
Parmley, S.F. and Smith, G.P., "Antibody-selectable filamentous fd phage vectors: affinity purification of target genes", *Gene*, 73, 305-18 (1988).
Pedersen, et al., "A Method for Directed Evolution and Functional Cloning of Enzymes", *Proc. Natl. Acad. Sci. USA*, 95: 10523-10528 (1998).
Perelson, A.S., "Theoretical Studies of Clonal Selection: Minimal Antibody Repertoire Size and Reliability of Self-Non-Self Discrimination", *J. Theor. Biol.*, 81: 645-670 (1979).
Pirrung et al., "A General Method for the Spatially Defined Immobilization of Biomolecules on Glass Surfaces Using 'Caged' Biotin", *Bioconjug. Chem.*, 7: 317-321 (1996).
Qi et al., "Acid Beta-Glucosidase: Intrinsic Fluorescence and Conformational Changes Induced by Phospholipids and Saposin C", *Biochem.*, 37(33): 11544-11554 (1998).
Ramstrom et al., "Drug Discovery by Dynamic Combinatorial Libraries", *Nat. Rev. Drug Discov.*, 1(1): 26-36 (2002).
Riess, J.G., "Fluorous Micro- and Nanophases with a Biomedical Perspective", *Tetrahedron*, 58: 4113-4131 (2002).
Roberts, R.W. & Szostak, J.W., "RNA-peptide fusions for the in vitro selection of peptides and proteins", *Proc. Natl. Acad. Sci. USA*, 94: 12297-12302 (1997).
Rolland et al., "Review Article: Fluorescence Polarization Assay by Flow Cytometry", *J. Immunol. Meth.*, 76(1): 1-10 (1985).
Sadtler et al., "Achieving Stable, Reverse Water-in-Fluorocarbon Emulsions", *Angew. Chem. Int. Ed. Engl.*, 35(17): 1976-1978 (1996).
Scott, R.L., "The Solubility of Fluorocarbons", *J. Am. Chem. Soc.*, 70: 4090-4093 (1948).
Sepp et al., "Microbead Display by In Vitro Compartmentalisation: Selection for Binding Using Flow Cytometry", *FEBS Lett.*, 532: 455-458 (2002).
Song et al., "A Microfluidic System for Controlling Reaction Networks in Time", *Angew. Chem. Int. Ed. Engl.*, 42(7): 767-772 (2003).
Song, H. and Ismagilov, R.F., "Millisecond kinetics on a microfluidic chip using nanoliters of reagents", *J Am Chem Soc.*, 125: 14613-14619 (2003).
Soumillion, et al., "Selection of β-Lactamase on Filamentous Bacteriophage by Catalytic Activity", *J Mol Biol*, 237: 415-22 (1994).
Strizhkov et al., "PCR amplification on a microarray of gel-immobilized oligonucleotides: Detection of bacterial toxin- and drug-resistant genes and their mutations." *Biotechniques*, 29(4): 844-857 (2000).
Studer et al., "Fluorous Synthesis: A Fluorous-Phase Strategy for Improving Separation Efficiency in Organic Synthesis", *Science* 275: 823-826 (1997).
Sugiura et al., "Interfacial tension driven monodispersed droplet formation from microfabricated channel array" *Langmuir*, 17: 5562-5566 (2001).
Sundberg et al., "Spatially-Addressable Immobilisation of Macromolecules on Solid Supports", *J. Am. Chem. Soc.*, 117: 12050-12057 (1995).
Tawfik, D.S., and Griffiths, A.D., "Man-made cell-like compartments for molecular evolution", *Nat Biotechnol.*, 16: 652-656 (1998).
Thorsen et al., "Dynamic Pattern Formation in a Vesicle-Generating Microfluidic Device", *Phys. Rev. Lett.*, 86(18): 4163-4166 (2001).
Tuerk, C. and Gold, L., "Systematic Evolution of Ligands by Exponential Enrichment: RNA Ligands to Bacteriophage T4 DNA Polymerase", *Science*, 249: 505-10 (1990).
Umbanhowar et al., "Monodisperse Emulsions Generated Via Drop Break Off in a Coflowing Steam", *Langmuir*, 16: 347-351 (2000).
Warburton, B., "Microcapsules for Multiple Emulsions", *Encapsulation and Controlled Release, Spec. Publ.-R. Soc. Chem.*, pp. 35-51 (1993).

(56) References Cited

OTHER PUBLICATIONS

Voss, E. W., "Kinetic Measurements of Molecular Interactions by Spectrofluorometry", *J. Mol. Recognition*, 6: 51-58 (1993).
Adang, A.E. et al., The contribution of combinatorial chemistry to lead generation: an interim analysis, Curr Med Chem 8: 985-998 (2001).
Advisory Action for U.S. Appl. No. 11/360,845, dated Jun. 14, 2010.
Advisory Action for U.S. Appl. No. 11/698,298 dated May 20, 2011.
Affholter and F. Arnold, Engineering a Revolution, Chemistry in Britain, Apr. 1999, p. 48.
Agrawal and Tang, Site-specific functionalization of oligodeoxynucleotides for non-radioactive labelling, Tetrahedron Letters 31:1543-1546 (1990).
Aharoni et al., High-Throughput screens and selections of enzyme-encoding genes, Curr Opin Chem Biol, 9(2): 210-6 (2005).
Ahn et al., Dielectrophoretic manipulation of drops for high-speed microluidic sorting devices, Applied Phys Lett 88, 024104 (2006).
Allen et al., High throughput fluorescence polarization: a homogeneous alternative to radioligand binding for cell surface receptors J Biomol Screen. 5(2):63-9 (2000).
Altman et al., Solid-state laser using a rhodamine-doped silica gel compound, IEEE Photonics technology letters 3(3):189-190 (1991).
Amstutz, P. et al., In vitro display technologies: novel developments and applications. Curr Opin Biotechnol, 12, 400-405 (2001).
Anarbaev et al., Klenow fragment and DNA polymerase alpha-primase fromserva calf thymus in water-in-oil microemulsions, Biochim Biophy Acta 1384:315-324 (1998).
Anderson et al., Preparation of a cell-free protein-synthesizing system from wheat germ, Methods Enzymol 101:635-44 (1983).
Anderson, J.E., Restriction endonucleases and modification methylases, Curr. Op. Struct. Biol., 3:24-30 (1993).
Ando, S. et al., PLGA microspheres containing plasmid DNA: preservation of supercoiled DNA via cryopreparation and carbohydrate stabilization, J Pharm Sci, 88(1):126-130 (1999).
Angell et al., Silicon micromechanical devices, Scientific American 248:44-55 (1983).
Anhuf et al., Determination of SMN1 and SMN2 copy number using TaqMan technology, Hum Mutat 22(1):74-78 (2003).
Anna et al., Formation of dispersions using flow focusing in microchannels, Applied Physics Letters,82(3): 364-366 (2003).
Arkin, M.R. et al., Probing the importance of second sphere residues in an esterolytic antibody by phage display, J Mol Biol 284(4):1083-94 (1998).
Armstrong et al., Multiple-Component Condensation Strategies for Combinatorial Library Synthesis, Acc. Chem. Res. 29(3):123-131 (1996).
Ashkin and Dziedzic, Optical trapping and manipulation of viruses and bacteria, Science 235(4795):1517-20 (1987).
Ashkin et al., Optical trapping and manipulation of single cells using infrared laser beams, Nature 330:769-771 (1987).
Auroux, Pierre-Alain et al., Micro Total Analysis Systems. 2. Analytical Standard Operations and Applications, Analytical Chemistry, vol. 74, No. 12, 2002, pp. 2637-2652.
Baccarani et al., *Escherichia coli* dihydrofolate reductase: isolation and characterization of two isozymes, Biochemistry 16(16):3566-72 (1977).
Baez et al., Glutathione transferases catalyse the detoxication of oxidized metabolites (o-quinones) of catecholamines and may serve as an antioxidant system preventing degenerative cellular processes, Biochem. J 324:25-28 (1997).
Bagwe et al, Improved drug delivery using microemulsions: rationale, recent progress, and new horizons, Crit Rev Ther Drug Carr Sys 18(1):77-140 (2001).
Baker, M., Clever PCR: more genotyping, smaller volumes, Nature Methods 7:351-356 (2010).
Ball and Schwartz, CMATRIX: software for physiologically based pharmacokinetic modeling using a symbolic matrix representation system, Comput Biol Med 24(4):269-76 (1994).

Ballantyne and Nixon, Selective Area Metallization by Electron-Beam Controlled Direct Metallic Deposition, J. Vac. Sci. Technol. 10:1094 (1973).
Barany F., The ligase chain reaction in a PCR World, PCR Methods and Applications 1(1):5-16 (1991).
Barany, F. Genetic disease detection and DNA amplification using cloned thermostable ligase, PNAS 88(1): 189-93 (1991).
Baret et al., Fluorescence-activated droplet sorting (FADS): efficient microfluidic cell sorting based on enzymatic activity, Lab on a Chip 9:1850-1858 (2009).
Baret et al., Kinetic aspects of emulsion stabilization by surfactants: a microfluidic analysis, Langmuir 25:6088-6093 (2009).
Bauer, J., Advances in cell separation: recent developments in counterflow centrifugal elutriation and continuous flow cell separation, J Chromotography, 722:55-69 (1999).
Beer et al., On-Chip, Real-Time, Single-Copy Polymerase Chain Reaction in Picoliter Droplets, Anal. Chem., 2007, v. 79, pp. 847-8475.
Bein, Thomas, Efficient Assays for Combinatorial methods for the Discovery of Catalysts, Agnew. Chem. Int. Ed. 38:3, 323-26 (1999).
Benichou et al., Double Emulsions Stabilized by New Molecular Recognition Hybrids of Natural Polymers, Polym. Adv. Tehcnol 13:1019-1031 (2002).
Benner, S.A., Expanding the genetic lexicon: incorporating non-standard amino acids into proteins by ribosome-based synthesis, Trends Biotechnol 12:158-63 (1994).
Benning, M.M. et al., The binding of substrate analogs to phosphotriesterase. J Biol Chem, 275, 30556-30560 (2000).
Berman et al., An agarose gel electrophoresis assay for the detection of DNA-binding activities in yeast cell extracts, Methods Enzymol 155:528-37 (1987).
Bernath et al, In Vitro Compartmentalization by Double Emulsions: Sorting and Gene Enrichment by Fluorescence Activated Cell Sorting, Anal. Biochem 325:151-157 (2004).
Bernath et al., Directed evolution of protein inhibitors of DNA-nucleases by in vitro compartmentalization (IVC) and nano-droplet delivery, J. Mol. Biol 345(5):1015-26 (2005).
Betlach, L. et al., A restriction endonuclease analysis of the bacterial plasmid controlling the EcoRI restriction and modification of DNA. Federation Proceedings, 35, 2037-2043 (1976).
Bibette et al., Emulsions: basic principles, Rep. Prog. Phys. 62: 969-1033 (1999).
Bico, Jose et al., Rise of Liquids and Bubbles in Angular Capillary Tubes, Journal of Colloid and Interface Science, 247:162-166 (2002).
Bico, Jose et al., Self-Propelling Slugs, J. Fluid Mech., 467:101-127 (2002).
Blattner and Dahlberg, RNA synthesis startpoints in bacteriophage lambda: are the promoter and operator transcribed, Nature New Biol 237(77):227-32 (1972).
Boder et al., Yeast surface display for screening combinatorial polypeptide libraries, Nat Biotechnol 15(6):553-7 (1997).
Bougueleret, L. et al., Characterization of the gene coding for the EcoRV restriction and modification system of *Escherichia coli*, Nucleic Acids Res, 12(8):3659-76 (1984).
Boyum, A., Separation of leukocytes from blood and bone marrow. Introduction, Scand J Clin Lab Invest Suppl 97:7 (1968).
Branebjerg et al., Fast mixing by lamination, MEMS Proceedings 9th Ann WO rkshop, San Diego, Feb. 11-15, 1996, 9:441-446 (1996).
Braslaysky et al., Sequence information can be obtained from single DNA molecules, PNAS 100(7):3960-3964 (2003).
Bringer et al., Microfluidic Systems for Chemical Kinetics That Rely on Chaotic Mixing in Droplets, Philos Transact a Math Phys Eng Sci 362:1-18 (2004).
Brody et al., A self-assembled microlensing rotational probe, Applied Physics Letters, 74:144-46 (1999).
Brown et al., Chemical synthesis and cloning of a tyrosine tRNA gene, Methods Enzymol 68:109-151 (1979).
Bru, R. et al., Catalytic activity of elastase in reverse micelles, Biochem Mol Bio Int, 31(4):685-92 (1993).
Bru, R. et al., Product inhibition of alpha-chymotrypsin in reverse micelles. Eur J Biochem 199(1): 95-103 (1991).

(56) References Cited

OTHER PUBLICATIONS

Brummelkamp et al., A system for stable expression of short interfering RNAs in mammalian cells, Science 296(5567):550-3 (2002).
Buckpitt et al.,Hepatic and pulmonary microsomal metabolism of naphthalene to glutathione adducts: factors affecting the relative rates of conjugate formation, J. Pharmacol. Exp. Ther. 231:291-300 (1984).
Buican et al., Automated single-cell manipulation and sorting by light trapping, Applied Optics 26(24):5311-5316 (1987).
Burbaum, J., Miniaturization technologies in HTS: how fast, how small, how soon Drug Discov Today 3:313-322 (1998).
Burns et al., Microfabricated structures for integrated DNA analysis, Proc. Natl. Acad. Sci. USA, 93:5556-5561(1996).
Burns, J.R. et al., The Intensification of Rapid Reactions in Multiphase Systems Using Slug Flow in Capillaries, Lab on a Chip, 1:10-15 (2001).
Burns, Mark et al., An Integrated Nanoliter DNA Analysis Device, Science, 282:484-487(1998).
Byrnes, P.J. et al., Sensitive fluorogenic substrates for the detection of trypsin-like proteases and pancreatic elastase, Anal Biochem, 126:447 (1982).
Cahill et al., Polymerase chain reaction and Q beta replicase amplification, Clin Chem 37(9):1482-5 (1991).
Caldwell, S.R. et al., Limits of diffusion in the hydrolysis of substrates by the phosphodiesterase from Pseudomonas diminuta, Biochemistry, 30: 7438-7444 (1991).
Calvert, P., Inkjet printing for materials and devices, Chem Mater 13: 3299-3305 (2001).
Caruthers, Gene synthesis machines: DNA chemistry and its uses, Science 230:281-285 (1985).
Chakrabarti, A.C. et al., Production of RNA by a polymerase protein encapsulated within phospholipid vesicles, J Mol Evol, 39(6):555-9 (1994).
Chamberlain and Ring, Characterization of T7-specific ribonucleic acid polymerase. 1. General properties of the enzymatic reaction and the template specificity of the enzyme, J Biol Chem 248:2235-44 (1973).
Chan, Emory M. et al., Size-Controlled Growth of CdSe Nanocrystals in Microfluidic Reactors, Nano Letters, 3(2):199-201(2003).
Chang and Su, Controlled double emulsification utilizing 3D PDMS microchannels, Journal of Micromechanics and Microengineering 18:1-8 (2008).
Chang, T.M., Recycling of NAD(P) by multienzyme systems immobilized by microencapsulation in artifical cells, Methods Enzymol, 136(67):67-82 (1987).
Chao et al., Control of Concentration and Volume Gradients in Microfluidic Droplet Arrays for Protein Crystallization Screening, 26th Annual International Conference of the IEEE Engineering in Medicine and Biology Society, San Francisco, California Sep. 1-5, 2004.
Chao et al., Droplet Arrays in Microfluidic Channels for Combinatorial Screening Assays, Hilton Head 2004: A Solid State Sensor, Actuator and Microsystems Workshop, Hilton Head Island, South Carolina, Jun. 6-10, 2004.
Chayen, Crystallization with oils: a new dimension in macromolecular crystal growth Journal of Crystal Growth,196:434-441(1999).
Chen et al., Capturing a Photoexcited Molecular Structure Through Time-Domain X-ray Absorption Fine Structure, Science 292(5515):262-264 (2001).
Chen et al., Microfluidic Switch for Embryo and Cell Sorting the 12th International Conference on Solid State Sensors, Actuators, and Microsystems, Boston, MA Jun. 8-12, 2003 Transducers, 1: 659-662 (2003).
Chen-Goodspeed et al., Structural Determinants of the substrate and stereochemical specificity of phosphotriesterase, Biochemistry, 40(5):1325-31 (2001).
Chen-Goodspeed, M. et al., Enhancement, relaxation, and reversal of the stereoselectivity for phosphotriesterase by rational evolution of active site residues, Biochemistry, 40: 1332-1339 (2001b).
Cheng, Z.,et al, Electro flow focusing inmicrofluidic devices, Microfluidics Poster, presented at DBAS, Frontiers in Nanoscience, presented Apr. 10, 2003.
Chetverin and Spirin, Replicable RNA vectors: prospects for cell-free gene amplification, expression, and cloning, Prog Nucleic Acid Res Mol Biol, 51:225-70 (1995).
Chiang, C.M. et al., Expression and purification of general transcription factors by FLAG epitope-tagging and peptide elution, Pept Res, 6: 62-64 (1993).
Chiba et al., Controlled protein delivery from biodegradable tyrosino-containing poly(anhydride-co-imide) microspheres, Biomaterials, 18(13): 893-901 (1997).
Chiou et al., A closed-cylce capillary polymerase chain reaction machine, Analytical Chemistry, American Chemical Society, 73:2018-21 (2001).
Chou et al., A mirofabricated device for sizing and sorting DNA molecules 96:11-13(1998).
Clackson, T. et al., In vitro selection from protein and peptide libraries, Trends Biotechnol, 12:173-84 (1994).
Clausell-Tormos et al., Droplet-based microfluidic platforms for the encapsulation and screening of Mammalian cells and multicellular organisms, Chem Biol 15(5):427-437 (2008).
Cohen, S. et al., Controlled delivery systems for proteins based on poly(lactic/glycolic acid) microspheres, Pharm Res, 8(6):713-720 (1991).
Collins et al., Optimization of Shear Driven Droplet Generation in a Microluidic Device, ASME International Mechanical Engineering Congress and R&D Expo, Washington (2003).
Collins, J. et al., Microfluidic flow transducer based on the measurements of electrical admittance, Lab on a Chip, 4:7-10 (2004).
Compton, J., Nucleic acid sequence-based amplification, Nature, 350(6313):91-2 (1991).
Cormack, B.P. et al., FACS-optimized mutants of the green fluorescent protein (GFP), Gene 173(1):33-38 (1996).
Cortesi et al., Production of lipospheres as carriers for bioactive compounds, Biomateials, 23(11): 2283-2294 (2002).
Courrier et al., Reverse water-in-fluorocarbon emulsions and microemulsions obtained with a fluorinated surfactant, Colloids and Surfaces A: Physicochem. Eng. Aspects 244:141-148 (2004).
Craig, D. et al., Fluorescence-based enzymatic assay by capillary electrophoresis laser-induced fluoresence detection for the determinination of a few alpha-galactosidase molecules, Anal. Biochem. 226: 147 (1995).
Creagh, A.L. et al., Structural and catalytic properties of enzymes in reverse micelles, Enzyme Microb Technol 15(5): 383-92 (1993).
Crosland-Taylor, A Device for Counting Small Particles suspended in a Fluid through a Tube, Nature 171:37-38 (1953).
Crowley, J. M., Electrical breakdown of bimolecular lipid membranes as an electromechanical instability, Biophys J. 13(7):711-724 (1973).
Curran, D.P., Strategy-level separations in organic synthesis: from planning to practice. Angew Chem Int Ed, 37: 1174-11-96 (1998).
Czarnik, A.W., Encoding methods for combinatorial chemistry, Curr Opin Chem Biol 1:60-66 (1997).
Dankwardt et al., Combinatorial synthesis of small-molecule libraries using 3-amino-5-hydroxybenzoic acid, 1:113-120 (1995).
Davis, J.A. et al., Deterministic hydrodynamics: Taking blood apart, PNAS 103:14779-14784 (2006).
Davis, S.S. et al., Multiple emulsions as targetable delivery systems, Methods in Enzymology, 149: 51-64 (1987).
de Gans, B.J. et al., Inkjet printing of polymers: state of the art and future developments, Advanced materials, 16: 203-213 (2004).
De-Bashan, L. E. et al., Removal of ammonium and phosphorus ions from synthetic wastewater by the microalgae *Chlorella vulgaris* coimmobilized in alginate beads with the microalgae growth-promoting bacterium *Azospirillum brasilense*, Water Research 36:2941-2948 (2002).
Delagrave, S. et al., Red-shifted excitation mutants of the green fluorescent protein, Biotechnology 13(2):151-4 (1995).

(56) References Cited

OTHER PUBLICATIONS

DelRaso, In vitro methodologies for enhanced toxicity testing, Toxicol. Lett. 68:91-99 (1993).
Dickinson, E., Emulsions and droplet size control, Wedlock, D.J., Ed., in Controlled Particle Droplet and Bubble Formulation, ButterWO rth-Heine-mann, 191-257 (1994).
DiMatteo, et al., Genetic conversion of an SMN2 gene to SMN1: A novel approach to the treatment of spinal muscular atrophy, Exp Cell Res. 314(4):878-886 (2008).
Dinsmore et al., Colioidosomes: Selectively Permeable Capsules Composed of Colloidal Particles, Science 298(5595):1006-1009. (2002).
Dittrich et al., A new embedded process for compartmentalized cell-free protein expression and on-line detection in microfluidic devices, Chembiochem 6(5):811-814 (2005).
Doi et al., In vitro selection of restriction endonucleases by in vitro compartmentilization, Nucleic Acids Res, 32(12): e95 (2004).
Doi, N. and Yanagawa, H. STABLE: protein-DNA fusion system for screening of combinatorial protein libraries in vitro, FEBS Lett., 457: 227-230 (1999).
Doman, T.N. et al., Molecular docking and high-throughput screening for novel inhibitors of protein tyrosine phosphatase-1B, J Med Chem, 45: 2213-2221 (2002).
Dove et al., In Brief, Nature Biotechnology 20:1213 (2002).
Dower et al., High efficiency transformation of *E. coli* by high voltage electroporation, Nucleic Acids Res 16:6127-6145 (1988).
Dressman et al., Transforming single DNA molecules into fluorescent magnetic particles for detection and enumeration of genetic variations, PNAS 100:8817-22 (2003).
Dreyfus et al., Ordered and disordered patterns in two phase flows in microchannels, Phys Rev Lett 90(14):144505-1-144505-4 (2003).
Drmanac et al., Sequencing by hybridization: towards an automated sequencing of one million M13 clones arrayed on membranes, Elctrophoresis 13:566-573 (1992).
Duffy et al., Rapid Protyping of Microfluidic Systems and Polydimethylsiloxane, Anal Chem 70:474-480 (1998).
Duggleby, R. G. Enzyme Kinetics and Mechanisms, Pt D. Academic Press 249:61-90 (1995).
Dumas, D.P., Purification and properties of the phosphotriesterase from Psuedomonas diminuta, J Biol Chem 264: 19659-19665 (1989).
Eckert and Kunkel, DNA polymerase fidelity and the polymerase chain reaction, Genome Res 1:17-24 (1991).
Edd et al., Controlled encapsulation of single-cells into monodisperse picolitre drops, Lab Chip 8(8):1262-1264 (2008).
Edel, Joshua B. et al., Microfluidic Routes to the Controlled Production of Nanopaticles, Chemical Communications, 1136-1137 (2002).
Edris et al., Encapsulation of orange oil in a spray dried double emulsion, Nahrung/Food, 45(2):133-137 (2001).
Effenhauser et al., Glass chips for high-speed capillary electrophoresis separations with submicrometer plate heights, Anal Chem 65:2637-2642 (1993).
Eggers, Jens et al., Coalescence of Liquid Drops, J. Fluid Mech.,401 : 293-310 (1999).
Ehrig, T. et al., Green-fluorescent protein mutants with altered fluorescence excitation spectra, Febs Lett, 367(2):163-66 (1995).
Eigen et al., hypercycles and compartments: compartments assists—but does not replace—hypercyclic organization of early genetic information, J Theor Biol, 85:407-11 (1980).
Eigen et al., The hypercycle: coupling of RNA and protein biosynthesis in the infection cycle of an RNA bacteriophage, Biochemistry, 30:11005-18 (1991).
Eigen, Wie entsteht information Prinzipien der selbstorganisation in der biologie, Berichte der punsen-gesellschaft fur physikalische chemi, 80:1059-81 (1976).
Ellman et al., Biosynthetic method for introducing unnatural amino acids site-specifically into proteins, Methods Enzymol, 202:301-36 (1991).
Endo et al. Kinetic determination of trace cobalt by visual autocatalytic indication, Talanta 47:349-353 (1998).
Endo et al., Autocatalytic decomposition of cobalt complexes as an indicator system for the determination of trace amounts of cobalt and effectors, Analyst 121:391-394 (1996).
Eow et al., Electrocoalesce-separators for the separation of aqueous drops from a flowing dielectric viscous liquid, Separation and Purification Tech 29:63-77 (2002).
Eow et al., Electrostatic enhancement of coalescence of water droplets in oil: a review of the technology, Chemical Engineeing Journal 85:357-368 (2002).
Eow et al., Motion, deformation and break-up of aqueous drops in oils under high electric field strengths, Chemical Eng Proc 42:259-272 (2003).
Eow et al., The behavior of a liquid-liquid interface and drop-interface coalescence under the influence of an electric field, Colloids and Surfaces A: Physiochern. Eng. Aspects 215:101-123 (2003).
Eow, et al. Electrostatic and hydrodynamic separation of aqueous drops in a flowing viscous oil, Chemical Eng Proc 41:649-657 (2002).
Extended European Search Report for EP 10181911.8 dated Jun. 1, 2011 (7 pages).
Extended European Search Report for EP 10184514.7 dated Dec. 20, 2010 (5 pages).
Faca et al., A mouse to human search for plasma proteome changes associated with pancreatic tumor development, PLoS Med 5(6):e123 (2008).
Fahy et al., Self-sustained sequence replication (3SR): an isothermal transcription-based amplification system alternative to PCR, PCR Methods Appl 1:25-33 (1991).
Fan and Harrison, Micromachining of capillary electrophoresis injectors and separators on glass chips and evaluation of flow at capillary intersections, Anal Chem 66:177-184 (1994).
Fastrez, J., In vivo versus in vitro screening or selection for catalytic activity in enzymes and abzymes, Mol Biotechnol 7(1):37-55 (1997).
Fettinger et al., Stacked modules for micro flow systems in chemical analysis: concept and studies using an enlarged model, Sens Actuat B. 17:19-25 (1993).
Fiedler et al., Dielectrophoretic sorting of particles and cells in a microsystem, Anal Chem 70(9):1909-1915 (1998).
Field, J. et al., Purification of a RAS-responsive adenylyl cyclase complex from *Saccharomyces cervisiae* by use of an epitope addition method. Mol Cell Biot, 8: 2159-2165 (1988).
Fields, S. and Song, O., A novel genetic system to detect protein-protein interactions, Nature 340(6230): 245-6 (1989).
Filella et al., TAG-72, CA 19.9 and CEA as tumor markers in gastric cancer, Acta Oncol. 33(7):747-751 (1994).
Finch, C.A., Encapsulation and controlled release, Spec Publ R Soc Chem, 138:35 (1993).
Finch, C.A., Industrial Microencapsulation: Polymers for Microcapsule Walls, 1-12 in Encapsulation and Controlled Release, Woodhead Publishing (1993).
Fire & Xu, Rolling replication of short DNA circles, PNAS 92(10):4641-5 (1995).
Firestine, S.M. et al., Using an AraC-based three hybrid system to detect biocatalysts in vivo, Nat Biotechnol 18: 544-547 (2000).
Fisch et al., A strategy of exon shuffling for making large peptide repertoires displayed on filamentous bacteriophage, PNAS 93:7761-6 (1996).
Fisher et al., Cell Encapsulation on a Microfluidic Platform, The Eighth International Conference on Miniaturised Systems for Chemistry and Life Scieces, MicroTAS 2004, Sep. 26-30, Malmo, Sweden.
Fletcher et al., Micro reactors: principles and applications in organic synthesis, Tetrahedron 58:4735-4757 (2002).
Fluri et al., Integrated capillary electrophoresis devices with an efficient postcolumn reactor in planar quartz and glass chips, Anal Chem 68:4285-4290 (1996).
Fornusek, L. et al., Polymeric microspheres as diagnostic tools for cell surface marker tracing, Crit Rev Ther Drug Carrier Syst, 2:137-74 (1986).

(56) References Cited

OTHER PUBLICATIONS

Fowler, Enhancement of Mixing by Droplet-Based Microfluidics, Int Conf MEMS 97-100 (2002).
Freese, E., The specific mutagenic effect of base analogues on Phage T4, J Mol Biol, 1: 87 (1959).
Frenz et al., Reliable microfluidic on-chip incubation of droplets in delay-lines, Lab on a Chip 9:1344-1348 (2008).
Fu et al., A microfabricated fluorescence-activated cell sorter, Nature Biotechnology, 17(11):1109-1111 (1999).
Fu et al., An Integrated Microfabricated Cell Sorter, Anal. Chem., 74: 2451-2457 (2002).
Fulton et al., Advanced multiplexed analysis with the FlowMetrix system, Clin Chem 43:1749-1756 (1997).
Fulwyler, Electronic Separation of Biological Cells by Volume, Science 150(3698):910-911 (1965).
Gallarate et al., On the stability of ascorbic acid in emulsified systems for topical and cosmetic use, Int J Pharm 188(2):233-241 (1999).
Ganan-Calvo, A.M., Perfectly Monodisperse Microbubbling by Capillary Flow Focusing, Phys Rev Lett 87(27): 274501-1-4 (2001).
Garcia-Ruiz et al. A super-saturation wave of protein crystallization, J. Crystal Growth, 232:149-155(2001).
Garcia-Ruiz et al., Investigation on protein crystal growth by the gel acupuncture method{, Acta, Cryst., 1994, D50, 99. pp. 484-490.
Garstecki, et al., Formation of monodisperse bubbles in a microfluidic flow-focusing device, Appl Phys Lett 85(13):2649-2651 (2004).
Gasperlin et al., The structure elucidation of semisolid w/o emulsion systems containing silicone surfactant, Intl J Pharm, 107:51-6 (1994).
Gasperlin et al., Viscosity prediction of lipophillic semisolid emulsion systems by neural network modeling, Intl J Pharm, 196:37-50 (2000).
Georgiou et al., Display of heterologous proteins on the surface of microorganisms: from the screenign of combinatiorial libraires to live recombinant vaccines. Nat Biotechnol 15(1), 29-34 (1997).
Georgiou, G., Analysis of large libraries of protein mutants using flow cytometry, Adv Protein Chem, 55: 293-315 (2000).
Gerdts et al., A Synthetic Reaction NetWork: Chemical Amplification Using Nonequilibrium Autocatalytic Reactions Coupled in Time, J. Am. Chem. Soc 126:6327-6331 (2004).
Ghadessy et al., Directed Evolution of Polymerase Function by Compartmentalized Self-Replication, PNSAS 98(8): 4552-4557 (2001).
Gibbs et al., Detection of single DNA base differences by competitive oligonucleotide priming, Nucleic Acids Res. 17(7): 2437-48 (1989).
Gilliland, G., Analysis of cytokine mRNA and DNA: Detection and quantitation by competitive polymerase chain reaction, PNAS, 87(7):2725-9 (1990).
Giusti et al., Synthesis and characterization of 5' fluorescent dye labeled oligonucleotides, Genome Res 2:223-227 (1993).
Goodall, J. L. et al., Operation of Mixed-Culture Immobilized Cell Reactors for the Metabolism of Meta- and Para-Nitrobenzoate by *Comamonas* Sp. JS46 and *Comamonas* Sp. JS47, Biotechnology and Bioengineering, 59 (1): 21-27 (1998).
Gordon and Balasubramanian, Solid phase synthesis—designer linkers for combinatorial chemistry: a review, J. Chem. Technol. Biotechnol., 74(9):835-851 (1999).
Gregoriadis, G., Enzyme entrapment in liposomes, Methods Enzymol 44:218-227 (1976).
Griffiths et al., Directed evolution of an extremely fast phosphotriesterase by in vitro compartmentalization, EMBO J, 22:24-35 (2003).
Griffiths et al., Isolation of high affinity human antibodies directly from large synthetic repertoires, Embo J 13(14):3245-60 (1994).
Griffiths et al., Man-made enzymes-from design to in vitro compartmentalisation, Curr Opin Biotechnol 11:338-353 (2000).
Griffiths, A., and Tawfik, D., Miniaturising the laboratory in emulsion droplets, Trend Biotech 24(9):395-402 (2006).
Griffiths, A.D. et al., Strategies for selection of antibodies by phage display, Curr Opin Biotechnol, 9:102-8 (1998).
Guatelli, J.C. et al., Isothermal, in vitro amplification of nucleic acids by a multienzyme reaction modeled after retroviral replication, PNAS, 87(5):1874-8 (1990).
Guixe et al., Ligand-Induced Conformational Transitions in *Escherichia coli* Phosphofructokinase 2: Evidence for an Allosteric Site for MgATP2n, Biochem., 37: 13269-12375 (1998).
Gupta, K.C., et al., A general method for the synthesis of 3'-sulfhydryl and phosphate group containing oligonucleotides, Nucl Acids Res 19 (11): 3019-3026 (1991).
Haber et al., Activity and spectroscopic properties of bovine liver catalase in sodium bis(2-ethylhexyl) sulfosuccinate/isooctane reverse micelles, Eur J Biochem 217(2): 567-73 (1993).
Habig and Jakoby, Assays for differentiation of glutathione S-transferases, Methods in Enzymology, 77: 398-405 (1981).
Hadd et al., Microchip Device for Performing Enzyme Assays, Anal. Chem 69(17): 3407-3412 (1997).
Haddad et al., A methodology for solving physiologically based pharmacokinetic models without the use of simulation software, Toxicol Lett. 85(2): 113-26 (1996).
Hagar and Spitzer, the effect of endotoxemia on concanavalin A induced alterations in cytoplasmic free calcium in rat spleen cells as determined with Fluo-3, Cell Calcium 13:123-130 (1992).
Hai et al., Investigation on the release of fluorescent markers from the w/o/w emulsions by fluorescence-activated cell sorter, J Control Release, 96(3): 393-402 (2004).
Haies et al., Morphometric study of rat lung cells. I. Numerical and dimensional characteristics of parenchymal cell population, Am. Rev. Respir. Dis. 123:533-54 (1981).
Hall, Experimental evolution of Ebg enzyme provides clues about the evolution of catalysis and to evolutionary potential, FEMS Microbiol Lett, 174(1):1-8 (1999).
Hall, The EBG system of *E. coli*: origin and evolution of a novel beta-galactosidase for the metabolism of lactose, Genetica 118(2-3):143-56 (2003).
Han et al., Quantum-dot-tagged Microbeads for Multiplexed Optical Coding of Biomolecules, Nat Biotech 19(7): 631-635 (2001).
Handen, J.S., High-throughput screening- challenges for the future, Drug Discov World, 47-50 (2002).
Handique, K. et al., On-Chip Thermopneumatic Pressure for Discrete Drop Pumping, Analytical Chemistry, 73:1831-1838 (2001).
Hanes et al., Degradation of porous poly(anhydide-co-imide) microspheres and implication for controlled macromolecule delivery, Biomaterials, 19(1-3): 163-172(1998).
Hansen et al., A robust and scalable microfluidic metering method that allows protein crystal growth by free interface diffusion, PNAS 99(26):16531-16536 (2002).
Harada et al., Monoclonal antibody G6K12 specific for membrane-associated differentiation marker of human stratified squamous epithelia and squamous cell carcinoma, J. Oral Pathol. Med 22(4):145-152 (1993).
Harder, K.W. et al., Characterization and kinetic analysis of the intracellular domain of human protein tyrosine phosphatase beta (HPTP beta) using synthetic phosphopeptides, Biochem J 298 (Pt 2): 395-401 (1994).
Harries et al., A Numerical Model for Segmented Flow in a Microreactor, Int J of Heat and Mass Transfer, 46:3313-3322 (2006).
Harris et al., Single-molecule DNA sequencing of a viral genome, Science 320(5872):106-109 (2008).
Harrison et al., Micromachining a miniaturized capillary electrophoresis-based chemical analysis system on a chip, Science 261(5123):895-897 (1993).
Hasina et al., Plasminogen activator inhibitor-2: a molecular biomarker for head and neck cancer progression, Cancer Research 63:555-559 (2003).
Haynes Principles of Digital PCR and Measurement IssueOct. 15, 2012.
Hayward et al., Dewetting Instability during the Formation of Polymersomes from BloceCopolymer-Stabilized Double Emulsions, Langmuir, 22(10): 4457-4461 (2006).

(56) References Cited

OTHER PUBLICATIONS

He et al., Selective encapsulation of single cells and subcellular organelles into picoliter- and femtoliter-volume droplets, Anal Chem 77(6):1539-1544 (2005).
Heim et al., Engineering Green Fluorescent Protein for Improved Brightness, Longer Wavelengths and Fluorescence Response Energy Transfer, Carr. Biol, 6(2): 178-182 (1996).
Hellman et al., Differential tissue-specific protein markers of vaginal carcinoma, Br J Cancer, 100(8): 1303-131 (2009).
Hergenrother et al., Small-Molecule Microarrays: Covalent Attachment and Screening of Alcohol-Containing Small Molecules on Glass Slides, J. Am. Chem. Soc, 122: 7849-7850 (2000).
Hildebrand et al., Liquid-Liquid Solubility of Perfluoromethylcyclohexane with Benzene, Carbon Tetrachloride, Chlorobenzene, Chloroform and Toluene, J. Am. Chem. Soc, 71:22-25 (1949).
Hjelmfelt et al, Pattern-Recognition in Coupled Chemical Kinetic Systems, Science, 260(5106):335-337 (1993).
Ho, S.N. et al., Site-directed mutageneiss by overlap extension using the polymerase chain reaction, Gene, 77(1):51-9 (1989).
Hoang, Physiologically based pharmacokinetic models: mathematical fundamentals and simulation implementations, Toxicol Lett 79(1-3):99-106 (1995).
Hochuli et al., New metal chelate adsorbent selective for proteins and peptides containing neighbouring histidine residues, J Chromatogr 411: 177-84 (1987).
Holmes et al., Reagents for Combinatorial Organic Synthesis: Development of a New O-Nitrobenzyl Photolabile Linder for Solid Phase Synthesis, J. OrgChem., 60: 2318-2319(1995).
Hong, S.B. et al., Stereochemical constraints on the substrate specificity of phosphodiesterase, Biochemistry, 38: 1159-1165 (1999).
Hoogenboom et al., Multi-subunit proteins on the surface of filamentous phage: methodologies for displaying antibody (Fab) heavy and light chains, Nucl Acids Res., 91: 4133-4137 (1991).
Hoogenboom, H.R., Designing and optimizing library selection strategies for generating high-affinity antibodies, Trends Biotechnol, 15:62-70 (1997).
Hopfinger & Lasheras, Explosive Breakup of a Liquid Jet by a Swirling Coaxial Jet, Physics of Fluids 8(7):1696-1700 (1996).
Hopman et al., Rapid synthesis of biotin-, digoxigenin-, trinitrophenyl-, and fluorochrome-labeled tyramides and their application for in situ hybridization using CARD amplification, J of Histochem and Cytochem, 46(6):771-77 (1998).
Horton et al., Engineering hybrid genes without the use of restriction enzymes: gene splicing by overlap extension, Gene 77(1), 61-8 (1989).
Hosokawa, Kazuo et al., Handling of Picoliter Liquid Samples in a Poly(dimethylsiloxane)-Based Microfluidic Device, Analytical Chemistry, 71(20):4781-4785 (1999).
Hsu et al., Comparison of process parameters for microencapsulation of plasmid DNA in poly(D, L-lactic-co-glycolic acid microspheres, J Drug Target, 7:313-23 (1999).
Huang L. R. et al., Continuous particle separation through deterministic lateral displacement, Science 304(5673):987-990 (2004).
Huang, Z. et al., A sensitive competitive ELISA for 2,4-dinitrophenol using 3,6-fluorescein diphosphate as a fluorogenic substrate, J Immunol Meth, 149:261 (1992).
Huang, Z.J., Kinetic assay of fluorescein mono-beta-D-galactosidase hydrolysis by beta-galactosidase: a front-face measurement for strongly absorbing fluorogenic substrates, Biochemistry, 30:8530-4 (1991).
Hubert et al. Data Concordance from a Comparison between Filter Binding and Fluorescence Polarization Assay Formats for Identification of RUOCK-II Inhibitors, J biomol Screen 8(4):399-409 (2003).
Huebner, A. et al., Quantitative detection of protein expression in single cells using droplet microfluidics, Chem Com 12:1218-1220 (2007).
Hung et al., Optimization of Droplet Generation by controlling PDMS Surface Hydrophobicity, 2004 ASME International Mechanical Engineering Congrees and RD&D Expo, Nov. 13-19, Anaheim, CA (2004).
Hung, et al, Controlled Droplet Fusion in Microfluidic Devices, MicroTAS 2004, Sep. 26-30, Malmo, Sweden (2004).
Hutchison et al., Cell-free cloning using Phi29 polymerase, PNAS 102(48):17332-17336 (2005).
Ibrahim, S.F. et al., High-speed cell sorting: fundamentals and recent advances, Curr Opin Biotchnol, 14(1):5-12 (2003).
Ikeda et al., Bioactivation of tegafur to 5-fluorouracil is catalyzed by cytochrome P-450 2A6 in human liver microsomes in vitro, Clin Cancer Res 6(11):4409-4415 (2000).
lnai et al., Immunohistochemical detection of an enamel protein-related epitope in rat bone at an early stage of osteogenesis, Histochemistry 99(5):335-362 (1993).
International Preliminary Report of Patentability for PCTUS2010061741 dated Sep. 16, 2011(4 pages).
International Preliminary Report on Patentability dated Sep. 20, 2007, for PCT/US2006/007772.
International Search Report and Written Opinion for PCT/US2009/050931 dated Nov. 26, 2009 (3 pages).
International Search Report and Written Opinion for PCTUS1154353 dated Apr. 20, 2012 (34 pages).
International Search Report and Written Opinion for PCTUS12024745 dated May 11, 2012 (21 pages).
International Search Report and Written Opinion for PCTUS1224741 dated Jun. 12, 2012 (12 pages).
International Search Report and Written Opinion for PCTUS125499 dated May 29, 2012 (10 pages).
International Search Report and Written Opinion in PCT/EP2010/065188 dated Jan. 12, 2011 (7 pages).
International Search Report and Written Opinion in PCT/US11/24615 dated Jul. 25, 2011 (37 pages).
International Search Report and Written Opinion in PCT/US2004/010903 dated Dec. 20, 2004 (16 pages).
International Search Report and Written Opinion in PCT/US2006/021286 dated Sep. 14, 2007 (16 pages).
International Search Report and Written Opinion in PCT/US2007/002063 dated Nov. 15, 2007 (20 pages).
International Search Report in PCT/US01/18400 dated Jan. 28, 2005 ( 37 pages).
Ismagilov, Integrated Microfluidic Systems, Angew. Chem. Int. Ed 42:4130-4132 (2003).
Jang et al., Controllable delivery of non-viral DNA from porous scaffold, J Controlled Release 86(1):157-168 (2003).
Japanese Office Action for JP 2006-509830 dated Jun. 1, 2011 (4 pages).
Jermutus et al., Recent advances in producing and selecting functional proteins by using cell-free translation, Curr Opin Biotechnol 9(5): 534-48 (1998).
Jo, et al, Encapsulation of Bovine Serum Albumin in Temperature-Programmed Shell-in-Shell Structures, Macromol. Rapid Comm 24:957-962 (2003).
Joerger et al., Analyte detection with DNA-labeled antibodies and polymerase chain reaction, Clin. Chem. 41(9):1371-7 (1995).
Johannsson et al., Amplification by Second Enzymes, in ELISA and Other Solid Phase Immunoassays, Kemeny et al (ed.), Chapter 4, pp. 85-106 John Wiley (1988).
Johannsson, A., Heterogeneous Enzyme Immunoassays, in Principles and Practice of Immunoassay, pp. 295-325 Stockton Press (1991).
Johnson, T.O. et al., Protein tyrosine phosphatase 1B inhibitors for diabetes, Nature Review Drug Discovery 1, 696-709 (2002).
Jones et al. Glowing jellyfish, luminescence and a molecule called coelenterazine, Trends Biotechnol. 17(12):477-81 (1999).
Jones, L.J. et al., Quenched BODIPY dye-labeled casein substrates for the assay of protease activity by direct fluorescence measurement, Anal Biochem, 251:144 (1997).
Joo et al., Laboratory evolution of peroxide-mediated cytochrome P450 hydroxylaion, Nature 399:670 (1999).
Joos et al., Covalent attachment of hybridizable oligonucleotides to glass supports, Analytical Biochemistry 247:96-101 (1997).

(56) References Cited

OTHER PUBLICATIONS

Kadir and Moore, Haem binding to horse spleen ferritin, Febs Lett, 276: 81-4 (1990).
Kallen, R.G. et al., The mechanism of the condensation of formaldehyde with tetrahydrofolic acid, J. Biol. Chem., 241:5851-63 (1966).
Kambara et al., Optimization of Parameters in a DNA Sequenator Using Fluorescence Detection, Nature Biotechnology 6:816-821 (1988).
Kamensky et al., Spectrophotometer: new instrument for ultrarapid cell analysis, Science 150(3696):630-631 (1965).
Kanouni et al., Preparation of a stable double emulsion (W1/0/W2): role of the interfacial films on the stability of the system, Adv. Collid. Interf. Sci., 99(3): 229-254 (2002).
Katanaev et al., Viral Q beta RNA as a high expression vector for mRNA translation in a cell-free system, Febs Lett, 359:89-92 (1995).
Katsura et al., Indirect micromanipulation of single molecules in water-in-oil emulsion, Electrophoresis, 22:289-93 (2001).
Kawakatsu et al., Regular-sized cell creation in microchannel emulsification by visual microprocessing method, Journal of the American Oil ChemistS Society, 74:317-21 (1997).
Keana J. & Cai, S. X., New reagents for photoaffinity labeling: synthesis and photolysis of functionalized perfluorophenyl azides, J. Org. Chem.55(11):3640-3647 (1990).
Keefe, A.D. et al., Functional proteins from a random-sequence library, Nature, 410: 715-718 (2001).
Keij et al., High-Speed Photodamage Cell Selection Using a Frequency-Doubled Argon Ion Laser, Cytometry, 19(3): 209-216 (1995).
Keij, J.F., et al., High-speed photodamage cell sorting: An evaluation of the ZAPPER prototype, Methods in cell biology, 42: 371-358 (1994).
Kelly et al., Miniaturizing chemistry and biology in microdroplets, Chem Commun 18:1773-1788 (2007).
Kerker, M., Elastic and inelastic light scattering in flow cytometry, Cytometry, 4:1-10 (1983).
Khandjian, UV crosslinking of RNA to nylon membrane enhances hybridization signals, Mol. Bio. Rep. 11: 107-115 (1986).
Kim et al., Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125 (2004).
Kim S. et al, Type II quantum dots: CdTe/CdSe (core/shell) and CdSe/ZnTe (core/shell) heterostructures, J. Am Chem Soc. 125:11466-11467 (2003).
Kircher et al., High-throughput DNA sequencing-concepts and limitations, Bioessays 32(6):524-536 (2010).
Kiss et al., High-throughput quantitative polymerase chain reaction in picoliter droplets, Anal. Chem 80:8975-8981 (2008).
Kitagawa et al., Manipulation of a single cell with microcapillary tubing based on its electrophoretic mobility, Electrophoresis 16:1364-1368 (1995).
Klug and Famulok, All you wanted to know about selex, Molecular Biology Reports, 20:97-107 (1994).
Klug and Schwabe, Protein motifs 5. Zinc fingers, FASEB J 9(8):597-604 (1995).
Klug, A., Gene Regulatory Proteins and Their Interaction with DNA, Ann NY Acad Sci, 758: 143-60 (1995).
Knaak et al., Development of partition coefficients, Vmax and Km values, and allometric relationships, Toxicol Lett. 79(I-3):87-98 (1995).
Knight, James B., Hydrodynamic Focusing on a Silicon Chip: Mixing Nanoliters in Microseconds, Physical Review Lett 80(17):3863-3866 (1998).
Kojima et al. PCR amplification from single DNA molecules on magnetic beads in emulsion: application for high-throughput screening of transcription factor targets. Nucleic Acids Res. 33:e150 (2005).
Kolb et al., Cotranslational folding of proteins, Biochem Cell Biol, 73:1217-20 (1995).
Komatsu et al., Roles of cytochromes P450 1A2, 2A6, and 2C8 in 5-fluorouracil formation rom tegafur, an anticancer prodrug, in human liver microsomes. Drug Met. Disp., 28:1457-1463 (2001).
Kopp et al., Chemical amplification: continuous flow PCR on a chip, Science, 280:1046-48 (1998).
Koster et al., Drop-based microfluidic devices for encapsulation of single cells, Lab on a Chip 8:1110-1115 (2008).
Kowalczykowski et al., Biochemistry of homologous recombination in *Escherichia coli*, Microbiol Rev 58(3):401-65 (1994).
Krafft et al., Emulsions and microemulsions with a fluorocarbon phase, Colloid and Interface Science 8(3):251-258 (2003).
Krafft, Fluorocarbons and fluorinated amphiphiles in drug delivery and biomedical research, Adv Rev Drug Disc 47:209-228 (2001).
Krafft et al., Synthesis and preliminary data on the biocompatibility and emulsifying properties of perfluoroalkylated phosphoramidates as injectable surfactants, Eur. J. Med. Chem., 26:545-550 (1991).
Kralj et al., Surfactant-enhanced liquid-liquid extraction in microfluidic channels with inline electric-field enhanced coalescence, Lab Chip 5:531-535 (2005).
Kricka and Wilding, Microchip PCR, Anal Bioanal Chem 377(5):820-825 (2003).
Kricka and Wilding, Micromachining: a new direction for clinical analyzers, Pure and Applied Chemistry 68(10):1831-1836 (1996).
Krumdiek, C.L. et al., Solid-phase synthesis of pteroylpolyglutamates, Methods Enzymol, 524-29 (1980).
Kumar, A. et al., Activity and kinetic characteristics of glutathione reductase in vitro in reverse micellar waterpool, Biochem Biophys Acta, 996(1-2):1-6 (1989).
Lage et al., Whole genome analysis of genetic alterations in small DNA samples using hyperbranched strand displacement amplification and array-CGH. Genome Res. 13: 294-307 (2003).
Lamprecht et al., pH-sensitive microsphere delivery increases oral bioavailability of calcitonin, Journal of Controlled Release, 98(1): 1-9(2004).
Lancet, D. et al., Probability model for molecular recognition in biuological receptor repertoirs: significance to the olfactory system, PNAS, 90(8):3715-9 (1993).
Landergren et al., A ligase mediated gene detection technique. Science 241(4869):1077-80 (1988).
Lasheras, et al., Breakup and Atomization of a Round Water Jet by a High Speed Annular Air Jet, J Fluid Mechanics 357:351-379 (1998).
Leary et al., Application of Advanced Cytometric and Molecular Technologies to Minimal Residual Disease Monitoring, Proceedings of SPIE 3913:36-44 (2000).
Lee et al, Investigating the target recognition of DNA cytosine-5 methyltransferase Hhal by library selection using in vitro compartmentalisation (IVC), Nucleic Acids Res 30:4937-4944 (2002).
Lee et al., Circulating flows inside a drop under time-periodic non-uniform electric fields, Phys Fuilds 12(8):1899-1910 (2000).
Lee, et al, Effective Formation of Silicone-in-Fluorocarbon-in-Water Double Emulsions: Studies on Droplet Morphology and Stability, Journal of Dispersion Sci Tech 23(4):491-497(2002).
Lee, et al, Preparation of Silica Paticles Encapsulating Retinol Using O/W/O Multiple Emulsions, Journal of Colloid and Interface Science, 240(1): 83-89 (2001).
Lemof, et al, An AC Magnetohydrodynamic Microfluidic Switch for Micro Total Analysis Systems, Biomedical Microdevices, 5(I):55-60 (2003).
Lesley et al., Use of in vitro protein synthesis from PCR-generated templates to study interaction of *E coli* transcription factors with core RNA polymerase, J Biol Chem 266(4):2632-8 (1991).
Lesley, S.A., Preparation and use of *E. coli* S-30 extracts, Methods Mol Biol, 37:265-78 (1995).
Leung et al., A method for random mutagenesis of a defined DNA segment using a modified polymerase chain reaction. Technique 1:11-15 (1989).
Li and Harrison, Transport, Manipulation, and Reaction of Biological Cells On-Chip Using Electrokinetic Effects, Analytical Chemistry 69(8):1564-1568 (1997).

(56) References Cited

OTHER PUBLICATIONS

Li et al., Nanoliter microfluidic hybrid method for simultaneous screening and optimization validated with crystallization of membrane proteins, PNAS 103: 19243-19248 (2006).
Li et al., Single-step procedure for labeling DNA strand breaks with fllourescein-or BODIPY-conjugated deoxynucleotides: detection of apoptosis and bromodeoxyuridine incorporation. Cytometry 20:172-180 (1995).
Liao et al., Isolation of a thermostable enzyme variant by cloning and selection in a thermophile, PNAS 83:576-80 (1986).
Lim et al., Microencapsulated islets as bioartificial endocrine pancreas, Science 210(4472):908-10 (1980).
Link et al, Geometrically Mediated Breakup of Drops in Microfluidic Devices, Phys. Rev. Lett., 92(5): 054503-1 thru 054503-4 (2004).
Lipinski et al., Experimental and Computational Approaches to Estimate Solubility and Permeability in Drug Discovery and Development Settings ,Adv. Drug Deliv. Rev., 46:3-26 (2001).
Lipkin et al., Biomarkers of increased susceptibility to gastreointestinal cancer: new application to studies of cancer prevention in human subjects, Cancer Research 48:235-245 (1988).
Liu et al., Fabrication and characterization of hydrogel-based microvalves, Mecoelectromech. Syst.11:45-53 (2002).
Liu et al., Passive Mixing in a Three-Dimensional Serpentine MicroChannel, J MEMS 9(2):190-197 (2000).
Lizardi et al., Mutation detection and single-molecule counting using isothermal rolling-circle amplification. Nat Genet 19(3):225-32 (1998).
Loakes and Brown, 5-Nitroindole as a universal base analogue. Nucleic Acids Res 22: 4039-4043 (1994).
Loakes et al., Stability and structure of DNA oligonucleotides containing non-specific base analogues. J. Mol. Biol 270:426-435 (1997).
Loeker et al., Colloids and Surfaces A: Physicochem. Eng. Aspects 214:143-150, (2003).
Lopez-Herrera, et al, Coaxial jets generated from electrified Taylor cones. Scaling laws, Aerosol Science, 34:535-552 (2003).
Lopez-Herrera, et al, One-Dimensional Simulation of the Breakup of Capillary Jets of Conducting Liquids Application to E.H.D. Spraying, Aerosol. Set, 30 (7): 895-912 (1999).
Lopez-Herrera, et al, The electrospraying of viscous and non-viscous semi-insulating liquids. Scalilng laws, Bulletin of the American Physical Society,40 (12):2041(1995).
Lorenceau et al, Generation of Polymerosomes from Double-Emulsions, Langmuir, 21(20): 9183-9186 (2005).
Lorenz et al, Isolation and expression of a cDNA encoding Renilla reniformis luciferase, PNAS 88(10):4438-42 (1991).
Loscertales, et al, Micro/Nano Encapsulation via Electrified Coaxial Liquid Jets, Science, 295(5560): 1695-1698 (2002).
Low N.M. et al., Mimicking somatic hypermutaion: affinity maturation of antibodies displayed on bacteriophage using a bacterila mutator strain. J Mol Biol 260(3), 359-68 (1996).
Lowe, K.C., Perfluorochemical respiratory gas carriers: benefits to cell culture systems, J Fluorine Chem 118:19-26 (2002).
Lowman et al., Selecting high affinity binding proteins by monovalent phage display, Biochemistry 30(45):10832-8 (1991).
Lu et al., Robust fluorescein-doped silica nanoparticles via dense-liquid treatment, Colloids and Surfaces a Physicachemical and Engineering Aspects, 303(3):207-210 (2007).
Luisi et al, Activity and Conformation of Enzymes in Reverse Micellar Solutions, Meth. Enzymol 136:188-216 (1987).
Lund et al., Assesment of methods for covalent binding of nucleic acids to magnetic beads, Dynabeads, and the characteristics of the bound nucleic acids in hybridization reactions, Nucleic Acids Research, Oxford University Press, 16(22) (1998).
Lunderberg et al., Solid-phase technology: magnetic beads to improve nucleic acid detection and analysis, Biotechnology Annual Review, 1:373-401 (1995).
Lundstrom, et al, Breakthrough in cancer therapy: Encapsulation of drugs and viruses, www.currentdrugdiscovery.com, Nov. 19-23, 2002.
Lyne, P.D., Structure-Based Virtual Screening: An Overview, Drug Discov. Today, 7(20):1047-1055 (2002).
Ma, C. et al., In vitro protein engineering using synthetic tRNA(Ala) with different anticodons, Biochemistry 32(31):7939-45 (1993).
Mackenzie et al., The application of flow microfluorimetry to biomedical research and diagnosis: a review, Dev Biol Stand 64:181-193 (1986).
Mackenzie, IABS Symposium on Reduction of Animal Usage in the Development and Control of Biological Products, London, UK, 1985.
Maclean, D. et al., Glossary of terms used in combinatorial chemistry, Pure Appl. Chem. 71(12):2349-2365 (1999).
Magdassi et al., Multiple Emulsions: HLB Shift Caused by Emulsifier Migration to External Interface, J. Colloid Interface Sci 97:374-379 (1984).
Mahajan et al., Bcl-2 and Bax Interactions in Mitochondria Probed with Green Florescent Protein and Fluorescence Resonance Energy Transfer, Nat. Biotechnol. 16(6): 547-552 (1998).
Manley et al., In vitro transcription: whole cell extract, Methods Enzymol, 101:568-82 (1983).
Manz et al., Micromachining of monocrystalline silicon and glass for chemical analysis systems a look into next century's technology or just a fashionable craze, Trends in Analytical Chemistry 10(5):144-149 (1991).
Mao et al., Kinetic behaviour of alpha-chymotrypsin in reverse micelles: a stopped-flow study, Eur J Biochem 208(1):165-70 (1992).
Mao, Q. et al., Substrate effects on the enzymatic activity of alphachymotrypsin in reverse micelles, Biochem Biophys Res Commun, 178(3):1105-12 (1991).
Mardis, E.R., The impact of next-generation sequencing technology on genetics, Trends Genet 24:133-141 (2008).
Margulies, M et al., Genome sequencing in microfabricated high-density picolitre reactors, Nature 437(7057):376-380 (2005).
Marques et al., Porous Flow within Concentric Cylinders, Bull Am Phys Soc Div Fluid Dyn 41:1768 (1996).
Mason, T.J. and Bibette, J. Shear Rupturing of Droplets in Complex Fluids, Langmuir, 13(17):4600-4613 (1997).
Mastrobattista et al., High-throughput screening of enzyme libraries: in vitro evolution of a beta-galactosidase by fluorescence-activated sorting of double emulsions, Chem. Biol. 12(12): 1291-1300 (2005).
Masui et ai., Probing of DNA-Binding Sites of *Escherichia coli* RecA Protein Utilizing 1-anilinonaphthalene-8-Sulfonic Acid, Biochem 37(35):12133-12143 (1998).
Matayoshi, E.D. et al., Novel fluorogenic substrates for assaying retroviral proteases by resonance energy transfer, Science 247:954 (1990).
Mayr, L.M., and Fuerst, P., The Future of High-Throughput Screening, JBiomol Screen 13:443-448 (2008).
Mazutis et al., Droplet-Based Microfluidic Systems for High-Throughput Single DNA Molecule Isothermal Amplification and Analysis, Anal Chem 81(12):4813-4821 (2009).
Mazutis et al., Multi-step microfluidic droplet processing: kinetic analysis of an in vitro translated enzyme, Lab Chip 9:2902-2908 (2009).
McDonald and Whitesides, Poly(dimethylsiloxane) as a material for fabricating microfluidic devices, Account Chem. Res. 35:491-499 (2002).
McDonald et al. Fabrication of microfluidic systems in poly(dimethylsiloxane), Electrophoresis 21(1):27-40 (2000).
Melton et al., Efficient in vitro synthesis of biologically active RNA and RNA hybridization probes from plasmids containing a bacteriophage SP6 promoter, Nucl. Acids Res. 12(18):7035-7056 (1984).
Mendel, D. et al., Site-Directed Mutagenesis with an Expanded Genetic Code, Annu Rev Biophys Biomol Struct, 24:435-62 (1995).
Menger and Yamada, Enzyme catalysis in water pools, J. Am. Chem. Soc., 101:6731-4 (1979).

(56) References Cited

OTHER PUBLICATIONS

Meylan and Howard, Atom/fragment contribution method for estimating octanol-water partition coefficients, J Pharm Sci. 84(1):83-92 (1995).
Miele et al., Autocatalytic replication of a recombinant RNA, J Mol Biol, 171:281-95 (1983).
Minshuil, J. and Stemmer, W.P., Protein evolution by molecular breeding, Curr Opin Chem Biol 3(3): 284-90 (1999).
Miroux and Walker, Over-production of proteins in *Escherichia coli:* mutant hosts that allow synthesis of some membrane proteins and globular proteins at high levels, J of Mol Biol 260(3):289-98 (1996).
Miyawaki et at., Fluorescent Indicators for Ca2+ Based on Green Fluorescent Proteins and Calmodulin, Nature, 388: 882-887 (1997).
Mize et al., Dual-enzyme cascade—an amplified method for the detection of alkaline phosphatase, Anal Biochem 179(2): 229-35 (1989).
Mock et al., A fluorometric assay for the biotin-avidin interaction based on displacement of the fluorescent probe 2-anilinonaphthalene-6-sulfonic acid, Anal Biochem, 151:178-81 (1985).
Moldavan, A., Photo-electric technique for the counting of microscopical cells, Science 80:188-189 (1934).
Montigiani, S. et al., Alanine substitutions in calmodulin-binding peptides result in unexpected affinity enhancement, J Mol Biol, 258:6-13 (1996).
Moore, M.J., Exploration by lamp light, Nature, 374:766-7 (1995).
Moudrianakis and Beer, Base sequence determination in nucelic acids with the electron microscope 3. Chemistry and microscopy of guanine-labeled DNA, PNAS 53:564-71 (1965).
Mueth et al., Origin of stratification in creaming emulsions, Physical Review Letters 77(3):578-581 (1996).
Mulbry, W.W. et al., Parathion hydrolase specified by the Flavobacterium opd gene: relationshio between the gene and protein. J Bacteriol, 171: 6740-6746 (1989).
Mulder et al., Characterization of two human monoclonal antibodies reactive with HLA-B12 and HLA-B60, respectively, raised by in vitro secondary immunization of peripheral blood lymphocytes, Hum. Immunol 36(3):186-192 (1993).
Nakano et al., High speed polymerase chain reaction in constant flow, Biosci Biotech and Biochem, 58:349-52 (1994).
Nakano et al., Single-molecule PCR using water-in-oil emulsion, J Biotech, 102:117-24 (2003).
Nakano et al., Single-molecule reverse transcription polymerase chain reaction using water-in-oil emulsion, J Biosci Bioeng 99:293-295 (2005).
Nametkin, S.N. et al., Cell-free translation in reversed micelles, FEB Letters, 309(3):330-32 (1992).
Narang et al, Improved phosphotriester method for the synthesis of gene fragments, Methods Enzymol, 68:90-98 (1979).
Nelson, P. S., et al., Bifunctional oligonucleotide probes synthesized using a novel CPG support are able to detect single base pair mutations, Nucl Acids Res 17(18): 7187-7194 (1989).
Ness, J.E. et al., Molecular Breeding: the natural approach to protein design. Adv Protein Chem, 55: 261-292 (2000).
Ng et al., Protein crystallization by capillary counter-diffusion for applied crystallographic structure determination, J. Struct. Biol, 142:218-231(2003).
Ng, B.L. et al., Factors affecting flow karyotype resolution, Cytometry, Part A 69A: 1028-1036 (2006).
Nguyen et al., Optical detection for droplet size control in microfluidic droplet-based analysis systems, Sensors and Actuators B 117(2):431-436 (2006).
Nihant et al., Polylactide Microparticles Prepared by Double Emulsion/Evaporation Technique. I. Effect of Primary Emulsion Stability, Pharmaceutical Research, 11(10):1479-1484 (1994).
Nisisako et al., Controlled formulation of monodisperse double emulsions in a multiple-phase microluidic system, Sot Matter, 1:23-27 (2005).
Nisisako et al., Formation of droplets using branch channels in a microfluidic circuit, Proceedings of the SICE Annual Conference. International Session Papers,1262-1264 (2002).
Nisisako et al., Microstructured Devices for Preparing Controlled Multiple Emulsions. Chem. Eng. Technol 31(8):1091-1098 (2008).
Nisisako, Takasi et al., Droplet Formation in a MicroChannel NetWO rk, Lab on a Chip, vol. 2, 2002, pp. 24-26.
Nissim, A. et al., Antibody fragments from a single pot phage display library as immunochemical reagents, Embo J, 13:692-8 (1994).
Nof and Shea, Drug-releasing scaffolds fabricated from drug-loaded microspheres, J. Biomed Mater Res 59:349-356 (2002).
Norman, A., Flow Cytometry, Med. Phys., 7(6):609-615 (1980).
Oberholzer et al., Enzymatic RNA replication in self-reproducing vesicles: an approach to a minimal cell, Biochem Biophys Res Commun 207(1):250-7 (1995).
Oberholzer et al., Polymerase chain reaction in liposomes, Chem. Biol. 2(10):677-82 (1995).
Obukowicz, M.G. et al., Secretion and export of IGF-1 in *Escerichia coli* strain JM101, Mol Gen Genet, 215:19-25 (1988).
Office Action for U.S. Appl. No. 11/246,911 dated Feb. 8, 2011.
Office Action for U.S. Appl. No. 11/360,845 dated Apr. 26, 2011.
Office Action for U.S. Appl. No. 11/360,845 dated Aug. 4, 2010.
Office Action for U.S. Appl. No. 11/698,298, dated Jun. 29, 2011.
Ogura, Y., Catalase activity at high concentrations of hydrogen peroxide, Archs Biochem Biophys, 57: 288-300 (1955).
Oh et al., Distribution of Macropores in Silica Particles Prepared by Using Multiple Emulsions, Journal of Colloid and Interface Science, 254(1): 79-86 (2002).
Okushima et al. Controlled production of monodisperse double emulsions by two-step droplet breakup in microfluidic devices, Langmuir 20(23): 9905-8 (2004).
Olsen et ai., Function-based isolation of novel enzymes from a large library, Nat Bioteoltnol 13(10):1071-4 (2000).
Omburo, G.A. et al., Characterization of the zinc binding site of bacterial phosphotriesterase, J of Biological Chem, 267:13278-83 (1992).
Oroskar et al., Detection of immobilized amplicons by ELISA-like techniques, Clin. Chem. 42:1547-1555 (1996).
Ostermeier, M. et al., A combinatorial approach to hybrid enzymes independent of DNA homology, Nat Biotechnol, 17(12):1205-9 (1999).
Ouelette, A new wave of microfluidic devices, Indust Physicist pp. 14-17 (2003).
Pabit et al., Laminar-Flow Fluid Mixer for Fast Fluorescence Kinetics Studies, Biophys J 83:2872-2878 (2002).
Paddison et al., Stable suppression of gene expression by RNAi in mammalian cells, PNAS 99(3):1443-1448 (2002).
Pannacci et al., Equilibrium and Nonequilibrium States in Microluidic Double Emulsions Physical Review Leters, 101(16):164502 (2008).
Park et al., Cylindrical compact thermal-cycling device for continuoflow polymeras chain reaction, Anal Chem, ACS, 75:6029-33 (2003).
Park et al., Model of Formation of Monodispersed Colloids, J. Phys. Chem. B 105:11630-11635 (2001).
Parker et al., Development of high throughput screening assays using fluorescence polarization: nuclear receptor-ligand-binding and kinase/phosphatase assays, J Biomol Screen, 5(2): 77-88 (2000).
Pelham and Jackson, An efficient mRNA-dependent translation system from reticulocyte lysates, Eur J Biochem 67:247-56 (1976).
Pelletier et al., An in vivo library-verslibrary selection of optimized protein-protein interactions, Nature Biotechnology, 17:683-90 (1999).
Peng et al., Controlled Production of Emulsions Using a Crossflow Membrane, Particle & Particle Systems Characterization 15:21-25 (1998).
Perelson et al., Theorectical studies of clonal selection: minimal antibody repertoire size and reliability of self-non-self discrimination. J Theor Biol 81(4):645-70 (1979).

(56) References Cited

OTHER PUBLICATIONS

Perez-Gilabert et al., Application of active-phase plot to the kinetic analysis of lipoxygenase in reverse micelles, Biochemistry J. 288:1011-1015 (1992).
Perrin, J., Polarisation de la lumiere de fluorescence vie moyenne des molecules dans letat excite, J. Phys. Rad. 1:390-401 (1926).
Petrounia, I.P. et al., Designed evolution of enzymatic properties, Curr Opin Biotechnol, 11:325-330 (2000).
Piemi et al., Transdermal delivery of glucose through hairless rat skin in vitro: effect of multiple and simple emulsions, Int J Pharm, 171:207-215 (1998).
Pirrung et al., A General Method for the Spatially Defined Immobilization of Biomolecules on Glass Surfaces Using 'Caged' Biotin, Bioconjug Chem 7: 317-321 (1996).
Ploem, in Fluorescent and Luminescent Probes for Biological Activity Mason, T. G. Ed., Academic Press, Landon, pp. 1-11, 1993.
Pluckthun, A. et al., In vitro selection and evolution of proteins, Adv Protein Chem, 55: 367-403 (2000).
Pollack et al., Electrowetting-based actuation of droplets for integrated microfluidics, Lab Chip 2:96-101 (2002).
Pollack et al., Selective chemical catalysis by an antibody, Science 234(4783):1570-3 (1986).
Pons et al, Synthesis of Near-Infrared-Emitting, Water-Soluble CdTeSe/CdZnS Core/Shell Quantum Dots, Chemistry of Materials 21(8):1418-1424 (2009).
Posner et al., Engineering specificity for folate into dihydrofolate reductase from *Escherichia coli*, Biochemistry, 35: 1653-63 (1996).
Poulin and Theil, "A priori" prediction of tissue: plasma partition coefficients of drugs to facilitate the use of physiologically-based pharmokinetic models in drug discovery, J Pharm Sci 89(1):16-35 (2000).
Priest, et al. Generation of Monodisperse Gel Emulsions in a Microfluidic Device, Applied Physics Letters, 88:024106 (2006).
Qi et al., Acid Beta-Glucosidase: Intrinsic Fluorescence and Conformational Changes Induced by Phospholipids and Saposin C, Biochem., 37(33): 11544-11554 (1998).
Raghuraman et al., Emulston Liquid Membranes for Wastewater Treatment: Equillibrium Models for Some Typical Metal-Extractant Systems,Environ. Sci. Technol 28:1090-1098 (1994).
Ralhan, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173 (2008).
Ramsey, J.M., The burgeoning power of the shrinking laboratory, Nat Biotechnol 17(11):1061-2 (1999).
Ramstrom and Lehn, Drug discovery by dynamic combinatorial libraries, Nat Rev Drug Discov 1:26-36 (2002).
Raushel, F.M. et al., Phosphotriesterase: an enzyme in search of its natural substrate, Adv Enzymol Relat Areas Mol Biol, 74: 51-93 (2000).
Rech et al., Introduction of a yeast artificial chromosome vector into *Sarrachomyeces cervesia* by electroporation, Nucleic Acids Res 18:1313 (1990).
Reyes et al., Micro Total Analysis Systems. 1. Introduction, Theory and Technology, Anal Chem 74(12):2623-2636 (2002).
Riess, J.S., Fluorous micro- and nanophases with a biomedical perspective, Tetrahedron 58(20):4113-4131 (2002).
Roach et al., Controlling nonspecific protein adsorption in a plug-based microfluidic system by controlling inteifacial chemistry using fluorophase surfactants, Anal. Chem. 77:785-796 (2005).
Roberts & Ja, In vitro selection of nucleic acids and proteins: What are we learning, Curr Opin Struct Biol 9(4): 521-9 (1999).
Roberts et al., Simian virus 40 DNA directs synthesis of authentic viral polypeptides in a linked transcription-translation cell-free system 72(5):1922-1926 (1975).
Roberts, J.W.,Termination factor for RNA synthesis, Nature, 224: 1168-74 (1969).
Roberts, R.W. Totally in vitro protein selection using mRNA-protein fusions and ribosome display. Curr Opin Chem Biol 3(3), 268-73 (1999).
Rodriguez-Antona et al., Quantitative RT-PCR measurement of human cytochrome P-450s: application to drug induction studies. Arch. Biochem. Biophys., 376:109-116 (2000).
Rolland et al., Fluorescence Polarization Assay by Flow Cytometry, J. Immunol. Meth., 76(1): 1-10 (1985).
Rosenberg et al.,Termination of transcription in bacteriophage lambda, J Biol Chem, 250: 4755-64 (1975).
Rosenberry, T.L., Acetylcholinesterase, Adv Enzymol Relat Areas Mol Biol, 43: 103-218 (1975).
Rotman, Measurement of activities of single molecules of beta-galactosidase, PNAS, 47:1981-91 (1961).
Russon et al., Single-nucleotide polymorphism analysis by allele-specific extension of fluorescently labeled nucleotides in a microfluidic flow-through device, Electrophoresis, 24:158-61 (2003).
Sadtler et al., Achieving stable, reverse water-in-fluorocarbon emulsions. Angew Chem Int Ed 35:1976-1978 (1996).
Saiki, R.K, et al, Primer directed enzymatic amplification of DNA with a thermostable DNA polymerase. Science 239(4839):487-91 (1988).
Sakamoto, Rapid and simple quantification of bacterial cells by using a microfluidic device, Appl Env Microb. 71:2 (2005).
Sanchez et al., Breakup of Charged Capillary Jets, Bulletin of the American Physical Society Division of Fluid Dynamics 41:1768-1768 (1996).
Sano, T. et al., Immuno-PCR-Very sensitive antigen-detection by means of sepcific antibody-DNA conjugates. Science 258(5079), 120-122 (1992).
SantaLucia, A unified view of polymer, dumbbell, and oligonucleotide DNA nearest-neighbor thermodynamics, PNAS 95(4):1460-5 (1998).
Santra et al., Fluorescence lifetime measurements to determine the core-shell nanostructure of FITC-doped silica nanoparticles: An optical approach to evaluate nanoparticle photostability, J Luminescence 117(1):75-82 (2006).
Schatz et al., Screening of peptide libraries linked to lac repressor, Methods Enzymol 267: 171-91 (1996).
Schneegass et al., Miniaturized flow-through PCR with different template types in a silicone chip thermocycler, Lab on a Chip, Royal Soc of Chem, 1:42-9 (2001).
Schubert et al., Designer Capsules, Nat Med 8:1362 (2002).
Schweitzer et al., Immunoassays with rolling circle DNA amplification: A versatile platform for ultrasensitive antigen detection, PNAS 97(18), 10113-10119 (2000).
Schweitzer, B. et al., Combining nucleic acid amplification and detection. Curr Opin Biotechnol 12(1):21-7 (2001).
Scott, R.L., The Solubility of Fluorocarbons, J. Am. Chem. Soc, 70: 4090-4093 (1948).
Seethala and Menzel, Homogeneous, Fluorescence Polarization Assay for Src-Family Tyrosine Kinases, Anal Biochem 253(2):210-218 (1997).
Seiler et al., Planar glass chips for capillary electrophoresis: repetitive sample injection, quantitation, and separation efficiency, Anal Chem 65(10):1481-1488 (1993).
Selwyn M. J., A simple test for inactivation of an enzyme during assay, Biochim Biophys Acta 105:193-195 (1965).
Seo et al., Microfluidic consecutive flow-focusing droplet generators, Soft Matter, 3:986-992 (2007).
Seong and Crooks, Efficient Mixing and Reactions Within Microfluidic Channels Using Microbead-Supported Catalysts, J Am Chem Soc 124(45):13360-1 (2002).
Seong et al., Fabrication of Microchambers Defined by Photopolymerized Hydrogels and Weirs Within Microfluidic Systems: Application to DNA Hybridization, Analytical Chem 74(14):3372-3377 (2002).
Sepp et al., Microbead display by in vitro compartmentalisation: selection for binding using flow cytometry, FEBS Letters 532:455-58 (2002).

(56) References Cited

OTHER PUBLICATIONS

Serpersu et al., Reversible and irreversible modification of erythrocyte membranse permeability by electric field, Biochim Biophys Acta 812(3):779-785 (1985).
Shapiro, H.M., Multistation multiparameter flow cytometry: a critical review and rationale, Cytometry 3: 227-243 (1983).
Shestopalov et al., Multi-Step Synthesis of Nanoparticles Performed on Millisecond Time Scale in a Microfluidic Droplet-Based System, The Royal Society of Chemistry 4:316-321(2004).
Shtern V, and Hussain F., Hysteresis in swirling jets, J. Fluid Mech. 309:1-44 (1996).
Sia &Whitesides, Microfluidic devices fabricated in poly(dimethylsiloxane) for biological studies, Electrophoresis 24(21):3563-3576 (2003).
Sidhu, S.S., Phage display in pharmaceutical biotechnology, Curr Opin Biotech 11:610-616 (2000).
Siemering et al., Mutations that suppress the thermosensitivity of green fluorescent protein, Current Biology 6:1653-1663 (1996).
Silva-Cunha et al., W/O/W multiple emulsions of insulin containing a protease inhibitor and an absorption enhancer: biological activity after oral administration to normal and diabetic rats, Int J Pharm 169:33-44 (1998).
Sims et al., Immunopolymerase chain reaction using real-time polymerase chain reaction for detection, Anal. Biochem. 281(2):230-2 (2000).
Slappendel et al., Normal cations and abnormal membrane lipids in the red blood cells of dogs with familial stomatocytosis hypertrophic gastritis, Blood 84:904-909 (1994).
Slob et al., Structural identifiability of PBPK models: practical consequences for modeling strategies and study designs, Crit Rev Toxicol. 27(3):261-72 (1997).
Smith et al., Direct mechanical measurements of the elasticity of single DNA molecules by using magnetic beads, Science 258(5085):1122-1126 (1992).
Smith et al., Fluorescence detection in automated DNA sequence analysis, Nature 321:674-679 (1986).
Smith et al., Phage display, Chemical Reviews 97(2), 391-410 (1997).
Smith et al., The synthesis of oligonucleotides containing an aliphatic amino group at the 5' terminus: synthesis of fluorescent DNA primers for use in DNA sequence analysis, Nucl. Acid Res. 13:2399-2412 (1985).
Smith G.P., Filamentous fusion phage: novel expression vectors that display cloned antigens on the virion surface, Science 228(4705): 1315-7(1985).
Smyth et al., Markers of apoptosis: methods for elucidating the mechanism of apoptotic cell death from the nervous system, Biotechniques 32:648-665 (2000).
Sohn, et al, Capacitance cytometry: Measuring biological cells one by one, PNAS 97(20):10687-10690 (2000).
Somasundaram and Ramalingam, Gain studies of Rhodamine 6G dye doped polymer laser, J Photochem Photobiol 125(1-3):93-98 (1999).
Song et al., A microfluidic system for controlling reaction networks in time, Angew. Chem. Int. Ed. 42(7):768-772 (2003).
Song et al., Experimental Test of Scaling of Mixing by Chaotic Advection in Droplets Moving Through Microfluidic Channels, App Phy Lett 83(22):4664-4666 (2003).
Song, H. and Ismagilov, R.F., Millisecond kinetics on a microluidic chip using nanoliters of reagents, J Am Chem Soc. 125: 14613-14619 (2003).
Soni and Meller, Progress toward ultrafast DNA sequencing using solid-state nanopores, Clin Chem 53:1996-2001 (2007).
Soumillion et al., Novel concepts for the selection of catalytic activity. Curr Opin Biotechnol 12:387-394 (2001).
Sproat et al., The synthesis of protected 5'-mercapto-2',5'-dideoxyribonucleoside-3'-0-phosphorainidites, uses of 5'-mercapto-oligodeoxyribonucleotides, Nucleic Acids Res 15:4837-4848 (1987).
Stauber, et a., Rapid generation of monoclonal antibody-secreting hybridomas against African horse sickness virus by in vitro immunization and the fusion/cloning technique, J. Immunol. Meth 161(2):157-168 (1993).
Stemmer, W.P., DNA shuffling by random fragmentation and reassembly: in vitro recombination for molecular evolution. PNAS 91(22):10747-51(1994).
Stemmer, W.P., Rapid evolution of a protein in vitro by DNA shuffling, Nature 370(6488):389-91 (1994).
Stober et al., Controlled growth of monodisperse silica spheres in the micron size range, J Colloid and Interface Sci 26(1):62-69 (1968).
Stofko, H.R. et al., A single step purification for recombinant proteins. Characterization of microtube associated protein (MAP2) fragment which associates with the type II cAMP-dependent protein kinase, Febs Lett 302: 274-278 (1992).
Stone et al., Engineering flows in small devices: Microfluidics toward a lab-on-a-chip, Ann. Rev. Fluid Mech. 36:381-441 (2004).
Stroock et al., Chaotic mixer for microchannels, Science 295(5555):647-651 (2002).
Studer et al., Fluorous Synthesis: A FluoroPhase Strategy for Improving Separation Efficiency in Organic Synthesis, Science 275: 823-826 (1997).
Sugiura et al., Effect of Channel Structure on MicroChannel Emuisification, Langmuir 18:5708-5712 (2002).
Sundberg et al., Spatially-Addressable Immobilisation of Macromolecules on Solid Supports, J. Am. Chem. Soc, 117:12050-12057 (1995).
Sung et al. Chip-based microfluidic devices coupled with electrospray ionization-mass spectrometry, Electrophoresis 26:1783-1791 (2005).
Suzuki et al., Random mutagenesis of thermus aquaticus DNA polmerase I: concordance of immutable sites in vivo with the crystal structure, PNAS USA, 93:96701-9675 (1996).
Tabatabai and Faghri, A New Two-Phase Flow Map and Transition Boundary Accounting for Surface Tension Effects in Horizontal Miniature and Micro Tubes, J Heat Transfer 123:958-968 (2001).
Tabatabai et al, Economic feasability study of polyelectrolyte-enhanced ultrafiltration (PEUF) for water softening, J Membrane Science 100(3):193-207 (1995).
Tabatabai et al., Reducing Surfactant Adsorption on Carbonate Reservoirs, SPE Resenroir Engineering 8(2):117-122 (1993).
Tabatabai, Water Softening Using polyelectrolyte-enhanced ultrafiltration, Separation Science Technology 30(2):21 1-224 (1995).
Takayama et al., Patterning Cells and Their Environments Using Multiple Laminar Fluid Flows in Capillary NetWO rks, PNAS 96:5545-5548 (1999).
Takeuchi et al., An Axisymmetric Flow-Focusing Microfluidic Device, Adv. Mater 17(8):1067-1072 (2005).
Taly et al., Droplets as Microreactors for High-Throughput Biology, Chembiochem 8(3):263-272 (2007).
Tan et al., Controlled Fission of Droplet Emulsions in Bifurcating Microfluidic Channels, Transducers Boston (2003).
Tan et al., Design of microluidic channel geometries for the control of droplet volume, chemical concentration, and sorting, Lab Chip, 4(4): 292-298 (2004).
Tan et al., Monodispersed microfluidic droplet generation by shear focusing microfluidic device, Sensors and Actuators 114:350-356 (2006).
Tan, Y.C., Microfluidic Liposome Generation from Monodisperse Droplet Emulsion-Towards the Realization of Artificial Cells, Summer Bioengineering Conference, Florida (2003).
Tan, Y.C., Monodisperse Droplet Emulsions in Co-Flow Microfluidic Channels, Micro TAS, Lake Tahoe (2003).
Tanaka et al., Ethanol Production from Starch by a Coimmobilized Mixed Culture System of Aspergillus awamori and Zymomonas mobilis, Biotechnol Bioeng XXVII:1761-1768 (1986).
Tang et al., A multi-color fast-switching microfluidic droplet dye laser, Lab Chip 9:2767-2771 (2009).
Taniguchi et al., Chemical Reactions in Microdroplets by Electrostatic Manipulation of Droplets in Liquid Media, Lab on a Chip 2:19-23 (2002).

(56) References Cited

OTHER PUBLICATIONS

Tawfik et al., catELISA: a facile general route to catalytic antibodies, PNAS 90(2):373-7 (1993).
Tawfik et al., Efficient and selective p-nitrophenyl-ester=hydrolyzing antibodies elicited by a p-nitrobenzyl phosphonate hapten, Eur J Biochem, 244:619-26 (1997).
Tawfik et al., Man-made cell-like compartments for molecular evolution, Nature Biotechnology, 7(16):652-56 (1998).
Tawfik, D.S. et al., 1,8-diabycyclo[5.4.0]undecane mediated transesterification of p-nitrophenyl phosphonates—a novel route to phosphono esters, Synthesis—Stuttgart, 10: 968-972 (1993).
Taylor et al., Characterization of chemisorbed monolayers by surface potential measurments, J. Phys. D. Appl. Phys. 24:1443 (1991).
Taylor, The formation of emulsions in definable field of flow, Proc R Soc London A 146(858):501-523 (1934).
Tchagang et al., Early detection of ovarian cancer using group biomarkers, Mol Cancer Ther 7:27-37 (2008).
Tencza et al., Development of a Fluorescence Polarization-Based Diagnostic Assay for Equine Infectious Anemia Virus, J Clinical Microbiol 38(5):1854-185 (2000).
Terray et al., Microfluidic Control Using Colloidal Devices,Science, 296(5574):1841-1844 (2002).
Terray, et al, Fabrication of linear colloidal structures for microfluidic applications, Applied Phys Lett 81(9):1555-1557 (2002).
Tewhey et al., Microdroplet-based PCR amplification for large scale targeted sequencing, Nat Biotechnol 27(11):1025-1031 (2009).
Theberge et al., Microdroplets in Microfluidics: An Evolving Platform for Discoveries in Chemistry and Biology, Angew. Chem. Int. Ed 49(34):5846-5868 (2010).
Thompson, L.F., Introduction to Lithography, ACS Symposium Series 219:1-13, (1983).
Thorsen et al., Dynamic pattern formation in a vesicle-generating microfluidic device, Phys Rev Lett 86(18):4163-4166 (2001).
Thorsen et al., Microfluidic Large-Scale Integration, Science 298:580-584 (2002).
Tice et al., Effects of viscosity on droplet formation and mixing in microfluidic channels, Analytica Chimica Acta 507:73-77 (2004).
Tice et al., Formation of droplets and mixing in multiphase microfluidics at low values of the reynolds and the capillary numbers, Langmuir 19:9127-9133 (2003).
Titomanlio et al., Capillary experiments of flow induced crystallization of HOPE, AlChe Journal, 36(1):13-18(1990).
Tleugabulova et al., Evaluating formation and growth mechanisms of silica particles using fluorescence anisotropy decay analysis, Langmuir 20(14):5924-5932 (2004).
Tokatlidis et al., Nascent chains: folding and chaperone intraction during elongation on ribosomes, Philos Trans R Soc Lond B Biol Sci, 348:89-95 (1995).
Tokeshi et al., ContinuoFlow Chemical Processing on a Microchip by Combining Microunit Operations and a Multiphase Flow NetWO rk, Anal Chem 74(7):1565-1571 (2002).
Tokumitsu, H. et al., Preparation of gadopentetic acid-loaded chitosan microparticles for gadolinium neutron-capture therapy of cancer by a novel emulsion-droplet coalescence technique, Chem and Pharm Bull 47(6):838-842 (1999).
Tramontano, A., Catalytic antibodies, Science 234(4783):1566-70 (1986).
Trindade, T., Nanocrystalline semiconductors: synthesis, properties, and perspectives, Chem. Mat. 13:3843-3858 (2001).
Tripet, B. et al., Engineering a de novo-designed coiled-coil heterodimerization domain off the rapid detection, purification and characterization of recombinantly expressed peptides and proteins, Protein Engng., 9:1029-42 (1996).
Umbanhowar et al., Monodisperse Emulsion Generation via Drop Break Off in a Coflowing Stream, Langmuir 16(2):347-351 (2000).
Unger et al., Monolithic microfabricated valves and pumps by multylayer soft lithography, Science 288(5463):113-116 (2000).
Utada, A. et al., Monodisperse double emulsions generated from a microcapillary device, Science, 308:537-541 (2005).
Vainshtein et al., Peptide rescue of an N-terminal truncation of the stoffel fragment of Taq DNA polymerase, Protein Science, 5:1785-92 (1996).
Van Bockstaele et al., Prognostic markers in chronic lymphocytic leukemia: a comprehensive review, Blood Rev 23(1):25-47 (2009).
Van Dilla et al., Cell Microfluorometry: A Method for Rapid Fluorescence Measurement, Science 163(3872):1213-1214 (1969).
Van Dilla et al., The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105, distributed Jan. 23, 1968.
Vanhooke et al., Three-dimensional structure of the zinc-containing phosphotrieesterase with the bound substrate analog diethy 4-methylbenzylphosphonate, Biochemistry 35:6020-6025 (1996).
Varga, J.M. et al., Mechanism of allergic cross-reactions-I. Multispecific binding of ligands to a mouse monoclonal anti-DNP IgE antibody. Mol Immunol 28(6), 641-54 (1991).
Vary, A homogeneous nucleic acid hybridization assay based on strand displacement, Nucl Acids Res 15(17):6883-6897 (1987).
Venkateswaran et al., Production of Anti-Fibroblast Growth Factor Receptor Monoclonal Antibodies by In Vitro Immunization, Hybirdoma, 11(6):729-739 (1992).
Venter et al., The sequence of the human genome, Science 291(5507):1304-51 (2001).
Vogelstein et al., Digital PCR, PNAS 96(16):9236-9241 (1999).
Voss, E.W., Kinetic measurements of molecular interactions by spectrofluorometry, J Mol Recognit, 6:51-58 (1993).
Wahler, D. et al., Novel methods for biocatalyst screening. Curr Opin Chem Biol, 5: 152-158 (2001).
Walde, P. et al., Oparin's reactions revisited: enzymatic synthesis of poly(adenylic acid) in micelles and self-reproducing vesicles. J Am Chem Soc, 116: 7541-7547 (1994).
Walde, P. et al., Spectroscopic and kinetic studies of lipases solubilized in reverse micelles, Biochemistry, 32(15):4029-34 (1993).
Walde, P. et al., Structure and activity of trypsin in reverse micelles, Eur J Biochem, 173(2):401-9 (1988).
Walker et al., Isothermal in vitro amplification of DNA by a restriction enzyme/DNA polymerase system, PNAS 89(1):392-6 (1992).
Walker et al., Strand displacement amplification—an isothermal, in vitro DNA amplification technique, Nucleic Acid Res, 20(7):1691-6 (1992).
Wang et al., DEP actuated nanoliter droplet dispensing using feedback control, Lab on a Chip 9:901-909 (2008).
Wang et al., Preparation of Titania Particles Utilizing the Insoluble Phase Interface in a MicroChannel Reactor, Chemical Communications 14:1462-1463 (2002).
Wang, A.M. et al., Quantitation of mRNA by the polymerase chain reaction. Proc natl Acad Sci USA 86(24), 9717-21 (1989).
Wang, G.T. et al., Design and synthesis of new fluorogenic HIV protease substrates based on resonance energy transfer, Tetrahedron Lett., 31:6493 (1990).
Wasserman et al., Structure and reactivity of allyl- siloxane monolayers formed by reaction of allcyltrichlorosilanes on silicon substrates, Langmuir 5:1074-1087 (1989).
Weil. et al., Selective and accurate initiation of transcription at the Ad2 major late promotor in a soluble system dependent on purified RNA polymerase II and DNA, Cell, 18(2):469-84 (1979).
Werle et al., Convenient single-step, one tube purification of PCR products for direct sequencing, Nucl Acids Res 22(20):4354-4355 (1994).
Wetmur et al., Molecular haplotyping by linking emulsion PCR: analysis of paraoxonase 1 haplotypes and phenotypes, Nucleic Acids Res 33(8):2615-2619 (2005).
Wick et al., Enzyme-containing liposomes can endogenously produce membrane-constituting lipids, Chem Biol 3(4):277-85 (1996).
Widersten and Mannervik, Glutathione Transferases with Novel Active Sites Isolated by Phage Display from a Library of Random Mutants, J Mol Biol 250(2):115-22 (1995).

(56) References Cited

OTHER PUBLICATIONS

Wiggins et al., Foundations of chaotic mixing, Philos Transact a Math Phys Eng Sci 362(1818):937-70 (2004).
Williams et al., Amplification of complex gene libraries by emulsion PCR, Nature Methods 3(7):545-550 (2006).
Williams et al., Methotrexate, a high-affinity pseudosubstrate of dihydrofolate reductase, Biochemistry, 18(12):2567-73 (1979).
Wilson, D.S. and Szostak, J.W., In vitro selection of functional nucleic acids, Ann. Rev. Biochem. 68: 611-647 (1999).
Winter et al., Making antibodies by phage display technology, Annu Rev Immunol 12:433-55 (1994).
Wittrup, K.D., Protein engineering by cell-surface display. Curr Opin Biotechnology, 12: 395-399 (2001).
Wolff et al., Integrating advanced functionality in a microfabricated high-throughput fluorescent-activated cell sorter, Lab Chip, 3(1): 22-27 (2003).
Wronski et al., Two-color, fluorescence-based microplate assay for apoptosis detection. Biotechniques, 32:666-668 (2002).
Wu et al., The ligation amplification reaction (LAR)-amplification of specific DNA sequences using sequential rounds of template-dependent ligation, Genomics 4(4):560-9 (1989).
Wyatt et al., Synthesis and purification of large amounts of RNA oligonucleotides, Biotechniques 11(6):764-9 (1991).
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xu, S. et al., Generation of monodisperse particles by using microfluidics: control over size, shape, and composition, Angew. Chem. Int. Ed. 44:724-728 (2005).
Yamagishi, J. et al., Mutational analysis of structure-activity relationships in human tumor necrosis factor-alpha, Protein Eng, 3:713-9 (1990).
Yamaguchi et al., Insulin-loaded biodegradable PLGA microcapsules: initial burst release controlled by hydrophilic additives, Journal of Controlled Release, 81(3): 235-249 (2002).
Yelamos, J. et al., Targeting of non-Ig sequences in place of the V segment by somatic hypermutation. Nature 376(6537):225-9 (1995).
Yershov et al., DNA analysis and diagnostics on oligonucleotide microchips, PNAS 93(10):4913-4918 (1996).
Yu et al. Responsive biomimetic hydrogel valve for microfluidics. Appl. Phys. Lett 78:2589-2591 (2001).
Yu et al., Quantum dot and silica nanoparticle doped polymer optical fibers, Optics Express 15(16):9989-9994 (2007).
Yu et al., Specifc inhibition of PCR by non-extendable oligonucleotides using a 5' to 3' exonuclease-deficient DNA polymerase, Biotechniques 23(4):714-6, 718-20 (1997).
Zaccolo, M. et al., An approach to random mutagenesis of DNA using mixtures of triphosphate derivatives of nucleoside analogues. J Mol Biol 255(4):589-603 (1996).
Zakrzewski, S.F., Preparation of tritiated dihydrofolic acid of high specific activity, Methods Enzymol, 539 (1980).
Zaug and Cech, The intervening sequence RNA of Tetrahymena is an enzyme, Science 231(4737):470-5 (1986).
Zaug and Cech, The Tetrahymena intervening sequence ribonucleic acid enzyme is a phosphotransferase and an acid phosphatase, Biochemistry 25(16):4478-82 (1986).
Zaug et al., The Tetrahymena ribozyme acts like an RNA restriction endonuclease, Nature 324(6096):429-33 (1986).
Zhang et al., A Simple Statistical Parameter for Use in Evaluation and Validation of High Throughput Screening Assays, Journal of Biomolecular Screening, 4(2): 67-73 (1999).
Zhang, Z.Y., Substrate specificity of the protein tyrosine phosphatases, PNAS 90: 4446-4450 (1993).
Zhao, B. et al., Control and Applications of Immiscible Liquids in Microchannels, J. Am. Chem. Soc, vol. 124:5284-5285 (2002).
Zhao, H. et al., Molecular evolution by staggered extension process (StEP) in vitro recombination. Nat Biotechnol 16(3):258-61 (1998).
Zheng et al., A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem.,116:1-4, (2004).
Zheng et al., A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17): 2520-2523 (2005).
Zheng et al., Formation of Droplets of Alternating Composition in Microfluidic Channels and Applications to Indexing of Concentrations in Droplet-Based /Assays, Anal. Chem.,76: 4977-4982 (2004).
Zheng et al., Screening of Protein Crystallization Conditions on a Microfluidic Chip Using Nanoliter-Size Droplets, J Am Chem Soc 125(37):11170-11171 (2003).
Zimmermann et al., Dielectric Breakdown of Cell Membranes, Biophys J 14(11):881-889 (1974).
Zimmermann et al., Microscale Production of Hybridomas by Hypo-Osmolar Electrofusion, Hum. Antibod. Hybridomas, 3(1): 14-18 (1992).
Zubay, G., In vitro synthesis of protein in microbial systems, Annu Rev Genet, 7: 267-87 (1973).
Zubay, G., The isolation and properties of CAP, the catabolite gene activator, Methods Enzymol, 65: 856-77 (1980).
Zuckermann, R. et al., Efficient Methods for Attachment of Thiol-Specific Probes to the 3{-end of Synthetic Oligodeoxyribonucleotides, Nucleic Acids Res. 15:5305-5321 (1987).
Non-Final Office Action dated Sep. 18, 2013 from corresponding U.S. Appl. No. 11/643,151.

* cited by examiner

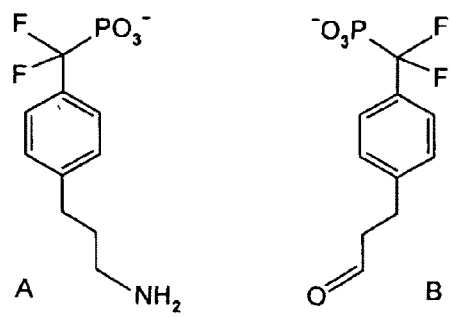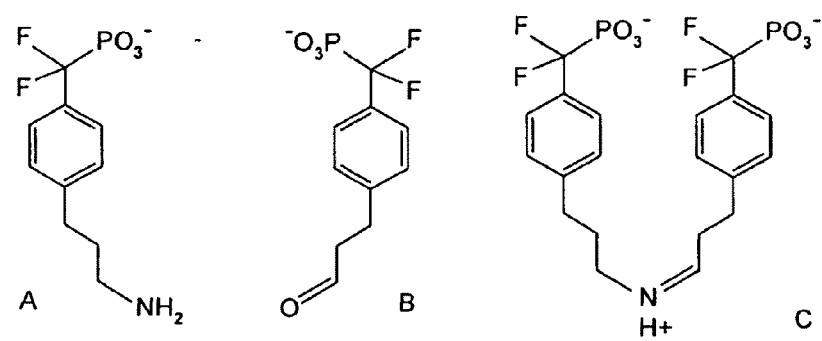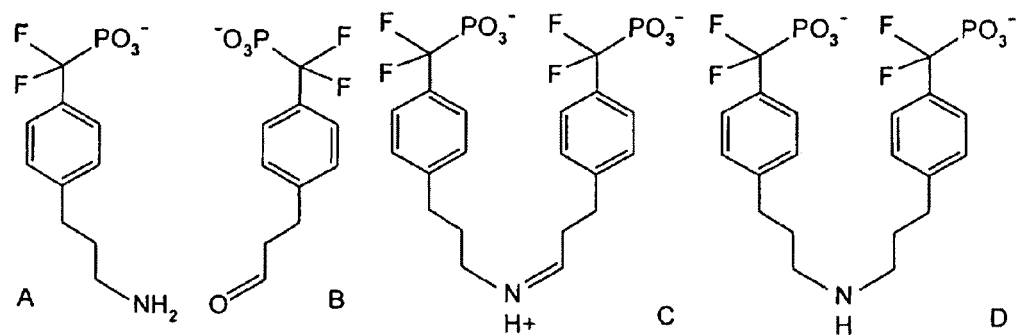
FIG. 22

COMPARTMENTALISED COMBINATORIAL CHEMISTRY BY MICROFLUIDIC CONTROL

RELATED APPLICATIONS

This application is a 35 U.S.C. §371 National Phase Application of PCT/GB2005/003927, filed Oct. 12, 2005; which is a continuation of U.S. Ser. No. 10/962,952 filed Oct. 12, 2004 now abandoned which is a continuation of PCT/GB2004/001352 filed Mar. 31, 2004, each of which is incorporated by reference in its entirety.

STATEMENT OF GOVERNMENT SUPPORT

This invention was made with government support under DMR-0213805 and DMR-0243715 awarded by the National Science Foundation. The government has certain rights in the invention.

The present invention relates to methods for use in the synthesis and identification of molecules which bind to a target component of a biochemical system or modulate the activity of a target.

Over the past decade, high-throughput screening (ITS) of compound libraries has become a cornerstone technology of pharmaceutical research. Investment into HTS is substantial. A current estimate is that biological screening and preclinical pharmacological testing alone account for ~14% of the total research and development (R&D) expenditures of the pharmaceutical industry (Handen, Summer 2002). HTS has seen significant improvements in recent years, driven by a need to reduce operating costs and increase the number of compounds and targets that can be screened. Conventional 96-well plates have now largely been replaced by 384-well, 1536-well and even 3456-well formats. This, combined with commercially available plate-handling robotics allows the screening of 100,000 assays per day, or more, and significantly cuts costs per assay due to the miniaturisafion of the assays.

HTS is complemented by several other developments. Combinatorial chemistry is a potent technology for creating large numbers of structurally related compounds for HTS. Currently, combinatorial synthesis mostly involves spatially resolved parallel synthesis. The number of compounds that can be synthesised is limited to hundreds or thousands but the compounds can be synthesised on a scale of milligrams or tens of milligrams, enabling full characterisation and even purification. Larger libraries can be synthesised using split synthesis on beads to generate one-bead-one compound libraries. This method is much less widely adopted due to a series of limitations including: the need for solid phase synthesis; difficulties characterising the final products (due to the shear numbers and small scale); the small amounts of compound on a bead being only sufficient for one or a few assays; the difficulty in identifying the structure of a hit compound, which often relies on tagging or encoding methods and complicates both synthesis and analysis. Despite this split synthesis and single bead analysis still has promise. Recently there have been significant developments in miniaturised screening and single bead analysis. For example, printing techniques allow protein-binding assays to be performed on a slide containing 10,800 compound spots, each of 1 nl volume (Hergenrother et al., 2000). Combichem has so far, however, generated only a limited number of lead compounds. As of April 2000, only 10 compounds with a combinatorial chemistry history had entered clinical development and all but three of these are (oligo)nucleotides or peptides (Adang and Hemikens, 2001). Indeed, despite enormous investments in both HTS and combinatorial chemistry during the past decade the number of new drugs introduced per year has remained constant at best.

Dynamic combinatorial chemistry (DCC) can also be used to create dynamic combinatorial libraries (DCLs) from a set of reversibly interchanging components, however the sizes of libraries created and screened to date are still fairly limited ($\leq 40,000$) (Ramstrom and Lehn, 2002).

Virtual screening (VS) (Lyne, 2002), in which large compound bases are searched using computational approaches to identify a subset of candidate molecules for testing may also be very useful when integrated with HTS. However, there are to date few studies that directly compare the performance of VS and HTS, and further validation is required.

Microfluidic technology has been applied to high throughput screening methods. For example, U.S. Pat. No. 6,508,988 describes combinatorial synthesis systems which rely on microfluidic flow to control the flow of reagents in a multichannel system. U.S. Pat. No. 5,942,056, and continuations thereof, describes a microfluidic test system for performing high throughput screening assays, wherein test compounds can be flowed though a plurality of channels to perform multiple reactions contemporaneously.

Despite all these developments, current screening throughput is still far from adequate. Recent estimates of the number of individual genes in the human genome (~30,000) and the number of unique chemical structures theoretically attainable using existing chemistries suggests that an enormous number of assays would be required to completely map the structure-activity space for all potential therapeutic targets (Burbaum, 1998).

Hence, a method with the capability to both create and screen vast numbers ($\geq 10^{10}$) of compounds quickly, using reaction volumes of only a few femtoliters, and at very low cost should be of enormous utility in the generation of novel drug leads.

SUMMARY OF THE INVENTION

The present inventors have found that the powerful technique of microfluidic control of microcapsules, in particular the electronic control of microfluid based technology can be applied to the compartmentalised microcapsule system described in Griffith & Tawfik (1998) which is herein incorporated by reference. The result is a novel method which is capable of creating and screening vast quantities of compounds both quickly and efficiently.

Thus, the invention, in a first aspect, provides a method for preparing a repertoire of compounds comprising the steps of:

(a) compartmentalising two or more sets of primary compounds into microcapsules; such that a proportion of the microcapsules contains multiple copies of one or more compounds representative of each of said sets, and wherein said one or more compounds represents a subset of the set of primary compounds; and (b) forming secondary compounds in the microcapsules by chemical reactions between primary compounds from different sets; wherein either one or both of steps (a) and (b) is performed under the microfluidic control of fluidic species.

A compound is "representative" of a set where is member of said set; advantageously, therefore, each microcapsule contains compound(s) from each set. Although a microcapsule may contain more than one different compound from each set, it contains only a proportion of said set—i.e. a subset. The subset of a set advantageously represents no more that 10% of the members of the set; preferably, this figure is 9%, 8%, 7%, 6%, 5%, 4%, 3%, 2%, 1% or less.

Most advantageously a microcapsule contains only a single compound from each set of primary compounds.

The sets of primary compounds used in the method of the invention can consist of any number of different compounds. At least a first set comprises two or more compounds; but the other set may be a single compound. Preferably, if a first set is a single compound, at least one further set comprises a repertoire of compounds. The larger this repertoire, the greater the number of different secondary compounds that will be generated.

Preferably, at least one set of compounds comprises a repertoire of different compounds. At least one set, however, may consist of a single compound, such that secondary compounds are all constructed based on or containing the single compound used in one set. The greater the number of sets, and the greater the diversity of each set, the greater the final diversity of the secondary compounds generated.

Advantageously, in step (a) the number of different compounds per compartment will be equivalent to the number of primary compounds forming the secondary compound in step (b).

In a second aspect, the invention provides a method for identifying primary compounds which react together to form secondary compounds capable of binding to or modulating the activity of a target, comprising the steps of:
(a) compartmentalising two or more sets of primary compounds into microcapsules; such that a proportion of the microcapsules contains two or more compounds;
(b) forming secondary compounds in: the microcapsules by chemical reactions between primary compounds from different sets; and
(c) identifying subsets of primary compounds which react to form secondary compounds which bind to or modulate the activity of the target; wherein one or more of steps (a), (b) and (c) is performed under the microfluidic control of fluidic species.

In a third aspect, the invention provides a method for synthesising compounds with enhanced ability to bind to or modulate the activity of the target, comprising the steps of:
(a) compartmentalising into microcapsules subsets of primary compounds identified in step (c) of the second aspect of the invention and, optionally, compartmentalising additional sets of primary compounds;
(b) forming secondary compounds in the microcapsules by chemical reactions between primary compounds from different sets; and
(c) identifying subsets of primary compounds which react to form secondary compounds which bind to or modulate the activity of the target; wherein one or more of steps (a), (b) and (c) is performed under the microfluidic control of fluidic species.

Advantageously, steps (a) to (c) can be repeated, but after the first cycle, step (a) comprises compartmentalising subsets of primary compounds identified in step (c) into microcapsules and, optionally, compartmentalising additional sets of compounds.

In a fourth aspect, the invention provides a method for identifying individual compounds which bind to or modulate the activity of the target, comprising the steps of:
(a) compartmentalising into microcapsules a primary compound identified in step (c) of the second or third aspect of the invention and additional sets of primary compounds;
(b) forming secondary compounds in the microcapsules by chemical reactions between primary compounds from different sets; and
(c) identifying subsets of primary compounds which react to form secondary compounds which bind to or modulate the activity of the target; wherein one or more of steps (a), (b) and (c) is performed under the microfluidic control of fluidic species.

If the secondary compound is formed by the chemical reaction between more than two primary compounds it can be identified by iteratively repeating steps (a) to (c), but after the first cycle, step (c) comprises compartmentalising the primary compound identified in step (c) of the second or third aspect of the invention, a primary compound identified in step (c) of each of the previous cycles (of the fourth aspect of the invention) and additional sets of primary molecules.

Preferably, the desired activity is selected from the group consisting of a binding activity and the modulation of the activity of a target. Advantageously, the target is compartmentalised into microcapsules together with the compounds.

Sets of compounds may be compartmentalised in different ways to achieve encapsulation of multiple copies of two or more compounds into microcapsules.

For example, small aliquots of an aqueous solution of each compound can be deposited into an oil phase (advantageously containing surfactants and/or other stabilising molecules) whilst applying mechanical energy, thereby dispersing each compound into multiple aqueous microcapsules, each of which contains (for the most part) a single sort of compound but multiple copies thereof. Advantageously, the compounds can be deposited into the oil phase in the form of droplets generated using inkjet printing technology (Calvert, 2001; de Gans et al., 2004), and more advantageously by piezoelectric drop-on-demand (DOD) inkjet printing technology. Inkjet printing technology can be used to mix primary compounds and, optionally, other reagents (e.g the target and reagents to assay target activity) immediately prior to forming the emulsion. Advantageously, multiple compounds can be mixed with multiple targets in a combinatorial manner.

Thus, step (a) above can be modified such that it comprises forming separate emulsion compartments containing two or more compounds and mixing the emulsion compartments to form an emulsified compound repertoire wherein a subset of the repertoire is represented in multiple copies in any one microcapsule.

Moreover, compound libraries can be compartmentalised in highly monodisperse microcapsules produced using microfluidic techniques. For example, aliquots of each compound can be compartmentalised into one or more aqueous microcapsules (with less than 1.5% polydispersity) in water-in-oil emulsions created by droplet break off in a co-flowing steam of oil (Umbanhowar et al., 2000). Advantageously, the aqueous microcapsules are then transported by laminar-flow in a stream of oil in microfluidic channels (Thorsen et al., 2001). The microcapsules containing single compounds can, optionally, be split into two or more smaller microcapsules using microfluidics (Link et al., 2004; Song et al., 2003). Microcapsules containing primary compounds can be fused with other microcapsules (Song et al., 2003) to form secondary compounds. Microcapsules containing compounds can also, optionally, be fused with microcapsules containing a target. A single microcapsule containing a target can, optionally, be split into two or more smaller microcapsules which can subsequently be fused with microcapsules containing different compounds, or compounds at different concentrations. Advantageously, a compound and a target can be mixed by microcapsule fusion prior to a second microcapsule fusion which delivers the reagents necessary to assay the activity of the target (e.g. the substrate for the target if the target is an enzyme). This allows time for the compound to bind to the target. The microcapsules can be analysed and, optionally, sorted using microfluidic devices (Fu et al., 2002).

In a further aspect, there is provided a method for preparing a repertoire of compounds comprising the steps of:
(a) attaching two or more sets of primary compounds onto microbeads;
(b) compartmentalising the microbeads into microcapsules such that a proportion of the microcapsules contains two or more microbeads;
(c) releasing at least one of the sets of primary compounds from the microbeads;
(d) forming secondary compounds in the microcapsules by chemical reactions between primary compounds from different sets; wherein one or more of steps (a), (b), (c) and (d) is performed under the microfluidic control of fluidic species.

Advantageously, the compounds are cleavable from the beads. Where more than two sets of compounds are used, all the sets with the exception of one are cleavable; preferably, they are all cleavable. The compounds may be attached to the microbeads by photochemically cleavable linkers.

In a still further aspect, the invention provides a method for identifying primary compounds which react together to form secondary compounds capable of binding to or modulating the activity of a target, comprising the steps of:
(a) attaching two or more sets of primary compounds onto microbeads;
(b) compartmentalising the microbeads into microcapsules together with the target such that many compartments contain two or more microbeads;
(c) releasing the primary compounds from the microbeads;
(d) forming secondary compounds in the microcapsules by chemical reactions between primary compounds from different sets; and
(e) identifying subsets of primary compounds which react to form secondary compounds which bind to or modulate the activity of the target; wherein one or more of steps (a), (b), (c), (d) and (e) is performed under the microfluidic control of fluidic species.

Advantageously, in step (b) the modal number of microbeads per compartment will be equivalent to the number of primary compounds forming the secondary compound in step (d).

In a further aspect, the invention provides a method for synthesising compounds with enhanced ability to bind to or modulate the activity of the target, comprising the steps of:
(a) attaching onto microbeads subsets of primary compounds identified in step (e) of the second aspect of the invention and, optionally, attaching additional sets of primary compounds;
(b) compartmentalising the microbeads into microcapsules together with the target such that many compartments contain two or more microbeads;
(c) releasing the primary compounds from the microbeads;
(d) forming secondary compounds in the microcapsules by chemical reactions between primary compounds from different sets; and
(e) identifying subsets of primary compounds which react to form secondary compounds which bind to or modulate the activity of the target; wherein one or more of steps (a), (b), (c), (d) and (e) is performed under the microfluidic control of fluidic species.

Advantageously, steps (a) to (e) can be repeated, but after the first cycle, step (a) comprises attaching onto microbeads subsets of primary compounds identified in step (e) and, optionally, attaching additional sets of compounds.

In a further aspect, the invention provides a method for identifying individual compounds which bind to or modulate the activity of the target, comprising the steps of:
(a) attaching onto microbeads a primary compound identified in step (e) of the second or third aspect of the invention and additional sets of primary compounds;
(b) compartmentalising the microbeads into microcapsules together with the target such that many compartments contain two or more microbeads;
(c) releasing the primary compounds from the microbeads;
(d) forming secondary compounds in the microcapsules by chemical reactions between primary compounds from different sets; and
(e) identifying subsets of primary compounds which react to form secondary compounds which bind to or modulate the activity of the target; wherein one or more of steps (a), (b), (c), (d) and (e) is performed under the microfluidic control of fluidic species.

If the secondary compound is formed by the chemical reaction between more than two primary compounds it can be identified by iteratively repeating steps (a) to (e), but after the first cycle, step (a) comprises attaching onto microbeads the primary compound identified in step (e) of the second or third aspect of the invention, a primary compound identified in step (e) of each of the previous cycles (of the fourth aspect of the invention) and additional sets of primary molecules.

Preferably, the desired activity is selected from the group consisting of a binding activity and the modulation of the activity of a target. Advantageously, the target is compartmentalised into microcapsules together with the microbeads.

According to a preferred implementation of the present invention, the compounds may be screened according to an activity of the compound or derivative thereof which makes the microcapsule detectable as a whole. Accordingly, the invention provides a method wherein a compound with the desired activity induces a change in the microcapsule, or a modification of one or more molecules within the microcapsule, which enables the microcapsule containing the compound and, optionally, the microbead carrying it to be identified. In this embodiment, therefore, the microcapsules are either: (a) physically sorted from each other according to the activity of the compound(s) contained therein, by for example, placing an electric charge on the microcapsule and 'steering' the microcapsule using an electric field, and the contents of the sorted microcapsules analysed to determine the identity of the compound(s) which they contain; or (b) analysed directly without sorting to determine the identity of the compound(s) which the microcapsules contain.

According to a preferred embodiment of the present invention, the screening of compounds may be performed by, for example:
(I) In a first embodiment, the microcapsules are screened according to an activity of the compound or derivative thereof which makes the microcapsule detectable as a whole. Accordingly, the invention provides a method wherein a compound with the desired activity induces a change in the microcapsule, or a modification of one or more molecules within the microcapsule, which enables the microcapsule containing the compound and the microbead carrying it to be identified. In this embodiment, therefore, the microcapsules are either: (a) physically sorted from each other according to the activity of the compound(s) contained therein, the contents of the sorted microcapsules optionally pooled into one or more common compartments, and the microcapsule contents analysed to determine the identity of the compound(s); or (b) analysed directly without sorting to determine the identity of the compound(s) which the microcapsules contained. Where the microcapsule contains microbeads, the microbeads can be analysed to determine the compounds with which they are coated.

(II) In a second embodiment, microbeads are analysed following pooling of the microcapsules into one or more common compartments. In this embodiment, a compound having the desired activity modifies the microbead which carried it (and which resides in the same microcapsule) in such a way as to make it identifiable in a subsequent step. The reactions are stopped and the microcapsules are then broken so that all the contents of the individual microcapsules are pooled. Modified microbeads are identified and either: (a) physically sorted from each other according to the activity of the compound(s) coated on the microbeads, and the sorted microbeads analysed to determine the identity of the compound(s) with which they are/were coated; or (b) analysed directly without sorting to determine the identity of the compound(s) with which the microbeads are/were coated. It is to be understood, of course, that modification of the microbead may be direct, in that it is caused by the direct action of the compound, or indirect, in which a series of reactions, one or more of which involve the compound having the desired activity, leads to modification of the microbead. Advantageously, the target is bound to the microbead and is a ligand and the compound within the microcapsule binds, directly or indirectly, to said ligand to enable the isolation of the microbead. In another configuration, a substrate for the target is and is bound to the microbead, and the activity of the compound within the microcapsule results, directly or indirectly, in the conversion of said substrate into a product which remains part of the microbead and enables its isolation. Alternatively, the activity of the compound may prevent or inhibit the conversion of said substrate into product. Moreover, the product of the activity of the compound within the microcapsule can result, directly or indirectly, in the generation of a product which is subsequently complexed with the microbead and enables its identification.

(III) In a third embodiment, the microbeads are analysed following pooling of the microcapsules into one or more common compartments. In this embodiment, a compound with a desired activity induces a change in the microcapsule containing the compound and the microbead which carries it. This change, when detected, triggers the modification of the microbead within the compartment. The reactions are stopped and the microcapsules are then broken so that all the contents of the individual microcapsules are pooled. Modified microbeads are identified and either: (a) physically sorted from each other according to the activity of the compound(s) coated on the microbeads, and the sorted microbeads analysed to determine the identity of the compound(s) with which they are/were coated; or (b) analysed directly without sorting to determine the identity of the compound(s) with which the microbeads are/were coated.

The microcapsules or microbeads may be modified by the action of the compound(s) such as to change their optical properties and/or electrical charge properties. For example, the modification of the microbead can enable it to be further modified outside the microcapsule so as to induce a change in its optical and/or electrical charge properties.

In another embodiment, the change in optical and/or electrical charge properties of the microcapsules or microbeads is due to binding of a compound with distinctive optical and/or electrical charge properties respectively to the target.

Moreover, the change in optical and/or electrical charge properties of the microcapsules or microbeads can be due to binding of a target with distinctive optical and/or electrical charge properties respectively by the compound.

The change in the optical and/or electrical charge properties of the microcapsule may be due to modulation of the activity of the target by the compound. The compound may activate or inhibit the activity of the target. For example, if the target is an enzyme, the substrate and the product of the reaction catalysed by the target can have different optical and/or electrical charge properties. Advantageously, the substrate and product have different fluorescence properties. In the case where the microcapsules contain microbeads, both the substrate and the product can have similar optical and/or electrical charge properties, but only the product of the reaction, and not the substrate, binds to, or reacts with, the microbead, thereby changing the optical and/or electrical charge properties of the microbead.

The change in optical and/or electrical charge properties of the microcapsules or microbeads can also be due to the different optical and/or electrical charge properties of the target and the product of the reaction being selected. Where both target and product have similar optical and/or electrical charge properties, only the product of the reaction being selected, and not the target, binds to, or reacts with, the microbead, thereby changing the optical and/or electrical charge properties of the microcapsules or microbeads.

In a further configuration, further reagents specifically bind to, or specifically react with, the product (and not the substrate) attached to or contained in the microcapsule or microbead, thereby altering the optical and/or electrical charge properties of the microcapsule or microbead.

Advantageously, microbeads modified directly or indirectly by the activity of the compound are further modified by Tyramide Signal Amplification (TSA™; NEN), resulting directly or indirectly in a change in the optical properties of said microcapsules or microbeads thereby enabling their separation.

It is to be understood that the detected change in the compartment may be caused by the direct action of the compound, or indirect action, in which a series of reactions, one or more of which involve the compound having the desired activity leads to the detected change.

Where the compounds are attached to beads, the density with which compounds are coated onto the microbeads, combined with the size of the microcapsule will determine the concentration of the compound in the microcapsule. High compound coating densities and small microcapsules will both give higher compound concentrations which may be advantageous for the selection of molecules with a low affinity for the target. Conversely, low compound coating densities and large microcapsules will both give lower compound concentrations which may be advantageous for the selection of molecules with a high affinity for the target.

Preferably, microencapsulation is achieved by forming an emulsion.

The microbead can be nonmagnetic, magnetic or paramagnetic.

Repertoires of compounds can be encapsulated so as to have multiple copies of a single compound in a microcapsule in different ways. For example, thin tubes connected to the microfluidic device can be dipped into reservoirs containing the desired compounds, and capillary action can be used to draw the desired compound from the reservoir into the microfluidic device. This method allows the microfluidic device to be loaded with compounds prepared outside the device.

Moreover, compound libraries can be compartmentalised in highly monodisperse microcapsules produced using microfluidic techniques. For example, aliquots of each compound can be compartmentalised into one or more aqueous microcapsules (with less than 1.5% polydispersity) in water-in-oil emulsions created by droplet break off in a co-flowing stream of oil (Umbanhowar et al., 2000). Advantageously, the aqueous microcapsules are then transported by laminar-flow in a stream of oil in microfluidic channels (Thorsen et al., 2001).The microcapsules containing single compounds can, optionally, be split into two or more smaller microcapsules using microfluidics (Link et al., 2004; Song et al., 2003). Microcapsules containing primary compounds can be fused with other microcapsules (Song et al., 2003) to form secondary compounds. Microcapsules containing compounds can also, optionally, be fused with microcapsules containing a target. A single microcapsule containing a target can, optionally, be split into two or more smaller microcapsules which can subsequently be fused with microcapsules containing different compounds, or compounds at different concentrations. Advantageously, a compound and a target can be mixed by microcapsule fusion prior to a second microcapsule fusion which delivers the reagents necessary to assay the activity of the target (e.g. the substrate for the target if the target is an enzyme). This allows time for the compound to bind to the target. The microcapsules can be analysed and, optionally, sorted using microfluidic devices (Fu et al., 2002).

Methods of controlling and manipulating of fluidic species are also described, for example, in U.S. Provisional Patent Application Ser. No. 60/498,091, filed Aug. 27, 2003, by Link, et. al.; U.S. Provisional Patent Application Ser. No. 60/392,195, filed Jun. 28, 2002, by Stone, et. al.; U.S. Provisional Patent Application Ser. No. 60/424,042, filed Nov. 5, 2002, by Link, et al.; U.S. Pat. No. 5,512,131, issued Apr. 30, 1996 to Kumar, et al.; International Patent Publication WO 96/29629, published Jun. 26, 1996 by Whitesides, et al.; U.S. Pat. No. 6,355,198, issued Mar. 12, 2002 to Kim, et al.; International Patent Application Serial No.: PCT/US01/16973, filed May 25, 2001 by Anderson, et al., published as WO 01/89787 on Nov. 29, 2001; International Patent Application Serial No. PCT/US03/20542, filed Jun. 30, 2003 by Stone, et al., published as WO 2004/002627 on Jan. 8, 2004; International Patent Application Serial No. PCT/US2004/010903, filed Apr. 9, 2004 by Link, et al.; and U.S. Provisional Patent Application Ser. No. 60/461,954, filed Apr. 10, 2003, by Link, et al.; each of which is incorporated herein by reference.

In various aspects of the invention, a fluidic system as disclosed herein may include a droplet formation system, a droplet fusing system, a droplet splitting system, a sensing system, a controller, and/or a droplet sorting and/or separation system, or any combination of these systems. Such systems and methods may be positioned in any suitable order, depending on a particular application, and in some cases, multiple systems of a given type may be used, for example, two or more droplet formation systems, two or more droplet separation systems, etc. As examples of arrangements, systems of the invention can be arranged to form droplets, to dilute fluids, to control the concentration of species within droplets, to sort droplets to select those with a desired concentration of species or entities (e.g., droplets each containing one molecule of reactant), to fuse individual droplets to cause reaction between species contained in the individual droplets, to determine reaction(s) and/or rates of reaction(s) in one or more droplets, etc. Many other arrangements can be practiced in accordance with the invention.

One aspect of the invention relates to systems and methods for producing droplets of a first liquid surrounded by a second liquid[2]. The first and second liquids may be essentially immiscible in many cases, i.e., immiscible on a time scale of interest (e.g., the time it takes a fluidic droplet to be transported through a particular system or device). In certain cases, the droplets may each be substantially the same shape or size, as further described below. The first liquid may also contain other species, for example, certain molecular species (e.g., as further discussed below), cells, particles, etc.

In one set of embodiments, electric charge may be created on a first liquid surrounded by a second liquid, which may cause the first liquid to separate into individual droplets within the second liquid. In some embodiments, the first liquid and the second liquid may be present in a channel, e.g., a microfluidic channel, or other constricted space that facilitates application of an electric field to the first liquid (which may be "AC" or alternating current, "DC" or direct current etc.), for example, by limiting movement of the first liquid with respect to the second liquid. Thus, the first liquid can be present as a series of individual charged and/or electrically inducible droplets within the second liquid. In one embodiment, the electric force exerted on the fluidic droplet may be large enough to cause the droplet to move within the second liquid. In some cases, the electric force exerted on the fluidic droplet may be used to direct a desired motion of the droplet within the second liquid, for example, to or within a channel or a microfluidic channel.

Electric charge may be created in the first liquid within the second liquid using any suitable technique, for example, by placing the first liquid within an electric field (which may be AC, DC, etc.), and/or causing a reaction to occur that causes the first liquid to have an electric charge, for example, a chemical reaction, an ionic reaction, a photocatalyzed reaction, etc. In one embodiment, the first liquid is an electrical conductor. As used herein, a "conductor" is a material having a conductivity of at least about the conductivity of 18 megohm (MOhm or M$\Omega$) water. The second liquid surrounding the first liquid may have a conductivity less than that of the first liquid. For instance, the second liquid may be an insulator, relative to the first liquid, or at least a "leaky insulator," i.e., the second liquid is able to at least partially electrically insulate the first liquid for at least a short period of time. Those of ordinary skill in the art will be able to identify the conductivity of fluids. In one non-limiting embodiment, the first liquid may be substantially hydrophilic, and the second liquid surrounding the first liquid may be substantially hydrophobic. In an alternative embodiment, the microcapsules or microbeads are analysed by detection of a change in their fluorescence. For example, microbeads can be analysed by flow cytometry and, optionally sorted using a fluorescence activated cell sorter (FACS). The different fluorescence properties of the target and the product can be due to fluorescence resonance energy transfer (FRET).

In a further embodiment, the internal environment of the microcapsules can be modified by the addition of one or more reagents to the continuous phase of the emulsion. This allows reagents to be diffused in to the microcapsules during the reaction, if necessary.

The invention moreover relates to a method according to the preceding aspects, further comprising the step of isolating the secondary compound produced by reaction of the primary compounds and optionally further comprising the step of manufacturing one or more secondary compounds.

The invention also provides for a product when identified according to the invention. As used in this context, a "product" may refer to any compound, selectable according to the invention.

Further embodiments of the invention are described in the detailed description below and in the accompanying claims.

BRIEF DESCRIPTION OF THE FIGURES

FIG. 22. Primary compounds for the synthesis of PTP1B inhibitors. An amine (A) and an aldehyde (B) with difluoromethylene phosphonate moieties. Amine A reacts with aldehyde B in the aqueous microcapsules of a water-in-oil emulsion to generate the imine C which is a potent PTP1B inhibitor. C can be reduced in situ using cyanoborohydride to generate the stable amine D.

DETAILED DESCRIPTION OF THE INVENTION

Definitions

Figure 1A:
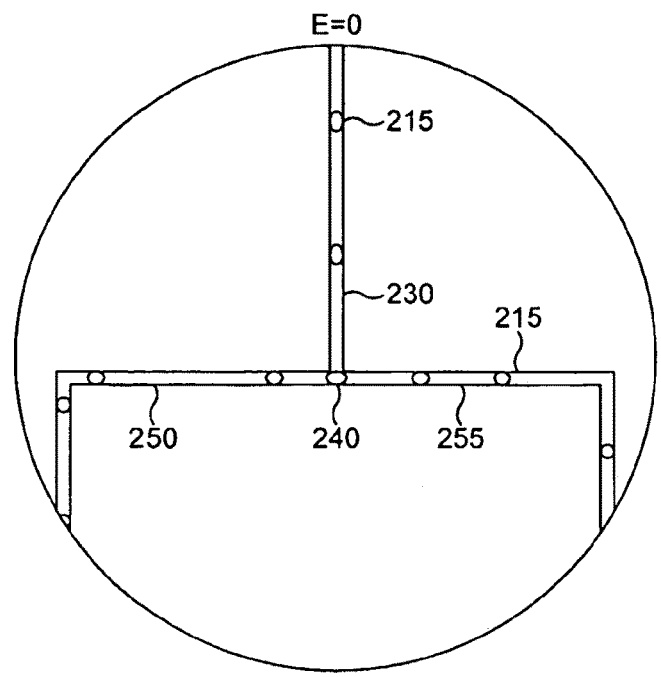
FIGS. 1A and 1B illustrate the splitting of droplets in accordance with one embodiment of the invention.

The term "microcapsule" is used herein in accordance with the meaning normally assigned thereto in the art and further described hereinbelow. In essence, however, a microcapsule is an artificial compartment whose delimiting borders restrict the exchange of the components of the molecular mechanisms described herein which allow the identification of the molecule with the desired activity. The delimiting borders preferably completely enclose the contents of the microcapsule. Preferably, the microcapsules used in the method of the present invention will be capable of being produced in very large numbers, and thereby to compartmentalise a library of compounds. Optionally, the compounds can be attached to microbeads. The microcapsules used herein allow mixing and sorting to be performed thereon, in order to facilitate the high throughput potential of the methods of the invention. Microcapsules according to the present invention can be a droplet of one fluid in a different fluid, where the confined components are soluble in the droplet but not in the carrier fluid, and in another embodiment there is another material defining a wall, such as a membrane (e.g. in the context of lipid vesicles; liposomes) or non-ionic surfactant vesicles, or those with rigid, nonpermeable membranes, or semipermeable membranes. Arrays of liquid droplets on solid surfaces, multiwell plates and "plugs" in microfluidic systems, that is fluid droplets that are not completely surrounded by a second fluid as defined herein, are not microcapsules as defined herein.

A "proportion" of the microcapsules, which is defined as comprising two or more compounds, or two or microbeads, is any fraction of the microcapsules in question, including all of said microcapsules. Advantageously, it is at least 25% thereof, preferably 50%, and more preferably 60%, 70%, 80%, 90% or 95%.

The term "microbead" is used herein in accordance with the meaning normally assigned thereto in the art and further described hereinbelow. Microbeads, are also known by those skilled in the art as microspheres, latex particles, beads, or minibeads, are available in diameters from 20 nm to 1 mm and can be made from a variety of materials including silica and a variety of polymers, copolymers and terpolymers. Highly uniform derivatised and non-derivatised nonmagnetic and paramagnetic microparticles (beads) are commercially available from many sources (e.g. Sigma, Bangs Laboratories, Luminex and Molecular Probes) (Fornusek and Vetvicka, 1986).

Microbeads can be "compartmentalised" in accordance with the present invention by distribution into microcapsules. For example, in a preferred aspect the microbeads can be placed in a water/oil mixture and emulsified to form a water-in-oil emulsion comprising microcapsules according to the invention. The concentration of the microbeads can be adjusted to control the number of microbeads, which on average, appear in each microcapsule. Advantageously, the concentration of the microbeads can be adjusted such that, on average a single microbead appears in only 10-20% of the microcapsules, thus assuring that there are very few microcapsules with more than one microbead.

The term "compound" is used herein in accordance with, the meaning normally assigned thereto in the art. The term compound is used in its broadest sense i.e. a substance comprising two or more elements in fixed proportions, including molecules and supramolecular complexes. This definition includes small molecules (typically <500 Daltons) which make up the majority of pharmaceuticals. However, the definition also includes larger molecules, including polymers, for example polypeptides, nucleic acids and carbohydrates, and supramolecular complexes thereof.

The term "primary compound" is used herein to indicate a compound which is compartmentalised in a microcapsule or coupled to a bead.

The term "secondary compound" is used herein to indicate a compound which is formed by the reaction between two or more primary compounds in a microcapsule, optionally after the release of at least one of the primary molecules from a microbead. Advantageously, all primary molecules are released from the microbeads. The secondary compound may be the result of a covalent or non-covalent reaction between the primary compounds.

The term "scaffold" is used herein in accordance with the meaning normally assigned thereto in the art. That is to say a core portion of a molecule common to all members of a combinatorial library (Maclean et al., 1999). Secondary compounds may optionally comprise scaffolds.

A "repertoire" of compounds is a group of diverse compounds, which may also be referred to as a library of compounds. Repertoires of compounds may be generated by any means known in the art, including combinatorial chemistry, compound evolution, or purchased from commercial sources such as Sigma Aldrich, Discovery Partners International, Maybridge and Tripos. A repertoire advantageously comprises at least $10^2$, $10^3$, $10^4$, $10^5$, $10^6$, $10^7$, $10^8$, $10^9$, $10^{10}$, $10^{11}$ or more different compounds, which may be related or unrelated in structure or function.

A "set" of compounds may be a repertoire of compounds or any, part of a repertoire, including a single compound species. The invention envisages the use of two or more sets of compounds, which are reacted together. The sets may be derived from a single repertoire, or a plurality of different repertoires.

Compounds can be "released" from a microbead by cleavage of a linker which effects the attachment of the compound to the microbead. Release of the compounds from the microbead allows the compounds to interact more freely with other contents of the microcapsule, and to be involved in reactions therein and optionally to become combined with other reagents to form new compounds, complexes, molecules or supramolecular complexes. Cleavage of linkers can be performed by any means, with means such as photochemical cleavage which can be effected from without the microcapsule being preferred. Photochemically cleavable linkers are known in the art (see for example (Gordon and Balasubramanian, 1999)) and further described below.

As used herein, the "target" is any compound, molecule, or supramolecular complex. Typical targets include targets of medical significance, including drug targets such as receptors, for example G protein coupled receptors and hormone receptors; transcription factors, protein kinases and phosphatases involved in signalling pathways; gene products specific to microorganisms, such as components of cell walls, replicases and other enzymes; industrially relevant targets, such as enzymes used in the food industry, reagents intended for research or production purposes, and the like.

An "activity", as referred to herein in connection with the modulation of an activity of a target, can be any activity of the target or an activity of a molecule which is influenced by the target, which is modulatable directly or indirectly by a compound or compounds as assayed herein. The activity of the target may be any measurable biological or chemical activity, including binding activity, an enzymatic activity, an activating or inhibitory activity on a third enzyme or other molecule, the ability to cause disease or influence metabolism or other functions, and the like. Activation and inhibition, as referred to herein, denote the increase or decrease of a desired activity 1.5 fold, 2 fold, 3 fold, 4 fold, 5 fold, 10 fold, 100 fold or more. Where the modulation is inactivation, the inactivation can be substantially complete inactivation. The desired activity may moreover be purely a binding activity, which may or may not involve the modulation of the activity of the target bound to.

A compound defined herein as "low molecular weight" or a "small molecule" is a molecule commonly referred to in the pharmaceutical arts as a "small molecule". Such compounds are smaller than polypeptides and other, large molecular complexes and can be easily administered to and assimilated by patients and other subjects. Small molecule drugs can advantageously be formulated for oral administration or intramuscular injection. For example, a small molecule may have a molecular weight of up to 2000 Dalton; preferably up to 1000 Dalton; advantageously between 250 and 750 Dalton; and more preferably less than 500 Dalton.

A "selectable change" is any change which can be measured and acted upon to identify or isolate the compound which causes it. The selection may take place at the level of the microcapsule, the microbead, or the compound itself, optionally when complexed with another reagent. A particularly advantageous embodiment is optical detection, in which the selectable change is a change in optical properties, which can be detected and acted upon for instance in a FACS device to separate microcapsules or microbeads displaying the desired change.

As used herein, a 'change in optical properties' refers to any change in absorption or emission of electromagnetic radiation, including changes in absorbance, luminescence, phosphorescence or fluorescence. All such properties are included in the term "optical". Microcapsules or microbeads can be identified and, optionally, sorted, for example, by luminescence, fluorescence or phosphorescence activated sorting. In a preferred embodiment, flow cytometry is employed to identify and, optionally, sort microcapsules or microbeads. A variety of optical properties can be used for analysis and to trigger sorting, including light scattering (Kerker, 1983) and fluorescence polarisation (Rolland et al., 1985). In a highly preferred embodiment microcapsules or microbeads are analysed and, optionally, sorted using a fluorescence activated cell sorter (FACS) (Norman, 1980; Mackenzie and Pinder, 1986).

The compounds in microcapsules or on beads can be identified using a variety of techniques familiar to those skilled in the art, including mass spectroscopy, chemical tagging or optical tagging.

As used herein, "or" is understood to mean "inclusively or," i.e., the inclusion of at least one, but including more than one, of a number or list of elements. In contrast, the term "exclusively or" refers to the inclusion of exactly one element of a number or list of elements.

The indefinite articles "a" and "an," as used herein in the specification and in the claims, should be understood to mean "at least one."

The term "about," as used herein in reference to a numerical parameter (for example, a physical, chemical, electrical, or biological property), will be understood by those of ordinary skill in the art to be an approximation of a numerical value, the exact value of which may be subject to errors such as those resulting from measurement errors of the numerical parameter, uncertainties resulting from the variability and/or reproducibility of the numerical parameter (for example, in separate experiments), and the like.

As used herein, a "cell" is given its ordinary meaning as used in biology. The cell may be any cell or cell type. For example, the cell may be a bacterium or other single-cell organism, a plant cell, or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a hepatocyte, a chondrocyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. In certain embodiments, the cell may be a Chinese hamster ovarian ("CHO") cell or a 3T3 cell.

"Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria.

Accordingly the term 'microfluidic control' (of a system/method) as described herein refers to a method/system which comprises the use of device or apparatus including at least one fluid channel having a cross-sectional dimension of less than 1 mm, and a ratio of length to largest cross-sectional dimension of at least 3:1.

Electronic microfluidic control (of a method/system) as referred to herein refers to a microfluidic method/system in which one or more steps of the method/system involves the production of an electronic charge on at least a proportion of the microcapsules used in the microfluidic method/system.

[These definitions of microfluidics etc. are a little different between the two filings—should they be made consistent?]

The "cross-sectional dimension" of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g. an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

As used herein, "integral" means that portions of components are joined in such a way that they cannot be separated from each other without cutting or breaking the components from each other.

A "droplet," as used herein is an isolated portion of a first fluid that is completely surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located.

The "average diameter" of a population of droplets is the arithmetic average of the diameters of the droplets. Those of ordinary skill in the art will be able to determine the average diameter of a population of droplets, for example, using laser light scattering or other known techniques. The diameter of a droplet, in a non-spherical droplet, is the mathematically-defined average diameter of the droplet, integrated across the entire surface. As non-limiting examples, the average diameter of a droplet may be less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers. The average diameter of the droplet may also be at least about 1 micrometer, at least about 2 micrometers, at least about 3 micrometers, at least about 5 micrometers, at least about 10 micrometers, at least about 15 micrometers, or at least about 20 micrometers in certain cases.

As used herein, a "fluid" is given its ordinary meaning, i.e., a liquid or a gas. Preferably a fluid is a liquid. The fluid may have any suitable viscosity that permits flow. If two or more fluids are present, each fluid may be independently selected among essentially any fluids (liquids, gases, and the like) by those of ordinary skill in the art, by considering the relationship between the fluids. The fluids may each be miscible or immiscible. For example, two fluids can be selected to be immiscible within the time frame of formation of a stream of fluids, or within the time frame of reaction or interaction. Where the portions remain liquid for a significant period of time then the fluids should be significantly immiscible. Where, after contact and/or formation, the dispersed portions are quickly hardened by polymerization or the like, the fluids need not be as immiscible. Those of ordinary skill in the art can select suitable miscible or immiscible fluids, using contact angle measurements or the like, to carry out the techniques of the invention.

As used herein, a first entity is "surrounded" by a second entity if a closed loop can be drawn around the first entity through only the second entity. A first entity is "completely surrounded" if closed loops going through only the second entity can be drawn around the first entity regardless of direction. In one aspect, the first entity is a particle. In yet another aspect of the invention, the entities can both be fluids. For example, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are substantially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, ethanol, salt solutions, etc. Examples of hydrophobic liquids include, but are not limited to, oils such as hydrocarbons, silicon oils, fluorocarbon oils, organic solvents etc.

The term "determining," as used herein, generally refers to the analysis or measurement of a species, for example, quantitatively or qualitatively, or the detection of the presence or absence of the species. "Determining" may also refer to the analysis or measurement of an interaction between two or more species, for example, quantitatively or qualitatively, or by detecting the presence or absence of the interaction. Example techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements.

General Techniques

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference) and chemical methods. In addition Harlow & Lane, A Laboratory Manual Cold Spring Harbor, N.Y., is referred to for standard Immunological Techniques.

(A) General Description

The microcapsules of the present invention require appropriate physical properties to allow the working of the invention.

First, to ensure that the compounds and the target may not diffuse between microcapsules, the contents of each microcapsule must be isolated from the contents of the surrounding microcapsules, so that there is no or little exchange of compounds and target between the microcapsules over the timescale of the experiment.

Second, the method of the present invention requires that there are only a limited number of beads per microcapsule. This ensures that the compounds and the target will be isolated from other beads.

Third, the formation and the composition of the microcapsules must not abolish the activity of the target.

Consequently, any microencapsulation system used must fulfil these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase should be removed or the biological systems in it inhibited or destroyed in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an oil) as the matrix in which these droplets are suspended (the nondisperse, continuous or external phase). Such emulsions are termed water-in-oil (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and decane. Suitable surfactants include: non-ionic surfactants (Schick, 1966) such as sorbitan monooleate (Span™80; ICI), sorbitan monostearate (Span™60; ICI), polyoxyethylenesorbitan monooleate (Tween™ 80; ICI), and octylphenoxyethoxyethanol (Triton X-100); ionic surfactants such as sodium cholate and sodium taurocholate and sodium deoxycholate; chemically inert silicone-based surfactants such as polysiloxane-polycetyl-polyethylene glycol copolymer (Cetyl Dimethicone Copolyol) (e.g. Abil™EM90; Goldschmidt); and cholesterol.

Emulsions with a fluorocarbon (or perfluorocarbon) continuous phase (Krafft et al., 2003; Riess, 2002) may be particularly advantageous. For example, stable water-in-perfluorooctyl bromide and water-in-perfluorooctylethane emulsions can be formed using F-alkyl dimorpholinophosphates as surfactants (Sadtler et al., 1996). Non-fluorinated compounds are essentially insoluble in fluorocarbons and perfluorocarbons (Curran, 1998; Hildebrand and Cochran, 1949; Hudlicky, 1992; Scott, 1948; Studer et al., 1997) and small drug-like molecules (typically <500 Da and Log P<5) (Lipinski et al., 2001) are compartmentalised very effectively in the aqueous microcapsules of water-in-fluorocarbon and water-in-perfluorocarbon emulsions—with little or no exchange between microcapsules.

Advantageously, compounds can be compartmentalised in microcapsules comprising non-aqueous (organic) solvents. Non-fluorinated organic solvents are essentially insoluble and immiscible with fluorocarbons and perfluorocarbons (Curran, 1998; Hildebrand and Cochran, 1949; Hudlicky, 1992; Scott, 1948; Studer et al., 1997) allowing the formation of emulsions with a fluorocarbon (or perfluorocarbon) continuous phase and a discontinuous phase formed from a non-aqueous solvent such as dichloromethane, chloroform, carbon tetrachloride, toluene, tetrahydrofuran, diethyl ether, and ethanol. The ability to form secondary compounds in microcapsules comprising non-aqueous solvents greatly expands the repertoire of chemical reactions that can be performed and secondary molecules that can be synthesised therein. Most of synthetic organic chemistry is carried out in organic solvents including dichloromethane, chloroform, carbon tetrachloride, toluene, tetrahydrofuran, diethyl ether, and ethanol. Organic molecules dissolve better in organic solvents. Electrostatic interactions are enhanced in organic solvents (due to the low dielectric constant), whereas they can be solvated and made less reactive in aqueous solvents. For example, much of contemporary organic chemistry involves reactions relating to carbonyl chemistry, including the use of metal enolates. Likewise for a growing number of other organometallic interactions. These reactions are often carried out under an inert atmosphere in anhydrous solvents (otherwise the reagents would be quenched by water). There are also a large number of reactions which use palladium catalysis including the Suzuki reaction and the Heck reaction.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Complicated biochemical processes, notably gene transcription and translation are also active in aqueous microcapsules formed in water-in-oil emulsions. This has enabled compartmentalisation in water-in-oil emulsions to be used for the selection of genes, which are transcribed and translated in emulsion microcapsules and selected by the binding or catalytic activities of the proteins they encode (Doi and Yanagawa, 1999; Griffiths and Tawfik, 2003; Lee et al., 2002; Sepp et al., 2002; Tawfik and Griffiths, 1998). This was possible because the aqueous microcapsules formed in the emulsion were generally stable with little if any exchange of nucleic acids, proteins, or the products of enzyme catalysed reactions between microcapsules.

The technology exists to create emulsions with volumes all the way up to industrial scales of thousands of liters (Becher, 1957; Sherman, 1968; Lissant, 1974; Lissant, 1984).

The preferred microcapsule size will vary depending upon the precise requirements of any individual screening process that is to be performed according to the present invention. In all cases, there will be an optimal balance between the size of the compound library and the sensitivities of the assays to determine the identity of the compound and target activity.

The size of emulsion microcapsules may be varied simply by tailoring the emulsion conditions used to form the emulsion according to requirements of the screening system. The larger the microcapsule size, the larger is the volume that will be required to encapsulate a given compound library, since the ultimately limiting factor will be the size of the microcapsule and thus the number of microcapsules possible per unit volume.

Water-in-oil emulsions can be re-emulsified to create water-in-oil-in water double emulsions with an external (continuous) aqueous phase. These double emulsions can be analysed and, optionally, sorted using a flow cytometer (Bernath et al., 2004).

Highly monodisperse microcapsules can be produced using microfluidic techniques. For example, water-in-oil emulsions with less than 1.5% polydispersity can be generated by droplet break off in a co-flowing stream of oil (Umbanhowar et al., 2000). Microfluidic systems can also be used for laminar-flow of aqueous microdroplets dispersed in a stream of oil in microfluidic channels (Thorsen et al., 2001). This allows the construction of microfluidic devices for flow analysis and, optionally, flow sorting of microdroplets (Fu et al., 2002).

Advantageously, highly monodisperse microcapsules can be formed using systems and methods for the electronic control of fluidic species. [One aspect of the invention relates to systems and methods for producing droplets of fluid surrounded by a liquid. The fluid and the liquid may be essentially immiscible in many cases, i.e., immiscible on a time scale of interest (e.g., the time it takes a fluidic droplet to be transported through a particular system or device). In certain cases, the droplets may each be substantially the same shape or size, as further described below. The fluid may also contain other species, for example, certain molecular species (e.g., as further discussed below), cells, particles, etc.

In one set of embodiments, electric charge may be created on a fluid surrounded by a liquid, which may cause the fluid to separate into individual droplets within the liquid. In some embodiments, the fluid and the liquid may be present in a channel, e.g., a microfluidic channel, or other constricted space that facilitates application of an electric field to the fluid (which may be "AC" or alternating current, "DC" or direct current etc.), for example, by limiting movement of the fluid with respect to the liquid. Thus, the fluid can be present as a series of individual charged and/or electrically inducible droplets within the liquid. In one embodiment, the electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc. As one example, in apparatus 5 in FIG. 3A, droplets 15 created by fluid source 10 can be electrically charged using an electric filed created by electric field generator 20.

Electric charge may be created in the fluid within the liquid using any suitable technique, for example, by placing the fluid within an electric field (which may be AC, DC, etc.), and/or causing a reaction to occur that causes the fluid to have an electric charge, for example, a chemical reaction, an ionic reaction, a photocatalyzed reaction, etc. In one embodiment, the fluid is an electrical conductor. As used herein, a "conductor" is a material having a conductivity of at least about the conductivity of 18 megohm (MOhm or M$\Omega$) water. The liquid surrounding the fluid may have a conductivity less than that of the fluid. For instance, the liquid may be an insulator, relative to the fluid, or at least a "leaky insulator," i.e., the liquid is able to at least partially electrically insulate the fluid for at least a short period of time. Those of ordinary skill in the art will be able to identify the conductivity of fluids. In one non-limiting embodiment, the fluid may be substantially hydrophilic, and the liquid surrounding the fluid may be substantially hydrophobic.

In some embodiments, the charge created on the fluid (for example, on a series of fluidic droplets) may be at least about $10^{-22}$ C/micrometer$^3$. In certain cases, the charge may be at least about $10^{-21}$ C/micrometer$^3$, and in other cases, the charge may be at least about $10^{-20}$ C/micrometer$^3$, at least about $10^{-19}$ C/micrometer$^3$, at least about $10^{-18}$ C/micrometer$^3$, at least about $10^{-17}$ C/micrometer$^3$, at least about $10^{-16}$ C/micrometer$^3$, at least about $10^{-15}$ C/micrometer$^3$, at least about $10^{-14}$ C/micrometer$^3$, at least about $10^{-13}$ C/micrometer$^3$, at least about $10^{-12}$ C/micrometer$^3$, at least about $10^{-11}$ C/micrometer$^3$, at least about $10^{-10}$ C/micrometer$^3$, or at least about $10^{-9}$ C/micrometer$^3$ or more. In certain embodiments, the charge created on the fluid may be at least about $10^{-21}$ C/micrometer$^2$, and in some cases, the charge may be at least about $10^{-20}$ C/micrometer$^2$, at least about $10^{-19}$ C/micrometer$^2$, at least about $10^{-18}$ C/micrometer$^2$, at least about $10^{-17}$ C/micrometer$^2$, at least about $10^{-16}$ C/micrometer$^2$, at least about $10^{-15}$ C/micrometer$^2$, at least about $10^{-14}$ C/micrometer$^2$, or at least about $10^{-13}$ C/micrometer$^2$ or more. In other embodiments, the charge may be at least about $10^{-14}$ C/droplet, and, in some cases, at least about $10^{-13}$ C/droplet, in other cases at least about $10^{-12}$ C/droplet, in other cases at least about $10^{-11}$ C/droplet, in other cases at least about $10^{-10}$ C/droplet, or in still other cases at least about $10^{-9}$ C/droplet.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can, be used. In certain embodiments, the electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more.

In some embodiments, an electric field may be applied to fluidic droplets to cause the droplets to experience an electric force. The electric force exerted on the fluidic droplets may be, in some cases, at least about $10^{-16}$ N/micrometer$^3$. In certain cases, the electric force exerted on the fluidic droplets may be greater, e.g., at least about $10^{-15}$ N/micrometer$^3$, at least about $10^{-14}$ N/micrometer$^3$, at least about $10^{-13}$ N/micrometer$^3$, at least about $10^{-12}$ N/micrometer$^3$, at least about $10^{-11}$ N/micrometer$^3$, at least about $10^{-10}$ N/micrometer$^3$, at least about $10^{-9}$ N/micrometer$^3$, at least about $10^{-8}$ N/micrometer$^3$, or at least about $10^{-7}$ N/micrometer$^3$ or more. In other embodiments, the electric force exerted on the fluidic droplets, relative to the surface area of the fluid, may be at least about $10^{-15}$ N/micrometer$^2$, and in some cases, at least about $10^{-14}$ N/micrometer$^2$, at least about $10^{-13}$ N/micrometer$^2$, at least about $10^{-12}$ N/micrometer$^2$, at least about $10^{-11}$ N/micrometer$^2$, at least about $10^{-10}$ N/micrometer$^2$, at least about $10^{-9}$ N/micrometer$^2$, at least about $10^{-8}$ N/micrometer$^2$, at least about $10^{-7}$ N/micrometer$^2$, or at least about $10^{-6}$ N/micrometer$^2$ or more. In yet other embodiments, the electric force exerted on the fluidic droplets may be at least about $10^{-9}$ N, at least about $10^{-8}$ N, at least about $10^{-7}$ N, at least about $10^{-6}$ N, at least about $10^{-5}$ N, or at least about $10^{-4}$ N or more in some cases.

In some embodiments of the invention, systems and methods are provided for at least partially neutralizing an electric charge present on a fluidic droplet, for example, a fluidic droplet having an electric charge, as described above. For example, to at least partially neutralize the electric charge, the fluidic droplet may be passed through an electric field and/or brought near an electrode, e.g., using techniques such as those described herein. Upon exiting of the fluidic droplet from the electric field (i.e., such that the electric field no longer has a strength able to substantially affect the fluidic droplet), and/or other elimination of the electric field, the fluidic droplet may become electrically neutralized, and/or have a reduced electric charge.

Figure 7A:
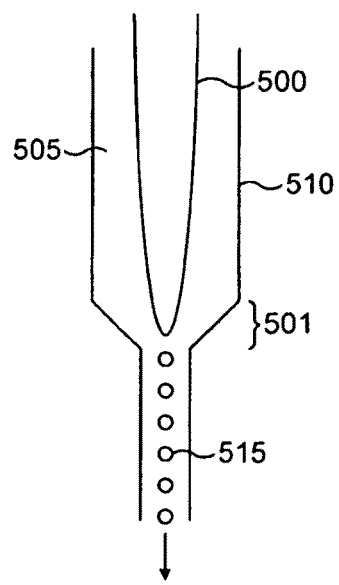
FIGS. 7a and 7b are schematic diagrams of the formation of microfluidic droplets in accordance with the present invention.

In another set of embodiments, droplets of fluid can be created from a fluid surrounded by a liquid within a channel by altering the channel dimensions in a manner that is able to induce the fluid to form individual droplets. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. One example is shown in FIG. 7A, where channel 510 includes a flowing fluid 500 (flowing downwards), surrounded by liquid 505. Channel 510 narrows at location 501, causing fluid 500 to form a series of individual fluidic droplets 515. In other embodiments, internal obstructions may also be used to cause droplet formation to occur. For instance, baffles, ridges, posts, or the like may be used to disrupt liquid flow in a manner that causes the fluid to coalesce into fluidic droplets.

Figure 7B:
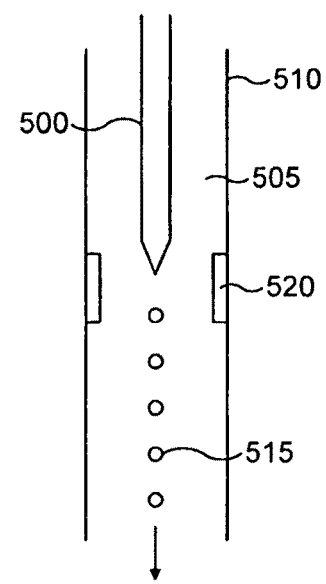

In some cases, the channel dimensions may be altered with respect to time (for example, mechanically or electro-mechanically, pneumatically, etc.) in such a manner as to cause the formation of individual fluidic droplets to occur. For example, the channel may be mechanically contracted ("squeezed") to cause droplet formation, or a fluid stream may be mechanically disrupted to cause droplet formation, for example, through the use of moving baffles, rotating blades, or the like. As a non-limiting example, in FIG. 7B, fluid 500 flows through channel 510 in a downward direction. Fluid 500 is surrounded by liquid 505. Piezoelectric devices 520 positioned near or integral to channel 510 may then mechanically constrict or "squeeze" channel 510, causing fluid 500 to break up into individual fluidic droplets 515.

Figure 14A:
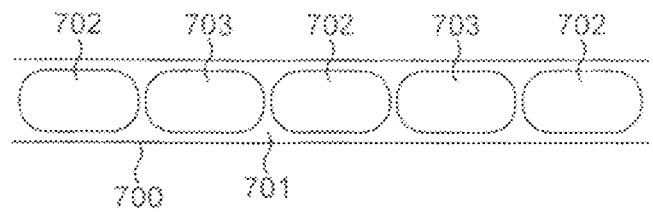
FIGS. 14a-c are illustrations of the formation and maintenance of microfluidic droplets using three immiscible liquids.
Figure 14B:
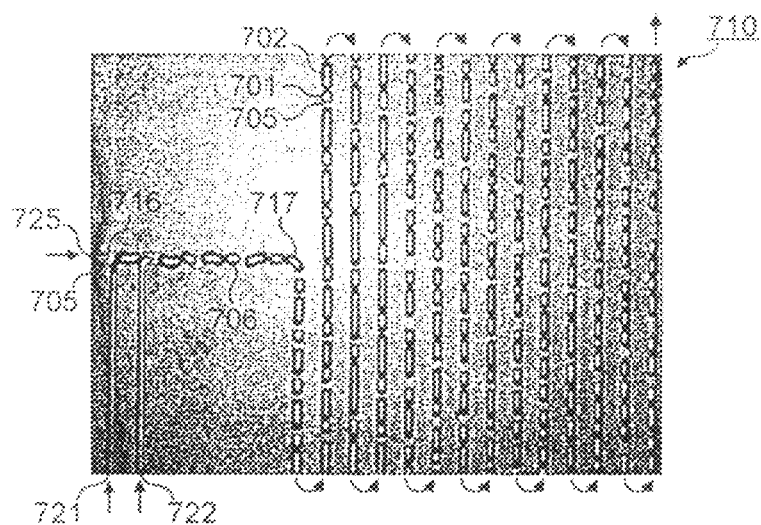
Figure 14C:
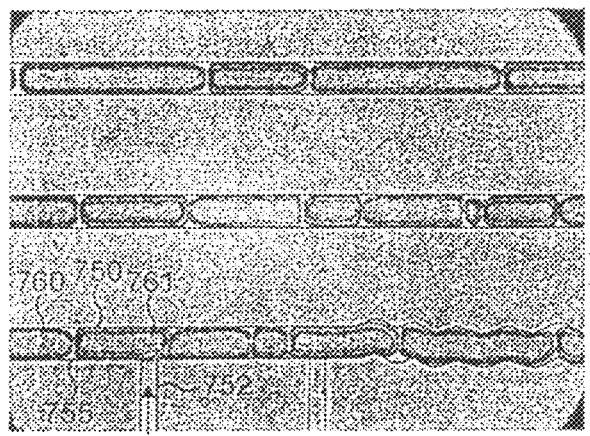

In yet another set of embodiments, individual fluidic droplets can be created and maintained in a system comprising three essentially mutually immiscible fluids (i.e., immiscible on a time scale of interest), where one fluid is a liquid carrier, and the second fluid and the third fluid alternate as individual fluidic droplets within the liquid carrier. In such a system, surfactants are not necessarily required to ensure separation of the fluidic droplets of the second and third fluids. As an example, with reference to FIG. 14A, within channel 700, a first fluid 701 and a second fluid 702 are each carried within liquid carrier 705. First fluid 701 and second fluid 702 alternate as a series of alternating, individual droplets, each carried by liquid carrier 705 within channel 700. As the first fluid, the second fluid, and the liquid carrier are all essentially mutually immiscible, any two of the fluids (or all three fluids) can come into contact without causing droplet coalescence to occur. A photomicrograph of an example of such a system is shown in FIG. 14B, illustrating first fluid 701 and second fluid 702, present as individual, alternating droplets, each contained within liquid carrier 705.

One example of a system involving three essentially mutually immiscible fluids is a silicone oil, a mineral oil, and an aqueous solution (i.e., water, or water containing one or more other species that are dissolved and/or suspended therein, for example, a salt solution, a saline solution, a suspension of water containing particles or cells, or the like). Another example of a system is a silicone oil, a fluorocarbon oil, and an aqueous solution. Yet another example of a system is a hydrocarbon oil (e.g., hexadecane), a fluorocarbon oil, and an aqueous solution. In these examples, any of these fluids may be used as the liquid carrier. Non-limiting examples of suitable fluorocarbon oils include octadecafluorodecahydronaphthalene:

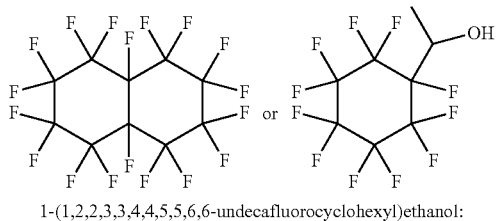

1-(1,2,2,3,3,4,4,5,5,6,6-undecafluorocyclohexyl)ethanol:

A non-limiting example of such a system is illustrated in FIG. 14B. In this figure, fluidic network 710 includes a channel containing liquid carrier 705, and first fluid 701 and second fluid 702. Liquid carrier 705 is introduced into fluidic network 710 through inlet 725, while first fluid 701 is introduced through inlet 721, and second fluid 702 is introduced through inlet 722. Channel 716 within fluidic network 710 contains liquid carrier 715 introduced from inlet 725. Initially, first fluid 701 is introduced into liquid carrier 705, forming fluidic droplets therein. Next, second fluid 702 is introduced into liquid 705, forming fluidic droplets therein that are interspersed with the fluidic droplets containing first fluid 701. Thus, upon reaching channel 717, liquid carrier 705 contains a first set of fluidic droplets containing first fluid 701, interspersed with a second set of fluidic droplets containing second fluid 702. In the embodiment illustrated, channel 706 optionally comprises a series of bends, which may allow mixing to occur within each of the fluidic droplets, as further discussed below. However, it should be noted that in this embodiment, since first fluid 701 and second fluid 702 are essentially immiscible, significant fusion and/or mixing of the droplets containing first fluid 701 with the droplets containing second fluid 702 is not generally expected.

Other examples of the production of droplets of fluid surrounded by a liquid are described in International Patent Application Serial No. PCT/US2004/010903, filed Apr. 9, 2004 by Link, et al. and International Patent Application Serial No. PCT/US03/20542, filed Jun. 30, 2003 by Stone, et al., published as WO 2004/002627 on Jan. 8, 2004, each incorporated herein by reference.

In some embodiments, the fluidic droplets may each be substantially the same shape and/or size. The shape and/or size can be determined, for example, by measuring the average diameter or other characteristic dimension of the droplets. The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasi-electric light scattering; polarimetry; refractometry; or turbidity measurements.

The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

In certain instances, the invention provides for the production of droplets consisting essentially of a substantially uniform number of entities of a species therein (i.e., molecules, compounds, cells, particles, etc.). For example, about 90%, about 93%, about 95%, about 97%, about 98%, or about 99%, or more of a plurality or series of droplets may each contain the same number of entities of a particular species. For instance, a substantial number of fluidic droplets produced, e.g., as described above, may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may each independently contain a range of entities, for example, less than 20 entities, less than 15 entities, less than 10 entities, less than 7 entities, less than 5 entities, or less than 3 entities in some cases. In one set of embodiments, in a liquid containing droplets of fluid, some of which contain a species of interest and some of which do not contain the species of interest, the droplets of fluid may be screened or sorted for those droplets of fluid containing the species as further described below (e.g., using fluorescence or other techniques such as those described above), and in some cases, the droplets may be screened or sorted for those droplets of fluid containing a particular number or range of entities of the species of interest, e.g., as previously described. Thus, in some cases, a plurality or series of fluidic droplets, some of which contain the species and some of which do not, may be enriched (or depleted) in the ratio of droplets that do contain the species, for example, by a factor of at least about 2, at least about 3, at least about 5, at least about 10, at least about 15, at least about 20, at least about 50, at least about 100, at least about 125, at least about 150, at least about 200, at least about 250, at least about 500, at least about 750, at least about 1000, at least about 2000, or at least about 5000 or more in some cases. In other cases, the enrichment (or depletion) may be in a ratio of at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, or more. For example, a fluidic droplet containing a particular species may be selected from a library of fluidic droplets containing various species, where the library may have about $10^5$, about $10^6$, about $10^7$, about $10^8$, about $10^9$, about $10^{10}$, about $10^{11}$, about $10^{12}$, about $10^{13}$, about $10^{14}$, about $10^{15}$, or more items, for example, a DNA library, an RNA library, a protein library, a combinatorial chemistry library, etc. In certain embodiments, the droplets carrying the species may then be fused, reacted, or otherwise used or processed, etc., as further described below, for example, to initiate or determine a reaction.

The use of microfluidic handling to create microcapsules according to the invention has a number of advantages:
a) They allow the formation of highly monodisperse microcapsules (<1.5% polydispersity), each of which functions as an almost identical, very small microreactor,
b) The microcapsules can have volumes ranging from about 1 femtoliter to about 1 nanoliter.
c) Compartmentalisation in microcapsules prevents diffusion and dispersion due to parabolic flow.
d) By using a perfluorocarbon carrier fluid it is possible to prevent exchange of molecules between microcapsules.
e) Compounds in microcapsules cannot react or interact with the fabric of the microchannels as they are separated by a layer of inert perfluorocarbon carrier fluid.
f) Microcapsules can be created at up to and including 10,000 $s^{-1}$ and screened using optical methods at the same rate. This is a throughput of ~$10^9$ per day.

Microcapsules can, advantageously, be fused or split. For example, aqueous microdroplets can be merged and split using microfluidics systems (Link et al., 2004; Song et al., 2003). Microcapsule fusion allows the mixing of reagents. Fusion, for example, of a microcapsule containing the target with a microcapsule containing the compound could initiate the reaction between target and compound. Microcapsule splitting allows single microcapsules to be split into two or more smaller microcapsules. For example a single microcapsule containing a compound can be split into multiple microcapsules which can then each be fused with a different microcapsule containing a different target. A single microcapsule containing a target can also be split into multiple microcapsules which can then each be fused with a different microcapsule containing a different compound, or compounds at different concentrations.

In one aspect, the invention relates to microfluidic systems and methods for splitting a fluidic droplet into two or more droplets. The fluidic droplet may be surrounded by a liquid, e.g., as previously described, and the fluid and the liquid are essentially immiscible in some cases. The two or more droplets created by splitting the original fluidic droplet may each be substantially the same shape and/or size, or the two or more droplets may have different shapes and/or sizes, depending on the conditions used to split the original fluidic droplet. In many cases, the conditions used to split the original fluidic droplet can be controlled in some fashion, for example, manually or automatically (e.g., with a processor, as discussed below). In some cases, each droplet in a plurality or series of fluidic droplets may be independently controlled. For example, some droplets may be split into equal parts or unequal parts, while other droplets are not split.

According to one set of embodiments, a fluidic droplet can be split using an applied electric field. The electric field may be an AC field, a DC field, etc. The fluidic droplet, in this embodiment, may have a greater electrical conductivity than the surrounding liquid, and, in some cases, the fluidic droplet may be neutrally charged. In some embodiments, the droplets produced from the original fluidic droplet are of approximately equal shape and/or size. In certain embodiments, in an applied electric field, electric charge may be urged to migrate from the interior of the fluidic droplet to the surface to be distributed thereon, which may thereby cancel the electric field experienced in the interior of the droplet. In some embodiments, the electric charge on the surface of the fluidic droplet may also experience a force due to the applied electric field, which causes charges having opposite polarities to migrate in opposite directions. The charge migration may, in some cases, cause the drop to be pulled apart into two separate fluidic droplets. The electric field applied to the fluidic droplets may be created, for example, using the techniques described above, such as with a reaction an electric field generator, etc.

Figure 1B:
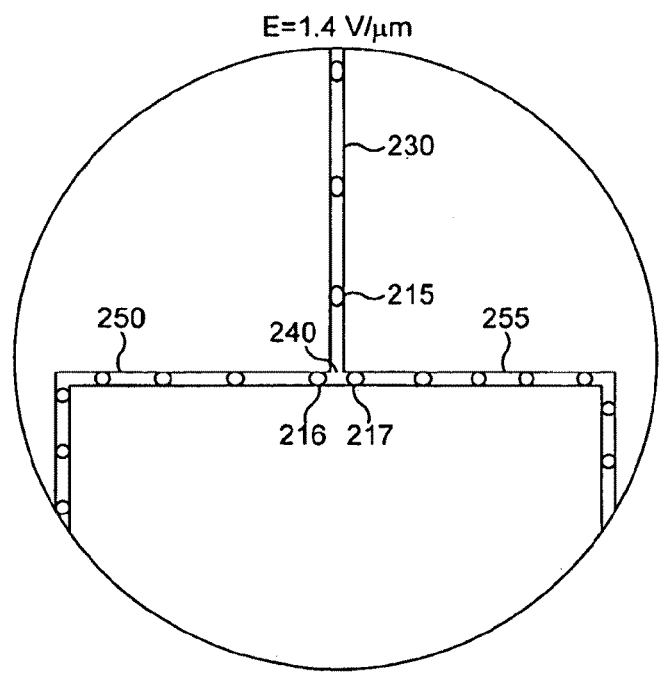

As a non-limiting example, in FIG. 1A, where no electric field is applied, fluidic droplets 215 contained in channel 230 are carried by a surrounding liquid, which flows towards intersection 240, leading to channels 250 and 255. In this example, the surrounding liquid flows through channels 250 and 255 at equal flowrates. Thus, at intersection 240, fluidic droplets 215 do not have a preferred orientation or direction, and move into exit channels 250 and 255 with equal probability due to the surrounding liquid flow. In contrast, in FIG. 1B, while the surrounding liquid flows in the same fashion as FIG. 1A, under the influence of an applied electric field of 1.4 V/micrometers, fluidic droplets 215 are split into two droplets at intersection 240, forming new droplets 216 and 217. Droplet 216 moves to the left in channel 250, while droplet 217 moves to the right in channel 255.

Figure 5:
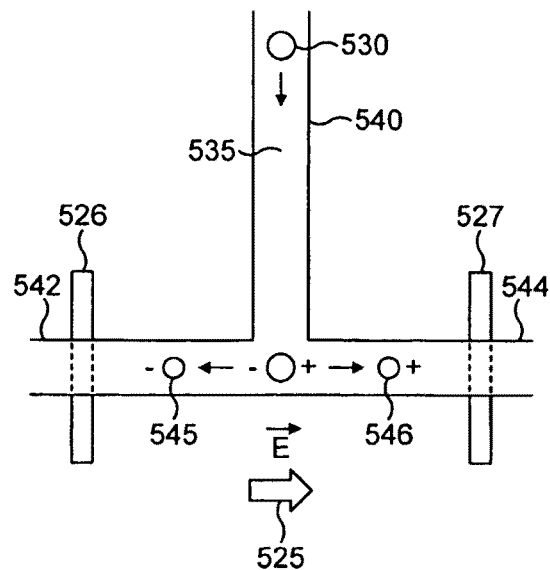
FIG. 5 is a schematic diagram of droplet splitting, in accordance with one embodiment of the invention.

A schematic of this process can be seen in FIG. 5, where a neutral fluidic droplet 530, surrounded by a liquid 535 in channel 540, is subjected to applied electric field 525, created by electrodes 526 and 527. Electrode 526 is positioned near channel 542, while electrode 527 is positioned near channel 544. Under the influence of electric field 525, charge separation is induced within fluidic droplet 530, i.e., such that a positive charge is induced at one end of the droplet, while a negative charge is induced at the other end of the droplet. The droplet may then split into a negatively charged droplet 545 and a positively charged droplet 546, which then may travel in channels 542 and 544, respectively. In some cases, one or both of the electric charges on the resulting charged droplets may also be neutralized, as previously described.

Other examples of splitting a fluidic droplet into two droplets are described in International Patent Application Serial No. PCT/US2004/010903, filed Apr. 9, 2004 by Link, et al.; U.S. Provisional Patent Application Ser. No. 60/498, 091, filed Aug. 27, 2003, by Link, et. al.; and International Patent Application Serial No. PCT/US03/20542, filed Jun. 30, 2003 by Stone, et al., published as WO 2004/002627 on Jan. 8, 2004, each incorporated herein by reference.

The invention, in yet another aspect, relates to systems and methods for fusing or coalescing two or more fluidic droplets into one droplet. For example, in one set of embodiments, systems and methods are provided that are able to cause two or more droplets (e.g., arising from discontinuous streams of fluid) to fuse or coalesce into one droplet in cases where the two or more droplets ordinarily are unable to fuse or coalesce, for example, due to composition, surface tension, droplet size, the presence or absence of surfactants, etc. In certain microfluidic systems, the surface tension of the droplets, relative to the size of the droplets, may also prevent fusion or coalescence of the droplets from occurring in some cases.

Figure 13A:
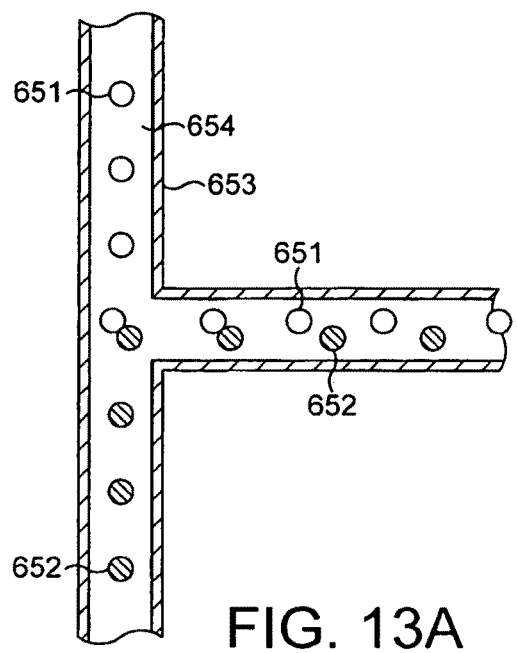
FIGS. 13a-d illustrate the use of oppositely charged droplets in the invention.
Figure 13B:
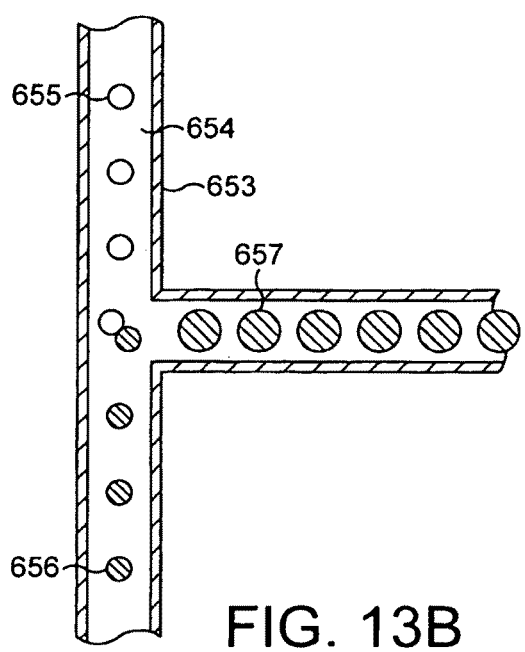

In one embodiment, two fluidic droplets may be given opposite electric charges (i.e., positive and negative charges, not necessarily of the same magnitude), which may increase the electrical interaction of the two droplets such that fusion or coalescence of the droplets can occur due to their opposite electric charges, e.g., using the techniques described herein. For instance, an electric field may be applied to the droplets, the droplets may be passed through a capacitor, a chemical reaction may cause the droplets to become charged, etc. As an example, as is shown schematically in FIG. 13A, uncharged droplets 651 and 652, carried by a liquid 654 contained within a microfluidic channel 653, are brought into contact with each other, but the droplets are not able to fuse or coalesce, for instance, due to their size and/or surface tension. The droplets, in some cases, may not be able to fuse even if a surfactant is applied to lower the surface tension of the droplets. However, if the fluidic droplets are electrically charged with opposite charges (which can be, but are not necessarily of, the same magnitude), the droplets may be able to fuse or coalesce. For instance, in FIG. 13B, positively charged droplets 655 and negatively charged droplets 656 are directed generally towards each other such that the electrical interaction of the oppositely charged droplets causes the droplets to fuse into fused droplets 657.

Figure 13C:
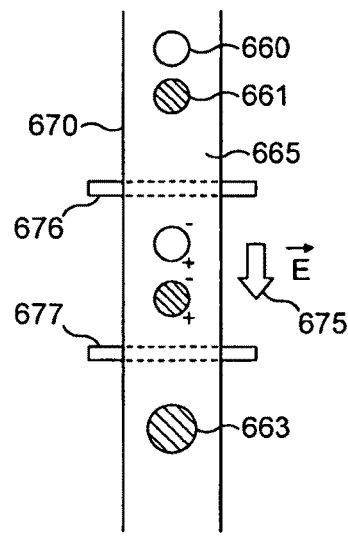
Figure 13D:
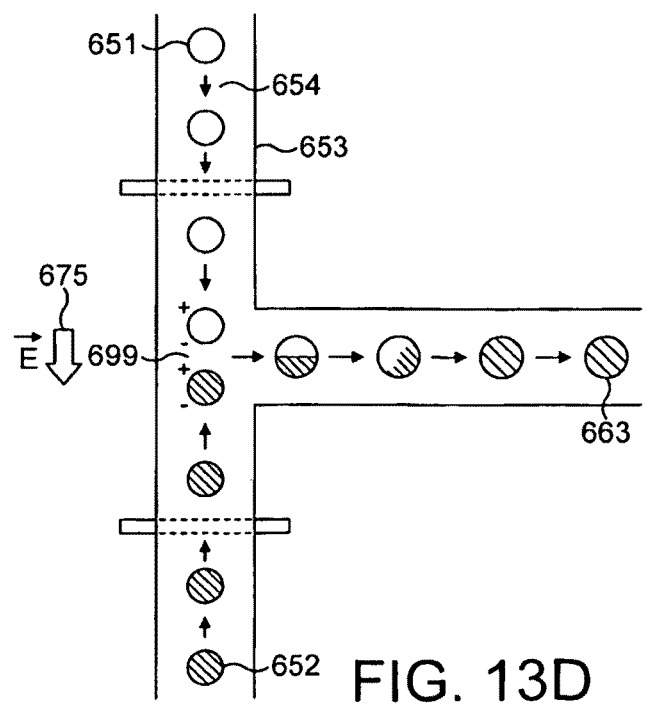

In another embodiment, the fluidic droplets may not necessarily be given opposite electric charges (and, in some cases, may not be given any electric charge), and are fused through the use of dipoles induced in the fluidic droplets that causes the fluidic droplets to coalesce. In the example illustrated in FIG. 13C, droplets 660 and 661 (which may each independently be electrically charged or neutral), surrounded by liquid 665 in channel 670, move through the channel such that they are the affected by an applied electric field 675. Electric field 675 may be an AC field, a DC field, etc., and may be created, for instance, using electrodes 676 and 677, as shown here. The induced dipoles in each of the fluidic droplets, as shown in FIG. 13C, may cause the fluidic droplets to become electrically attracted towards each other due to their local opposite charges, thus causing droplets 660 and 661 to fuse to produce droplet 663. In FIG. 13D, droplets 651 and 652 flow together to fuse to form droplet 653, which flows in a third channel.

Figure 12A:
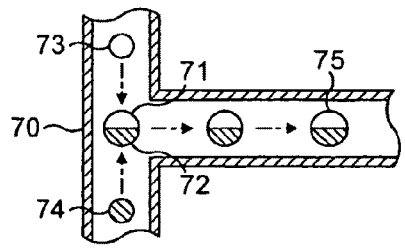
FIGS. 12a-j illustrate flow patterns for droplets in microfluidic systems in accordance with the invention.
Figure 12B:
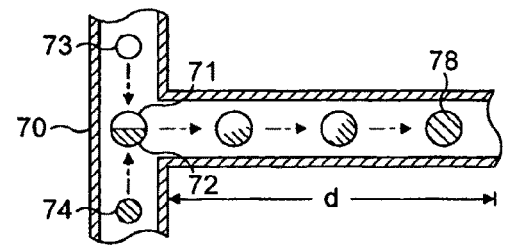
Figure 12C:
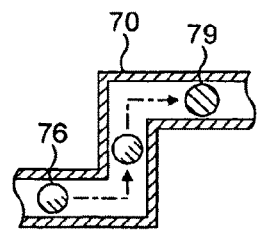
Figure 12D:
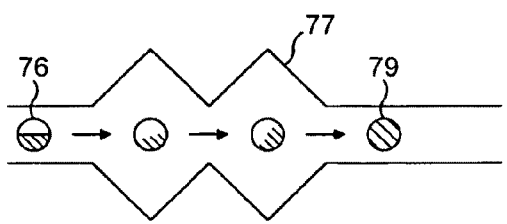
Figure 12E:
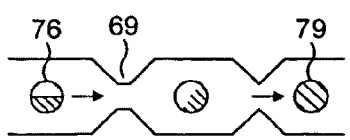
Figure 12F:
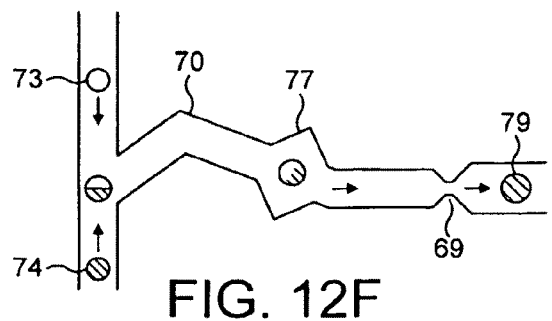
Figure 12G:
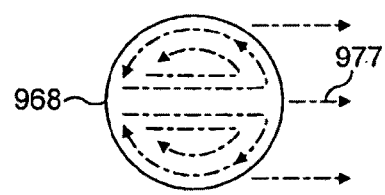
Figure 12H:
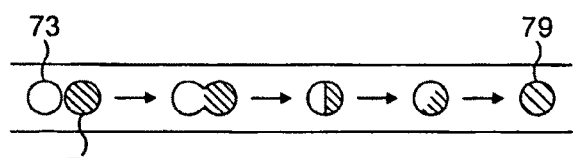
Figure 12I:
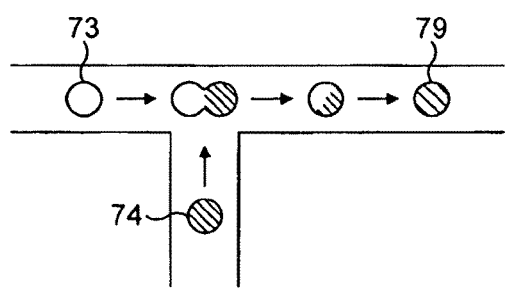
Figure 12J:
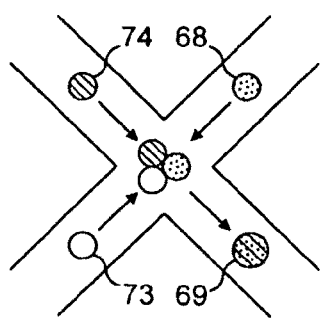

It should be noted that, in various embodiments, the two or more droplets allowed to coalesce are not necessarily required to meet "head-on." Any angle of contact, so long as at least some fusion of the droplets initially occurs, is sufficient. As an example, in FIG. 12H, droplets 73 and 74 each are traveling in substantially the same direction (e.g., at different velocities), and are able to meet and fuse. As another example, in FIG. 12I, droplets 73 and 74 meet at an angle and fuse. In FIG. 12J, three fluidic droplets 73, 74 and 68 meet and fuse to produce droplet 79.

Other examples of fusing or coalescing fluidic droplets are described in International Patent Application Serial No. PCT/US2004/010903, filed Apr. 9, 2004 by Link, et al., incorporated herein by reference.

Fluidic handling of microcapsules therefore results in further advantages:
a) Microcapsules can be split into two or more smaller microdroplets allowing the reagents contained therein to be reacted with a series of different molecules in parallel or assayed in multiplicate.
b) Microcapsules can be fused. This allows molecules to be: (a) diluted, (b) mixed with other molecules, and (c) reactions initiated, terminated or modulated at precisely defined times.
c) Reagents can be mixed very rapidly (in <2 ms) in microcapsules using chaotic advection, allowing fast kinetic measurements and very high throughput.
d) Reagents can be mixed in a combinatorial manner. For example, allowing the effect of all possible pairwise combinations of compounds in a compound library on a target to be tested Creating and manipulated microcapsules in microfluidic systems means that:
a) Stable streams of microcapsules can be formed in microchannels and identified by their relative positions.
b) If the reactions are accompanied by an optical signal (e.g. a change in fluorescence) a spatially-resolved optical image of the microfluidic network allows time resolved measurements of the reactions in each microcapsules.
c) Microcapsules can be separated using a microfluidic flow sorter to allow recovery and further analysis or manipulation of the molecules they contain.

Screening/Sorting of Microcapsules

In still another aspect, the invention provides systems and methods for screening or sorting fluidic droplets in a liquid, and in some cases, at relatively high rates. For example, a characteristic of a droplet may be sensed and/or determined in some fashion (e.g., as further described below), then the droplet may be directed towards a particular region of the device, for example, for sorting or screening purposes.

In some embodiments, a characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In some cases, high sorting speeds may be achievable using certain systems and methods of the invention. For instance, at least about 10 droplets per second may be determined and/or sorted in some cases, and in other cases, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second, at least about 1,500,000 droplets per second, at least about 2,000,000 or more droplets per second, or at least about 3,000,000 or more droplets per second may be determined and/or sorted in such a fashion.

Figure 2A:
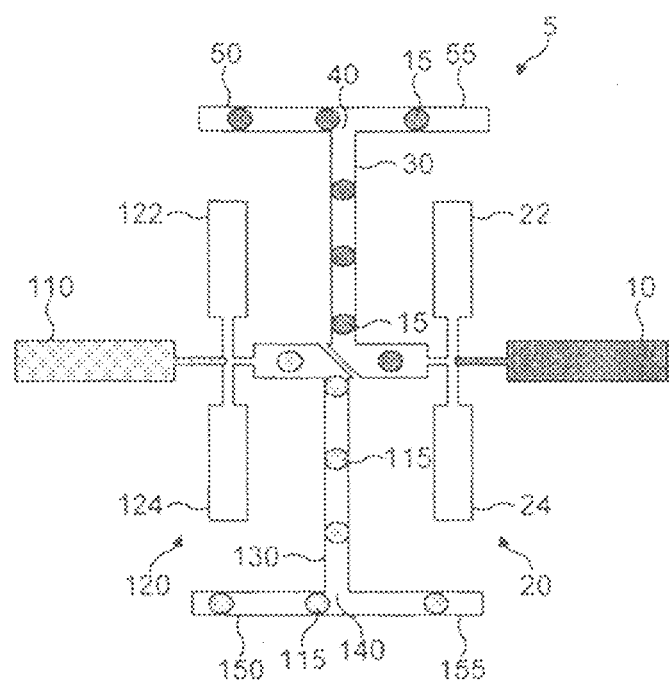
FIGS. 2A and 2B illustrate an apparatus in accordance with an embodiment of the invention, before the application of an electric field thereto.

In one set of embodiments, a fluidic droplet may be directed by creating an electric charge (e.g., as previously described) on the droplet, and steering the droplet using an applied electric field, which may be an AC field, a DC field, etc. As an example, in reference to FIGS. 2-4, an electric field may be selectively applied and removed (or a different electric field may be applied, e.g., a reversed electric field as shown in FIG. 4A) as needed to direct the fluidic droplet to a particular region. The electric field may be selectively applied and removed as needed, in some embodiments, without substantially altering the flow of the liquid containing the fluidic droplet. For example, a liquid may flow on a substantially steady-state basis (i.e., the average flowrate of the liquid containing the fluidic droplet deviates by less than 20% or less than 15% of the steady-state flow or the expected value of the flow of liquid with respect to time, and in some cases, the average flowrate may deviate less than 10% or less than 5%) or other predetermined basis through a fluidic system of the invention (e.g., through a channel or a microchannel), and fluidic droplets contained within the liquid may be directed to various regions, e.g., using an electric field, without substantially altering the flow of the liquid through the fluidic system. As a particular example, in FIGS. 2A, 3A and 4A, a liquid containing fluidic droplets 15 flows from fluid source 10, through channel 30 to intersection 40, and exits through channels 50 and 55. In FIG. 2A, fluidic droplets 15 are directed through both channels 50 and 55, while in FIG. 3A, fluidic droplets 15 are directed to only channel 55 and, in FIG. 4A, fluidic droplets 15 are directed to only channel 50.

In another set of embodiments, a fluidic droplet may be sorted or steered by inducing a dipole in the fluidic droplet (which may be initially charged or uncharged), and sorting or steering the droplet using an applied electric field. The electric field may be an AC field, a DC field, etc. For example, with reference to FIG. 9A, a channel 540, containing fluidic droplet 530 and liquid 535, divides into channel 542 and 544. Fluidic droplet 530 may have an electric charge, or it may be uncharged. Electrode 526 is positioned near channel 542, while electrode 527 is positioned near channel 544. Electrode 528 is positioned near the junction of channels 540, 542, and 544. In FIGS. 9C and 9D, a dipole is induced in the fluidic droplet using electrodes 526, 527, and/or 528. In FIG. 9C, a dipole is induced in droplet 530 by applying an electric field 525 to the droplet using electrodes 527 and 528. Due to the strength of the electric field, the droplet is strongly attracted to the right, into channel 544. Similarly, in FIG. 9D, a dipole is induced in droplet 530 by applying an electric field 525 to the droplet using electrodes 526 and 528, causing the droplet to be attracted into channel 542. Thus, by applying the proper electric field, droplet 530 can be directed to either channel 542 or 544 as desired.

Figure 10A:
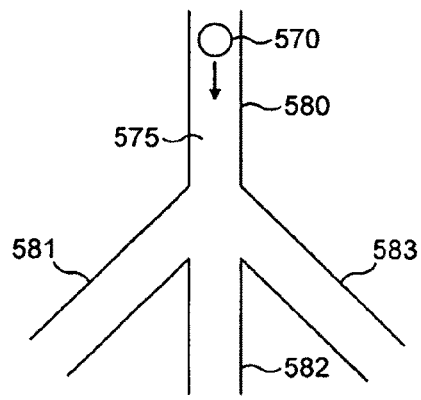
FIGS. 10a-d illustrate the sorting of microcapsules by altering the flow of carrier fluid in a microfluidic system.
Figure 10B:
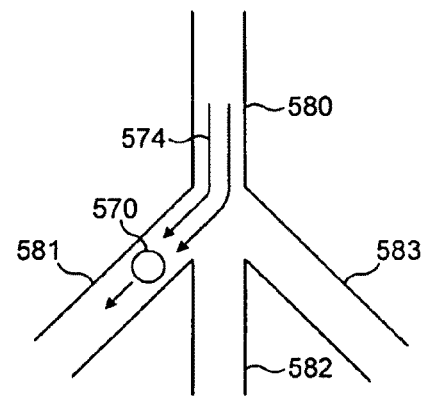
Figure 10C:
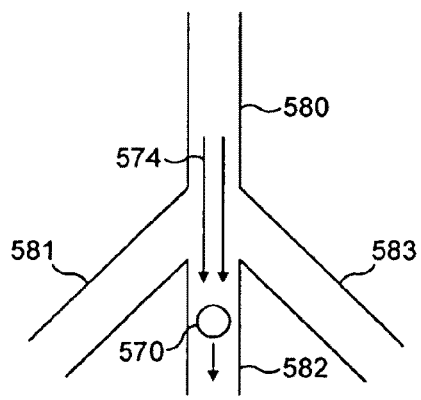
Figure 10D:
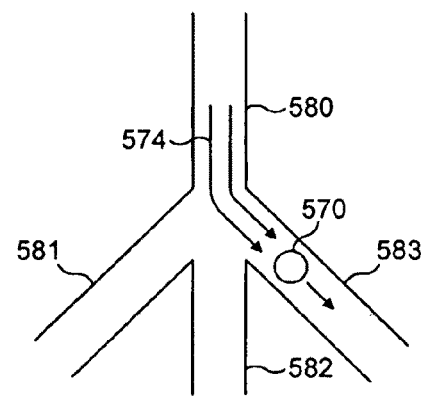

In other embodiments, however, the fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. As a non-limiting example, with reference to FIG. 10A, fluidic droplet 570 is surrounded by a liquid 575 in channel 580. Channel 580 divides into three channels 581, 582, and 583. The flow of liquid 575 can be directed into any of channels 581, 582, and 583 as desired, for example, using flow-controlling devices known to those of ordinary skill in the art, for example, valves, pumps, pistons, etc. Thus, in FIG. 10B, fluidic droplet 570 is directed into channel 581 by directing liquid 575 to flow into channel 581 (indicated by arrows 574); in FIG. 10C, fluidic droplet 570 is directed into channel 582 by directing liquid 575 to flow into channel 582 (indicated by arrows 574); and in FIG. 10D, fluidic droplet 570 is directed into channel 583 by directing liquid 575 to flow into channel 583 (indicated by arrows 574).

However, it is preferred that control of the flow of liquids in microfluidic systems is not used to direct the flow of fluidic droplets therein, but that an alternative method is used. Advantageously, therefore, the microcapsules are not sorted by altering the direction of the flow of a carrier fluid in a microfluidic system.

In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. The liquid reservoirs may be positioned such that, when activated, the movement of liquid caused by the activated reservoirs causes the liquid to flow in a preferred direction, carrying the fluidic droplet in that preferred direction. For instance, the expansion of a liquid reservoir may cause a flow of liquid towards the reservoir, while the contraction of a liquid reservoir may cause a flow of liquid away from the reservoir. In some cases, the expansion and/or contraction of the liquid reservoir may be combined with other flow-controlling devices and methods, e.g., as described herein. Non-limiting examples of devices able to cause the expansion and/or contraction of a liquid reservoir include pistons and piezoelectric components. In some cases, piezoelectric components may be particularly useful due to their relatively rapid response times, e.g., in response to an electrical signal.

Figure 11A:
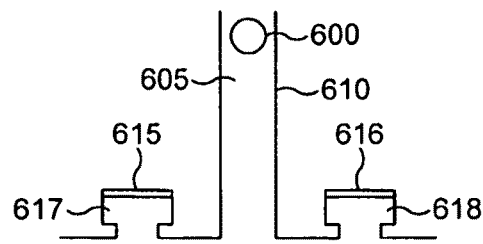
FIGS. 11a-c illustrate the use of pressure changes in the microfluidic system to control the direction of flow of droplets.
Figure 11B:
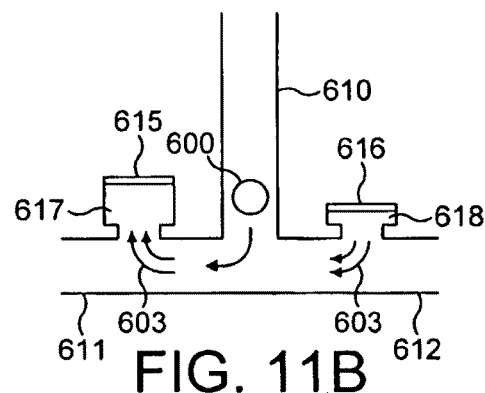
Figure 11C:
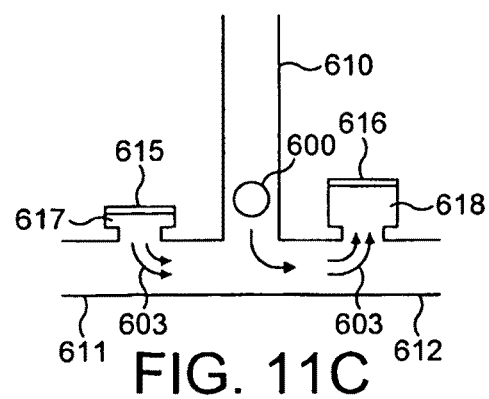

As a non-limiting example, in FIG. 11A, fluidic droplet 600 is surrounded by a liquid 605 in channel 610. Channel 610 divides into channels 611, 612. Positioned in fluidic communication with channels 611 and 612 are liquid reservoirs 617 and 618, which may be expanded and/or contracted, for instance, by piezoelectric components 615 and 616, by a piston (not shown), etc. In FIG. 11B, liquid reservoir 617 has been expanded, while liquid reservoir 618 has been contracted. The effect of the expansion/contractions of the reservoirs is to cause a net flow of liquid towards channel 611, as indicated by arrows 603. Thus, fluidic droplet 600, upon reaching the junction between the channels, is directed to channel 611 by the movement of liquid 605. The reverse situation is shown in FIG. 11C, where liquid reservoir 617 has contracted while liquid reservoir 618 has been expanded. A net flow of liquid occurs towards channel 612 (indicated by arrows 603), causing fluidic droplet 600 to move into channel 612. It should be noted, however, that reservoirs 617 and 618 do not both need to be activated to direct fluidic droplet 600 into channels 611 or 612. For example, in one embodiment, fluidic droplet 600 may be directed to channel 611 by the expansion of liquid reservoir 617 (without any alteration of reservoir 618), while in another embodiment, fluidic droplet 600 may be directed to channel 611 by the contraction of liquid reservoir 618 (without any alteration of reservoir 617). In some cases, more than two liquid reservoirs may be used.

Figure 6A:
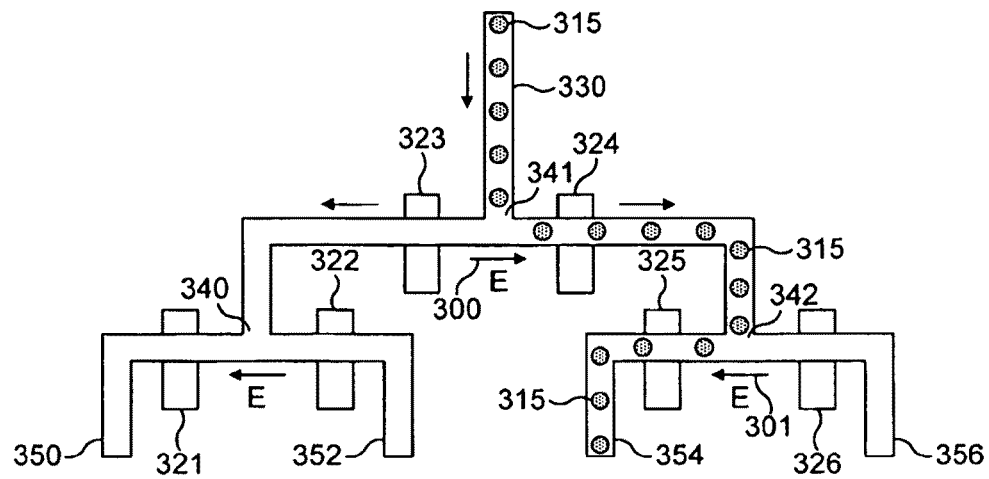
FIGS. 6A and 6B are schematic diagrams of additional embodiments of the invention.
Figure 6B:
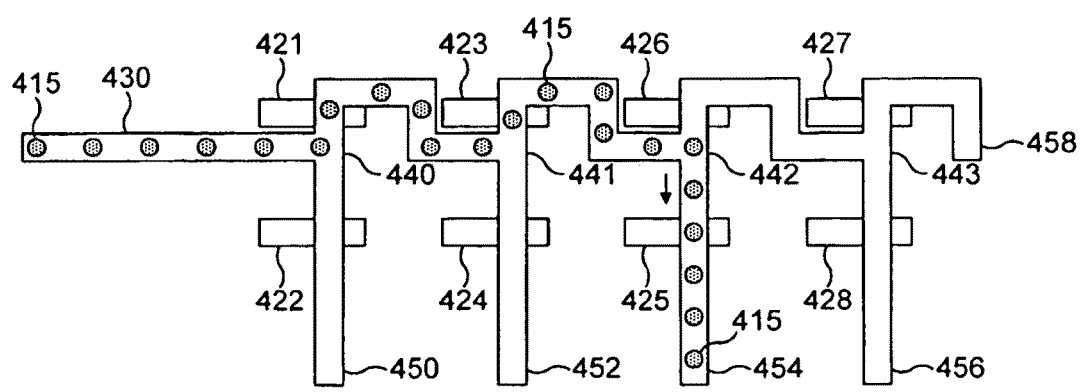

In some embodiments, the fluidic droplets may be sorted into more than two channels. Non-limiting examples of embodiments of the invention having multiple regions within a fluidic system for the delivery of droplets are shown in FIGS. 6A and 6B. Other arrangements are shown in FIGS. 10A-10D. In FIG. 6A, charged droplets 315 in channel 330 may be directed as desired to any one of exit channels 350, 352, 354, or 356, by applying electric fields to control the movement of the droplets at intersections 340, 341, and 342, using electrodes 321/322, 323/324, and 325/326, respectively. In FIG. 6A, droplets 315 are directed to channel 354 using applied electric fields 300 and 301, using principles similar to those discussed above. Similarly, in FIG. 6B, charged droplets 415 in channel 430 can be directed to any one of exit channels 450, 452, 454, 456, or 458, by applying electric fields to control the movement of the droplets at intersections 440, 441, 442, and 443, using electrodes 421/422, 423/424, 425/426, and 427/428, respectively. In this figure, droplets 415 are directed to channel 454; of course, the charged droplets may be directed to any other exit channel as desired.

Figure 2B:
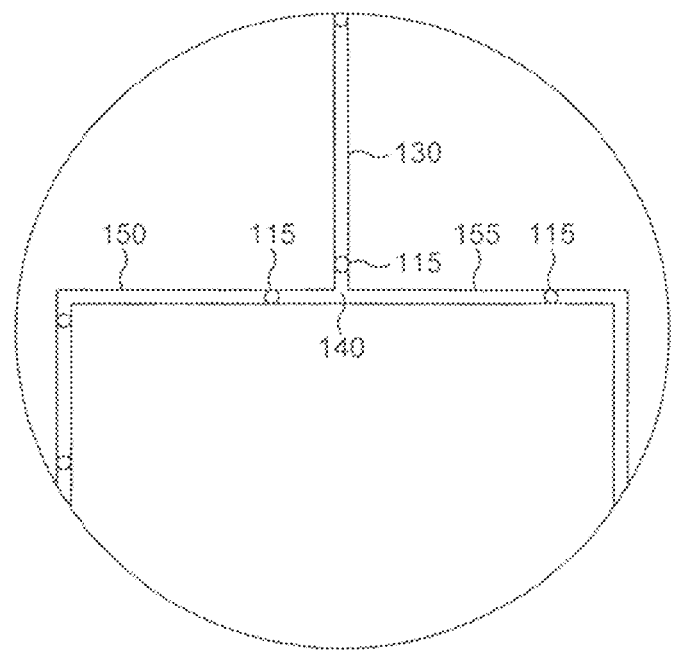

In another example, in apparatus 5, as schematically illustrated in FIG. 2A, fluidic droplets 15 created by fluid source 10 are positively charged due to an applied electric field created using electric field generator 20, which comprises two electrodes 22, 24. Fluidic droplets 15 are directed through channel 30 by a liquid containing the droplets, and are directed towards intersection 40. At intersection 40, the fluidic droplets do not have a preferred orientation or direction, and move into exit channels 50 and 55 with equal probability (in this embodiment, liquid drains through both exit channels 50 and 55 at substantially equal rates). Similarly, fluidic droplets 115 created by fluid source 110 are negatively charged due to an applied electric field created using electric field generator 120, which comprises electrodes 122 and 124. After traveling through channel 130 towards intersection 140, the fluidic droplets do not have a preferred orientation or direction, and move into exit channels 150 and 155 with equal probability, as the liquid exits through exit channels 150 and 155 at substantially equal rates. A representative photomicrograph of intersection 140 is shown in FIG. 2B.

Figure 3A:
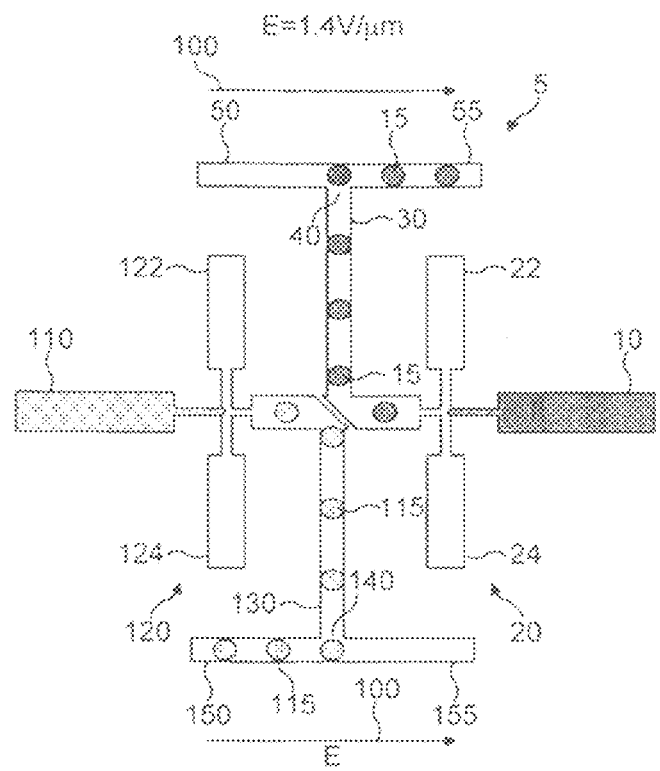
FIGS. 3A and 3B illustrate the apparatus of FIGS. 2A and 2B after the application of an electric field thereto.
Figure 3B:
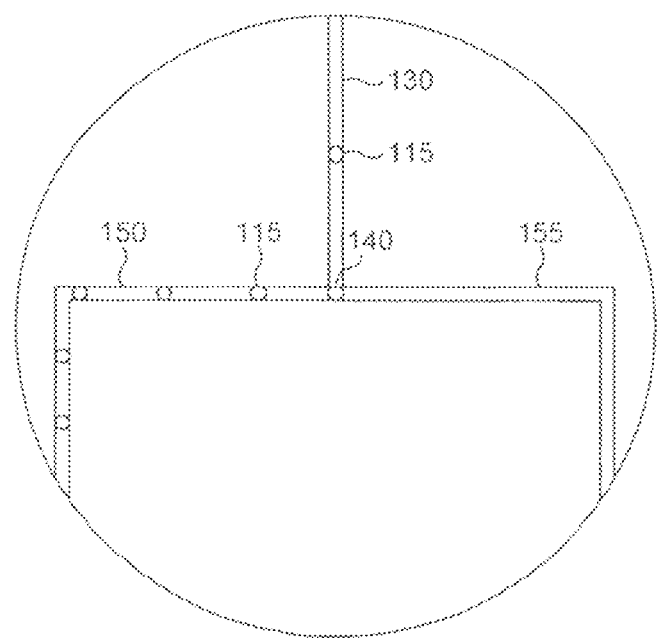
Figure 4A:
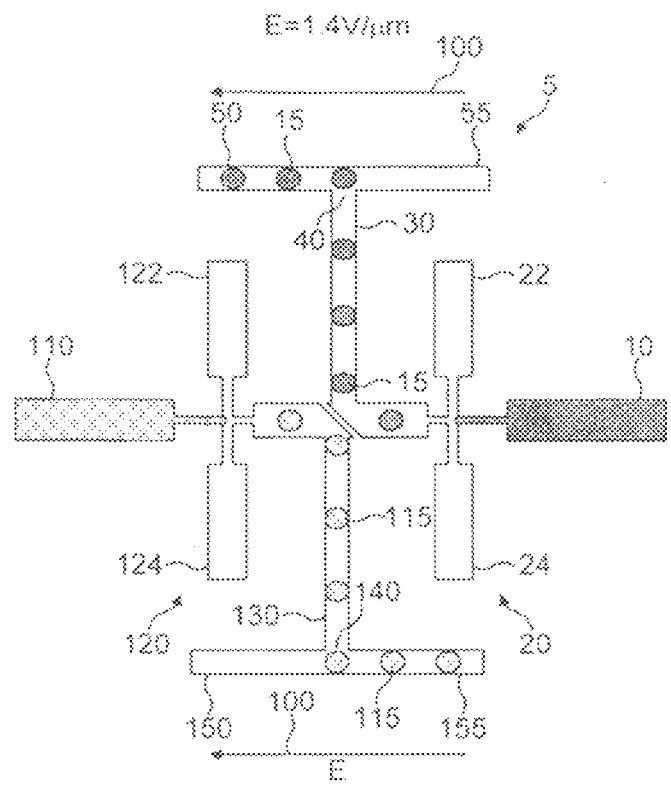
FIGS. 4A and 4B illustrate the apparatus of FIGS. 2A and 2B after the application of a reversed electric field thereto.

In the schematic diagram of FIG. 3A, an electric field 100 of 1.4 V/micrometer has been applied to apparatus 5 of FIG. 2A, in a direction towards the right of apparatus 5. Positively-charged fluidic droplets 15 in channel 30, upon reaching intersection 40, are directed to the right in channel 55 due to the applied electric field 100, while the liquid containing the droplets continues to exit through exit channels 50 and 55 at substantially equal rates. Similarly, negatively-charged fluidic droplets 115 in channel 130, upon reaching intersection 140, are directed to the left in channel 150 due to the applied electric field 100, while the liquid fluid continues to exit the device through exit channels 150 and 155 at substantially equal rates. Thus, electric field 100 can be used to direct fluidic droplets into particular channels as desired. A representative photomicrograph of intersection 140 is shown in FIG. 3B.

Figure 4B:
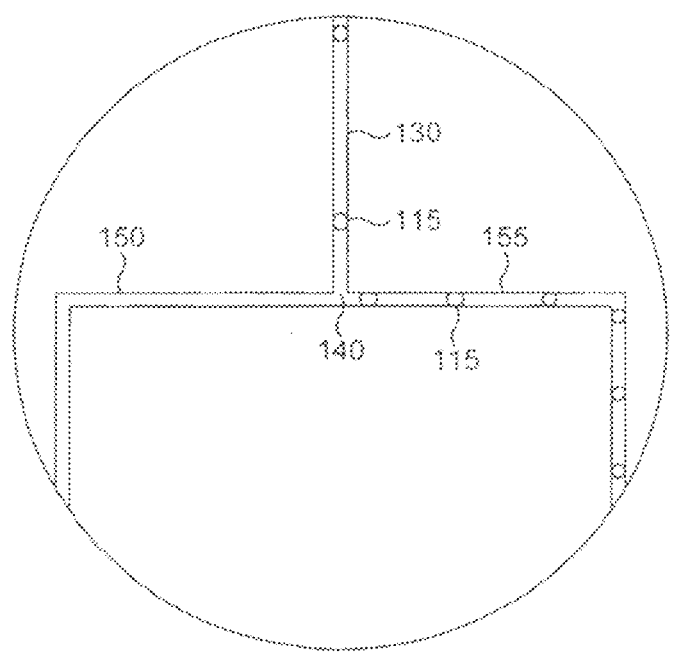

FIG. 4A is a schematic diagram of apparatus 5 of FIG. 2A, also with an applied electric field 100 of 1.4 V/micrometer, but in the opposite direction (i.e., −1.4 V/micrometer). In this figure, positively-charged fluidic droplets 15 in channel 30, upon reaching intersection 40, are directed to the left into channel 50 due to the applied electric field 100, while negatively-charged fluidic droplets 115 in channel 130, upon reaching intersection 140, are directed to the right into channel 155 due to applied electric field 100. The liquid containing the droplets exits through exit channels 50 and 55, and 150 and 155, at substantially equal rates. A representative photomicrograph of intersection 140 is shown in FIG. 4B.

In some embodiments of the invention, a fluidic droplet may be sorted and/or split into two or more separate droplets, for example, depending on the particular application. Any of the above-described techniques may be used to spilt and/or sort droplets. As a non-limiting example, by applying (or removing) a first electric field to a device (or a portion thereof), a fluidic droplet may be directed to a first region or channel; by applying (or removing) a second electric field to the device (or a portion thereof), the droplet may be directed to a second region or channel; by applying a third electric field to the device (or a portion thereof), the droplet may be directed to a third region or channel; etc., where the electric fields may differ in some way, for example, in intensity, direction, frequency, duration, etc. In a series of droplets, each droplet may be independently sorted and/or split; for example, some droplets may be directed to one location or another, while other droplets may be split into multiple droplets directed to two or more locations.

Figure 8A:
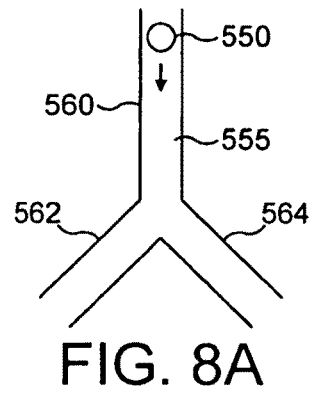
FIGS. 8a-f illustrate the splitting of droplets in accordance with the invention.
Figure 8B:
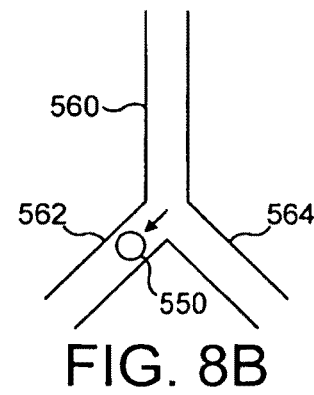
Figure 8C:
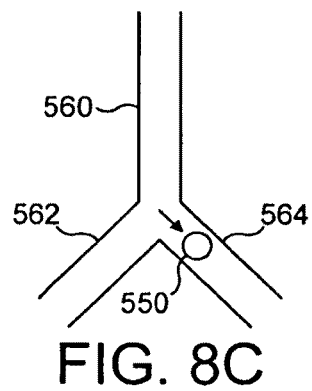
Figure 8D:
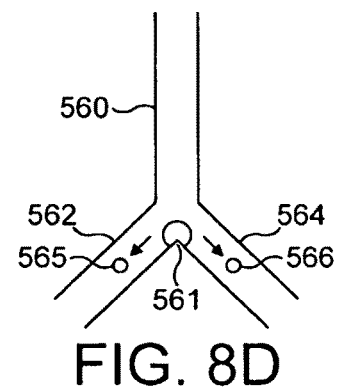
Figure 8E:
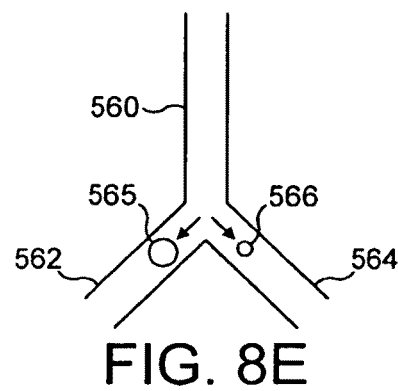
Figure 8F:
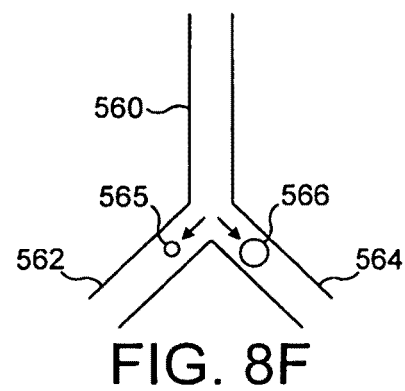

As one particular example, in FIG. 8A, fluidic droplet 550, surrounding liquid 555 in channel 560 may be directed to channel 556, channel 557, or be split in some fashion between channels 562 and 564. In FIG. 8B, by directing surrounding liquid 555 towards channel 562, fluidic droplet 550 may be directed towards the left into channel 562; in FIG. 8C, by directing surrounding liquid 555 towards channel 564, fluidic droplet 550 may be directed towards the right into channel 564, In FIG. 8D, an electric field may be applied, in combination with control of the flow of liquid 555 surrounding fluidic droplet 550, that causes the droplet to impact junction 561, which may cause the droplet to split into two separate fluidic droplets 565, 566. Fluidic droplet 565 is directed to channel 562, while fluidic droplet 566 is directed to channel 566. A high degree of control of the applied electric field may be achieved to control droplet formation; thus, for example, after fluidic droplet 565 has been split into droplets 565 and 566, droplets 565 and 566 may be of substantially equal size, or either of droplets 565 and 566 may be larger, e.g., as is shown in FIGS. 8E and 8F, respectively.

Figure 9A:
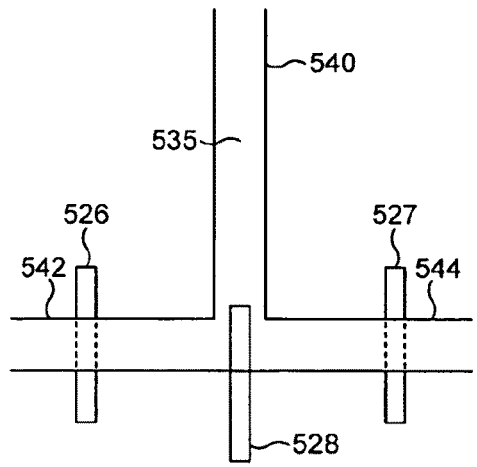
FIGS. 9a-d illustrate the induction of dipoles in droplets in accordance with the invention.
Figure 9B:
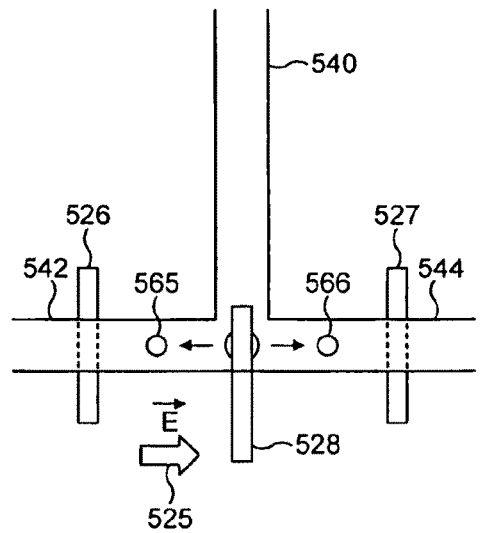
Figure 9C:
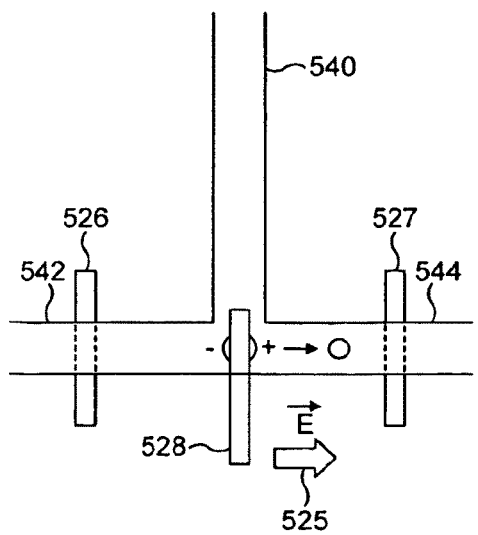
Figure 9D:
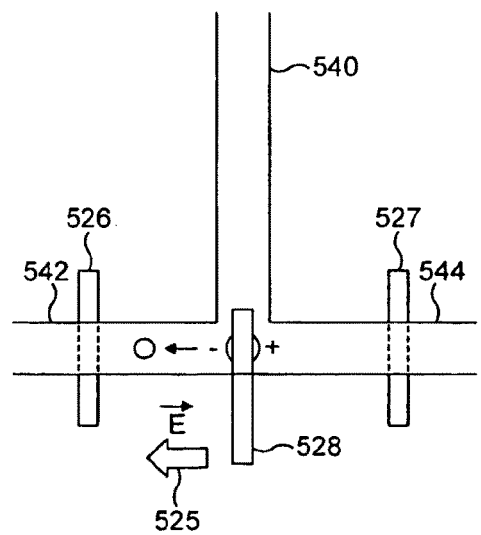

As another example, in FIG. 9A, channel 540, carrying fluidic droplet 530 and liquid 535, divides into channel 542 and 544. Fluidic droplet 530 may be electrically charged, or it may uncharged. Electrode 526 is positioned near channel 542, while electrode 527 is positioned near channel 544. Electrode 528 is positioned near the junction of channels 540, 542, and 544. When fluidic droplet 530 reaches the junction, it may be subjected to an electric field, and/or directed to a channel or other region, for example, by directing the surrounding liquid into the channel. As shown in FIG. 9B, fluidic droplet 530 may be split into two separate droplets 565 and 566 by applying an electric field 525 to the droplet using electrodes 526 and 527. In FIG. 9C, a dipole can be induced in droplet 530 by applying an electric field 525 to the droplet using electrodes 527 and 528. Due to the strength of the applied electric field, the droplet may be strongly attracted to the right, into channel 544. Similarly, in FIG. 9D, a dipole may be induced in droplet 530 by applying an electric field 525 to the droplet using electrodes 526 and 528, causing the droplet to be attracted into channel 542. By controlling which electrodes are used to induce an electric field across droplet 530, and/or the strength of the applied electric field, one or more fluidic droplets within channel 540 may be sorted and/or split into two droplets, and each droplet may independently be sorted and/or split.

For example, highly monodisperse microcapsules containing a target enzyme can be fused with highly monodisperse microcapsules each of which contain a different compound from a compound library. The fused microcapsules flow along a microfluidic channel, allowing time for the compounds to bind to the target enzyme. Each microcapsule is then fused with another microdroplet containing, for example, a fluorogenic enzyme substrate. The rate of the enzymatic reaction is determined by measuring the fluorescence of each microdroplet, ideally at multiple points (corresponding to different times).

Microcapsules can be optically tagged by, for example, incorporating fluorochromes. In a preferred configuration, the microcapsules are optically tagged by incorporating quantum dots: quantum dots of 6 colours at 10 concentrations would allow the encoding of $10^6$ microcapsules (Han et al., 2001). Microcapsules flowing in an ordered sequence in a microfluidic channel can be encoded (wholly or partially) by their sequence in the stream of microcapsules (positional encoding).

Microbeads, also known by those skilled in the art as microspheres, latex particles, beads, or minibeads, are available in diameters from 20 nm to 1 mm and can be made from a variety of materials including silica and a variety of polymers, copolymers and terpolymers including polystyrene (PS), polymethylmethacrylate (PMMA), polyvinyltoluene (PVT), styrene/butadiene (S/B) copolymer, and styrene/vinyltoluene (S/VT) copolymer. They are available with a variety of surface chemistries from hydrophobic surfaces (e.g. plain polystyrene), to very hydrophilic surfaces imparted by a wide variety of functional surface groups: aldehyde, aliphatic amine, amide, aromatic amine, carboxylic acid, chloromethyl, epoxy, hydrazide, hydroxyl, sulfonate and tosyl. The functional groups permit a wide range of covalent coupling reactions for stable or reversible attachment of compounds to the microbead surface.

Microbeads can be optically tagged by, for example, incorporating fluorochromes. For example, one hundred different bead sets have been created, each with a unique spectral address due to labelling with precise ratios of red (>650 nm) and orange (585 nm) fluorochromes (Fulton et al., 1997) and sets of up to $10^6$ beads can be encoded by incorporating quantum dots of 10 intensities and 6 colours (Han et al., 2001).

The compounds can be connected to the microbeads either covalently or non-covalently by a variety of means that will be familiar to those skilled in the art (see, for example, (Hermanson, 1996)). Advantageously, the compounds are attached via a cleavable linker. A variety of such linkers are familiar to those skilled in the art (see for example (Gordon and Balasubramanian, 1999)), including for example, linkers which can be cleaved photochemically and reversible covalent bonds which can be controlled by changing the pH (e.g. imines and acylhydrazones), by adjusting the oxido-reductive properties (e.g. disulphides), or using an external catalyst (e.g. cross-metathesis and transamidation).

The method of the present invention permits the identification of compounds which modulate the activity of the target in a desired way in pools (libraries or repertoires) of compounds.

In a highly preferred application, the method of the present invention is useful for screening libraries of compounds. The invention accordingly provides a method according to preceding aspects of the invention, wherein compounds are identified from a library of compounds.

The compounds identified according to the invention are advantageously of pharmacological or industrial interest, including activators or inhibitors of biological systems, such as cellular signal transduction mechanisms suitable for diagnostic and therapeutic applications. In addition the compounds identified according to the invention may be non-biological in nature. In a preferred aspect, therefore, the invention permits the identification of clinically or industrially useful products. In a further aspect of the invention, there is provided a product when isolated by the method of the invention.

The selection of suitable encapsulation conditions is desirable. Depending on the complexity and size of the compound library to be screened, it may be beneficial to set up the encapsulation procedure such that one or less than one secondary compound is formed per microcapsule. This will provide the greatest power of resolution. Where the library is larger and/or more complex, however, this may be impracticable; it may be preferable to form several secondary compounds together and rely on repeated application of the method of the invention to identify the desired compound. A combination of encapsulation procedures may be used to identify the desired compound.

Theoretical studies indicate that the larger the number of compounds created the more likely it is that a compound will be created with the properties desired (see (Perelson and Oster, 1979) for a description of how this applies to repertoires of antibodies). It has also been confirmed practically that larger phage-antibody repertoires do indeed give rise to more antibodies with better binding affinities than smaller repertoires (Griffiths et al., 1994). To ensure that rare variants are generated and thus are capable of being identified, a large library size is desirable. Thus, the use of optimally small microcapsules is beneficial.

The largest repertoires of compounds that can be screened in a single experiment to date, using two dimensional microarrays of 1 nl volume spots, is ~$10^3$ (Hergenrother et al., 2000). Using the present invention, at a microcapsule diameter of 2.6 mm (Tawfik and Griffiths, 1998), by forming a three-dimensional dispersion, a repertoire size of at least $10^{11}$ can be screened using 1 ml aqueous phase in a 20 ml emulsion.

In addition to the compounds, or microbeads coated with compounds, described above, the microcapsules according to the invention will comprise further components required for the screening process to take place. They will comprise the target and a suitable buffer. A suitable buffer will be one in which all of the desired components of the biological system are active and will therefore depend upon the requirements of each specific reaction system. Buffers suitable for biological and/or chemical reactions are known in the art and recipes provided in various laboratory texts, such as (Sambrook and Russell, 2001).

Other components of the system will comprise those necessary for assaying the activity of the target. These may for example comprise substrate(s) and cofactor(s) for a reaction catalysed by the target, and ligand(s) bound by the target. They may also comprise other catalysts (including enzymes), substrates and cofactors for reactions coupled to the activity of the target which allow for the activity of the target to be detected.

(B) Screening Procedures

To screen compounds which bind to or modulate the activity of a target, the target is compartmentalised in microcapsules together with one or more compounds or compound-coated microbeads. Advantageously each microcapsule contains only a single sort of secondary compound, but many copies thereof. Advantageously each microbead is coated with only a single sort of compound, but many copies thereof. Advantageously the compounds are connected to the microbeads via a cleavable linker, allowing them to be released from the microbeads in the compartments. Advantageously, each microcapsule or microbead is optically tagged to allow identification of the compounds contained within the microcapsule of attached to the microbead.

(i) Screening for Binding

Compounds can be screened directly for binding to a target. In this embodiment, if the compound is attached to a microbead and has affinity for the target it will be bound by the target. At the end of the reaction, all of the microcapsules are combined, and all microbeads pooled together in one environment. Microbeads carrying compounds exhibiting the desired binding can be selected by affinity purification using a molecule that specifically binds to, or reacts specifically with, the target.

In an alternative embodiment, the target can be attached to microbeads by a variety of means familiar to those skilled in the art (see for example (Hermanson, 1996)). The compounds to be screened contain a common feature—a tag. The compounds are released from the microbeads and if the compound has affinity for the target, it will bind to it. At the end of the reaction, all of the microcapsules are combined, and all microbeads pooled together in one environment. Microbeads carrying compounds exhibiting the desired binding can be selected by affinity purification using a molecule that specifically binds to, or reacts specifically with, the "tag".

In an alternative embodiment, microbeads may be screened on the basis that the compound, which binds to the target, merely hides the ligand from, for example, further binding partners. In this eventuality, the microbead, rather than being retained during an affinity purification step, may be selectively eluted whilst other microbeads are bound.

Sorting by affinity is dependent on the presence of two members of a binding pair in such conditions that binding may occur. Any binding pair may be used for this purpose. As used herein, the term binding pair refers to any pair of molecules capable of binding to one another. Examples of binding pairs that may be used in the present invention include an antigen and an antibody or fragment thereof capable of binding the antigen, the biotin-avidin/streptavidin pair (Savage et al., 1994), a calcium-dependent binding polypeptide and ligand thereof (e.g. calmodulin and a calmodulin-binding peptide (Montigiani et al., 1996; Stofko et al., 1992), pairs of polypeptides which assemble to form a leucine zipper (Tripet et al., 1996), histidines (typically hexahistidine peptides) and chelated $Cu^{2+}$, $Zn^{2+}$ and $Ni^{2+}$, (e.g. Ni-NTA; (Hochuli et al., 1987)), RNA-binding and DNA-binding proteins (Klug, 1995) including those containing zinc-finger motifs (Klug and Schwabe, 1995) and DNA methyltransferases (Anderson, 1993), and their nucleic acid binding sites.

In an alternative embodiment, compounds can be screened for binding to a target using a change in the optical properties of the microcapsule or the microbead.

The change in optical properties of the microcapsule or the microbead after binding of the compound to the target may be induced in a variety of ways, including:

(1) the compound itself may have distinctive optical properties, for example, it is fluorescent
(2) the optical properties of the compound may be modified on binding to the target, for example, the fluorescence of the compound is quenched or enhanced on binding (Voss, 1993; Masui and Kuramitsu, 1998).
(3) the optical properties of the target may be modified on binding of the compound, for example, the fluorescence of the target is quenched or enhanced on binding (Guixe et al., 1998; Qi and Grabowski, 1998)
(4) the optical properties of both target and compound are modified on binding, for example, there can be a fluorescence resonance energy transfer (FRET) from target to compound (or vice versa) resulting in emission at the "acceptor" emission wavelength when excitation is at the "donor" absorption wavelength (Heim & Tsien, 1996; Mahajan et al., 1998; Miyawaki et al., 1997).

The invention provides a method wherein a compound with the desired activity induces a change in the optical properties of the microcapsule, which enables the microcapsule containing the compound and the microbeads contained therein to be identified, and optionally, sorted.

In an alternative embodiment, the invention provides a method wherein microbeads are analysed following pooling of the microcapsules into one or more common compartments. In this embodiment, a compound having the desired activity modifies the optical properties of the microbead which carried it (and which resides in the same microcapsule) to allow it to be identified, and optionally, sorted.

In this embodiment, it is not necessary for binding of the compound to the target to directly induce a change in optical properties.

In this embodiment, if the compound attached to the microbead has affinity for the target it will be bound by the target. At the end of the reaction, all of the microcapsules are combined, and all microbeads pooled together in one environment. Microbeads carrying compounds exhibiting the desired binding can be identified by adding reagents that specifically bind to, or react specifically with, the target and thereby induce a change in the optical properties of the microbeads allowing their identification. For example, a fluorescently-labelled anti-target antibody can be used, or an anti-target antibody followed by a second fluorescently labelled antibody which binds the first.

In an alternative embodiment, the target can be attached to the microbeads by a variety of means familiar to those skilled in the art (see for example (Hermanson, 1996)). The compounds to be screened contain a common feature—a tag. The compounds are released from the microbeads and if the compound has affinity for the target, it will bind to it. At the end of the reaction, all of the microcapsules are combined, and all microbeads pooled together in one environment. Microbeads carrying compounds exhibiting the desired binding can be identified by adding reagents that specifically bind to, or react specifically with, the "lag" and thereby induce a change in the optical properties of the microbeads allowing their identification. For example, a fluorescently-labelled anti-"tag" antibody can be used, or an anti-"lag" antibody followed by a second fluorescently labelled antibody which binds the first.

In an alternative embodiment, microbeads may be identified on the basis that the gene product, which binds to the ligand, merely hides the ligand from, for example, further binding partners which would otherwise modify the optical properties of the microbeads. In this case microbeads with unmodified optical properties would be selected.

Fluorescence may be enhanced by the use of Tyramide Signal Amplification (TSA™) amplification to make the microbeads fluorescent (Sepp et al., 2002). This involves peroxidase (linked to another compound) binding to the microbeads and catalysing the conversion of fluorescein-tyramine in to a free radical form which then reacts (locally)

with the microbeads. Methods for performing TSA are known in the art, and kits are available commercially from NEN.

TSA may be configured such that it results in a direct increase in the fluorescence of the microbeads, or such that a ligand is attached to the microbeads which is bound by a second fluorescent molecule, or a sequence of molecules, one or more of which is fluorescent.

(ii) Screening for Regulation of Binding

In an alternative embodiment, the invention can be used to screen compounds which act to regulate a biochemical process. If the compound activates a binding activity of a target, a ligand for the target which is activated can be attached to microbeads by a variety of means familiar to those skilled in the art (see for example (Hermanson, 1996)). At the end of the reaction, all of the microcapsules are combined, and all microbeads pooled together in one environment. Microbeads carrying compounds exhibiting the desired binding can be selected by affinity purification using a molecule that specifically binds to, or reacts specifically with, the target.

In an alternative embodiment, microbeads may be screened on the basis that the compound inhibits the binding activity of a target. In this eventuality, the microbead, rather than being retained during an affinity purification step, may be selectively eluted whilst other microbeads are bound.

In an alternative embodiment, compounds can be screened for the ability to modulates a binding activity of a target using a change in the optical properties of the microcapsule or the microbead.

The change in optical properties of the microcapsule or the microbead after binding of the target to its ligand may be induced in a variety of ways, including:

(1) the ligand itself may have distinctive optical properties, for example, it is fluorescent
(2) the optical properties of the ligand may be modified on binding to the target, for example, the fluorescence of the ligand is quenched or enhanced on binding (Voss, 1993; Masui and Kuramitsu, 1998).
(3) the optical properties of the target may be modified on binding of the ligand, for example, the fluorescence of the target is quenched or enhanced on binding (Guixe et al., 1998; Qi and Grabowski, 1998)
(4) the optical properties of both target and ligand are modified on binding, for example, there can be a fluorescence resonance energy transfer (FRET) from target to ligand (or vice versa) resulting in emission at the "acceptor" emission wavelength when excitation is at the "donor" absorption wavelength (Heim & Tsien, 1996; Mahajan et al., 1998; Miyawaki et al., 1997).

The invention provides a method wherein a compound with the desired activity induces a change in the optical properties of the microcapsule, which enables the microcapsule containing the compound and the microbeads contained therein to be identified, and optionally, sorted.

In an alternative embodiment, the invention provides a method wherein microbeads are analysed following pooling of the microcapsules into one or more common compartments. In this embodiment, a compound having the desired activity modifies the optical properties of the microbead which carried it (and which resides in the same microcapsule) to allow it to be identified, and optionally, sorted.

In this embodiment, it is not necessary for binding of the target to the ligand to directly induce a change in optical properties.

In this embodiment, if a ligand attached to the microbead has affinity for the target it will be bound by the target. At the end of the reaction, all of the microcapsules are combined, and all microbeads pooled together in one environment. Microbeads carrying compounds which modulate the binding activity can be identified by adding reagents that specifically bind to, or react specifically with, the target and thereby induce a change in the optical properties of the microbeads allowing their identification. For example, a fluorescently-labelled anti-target antibody can be used, or an anti-target antibody followed by a second fluorescently labelled antibody which binds the first.

In an alternative embodiment, the target can be attached to the microbeads by a variety of means familiar to those skilled in the art (see for example (Hermanson, 1996)). The ligand to be screened contains a feature—a tag. At the end of the reaction, all of the microcapsules are combined, and all microbeads pooled together in one environment. Microbeads carrying compounds which modulate binding can be identified by adding reagents that specifically bind to, or react specifically with, the "tag" and thereby induce a change in the optical properties of the microbeads allowing their identification. For example, a fluorescently-labelled anti-"tag" antibody can be used, or an anti-"tag" antibody followed by a second fluorescently labelled antibody which binds the first.

Fluorescence may be enhanced by the use of Tyramide Signal Amplification (TSA™) amplification to make the microbeads fluorescent (Sepp et al., 2002), as above.

(iii) Screening for Regulation of Catalysis

In an alternative embodiment, the invention provides a method wherein a compound with the desired activity induces a change in the optical properties of the microcapsule, which enables the microcapsule containing the compound and, optionally, the microbeads contained therein to be identified, and optionally, sorted. The optical properties of microcapsules can be modified by either:

(a) the substrate and product of the regulated reaction having different optical properties (many fluorogenic enzyme substrates are available commercially, see for example (Haugland, 1996) including substrates for glycosidases, phosphatases, peptidases and proteases, or
(b) the presence of reagents which specifically bind to, or react with, the product (or substrate) of the regulated reaction in the microcapsule and which thereby induce a change in the optical properties of the microcapsules allowing their identification.

A wide range of assays for screening libraries of compounds for those which modulate the activity of a target are based on detecting changes in optical properties and can be used to screen compounds according to this invention. Such assays are well known to those skilled in the art (see for example Haugland, 1996).

Alternatively, selection may be performed indirectly by coupling a first reaction to subsequent reactions that takes place in the same microcapsule. There are two general ways in which this may be performed. First, the product of the first reaction could be reacted with, or bound by, a molecule which does not react with the substrate(s) of the first reaction. A second, coupled reaction will only proceed in the presence of the product of the first reaction. A regulatory compound can then be identified by the properties of the product or substrate of the second reaction.

Alternatively, the product of the reaction being selected may be the substrate or cofactor for a second enzyme-catalysed reaction. The enzyme to catalyse the second reaction can be incorporated in the reaction mixture prior to microencapsulation. Only when the first reaction proceeds will the coupled enzyme generate an identifiable product.

This concept of coupling can be elaborated to incorporate multiple enzymes, each using as a substrate the product of the previous reaction. This allows for selection of regulators of enzymes that will not react with an immobilised substrate. It can also be designed to give increased sensitivity by signal amplification if a product of one reaction is a catalyst or a cofactor for a second reaction or series of reactions leading to a selectable product (for example, see (Johannsson, 1991; Johannsson and Bates, 1988). Furthermore an enzyme cascade system can be based on the production of an activator for an enzyme or the destruction of an enzyme inhibitor (see (Mize et al., 1989)). Coupling also has the advantage that a common screening system can be used for a whole group of enzymes which generate the same product and allows for the selection of regulation of complicated multi-step chemical transformations and pathways.

In an alternative embodiment, if the target is itself an enzyme, or regulates a biochemical process which is enzymatic, the microbead in each microcapsule may be coated with the substrate for the enzymatic reaction. The regulatory compound will determine the extent to which the substrate is converted into the product. At the end of the reaction the microbead is physically linked to the product of the catalysed reaction. When the microcapsules are combined and the reactants pooled, microbeads which were coated with activator compounds can be identified by any property specific to the product. If an inhibitor is desired, selection can be for a chemical property specific to the substrate of the regulated reaction.

It may also be desirable, in some cases, for the substrate not to be attached to the microbead. In this case the substrate would contain an inactive "tag" that requires a further step to activate it such as photoactivation (e.g. of a "caged" biotin analogue, (Pirrung and Huang, 1996; Sundberg et al., 1995)). After convertion of the substrate to product the "tag" is activated and the "tagged" substrate and/or product bound by a tag-binding molecule (e.g. avidin or streptavidin) attached to the microbead. The ratio of substrate to product attached to the nucleic acid via the "tag" will therefore reflect the ratio of the substrate and product in solution. A substrate tagged with caged biotin has been used to select for genes encoding enzymes with phosphotriesterase activity using a procedure based on compartmentalisation in microcapsules (Griffiths and Tawfik, 2003). The phosphotriesterase substrate was hydrolysed in solution in microcapsules containing active enzyme molecules, and after the reaction was completed, the caging group was released by irradiation to allow the product to bind, via the biotin moiety, to microbeads to which the gene encoding the enzyme was attached.

After the microbeads and the contents of the microcapsules are combined, those microbeads coated with regulators can be selected by affinity purification using a molecule (e.g. an antibody) that binds specifically to the product or substrate as appropriate.

In an alternative embodiment, the invention provides a method wherein the microbeads are analysed following pooling of the microcapsules into one or more common compartments. Microbeads coated with regulator compounds can be identified using changes in optical properties of the microbeads. The optical properties of microbeads with product (or substrate) attached can be modified by either:

(1) the product-microbead complex having characteristic optical properties not found in the substrate-microbead complex, due to, for example;

(a) the substrate and product having different optical properties (many fluorogenic enzyme substrates are available commercially (see for example Haugland, 1996) including substrates for glycosidases, phosphatases, peptidases and proteases, or (b) the substrate and product having similar optical properties, but only the product, and not the substrate binds to, or reacts with, the microbead;

(2) adding reagents which specifically bind to, or react with, the product (or substrate) and which thereby induce a change in the optical properties of the microbeads allowing their identification (these reagents can be added before or after breaking the microcapsules and pooling the microbeads). The reagents;

(a) bind specifically to, or react specifically with, the product, and not the substrate, (or vice versa) if both substrate and product are attached to the microbeads, or (b) optionally bind both substrate and product if only the product, and not the substrate binds to, or reacts with, the microbeads (or vice versa).

In this scenario, the substrate (or one of the substrates) can be present in each microcapsule unlinked to the microbead, but has a molecular "tag" (for example biotin, DIG or DNP or a fluorescent group). When the regulated enzyme converts the substrate to product, the product retains the "tag" and is then captured in the microcapsule by the product-specific antibody. When all reactions are stopped and the microcapsules are combined, these microbeads will be "tagged" and may already have changed optical properties, for example, if the "tag" was a fluorescent group. Alternatively, a change in optical properties of "tagged" microbeads can be induced by adding a fluorescently labelled ligand which binds the "tag" (for example fluorescently-labelled avidin/streptavidin, an anti-"tag" antibody which is fluorescent, or a non-fluorescent anti-"tag" antibody which can be detected by a second fluorescently-labelled antibody).

(iv) Screening for Compound Specificity/Selectivity

Compounds with specificity or selectivity for certain targets and not others can be specifically identified by carrying out a positive screen for regulation of a reaction using one substrate and a negative screen for regulation of a reaction with another substrate. For example, two substrates, specific for two different target enzymes, are each labelled with different fluorogenic moieties. Each target enzymes catalyse the generation of a product with a different fluorescence spectrum resulting in different optical properties of the microcapsules depending on the specificity of the compound for two targets.

(v) Screening Using Cells

In the current drug discovery paradigm, validated recombinant targets form the basis of in vitro high-throughput screening (HTS) assays. Isolated proteins cannot, however, be regarded as representative of complex biological systems; hence, cell-based systems can provide greater confidence in compound activity in an intact biological system. A wide range of cell-based assays for drug leads are known to those skilled in the art. Cells can be compartmentalised in microcapsules, such as the aqueous microdroplets of a water-in-oil emulsion (Ghadessy, 2001). The effect of a compound(s) on a target can be determined by compartmentalising a cell (or cells) in a microcapsule together with a compound(s) and using an appropriate cell-based assay to identify those compartments containing compounds with the desired effect on the cell(s). The use of water-in-fluorocarbon emulsions may be particularly advantageous: the high gas dissolving capacity of fluorocarbons can support the exchange of respiratory gases and has been reported to be beneficial to cell culture systems (Lowe, 2002).

(vi) Flow Cytometry
(vi) Flow Analysis and Sorting

In a preferred embodiment of the invention the microcapsules or microbeads will be analysed and, optionally, sorted by flow cytometry. Many formats of microcapsule can be analysed and, optionally, sorted directly using flow cytometry.

In a highly preferred embodiment, microfluidic devices for flow analysis and, optionally, flow sorting (Fu, 2002) of microdroplets and microbeads will be used.

A variety of optical properties can be used for analysis and to trigger sorting, including light scattering (Kerker, 1983) and fluorescence polarisation (Rolland et al., 1985). In a highly preferred embodiment the difference in optical properties of the microcapsules or microbeads will be a difference in fluorescence and, if required, the microcapsules or microbeads will be sorted using a microfluidic or conventional fluorescence activated cell sorter (Norman, 1980; Mackenzie and Pinder, 1986), or similar device. Flow cytometry has a series of advantages:

(1) fluorescence activated cell sorting equipment from established manufacturers (e.g. Becton-Dickinson, Coulter, Cytomation) allows the analysis and sorting at up to 100,000 microcapsules or microbeads $s^{-1}$.

(2) the fluorescence signal from each microcapsule or microbead corresponds tightly to the number of fluorescent molecules present. As little as few hundred fluorescent molecules per microcapsules or microbeads can be quantitatively detected;

(3) the wide dynamic range of the fluorescence detectors (typically 4 log units) allows easy setting of the stringency of the sorting procedure, thus allowing the recovery of the optimal number microcapsules or microbeads from the starting pool (the gates can be set to separate microcapsules or microbeads with small differences in fluorescence or to only separate out microcapsules or microbeads with large differences in fluorescence, dependant on the selection being performed);

(4) fluorescence-activated cell sorting equipment can perform simultaneous excitation and detection at multiple wavelengths (Shapiro, 1995) allowing positive and negative selections to be performed simultaneously by monitoring the labelling of the microcapsules or microbeads with two to thirteen (or more) fluorescent markers, for example, if substrates for two alternative targets are labelled with different fluorescent tags the microcapsules or microbeads can labelled with different fluorophores dependent on the target regulated.

If the microcapsules or microbeads are optically tagged, flow cytometry can also be used to identify the compound or compounds in the microcapsule or coated on the microbeads (see below). Optical tagging can also be used to identify the concentration of the compound in the microcapsule (if more than one concentration is used in a single experiment) or the number of compound molecules coated on a microbead (if more than one coating density is used in a single experiment). Furthermore, optical tagging can be used to identify the target in a microcapsule (if more than one target is used in a single experiment). This analysis can be performed simultaneously with measuring activity, after sorting of microcapsules containing microbeads, or after sorting of the microbeads.

(vii) Microcapsule Identification and Sorting

The invention provides for the identification and, optionally, the sorting of intact microcapsules where this is enabled by the sorting techniques being employed. Microcapsules may be identified and, optionally, sorted as such when the change induced by the desired compound either occurs or manifests itself at the surface of the microcapsule or is detectable from outside the microcapsule. The change may be caused by the direct action of the compound, or indirect, in which a series of reactions, one or more of which involve the compound having the desired activity leads to the change. For example, where the microcapsule is a membranous microcapsule, the microcapsule may be so configured that a component or components of the biochemical system comprising the target are displayed at its surface and thus accessible to reagents which can detect changes in the biochemical system regulated by the compound on the microbead within the microcapsule.

In a preferred aspect of the invention, however, microcapsule identification and, optionally, sorting relies on a change in the optical properties of the microcapsule, for example absorption or emission characteristics thereof, for example alteration in the optical properties of the microcapsule resulting from a reaction leading to changes in absorbance, luminescence, phosphorescence or fluorescence associated with the microcapsule. All such properties are included in the term "optical". In such a case, microcapsules can be identified and, optionally, sorted by luminescence, fluorescence or phosphorescence activated sorting. In a highly preferred embodiment, flow cytometry is employed to analyse and, optionally, sort microcapsules containing compounds having a desired activity which result in the production of a fluorescent molecule in the microcapsule.

The methods of the current invention allow reagents to be mixed rapidly (in <2 ms), hence a spatially-resolved optical image of microcapsules in microfluidic network allows time resolved measurements of the reactions in each microcapsule. Microcapsules can, optionally, be separated using a microfluidic flow sorter to allow recovery and further analysis or manipulation of the molecules they contain. Advantageously, the flow sorter would be an electronic flow sorting device. Such a sorting device can be integrated directly on the microfluidic device, and can use electronic means to sort the microcapsules. Optical detection, also integrated directly on the microfluidic device, can be used to screen the microcapsules to trigger the sorting. Other means of control of the microcapsules, in addition to charge, can also be incorporated onto the microfluidic device.

In an alternative embodiment, a change in microcapsule fluorescence, when identified, is used to trigger the modification of the microbead within the compartment. In a preferred aspect of the invention, microcapsule identification relies on a change in the optical properties of the microcapsule resulting from a reaction leading to luminescence, phosphorescence or fluorescence within the microcapsule. Modification of the microbead within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the microbead or molecules attached to it. A similar procedure has been described previously for the rapid sorting of cells (Keij et al., 1994). Modification of the microbead may result, for example, from coupling a molecular "tag", caged by a photolabile protecting group to the microbeads: bombardment with photons of an appropriate wavelength leads to the removal of the cage. Afterwards, all microcapsules are combined and the microbeads pooled together in one environment. Microbeads coated with compounds exhibiting the desired activity can be selected by affinity purification using a molecule that specifically binds to, or reacts specifically with, the "tag".

(C) Compound Libraries (i) Primary Compound Libraries

Libraries of primary compounds can be obtained from a variety of commercial sources. The compounds in the library can be made by a variety of means well known to those skilled in the art. Optionally, compound libraries can be made by combinatorial synthesis using spatially resolved parallel synthesis or using split synthesis, optionally to generate one-bead-one-compound libraries. The compounds can, optionally, be synthesised on beads. These beads can be compartmentalised in microcapsules directly or the compounds released before compartmentalisation.

Advantageously, only a single type of compound, but multiple copies thereof is present in each microcapsule.

The compounds can, optionally, be connected to microbeads either covalently or non-covalently by a variety of means that will be familiar to those skilled in the art (see, for example, (Hermanson, 1996)).

Microbeads are available with a variety of surface chemistries from hydrophobic surfaces (e.g. plain polystyrene), to very hydrophilic surfaces imparted by a wide variety of functional surface groups: aldehyde, aliphatic amine, amide, aromatic amine, carboxylic acid, chloromethyl, epoxy, hydrazide, hydroxyl, sulfonate and tosyl. The functional groups permit a wide range of covalent coupling reactions, well known to those skilled in the art, for stable or reversible attachment of compounds to the microbead surface.

Advantageously, the compounds are attached to the microbeads via a cleavable linker. A variety of such linkers are familiar to those skilled in the art (see for example (Gordon and Balasubramanian, 1999)), including for example, linkers which can be cleaved photochemically and reversible covalent bonds which can be controlled by changing the pH (e.g. imines and acylhydrazones), by adjusting the oxido-reductive properties (e.g. disulphides), or using an external catalyst (e.g. cross-metathesis and transamidation).

Advantageously, only a single type of compound, but multiple copies thereof is attached to each bead.

(ii) Secondary Compound Libraries

Secondary compound libraries are created by reactions between primary compounds in microcapsules. Secondary compounds can be created by a variety of two component, and multi-component reactions well known to those skilled in the art (Armstrong et al., 1996; Domling, 2002; Domling and Ugi, 2000; Ramstrom and Lehn, 2002).

To form secondary compound libraries by a two-component reaction, two sets of compounds are compartmentalised in microcapsules such that many compartments contain two or more compounds. Advantageously, the modal number of compounds per microcapsule is two. Advantageously, the microcapsules contain at least one type of compound from each set of compounds. Advantageously, the microcapsules contain one type of compound from each set of compounds. The secondary compounds are formed by chemical reactions between primary compounds from different sets. The secondary compound may be the result of a covalent or non-covalent reaction between the primary compounds.

A variety of chemistries, familiar to those skilled in the art, are suitable to form secondary compounds in two-component reactions. For example, reversible covalent bonds which can be controlled by changing the pH (e.g. imines and acylhydrazones), by adjusting the oxido-reductive properties (e.g. disulphides), or using an external catalyst (e.g. cross-metathesis and transamidation), can be used (Ramstrom and Lehn, 2002).

In a further embodiment, the method can also be used to create secondary compound libraries using three-component, four-component and higher order multi-component reactions. Three, four or more sets of compounds (as appropriate) are compartmentalised in microcapsules. The compounds are compartmentalised in microcapsules such that many compartments contain multiple compounds. Advantageously, the modal number of compounds per microcapsule is equal to the number of components in the reaction. Advantageously, the microcapsules contain at least one type of compound from each set of compounds. Advantageously, the microcapsules contain one type of compound from each set of compounds. The secondary compounds are formed by chemical reactions between primary compounds from different sets. The secondary compound may be the result of covalent or non-covalent reactions between the primary compounds.

Examples of suitable multi-component reactions are the Strecker, Hantzsch, Biginelli, Mannich, Passerini, Bucherer-Bergs and Pauson-Khand three-component reactions and the Ugi four-component reaction (Armstrong et al., 1996; Domling, 2002; Domling and Ugi, 2000).

Secondary compound libraries may also be built using a scaffold molecule which is common to all the secondary compounds (Ramstrom and Lehn, 2002). This scaffold molecule may be compartmentalised into microcapsules together with the other primary compounds.

In a further embodiment, to form secondary compound libraries by a two-component reaction, two sets of compounds are attached to microbeads, advantageously to give only a single type of molecule per microbead. The microbeads are compartmentalised in microcapsules such that many compartments contain two or more microbeads. Advantageously, the modal number of beads per microcapsule is two. The compounds comprising at least one of the two sets are released from the microbeads. The secondary compounds are formed by chemical reactions between primary compounds from different sets. The secondary compound may be the result of a covalent or non-covalent reaction between the primary compounds.

In a further embodiment, the method can also be used to create secondary compound libraries using three-component, four-component and higher order multi-component reactions. Three, four or more sets of compounds (as appropriate) are attached to microbeads, advantageously to give only a single type of molecule per microbead. The microbeads are compartmentalised in microcapsules such that many compartments contain multiple microbeads. Advantageously, the modal number of beads per microcapsule is equal to the number of components in the reaction. The compounds comprising either all, or all bar one, of the sets are released from the microbeads. The secondary compounds are formed by chemical reactions between primary compounds from different sets. The secondary compound may be the result of covalent or non-covalent reactions between the primary compounds.

Advantageously, the same reversible covalent bond can used to couple the primary compound to the microbead as is used to form the secondary compound.

Secondary compound libraries may also be built using a scaffold molecule which is common to all the secondary compounds (Ramstrom and Lehn, 2002). This scaffold molecule may be compartmentalised into microcapsules together with the microbeads.

(D) Identification of Compounds

The compounds in microcapsules or on microbeads can be identified in a variety of ways. If the identified microcapsules are sorted (e.g. by using a fluorescence activated cell sorter—FACS) the compounds can be identified by direct analysis, for example by mass-spectroscopy. If the compounds remain attached to beads isolated as a result of selection (for example by affinity purification) or sorting (for example using a FACS) they can also be identified by direct analysis, for example by mass-spectroscopy. The microcapsules or beads can also be tagged by a variety of means well known to those skilled in the art and the tag used to identify the compound attached to the beads (Czarnik, 1997). Chemical, spectrometric, electronic, and physical methods to encode the compounds may all be used. In a preferred embodiment microcapsules or beads have different optical properties and are thereby optically encoded. In a preferred embodiment encoding is based on microcapsules or beads having different fluorescence properties. In a highly preferred embodiment the microcapsules or beads are encoded using fluorescent quantum dots present at different concentrations in the microcapsule or bead (Han, 2001). Microcapsules flowing in an ordered sequence in a microfluidic channel can also be encoded (wholly or partially) by their sequence in the stream of microcapsules (positional encoding).

Advantageously, each compounds is present in different microcapsules at different concentrations (typically at concentrations varying from mM to nM) allowing the generation of a dose-response curve. Fusing microcapsules to give all possible permutations of several different substrate concentrations and compound concentrations would allow the determination of the mode of inhibition (e.g. competitive, noncompetitive, uncompetitive or mixed inhibition) and inhibition constant ($K^i$) of an inhibitory compound. The concentration of the compounds in the microcapsules can be determined by, for example, optical encoding or positional encoding of the microcapsules or microbeads as above.

(E) Identification of Targets

Advantageously, multiple different targets can be compartmentalised in microcapsules such that each microcapsule contains multiple copies of the same target. For example, multiple protein kinases, or multiple polymorphic variants of a single target, can be compartmentalised to allow the specificity of compounds to be determined. The identity of the target in a microcapsule can be determined by, for example, optical encoding or positional encoding of the microcapsules or microbeads as above.

Expressed in an alternative manner, there is provided a method for the synthesis and identification of compounds which bind to a target component of a biochemical system or modulate the activity of the target, comprising the steps of:
(a) compartmentalising two or more sets of primary compounds into microcapsules together with the target such that many compartments contain two or more primary compounds;
(b) forming secondary compounds in the microcapsules by chemical reactions between primary compounds from different sets; and
(c) identifying subsets of primary compounds which react to form secondary compounds which bind to or modulate the activity of the target.

There is also provided a method for the synthesis and identification of compounds which bind to a target component of a biochemical system or modulate the activity of the target, comprising the steps of:
(1) attaching two or more sets of primary compounds onto microbeads;
(2) compartmentalising the microbeads into microcapsules together with the target such that many compartments contain two or more microbeads;
(3) releasing the primary compounds from the microbeads;
(4) forming secondary compounds in the microcapsules by chemical reactions between primary compounds from different sets; and
(5) identifying subsets of primary compounds which react to form secondary compounds which bind to or modulate the activity of the target.

If the primary compounds react, not only with other primary compounds in the same compartment, but also with other microbeads in the compartment, the primary compounds which react together to form a secondary compound can be identified by direct analysis of the compounds present on a microbeads isolated as a result of selection or sorting. For example, if the primary compounds are linked to the beads via a disulphide bond when they are released in the compartment the primary compounds will react both with each other to form a secondary compound and with the sulfhydryl groups on the beads. Hence, if two beads are co-compartmentalised, each bead will end up carrying both primary compounds. After isolation of these beads both primary compounds which reacted to form the secondary compound can be identified.

(F) Rapid Mixing of Reagents in Microcapsules

Advantageously, after fusion of microcapsules, the reagents contained in the fused microcapsule can be mixed rapidly using chaotic advection. By passing the droplets through channels that disrupt the laminar flow lines of the fluid within the droplets, their contents can be rapidly mixed, fully initiating any chemical reactions.

(G) Sensing Microcapsule Characteristics

In certain aspects of the invention, sensors are provided that can sense and/or determine one or more characteristics of the fluidic droplets, and/or a characteristic of a portion of the fluidic system containing the fluidic droplet (e.g., the liquid surrounding the fluidic droplet) in such a manner as to allow the determination of one or more characteristics of the fluidic droplets. Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

In some cases, the sensor may be connected to a processor, which in turn, cause an operation to be performed on the fluidic droplet, for example, by sorting the droplet, adding or removing electric charge from the droplet, fusing the droplet with another droplet, splitting the droplet, causing mixing to occur within the droplet, etc., for example, as previously described. For instance, in response to a sensor measurement of a fluidic droplet, a processor may cause the fluidic droplet to be split, merged with a second fluidic droplet, sorted etc.

One or more sensors and/or processors may be positioned to be in sensing communication with the fluidic droplet. "Sensing communication," as used herein, means that the sensor may be positioned anywhere such that the fluidic droplet within the fluidic system (e.g., within a channel), and/or a portion of the fluidic system containing the fluidic droplet may be sensed and/or determined in some fashion. For example, the sensor may be in sensing communication with the fluidic droplet and/or the portion of the fluidic system containing the fluidic droplet fluidly, optically or visually, thermally, pneumatically, electronically, or the like. The sensor can be positioned proximate the fluidic system, for example, embedded within or integrally connected to a wall of a channel, or positioned separately from the fluidic system but with physical, electrical, and/or optical communication with the fluidic system so as to be able to sense and/or determine the fluidic droplet and/or a portion of the fluidic system containing the fluidic droplet (e.g., a channel or a microchannel, a liquid containing the fluidic droplet, etc.). For example, a sensor may be free of any physical connection with a channel containing a droplet, but may be positioned so as to detect electromagnetic radiation arising from the droplet or the fluidic system, such as infrared, ultraviolet, or visible light. The electromagnetic radiation may be produced by the droplet, and/or may arise from other portions of the fluidic system (or externally of the fluidic system) and interact with the fluidic droplet and/or the portion of the fluidic system containing the fluidic droplet in such as a manner as to indicate one or more characteristics of the fluidic droplet, for example, through absorption, reflection, diffraction, refraction, fluorescence, phosphorescence, changes in polarity, phase changes, changes with respect to time, etc. As an example, a laser may be directed towards the fluidic droplet and/or the liquid surrounding the fluidic droplet, and the fluorescence of the fluidic droplet and/or the surrounding liquid may be determined. "Sensing communication," as used herein may also be direct or indirect. As an example, light from the fluidic droplet may be directed to a sensor, or directed first through a fiber optic system, a waveguide, etc., before being directed to a sensor.

Non-limiting examples of sensors useful in the invention include optical or electromagnetically-based systems. For example, the sensor may be a fluorescence sensor (e.g., stimulated by a laser), a microscopy system (which may include a camera or other recording device), or the like; As another example, the sensor may be an electronic sensor, e.g., a sensor able to determine an electric field or other electrical characteristic. For example, the sensor may detect capacitance, inductance, etc., of a fluidic droplet and/or the portion of the fluidic system containing the fluidic droplet.

As used herein, a "processor" or a "microprocessor" is any component or device able to receive a signal from one or more sensors, store the signal, and/or direct one or more responses (e.g., as described above), for example, by using a mathematical formula or an electronic or computational circuit. The signal may be any suitable signal indicative of the environmental factor determined by the sensor, for example a pneumatic signal, an electronic signal, an optical signal, a mechanical signal, etc.

(H) Materials

A variety of materials and methods, according to certain aspects of the invention, can be used to form any of the above-described components of the microfluidic systems and devices of the invention. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one embodiment, a bottom wall is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

Various aspects and embodiments of the present invention are illustrated in the following examples. It will be appreciated that modification of detail may be made without departing from the scope of the invention.

EXAMPLES

Example 1

Figure 15:
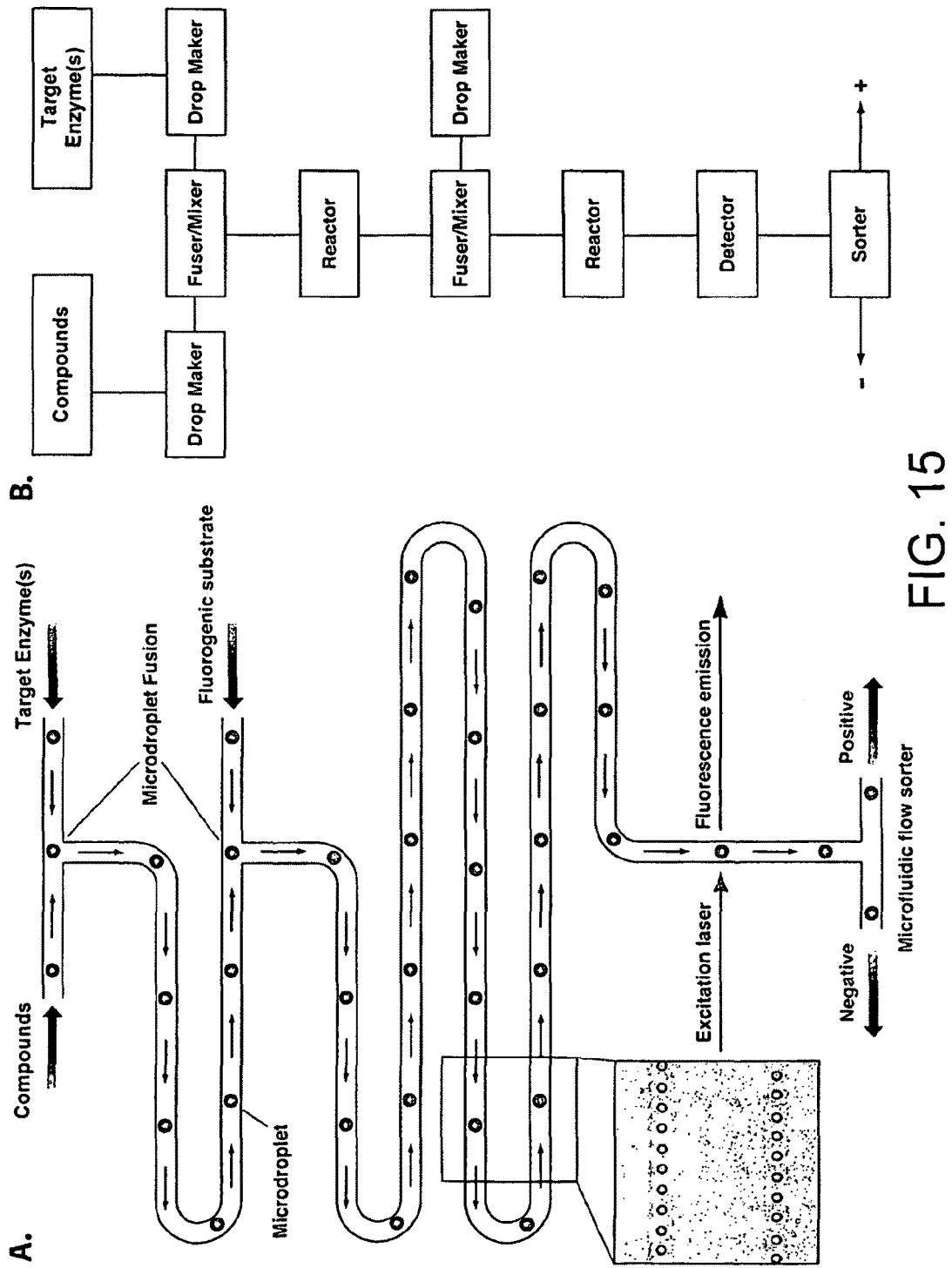
FIG. 15. Compound screening using microdroplets in a microfluidic system. Panel A: schematic of the core system. Panel B: process block diagram showing the modules in the core system. Microdroplets containing a target enzyme are fused with microdroplets each of which contain a different compound from a compound library. After allowing time for the compounds to bind to the target enzyme each microdroplet is fused with another microdroplet containing a fluorogenic enzyme substrate. The rate of the enzymatic reaction is determined by measuring the fluorescence of each microdroplet, ideally at multiple points (corresponding to different times). Microdroplets containing compounds with desired activities can, if required, be sorted and collected.
Figure 16:
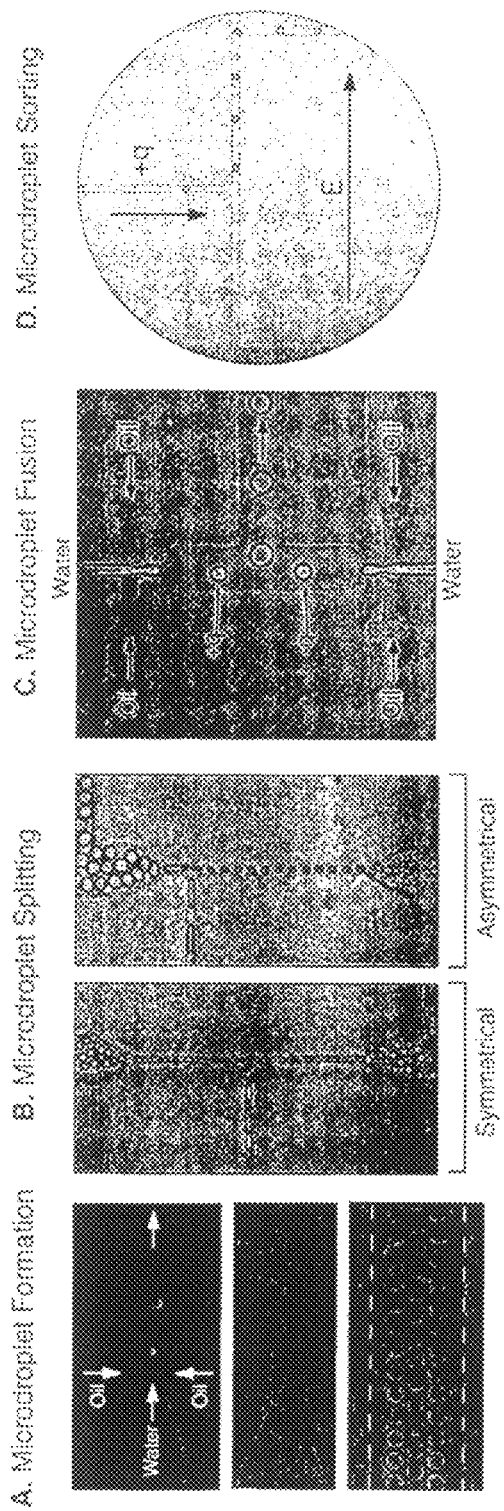
FIG. 16. Examples of microdroplet formation and manipulation using microfluidics. Panel A: microdroplets can be created at up to $10^4$ sec$^{-1}$ by hydrodynamic-focusing (top two panels) and show <1.5% polydispersity (bottom panel). Panel B: microdroplets can be split symmetrically or asymmetrically. Panel C: microdroplets carrying positive (+q) and negative (−q) electrical charges fuse spontaneously. Panel D: charged microdroplets can also be steered using an applied electrical field (E).

Microfluidic Device for Combinatorial Chemistry and Screening Using in vitro Compartmentalisation A schematic representation of the microfluidic device is shown in FIG. 15. Microchannels are fabricated with rectangular cross-sections using rapid prototyping in poly(dimethylsiloxane) (PDMS) (McDonald and Whitesides, 2002) and rendered hydrophobic as (Song and Ismagilov, 2003). Syringe pumps were used to drive flows (Harvard Apparatus PHD 2000 Infusion pumps). For aqueous solutions, 250 µl Hamilton Gastight syringes (1700 series, TLL) with removable needles of 27-gauge are used with 30-gauge Teflon tubing (Weico Wire and Cable). For the carrier fluid, 1 ml Hamilton Gastight syringes (1700 series, TLL) are used with 30-gauge Teflon needles with one hub from Hamilton (Song and Ismagilov, 2003). The carrier fluid is 9% (v/v) $C_6F_{11}C_2H_4OH$ in perfluorodecaline (PFD) (Song et al., 2003). The microfluidic device consists of a series of interconnected modules, Each module has a specific function. These include modules that will produce droplets, fuse droplets, mix droplets, react droplets, detect droplets, and sort droplets (see FIG. 16). In one example, droplets are made, consisting of different molecules or different concentrations of molecules. Droplets are made at rates of up to $10^4$ $sec^{-1}$, and are made with a polydispersity of less than 1.5% and with sizes ranging from 1 µm to 100 µm. Each droplet is fused with a second droplet containing a second set of reactants, and is rapidly mixed to initiate the chemical reaction. This chemical reaction is allowed to proceed in each droplet by passing it through a delay channel. Each droplet is then fused with another droplet containing a second set of reactants, and is subsequently rapidly mixed to initiate the second set of chemical reactions. After the second reaction has proceeded in a delay module, the results of the reaction is determined using an optical sensor or other form of detection module. Finally, the desired droplets are sorted into two populations based on signal form the optical detection module, one population is kept for further processing and the other discarded. These and other modules can be used in this combination, or in other combinations.

Droplet generation module: We use a flow-focusing geometry to form the drops. A water stream is infused from one channel through a narrow constriction; counter propagating oil streams hydrodynamically focus the water stream reducing its size as it passes through the constriction as shown in FIG. 23A. This droplet generator can be operated in a flow regime that produces a steady stream of uniform droplets of water in oil. The size of the water droplets is controlled by the relative flow rates of the oil and the water; the viscous forces overcome surface tension to create uniform droplets. If the flow rate of the water is too high a longer jet of fluid passes through the orifice and breaks up into droplets further down stream; these droplets are less uniform in size. If the flow rate of the water is too low, the droplet breakup in the orifice becomes irregular again, producing a wider range of droplet sizes. While this emulsification technology is robust, it is limited to producing droplets of one size at any given flow rate; this droplet size is largely determined by the channel dimensions. Moreover, the timing of the droplet production cannot be controlled.

Figure 23:
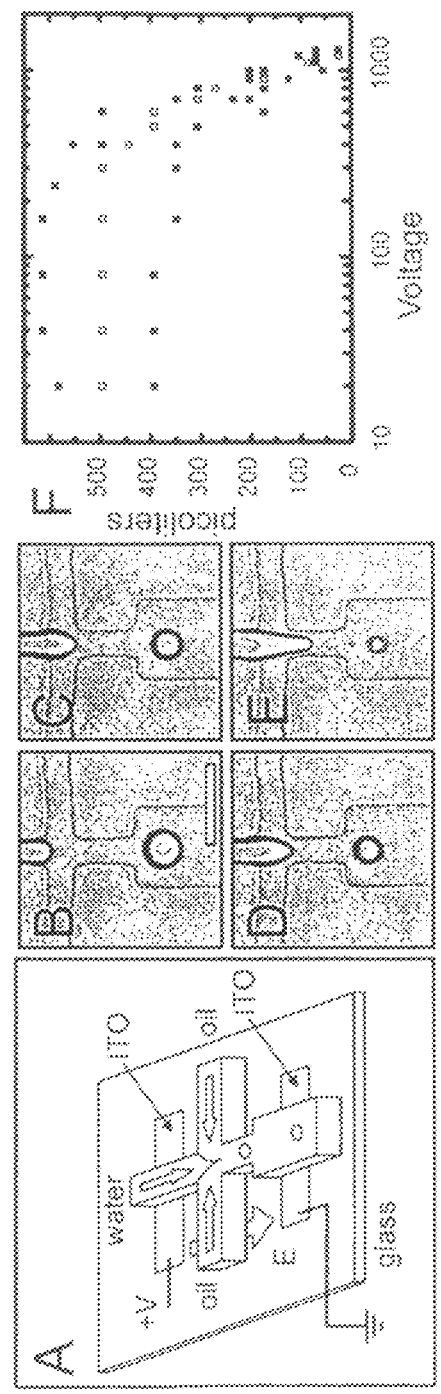
FIG. 23 Charged droplet generation. (A), Oil and water streams converge at a 30 micron orifice. A voltage V applied to indium-tin-oxide (ITO) electrodes on the glass produces an electric field E to capacitively charges the aqueous-oil interface. Drop size is independent of charge at low field strengths but decreases at higher fields, as shown in the photomicrographs, [(B) V=0, (C) V=400, (D) V=600 and (E) V=800] at higher fields. (F) Droplet size as a function of voltage showing the crossover between flow-dominated and field-dominated snap-off for three different flow rates of the continuous phase oil ($Q_c$=80 nL/s, 110 nL/s, and 140 nL/s). The infusion rate of the water is constant $Q_d$=20 nL/s.}

We overcome these limitations by incorporating electric fields to create an electrically addressable emulsification system. To achieve this, we apply high voltage to the aqueous stream and charge the oil water interface, as shown schematically in FIG. 23A. The water stream behaves as a conductor while the oil is an insulator; electrochemical reactions charge the fluid interface like a capacitor. At snap-off, charge on the interface remains on the droplet. In addition, the droplet volume, $V_{dr}$ and frequency, f, can be tailored over nearly three orders of magnitude without changing the infusion rate of the oil or water. Droplet size and frequency are not independent; instead their product is determined by the infusion rate of the dispersed phase $Q_d=fV_d$. The droplet size decreases with increasing field strength, as shown in FIGS. 23, B to E. The dependence of the droplet size on applied voltage for three different flow rates is summarized in FIG. 23F. At low applied voltages the electric field has a negligible effect, and droplet formation is driven exclusively by the competition between surface tension and viscous flow. By contrast, at high electric field strengths, there is a significant additional force on the growing drop, F=qE, where q is the charge on the droplet. Since the droplet interface behaves as a capacitor, q is proportional to the applied voltage, V. This leads to a $V^2$ dependence of the force, which accounts for the decrease in droplet size with increasing applied field shown in FIG. 23F. If the electric field becomes too large, the charged interface of the water stream is repelled by the highly charged drops; this destabilizes the production and increases the variation in droplet size.

The electronic control afforded by the field-induced droplet formation provides an additional valuable benefit: it allows the phase of the droplet break-off to be adjusted within the production cycle. This is accomplished by increasing the field above the critical break-off field only at the instant the droplet is required. This provides a convenient means to precisely synchronize the production and arrival of individual droplets at specific locations.

Droplet coalescer module: An essential component in any droplet-based reaction-confinement system is a droplet coalescing module which combines two or more reagents to initiate a chemical reaction. This is particularly difficult to achieve in a microfluidic device because surface tension, surfactant stabilization, and drainage forces all hinder droplet coalescence; moreover, the droplets must cross the stream lines that define their respective flows and must be perfectly synchronized to arrive at a precise location for coalescence.

Figure 24:
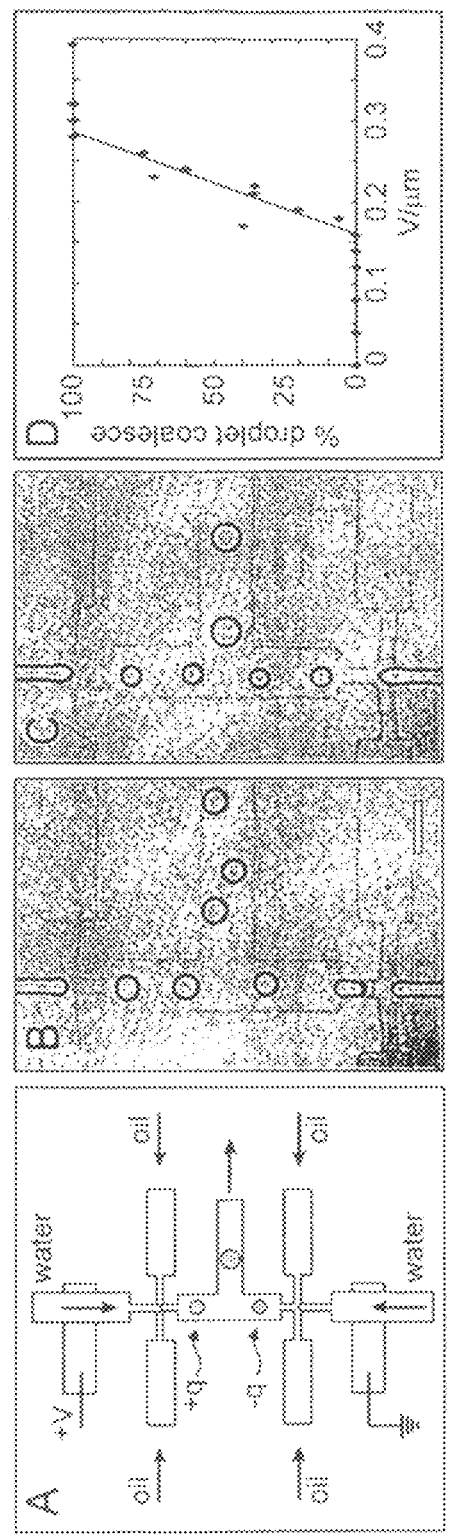
FIG. 24 Coalescing drops. (A) Drops having opposite sign of electrostatic charge can be generated by applying a voltage across the two aqueous streams. (B) In the absence of the field the frequency and timing of drop formation at the two nozzles are independent and each nozzle produces a different size drop at a different frequency; infusion rates are the same at both nozzles. After the confluence of the two streams, drops from the upper and lower nozzles stay in their respective halves of the stream and due to surfactant there are no coalescence events even in the case of large slugs that fill the channel width. (C) With an applied voltage of 200V across the 500 micron separation of the nozzles, the drops simultaneously break-off from the two nozzles and are identical; simultaneous drop formation can be achieved for unequal infusion rates of the aqueous streams even up to a factor of two difference in volumes. (D) The fraction of the drops that encounter each other and coalesce increases linearly above a critical field when a surfactant, sorbiton-monooleate 3% is present.

Use of electrostatic charge overcomes these difficulties; placing charges of opposite sign on each droplet and applying an electric field forces them to coalesce. As an example we show a device consisting of two separate nozzles that generate droplets with different compositions and opposite charges, sketched in FIG. 24A. The droplets are brought together at the confluence of the two streams. The electrodes used to charge the droplets upon formation also provide the electric field to force the droplets across the stream lines, leading to coalesce. Slight variations in the structure of the two nozzles result in slight differences in the frequency and phase of their droplet generation in the absence of a field. Thus the droplets differ in size even though the infusion rates are identical. Moreover, the droplets do not arrive at the point of confluence at exactly the same time. As a result the droplets do not coalesce as shown in FIG. 24B. By contrast, upon application of an electric field, droplet formation becomes exactly synchronized, ensuring that pairs of identically sized droplets each reach the point of confluence simultaneously. Moreover, the droplets are oppositely charged, forcing them to traverse the stream lines and contact each other, thereby causing them to coalesce, as shown in FIG. 24C. The remarkable synchronization of the droplet formation results from coupling of the break-off of each of the pair of droplets as mediated by the electric field; the magnitude of the electric field varies as the separation between the leading edges of the two droplets changes and the frequency of droplet break-off is mode-locked to the electric field. A minimum charge is required to cause droplets to coalesce, presumably because of the stabilizing effects of the surfactant coating; this is clear from FIG. 24D which shows the voltage dependence of the percentage of drops that contact each other that actually coalesce.

Figure 25:
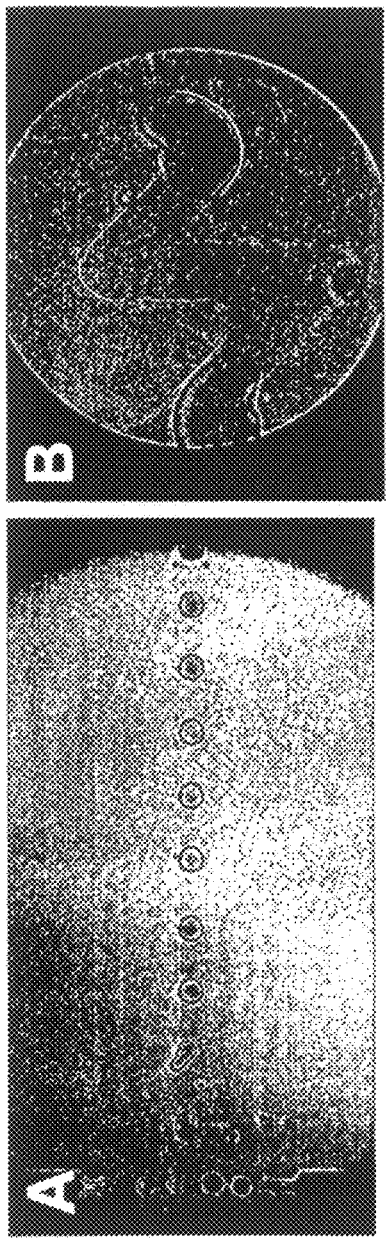
FIG. 25: (A) Droplets carrying a pH sensitive dye coalesce with droplets of a different pH fluid. (B) Chaotic advection rapidly mixes the two fluids through a combination of translation and rotation as the droplets pass around corners.
Figure 26:
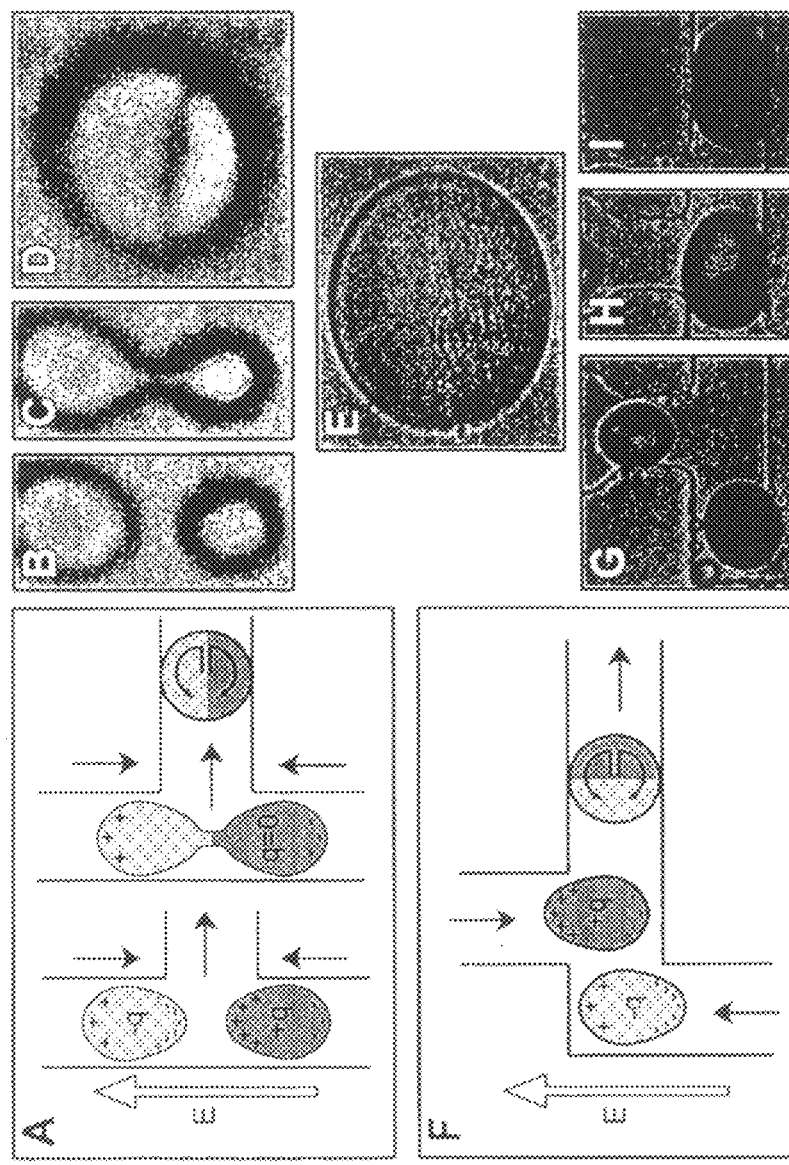
FIG. 26: Diffusion limited and rapid mixing strategies. (A) Drops meet and coalesce along the direction of E and then move off in a perpendicular direction, as sketched the counter rotating vortices after coalescence do not mix the two fluid parts as each vortex contains a single material. (B) As the drops approach each other the increasing field causes there interfaces to deform and (C) a bridge to jump out connecting the drops, to create (D) in the case of 20 nm silica particles and MgCl_2 a sharp interface where the particles begin to gel. (E) A typical unmixed droplet with particles in one hemisphere. (F) To achieve fast mixing, droplets are brought together in the direction perpendicular to the electric field and move off in the direction parallel to the direction they merged along. Counter rotating vortexes are then created where each vortex is composed of half of the contents from each of the premerger-droplets. (G) Shows a pH sensitive dye in the lower drop and a different pH fluid in the upper droplet. (H) After merger the droplets are split by a sharp line. (I) A uniform intensity indicating that mixing has been occurred is achieved in the droplet after it translates one diameter, typically this takes 1 to 2 ms.

Droplet mixer module: Rapid mixing is achieved through either successive iterations of translation and rotation, FIG. 25, or by coalescing drops along the direction parallel to the flow direction, FIG. 26.

Figure 27:
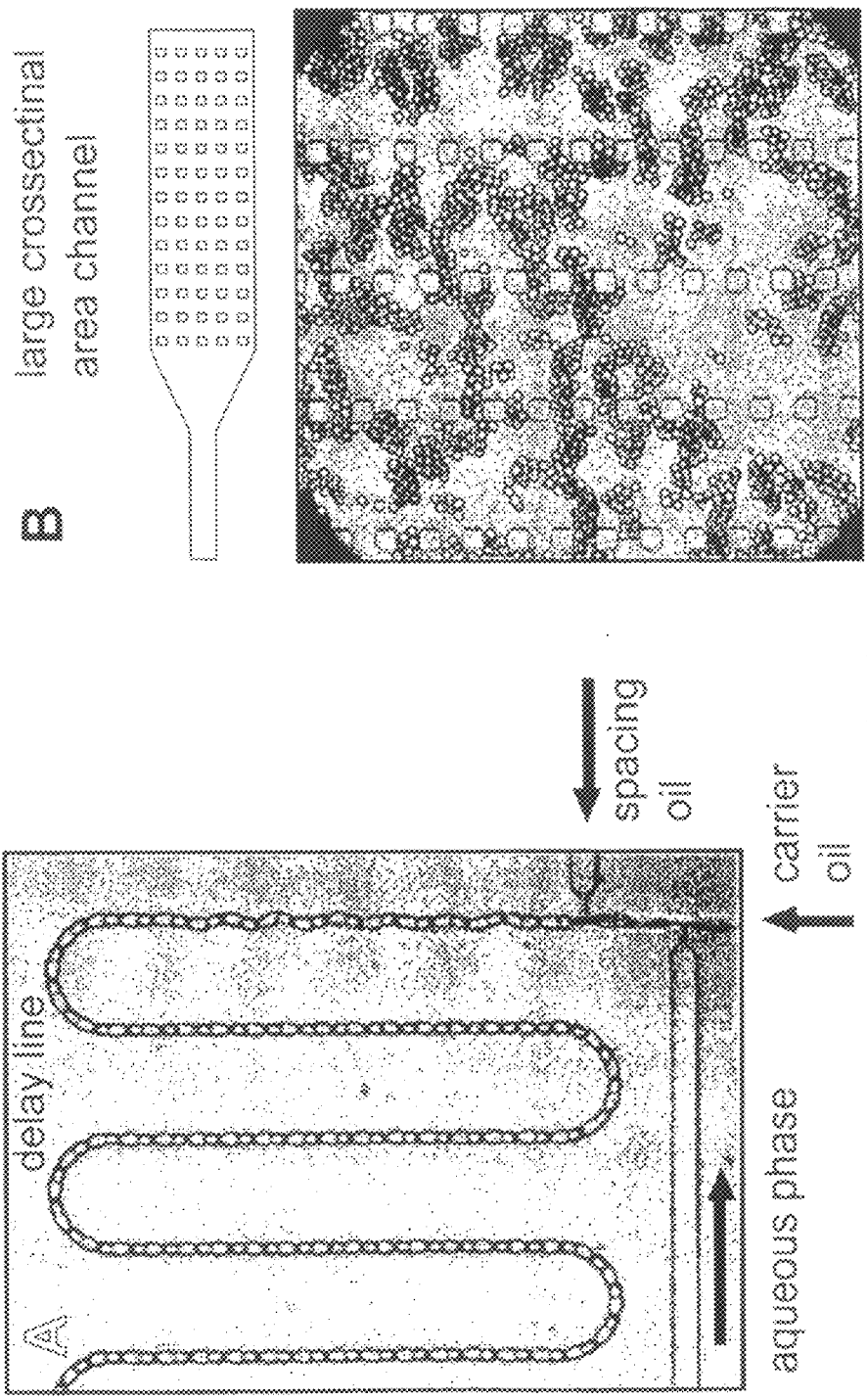
FIG. 27 Time delay reaction module. (A) Droplets of perfluorodecaline alternate with aqueous droplets in a hexadecane carrier fluid. The 'single-file' ordering of the droplets provides for long delays with essentially no deviation in the precise spacing of aqueous droplets or droplet order. (B) Increasing the width and height of the channel to create a 'large cross-sectional area' channel provides for extremely long time delays from minutes to hours. The exact ordering and spacing between the droplets is not maintained in this type of delay line.

Droplet reactor/time delay module: A delay line is used to provide a fixed time for a reaction. Two non-limiting examples of how this can be achieved are 'single file' and 'large cross-section' channels. The 'single file' delay line uses length to achieve a fixed reaction time. As this often results in exceptionally long channels, it is desirable to place spacer droplets of a third fluid, immiscible with both the carrier oil and the aqueous droplets inbetween aqueous droplet pairs. There is then an alternation between aqueous and non-aqueous droplets in a carrier oil. This is shown in FIG. 27A. A second possibility for achieving a long time delay is to use wide and deep channel having a 'large cross-sectional area' to slow the average velocity of the droplets. An example of this is shown in FIG. 27B.

Figure 28:
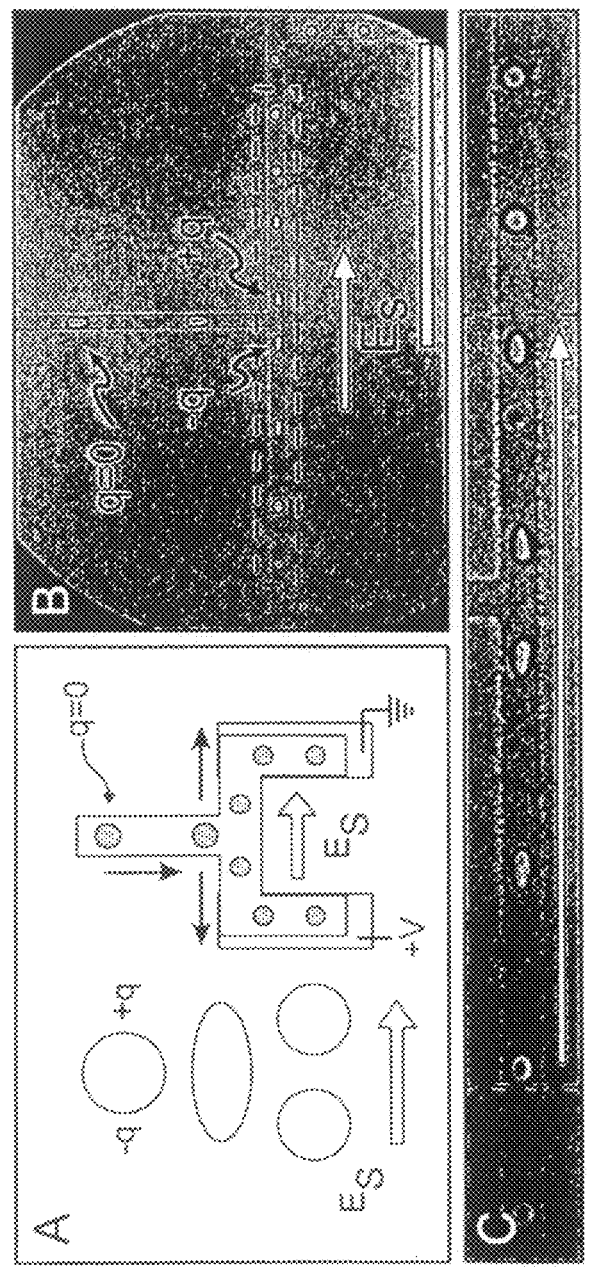
FIG. 28. Recharging neutral drops. (A) Schematic to recharge neutral drops by breaking them in the presence of an electric field. Uncharged drops (q=0) are polarized in an electric field ($E_S$≠0), and provided $E_S$ is sufficiently large, as shown in the photomicrograph of (B), they break into two oppositely charged daughter drops in the extensional flow at a bifurcation. The enlargement of the dashed rectangle, shown in (C), reveals that the charged drops are stretched in the electric field $E_S$ but return to spherical on contacting the electrodes indicated by dashed vertical lines.

Recharging module: The use of oppositely charged droplets and an electric field to combine and mix reagents is extremely robust, and 100% of the droplets coalesce with their partner from the opposite stream. However, after they coalesce the resultant drops carry no electrostatic charge. While it is convenient to charge droplets during formation, other methods must be employed in any robust droplet-based microfluidic system to recharge the mixed droplets if necessary for further processing. This is readily accomplished through the use of extensional flow to split neutral droplets in the presence of an electric field which polarizes them, resulting in two oppositely charged daughter droplets; this is sketched in FIG. 28A. The photomicrograph in FIG. 28B shows neutral droplets entering a bifurcation and splitting into charged daughter droplets. The dashed region in FIG. 28B is enlarged in FIG. 28C to illustrate the asymmetric stretching of the charged droplets in the electric field. The vertical dashed lines indicate the edges of the electrodes where the droplets return to their symmetric spherical shape. The electric field also allows precision control of the droplet splitting providing the basis for a robust droplet division module which allows the splitting of the contents into two or more aliquots of identical reagent, facilitating multiple assays on the contents of the same microreactor.

Figure 29:
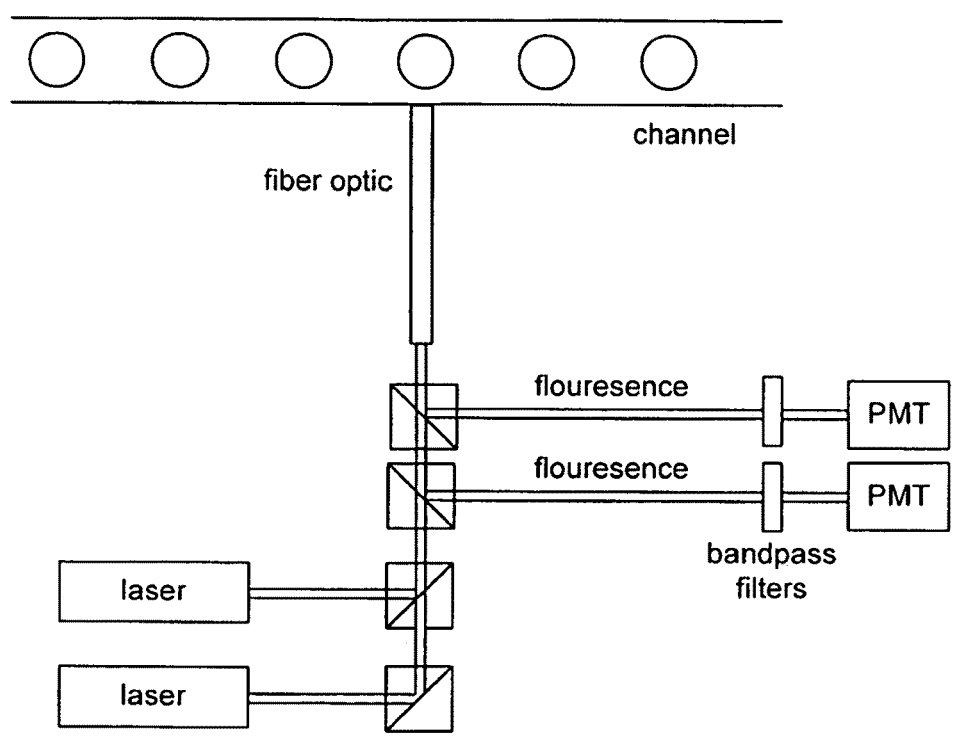
FIG. 29 Detection module. One or more lasers are coupled to an optical fibre that is used to excite the fluorescence in each droplet as it passes over the fibre. The fluorescence is collected by the same fibre and dichroic beam splitters separate off specific wavelengths of the fluorescent light and the intensity of the fluorescence is measured with a photomultiplier tube (PMT) after the light passes through a band-pass filter.

Detection module: The detection module consists of an optical fiber, one or more laser, one or more dichroic beam splitter, bandpass filters, and one or more photo multiplying tube (PMT) as sketched in FIG. 29.

Sorting module: The contents of individual droplets must be probed, and selected droplets sorted into discreet streams.

Figure 30:
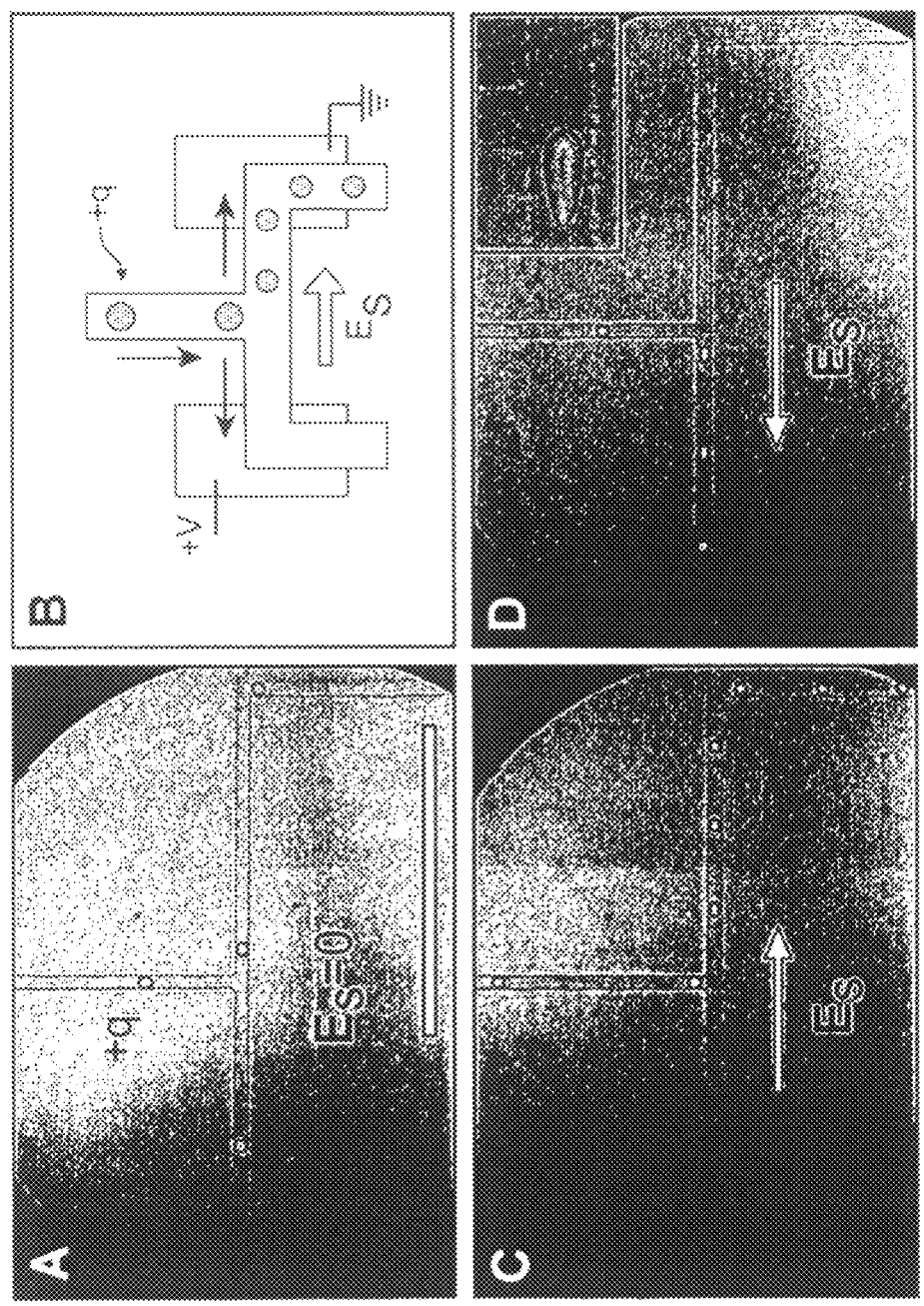
FIG. 30 Manipulating charged drops. In (A) charged drops alternately enter the right and left channels when there is no field applied ($E_S$=0). The sketch in (B) shows the layout for using an electric field $E_S$ to select the channel charged drops will enter at a bifurcation. When an electric field is applied to the right (C), the drops enter the right branch at the bifurcation; they enter the left branch when the field is reversed (D). After the bifurcation, the distance between drops is reduced to half what it was before indicating the oil stream is evenly divided. The inset of (D) shows the deformation in the shape of a highly charged drop in an electric field.

The use of electrostatic charging of droplets provides a means for sorting that can be precisely controlled, can be switched at high frequencies, and requires no moving parts. Electrostatic charge on the droplets enables drop-by-drop sorting based on the linear coupling of charge to an external electric field. As an example, a T-junction bifurcation that splits the flow of carrier fluid equally will also randomly split the droplet population equally into the two streams, as shown in FIG. 30A. However, a small electric field applied at the bifurcation precisely dictates which channel the drops enter; a schematic of the electrode configuration is shown in FIG. 30B. Varying the direction of the field varies the direction of the sorted droplets as shown in FIGS. 30C and 30D. The large forces that can be imparted on the droplets and the high switching frequency make this a fast and robust sorting engine with no moving parts; thus the processing rate is limited only by the rate of droplet generation.

Example 2

Screening for Protein Tyrosine Phosphatase 1B (PTP1B) Inhibitors Using Microcapsules in Microfluidic Systems PTP1B is a negative regulator of insulin and leptin signal transduction. Resistance to insulin and leptin are hallmarks of type 2 diabetes mellitus and obesity and hence PTP1B is an attractive drug target for diabetes and obesity therapy (Johnson et al., 2002). Using a microfluidic device as described in Example 1, we describe how PTP1B inhibitors can be screened using microcapsules in a microfluidic system.

Figure 17:
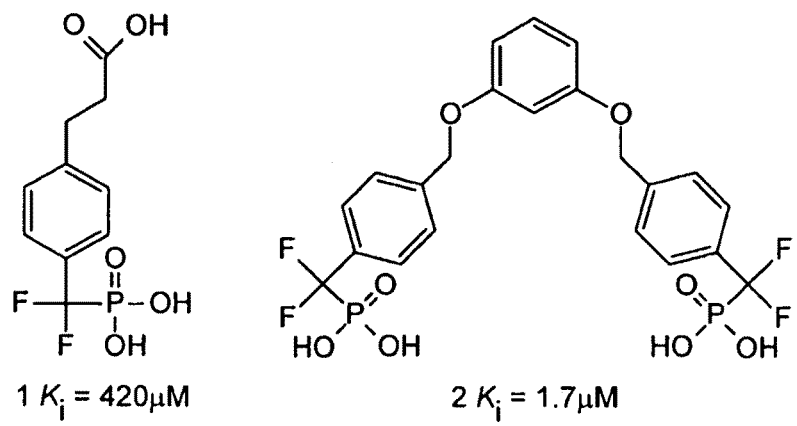
FIG. 17. Examples of PTP1B inhibitors. Compounds with a bis-difluoromethylene phosphonate moiety (e.g. 2) have significantly more potency than those with a single moiety (e.g. 1).
Figure 18:
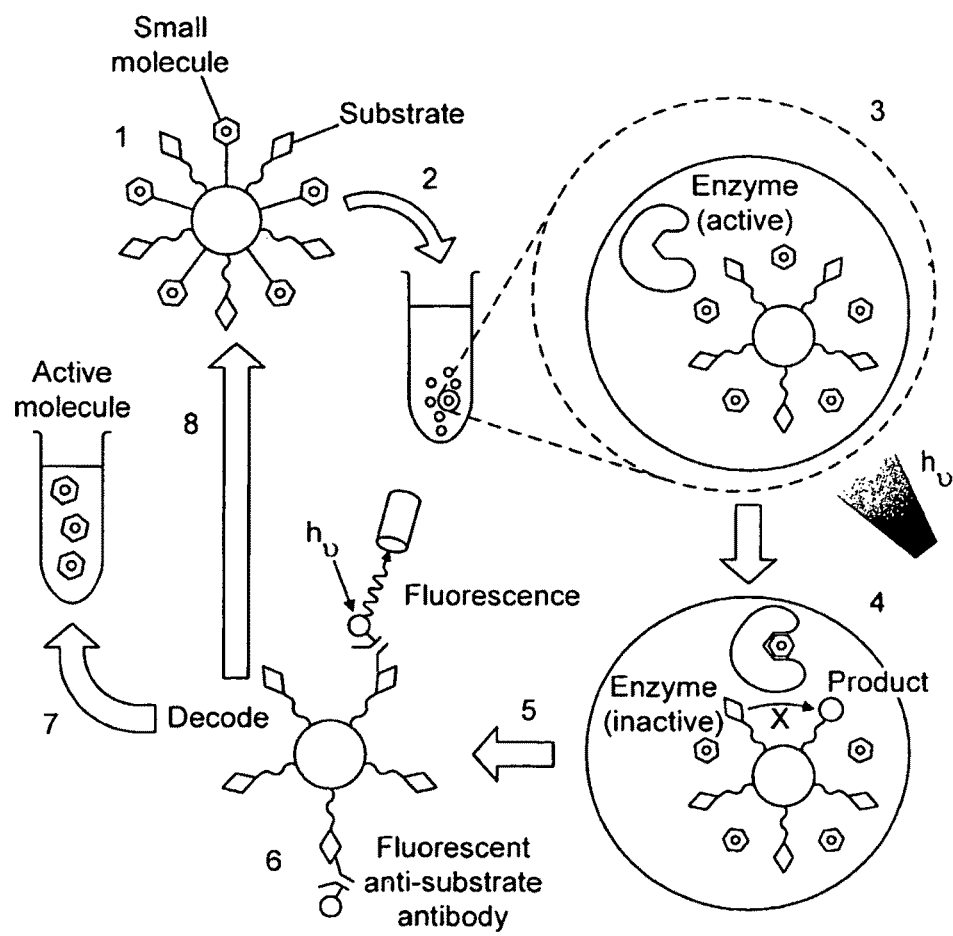
FIG. 18. Screening PTP1B inhibitors using microencapsulation. Polystyrene beads with surface carboxylate groups, died with orange or red fluorochromes (Fulton et al., 1997), are derivatised with a phosphopeptide PTP1B substrate, and either PTP1B inhibitors or non-inhibitory compounds, attached via a cleavable linker (1). After mixing the beads, single beads and target enzyme (PTP1B) are colocalised in a microcompartment by forming a water-in-oil emulsion using a microfluidic device (2). The compound is released (photochemically) (3). Inhibitors reduce the amount of substrate converted to product (dephosphorylated peptide) (4). The enzyme reaction is stopped and the emulsion is broken (5). After labelling with green fluorescent anti-substrate antibodies, beads are analysed by 3-colour flow cytometry to simultaneously determine extent of inhibition and the compound on the beads (6). Compound libraries can be coupled to optically tagged beads (see below) and rapidly decoded by flow cytometry (at up to 100,000 beads s$^{-1}$). Hit compounds are re-synthesised for further characterisation (7) or elaborated and rescreened in a process of synthetic evolution (8).

All water-soluble reagents are dissolved in (25 mM HEPES, pH 7.4, 125 mM NaCl, 1 mM EDTA), a buffer compatible with PTP1B activity. A solution of the target enzyme (human recombinant PTP1B, residues 1-322; Biomol Research Laboratories, Inc.) at 50 mU/ml and a solution of either a) 100 µM compound 2 (FIG. 17), which has a bis-difluoromethylene phosphonate and is a known PTP1B inhibitor (Johnson et al., 2002), or b) 100 µM hydrocinnamic acid (Aldrich), a compound that is not a PTP1B inhibitor are compartmentalised into microcapsules using the device. Each microcapsule containing target enzyme is fused with a microcapsule containing compound 2 or a microcapsule containing hydrocinnamic acid. Microcapsules containing either compound 2 or hydrocinnamic acid can be formed by switching between injection with syringes containing compound 2 and hydrocinnamic acid.

After microcapsule fusion the contents are rapidly mixed. After this point the microcapsules are run for up to 1 min through a 60 cm long microchannel (to allow inhibitor binding). This microchannel is then merged with a second microchannel containing aqueous microcapsules containing the fluorogenic PTP1B substrate 6,8-difluoro-4-methylumbelliferyl phosphate (DiFMUP) (Molecular Probes) in 25 mM HEPES, pH 7.4, 125 mM NaCl, 1 mM EDTA and the microcapsules fused pairwise. The fused microcapsules are then run for up to 2 min through a 60 cm long microchannel. Fluorescence of the microcapsules due to production of DiFMU (excitation/emission maxima 358/452 nm; blue fluorescence) is measured. Predominantly, microcapsules exhibiting blue fluorescence are those containing hydrocinnamic acid whereas microcapsules containing compound 2 exhibit low fluorescence due to inhibition of PTP1B.

Example 3

Screening of PTP1B Inhibitors from a Compound Library 96 aqueous mixtures are made on ice (to prevent reaction). The first mixture contains 100 µM compound 2 (FIG. 17), which has a bis-difluoromethylene phosphonate and is a known PTP1B inhibitor (Johnson et al., 2002), and a pre-defined ratio of Qdot™ Streptavidin Conjugates with emission maxima at 585 nm, 655 nm and 705 nm (Quantum Dot Corporation, Hayward Calif.) in a buffer compatible with PTP1B activity (25 mM HEPES, pH 7.4, 125 mM NaCl, 10% glycerol, 1 mM EDTA) (Doman et al., 2002). The 95 other aqueous mixtures are identical to the above but each contain one of 95 carboxylic acids from the Carboxylic Acid Organic Building Block Library (Aldrich) in place of compound 2, and different ratios of Qdot™ Streptavidin Conjugates with emission maxima at 585 nm, 655 nm and 705 nm. In all mixtures the concentration of the 705 nm Qdot™, Streptavidin Conjugates is 100 nM, and the concentrations of the 585 nm and 655 nm Qdot™ Streptavidin Conjugates is either 0, 11, 22, 33, 44, 55, 66, 77, 88 or 100 nM. Hence, there are 100 (10×10) permutations of Qdot™ Streptavidin Conjugate concentrations which allows the microcapsules containing each compound to have a unique fluorescence signature which is read by determining the fluorescence ratio of fluorescence at 705 nm, 585 nm and 655 nm.

The 96 mixtures are distributed into 96 wells of a microtitre plate. Aliquots from each well of the plate are loaded sequentially into the microfluidic device described in Example 1 using thin tubes connected to the microfluidic device which are dipped into reservoirs containing the desired compounds, and capillary action is used to draw the desired compound from the reservoir into the microfluidic device. The mixtures are compartmentalised into microcapsules in the device. Each microcapsule is fused with another microcapsule containing the target enzyme (human recombinant PTP1B, residues 1-322; Biomol Research Laboratories, Inc.) at 5 mU/ml and rapidly mixed. After incubating for 10 min, at 37° C. in a delay line the microcapsule is fused with a further microcapsule containing the fluorogenic PTP1B substrate 6,8-difluoro-4-methylumbelliferyl phosphate (DiFMUP) (Molecular Probes), and incubated at 37° C. for 30 min. in a delay line. Inhibitors reduce the amount of non-fluorescent substrate (DiFMUP) converted to the dephosphorylated product (DiFMU; excitation/emission maxima 358/452 nm; blue fluorescence). Microcapsule fluorescence is then analysed. Predominantly, all microcapsules exhibited blue fluorescence due to dephosphorylation of DiFMUP by PTP1B except those with the Qdot fluorescence signature of the microcapsules containing compound 2.

Example 4

Attachment of a Compound Library to Microbeads 5.5 µm diameter polystyrene microbeads that bear carboxylate functional groups on the surface are commercially available (Luminex Corporation) in an optically tagged form, as a result of incorporation of precise ratios of orange (585 nm), and red (>650 mm) fluorochromes (Fulton et al., 1997). A set of 100 such beads, each with a unique optical signature are modified with an excess of ethylenediamine and EDC (1-ethyl-3-(3-dimethylaminopropyl)carbodiimide hydrochloride (Pierce) as (Hermanson, 1996) to create primary amino groups on the surface. The photocleavable linker 4-(4-hydroxymethyl-2-methoxy-5-nitrophenoxy)butanoic acid (NovaBiochem) (Holmes and Jones, 1995) is then attached to the beads by forming an amide bond using EDC as above. 100 different carboxylic acids from the Carboxylic Acid Organic Building Block Library (Aldrich) are then coupled to the beads, by reacting with the linker alcohol to form a carboxylate ester, each of the 100 different optically tagged beads being coupled to a different carboxylic acid, and each bead being derivatised with ~$10^6$ molecules of carboxylic acid. Irradiation for 4 min on ice using a B100 AP 354 nm UV lamp (UVP) from a distance of ~5 cm results in release of the compounds from the beads as carboxylic acids.

Example 5

Screening for Inhibitors of the Enzyme Protein Tyrosine Phosphatase 1B (PTP1B) Using Compounds Attached to Microbeads 5.5 μm diameter polystyrene microbeads that bear carboxylate functional groups on the surface are commercially available (Luminex Corporation) in an optically tagged form, as a result of incorporation of precise ratios of orange (585 nm), and red (>650 nm) fluorochromes (Fulton et al., 1997). First, the carboxylate functional groups on the microbeads are converted to primary amines using ethylenediamine and EDC as in example 6. A phosphopeptide substrate for PTP1B, the undecapeptide EGFR$_{988-998}$ (DADEpYLIPQQG; SEQ ID NO: 1) (Zhang et al., 1993), is then coupled to both sets of microbeads via the surface amino groups using EDC. This peptide is made by solid phase synthesis on Sieber Amide resin (9-Fmoc-aminoxanthen-3-yloxy-Merrifield resin) (Novabiochem) with orthogonal protection on the side chain carboxylate groups using carboxylate-O-allyl esters. A linker comprised of tetradecanedioic acid is coupled to the N-terminus and the peptide cleaved from the beads using 1% TFA to yield a peptide with a C-terminal amide The peptide is coupled to the beads (using EDC) via the linker to give ~$10^5$ peptides per bead. The remaining surface amino groups are then modified by attaching the photochemically cleavable linker 4-(4-hydroxymethyl-2-methoxy-5-nitrophenoxy)butanoic acid as in example 6. The protecting groups on the side chain carboxylates of the peptide are then removed using Pd(Ph$_3$)$_4$/CHCl$_3$/HOAc/N-methyl morpholine. A first set of microbeads is derivatised with 3-(4-difluorophosphonomethylphenyl)propanoic acid (compound 1, FIG. 17), a compound that is a known PTP1B inhibitor (Johnson et al., 2002). A second set of beads, with a distinct optical tag from the first set of beads, is derivatised with hydrocinnamic acid (Aldrich), a compound that is not a PTP1B inhibitor. In each case the compound is coupled by reacting with the linker alcohol to form a carboxylate ester as in example 6. Each microbead is derivatised with ~$10^6$ molecules (Fulton et al., 1997).

The microbeads are then screened using the microfluidic system outlined in FIG. 15. The two sets of microbeads are mixed in ratios varying from 1:1000 to 1:1 (compound 1 beads: hydrocinnamic acid beads) and $10^8$ total microbeads are mixed with the target enzyme (human recombinant PTP1B, residues 1-322; Biomol Research Laboratories, Inc.) at a concentration of 10 nM, on ice (to prevent reaction) in a buffer compatible with PTP1B activity (25 mM HEPES, pH 7.4, 125 mM NaCl, 10% glycerol, 1 mM EDTA) (Doman et al., 2002). Single beads and target enzyme (PTP1B) are then colocalised in microcapsules by forming microcapsules using the microfluidic system described in Example 1. The concentration of beads is such that most microcapsules contain one or no beads. Each microcapsule is fused with another microcapsule containing the target enzyme (human recombinant PTP1B, residues 1-322; Biomol Research Laboratories, Inc.) at 5 mU/ml and rapidly mixed. The compound is released photochemically (as in example 4). After incubating for 10 min, at 37° C. in a delay line the microcapsule is fused with a further microcapsule containing the fluorogenic PTP1B substrate 6,8-difluoro-4-methylumbelliferyl phosphate (DiFMUP) (Molecular Probes), and incubated at 37° C. for 30 min. in a delay line. Inhibitors reduce the amount of substrate converted to product (dephosphorylated peptide). The microcapsules are collected, cooled to 4° C. and broken as (Griffiths and Tawfik, 2003) into 100 μM vanadate to stop the reaction (Harder et al., 1994). After labelling with an anti-substrate (anti-phosphotyrosine) antibody labelled with the green (530 nm) fluorochrome fluorescein isothiocyanate (mouse monoclonal IgG$_{2b}$ PY20 (Santa Cruz) according to the manufacturer's instructions, beads are analysed by 3-colour flow cytometry using a FACScan (Becton-Dickinson), FACScalibur (Becton-Dickinson) or MoFlo (Cytomation) flow cytometers to simultaneously determine the extent of inhibition and the compound on the beads. Predominantly, dephosphorylation of the peptide is only observed on those microbeads which were coated with PTP1B inhibitors, and not on other microbeads.

Example 6

Screening of PTP1B Inhibitors from a Compound Library Attached to Microbeads

A set of 100 5.5 μm diameter polystyrene microbeads, bearing carboxylate functional groups on the surface and each with a unique optical signature (Luminex Corporation) as a result of incorporation of precise ratios of orange (585 nm), and red (>650 nm) fluorochromes (Fulton et al., 1997) are derivatised with a phosphopeptide substrate for PTP1B, the undecapeptide EGFR$_{988-998}$(DADEpYLIPQQG; SEQ ID NO: 1) (Zhang et al., 1993), and 100 different carboxylic acids, each attached via a photochemically cleavable linker, as in example 4. One of these carboxylic acids is 3-(4-difluorophosphonomethylphenyl) propanoic acid (compound 1, FIG. 17), a compound that is a known PTP1B inhibitor (Johnson et al., 2002). The other 99 carboxylic acids are from the Carboxylic Acid Organic Building Block Library (Aldrich) as example 4. Equal numbers of each of the 100 bead sets are then mixed and screened as for example 5. Predominantly, dephosphorylation of the peptide is only observed on those microbeads which were coated with the PTP1B inhibitor 3-(4-difluorophosphonomethylphenyl) propanoic acid (compound 1, FIG. 17), and not on microbeads coated with other compounds.

Example 7

Compartmentalisation of Small Molecules in a Water-in-Fluorocarbon Emulsions

Figure 19:
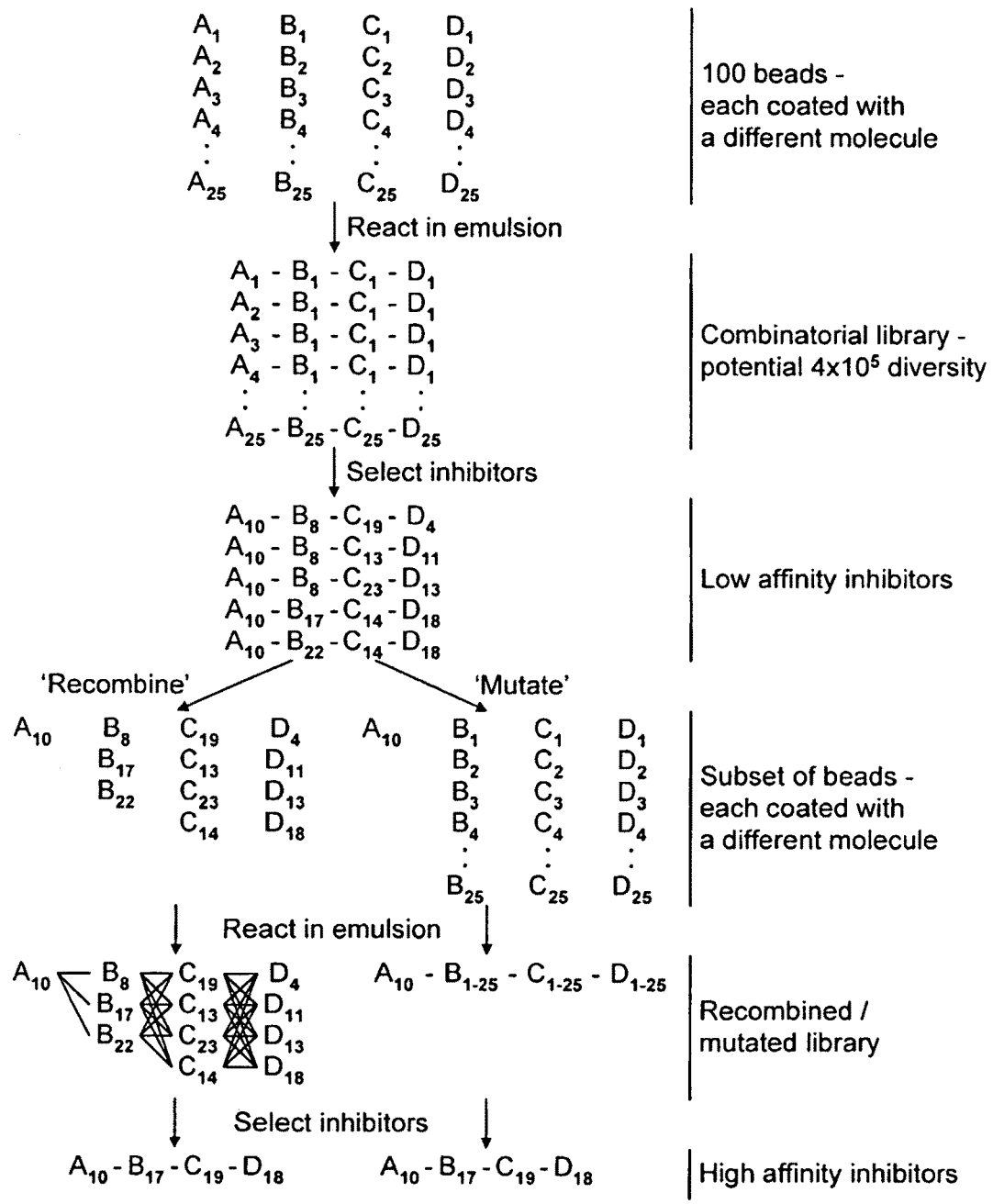
FIG. 19. Synthesising PTP1B inhibitors in an emulsion. Two types of beads are created, differentially labelled with orange and red fluorochromes, and derivatised with two types of molecule, A or B (neither, one, or both of which contain a difluoromethylene phosphonate moiety), attached via a reversible connection (a Schiff base). Beads are emulsified using a microfluidic device to give, on averages two beads per compartment. The molecules, A & B, are released from the beads in the compartment and react to form a new molecule, A-B, (in solution). If A-B is a PTP1B inhibitor the PTP1B substrate also on the beads is not dephosphorylated and these beads identified by flow cytometry as FIG. 18.
Figure 20:
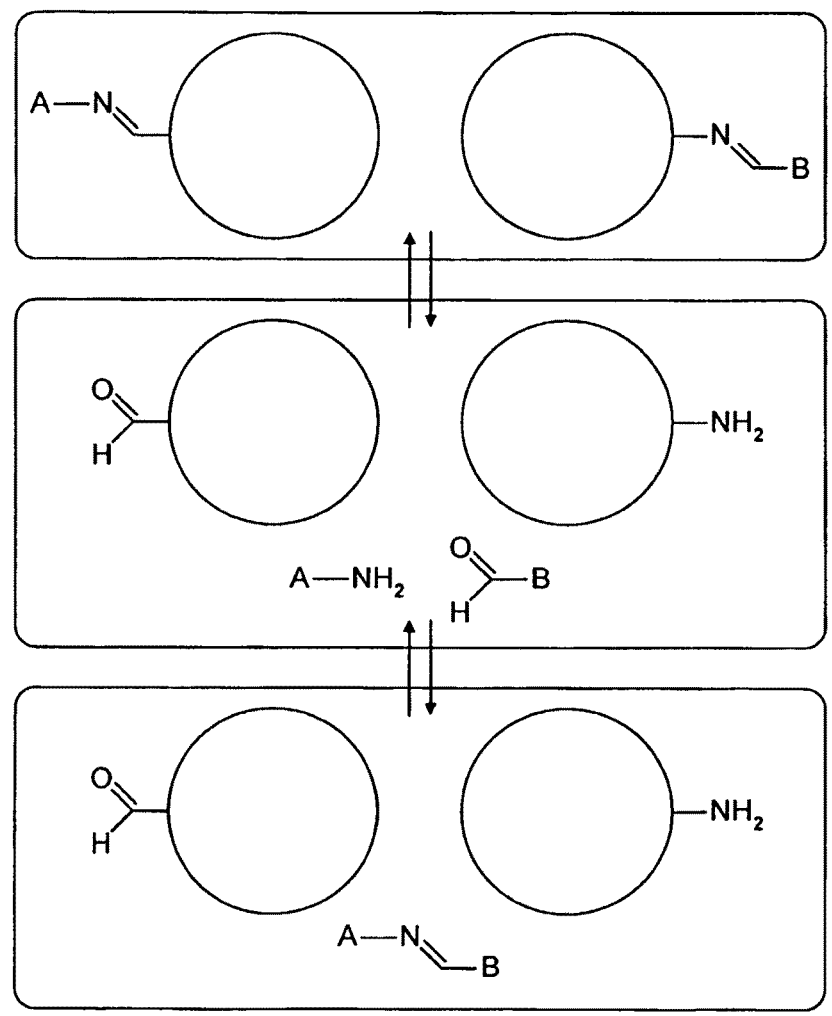
FIG. 20. Small molecule evolution using four-component reactions. Four sets of 25 beads are created, each derivatised with one of 25 variants of molecules A, B, C or D, emulsified to give, on average, 4 beads per compartment, the compounds released to synthesise a large combinatorial repertoire (4×10$^5$) in situ and screened as FIG. 18. Low affinity inhibitors will be 'recombined' by re-screening mixtures of beads carrying moieties identified in inhibitors. Beads carrying a moiety found in inhibitors (e.g. $A_{10}$) can also be mixed with complete sets of beads coated with B, C and D and screened. If a moiety (say $B_8$) is then identified as a component of an inhibitor, beads coated with $A_{10}$ and $B_8$ can be mixed with complete sets of beads C and D and the process repeated. This process of 'mutation' also results in deconvolution. After fixing three of the four moieties in active compounds, deconvolution can be completed using multiplex bead analysis as above. Compounds can be re-diversified or 'mutated' using bead sets carrying variant, exploded sets of the molecules used in the original libraries.
Figure 21:
FIG. 21. Compartmentalisation of small molecules in water-in-fluorocarbon emulsions. Water-in-perfluorooctyl bromide emulsions were made containing texas red (1 mM) and calcein (1 mM) in the aqueous phase by homogenisation as described in example 6 The two emulsions were mixed by vortexing and imaged by epifluorescence microscopy after 24 hours. No exchange of texas-red (red fluorescence) and calcein (green fluorescence) between microdroplets could be observed.

Water-in-fluorocarbon emulsions containing 95% (v/v) perfluorooctyl bromide, 5% (v/v) phosphate buffered saline containing the molecule of interest in solution, and 2% (w/v) C$_8$F$_{17}$C$_{11}$H$_{22}$OP(O)[N(CH$_2$CH$_2$)$_2$O]$_2$ (F8H11DMP) as surfactant were formed essentially as (Sadtler et al., 1996) by extrusion (15 times) through 14 µm filters (Osmonics) or by homogenising for 5 min at 25,000 r.p.m. using an Ultra-Turrax T8 Homogenizer (IKA) with a 5 mm dispersing tool. Emulsions were made containing a series of small fluorescent molecules dissolved in the aqueous phase at concentrations from 100 µm to 2 mM. These molecules, including calcein, texas red, fluorescein, coumarin 102, 7-hydroxycoumarin-3-carboxylic acid and 7-diethylamino-4-methyl coumarin (coumarin 1), had molecular weights from 203 to 625 Da and LogP values—calculated using SRC's LogKow/KowWin Program (Meylan and Howard, 1995)—ranging from −0.49 to 4.09. Emulsions containing different coloured fluorochromes were mixed by vortexing. Compartmentalisation was observed by epifluorescence microscopy of the mixed emulsions. No exchange between compartments was observed 24 hours after mixing (see FIG. 19).

Example 8

Compartmentalisation of Small Molecules in a Water-in-Fluorocarbon Emulsions Made Using Microfluidic Systems Water-in-fluorocarbon emulsions containing 95% (v/v) perfluorooctyl bromide, 5% (v/v) phosphate buffered saline containing the molecule of interest in solution, and 2% (w/v) $C_8F_{17}C_{11}H_{22}OP(O)[N(CH_2CH_2)_2O]_2$ (F8H11DMP) as surfactant were formed essentially using multiple droplet generation modules as described in Example 1. The aqueous phase at each of the nozzles contained a different small fluorescent molecules dissolved at concentrations from 100 µM to 2 mM. These molecules, including calcein, texas red, fluorescein, coumarin 102, 7-hydroxycoumarin-3-carboxylic acid and 7-diethylamino-4-methyl coumarin (coumarin 1), had molecular weights from 203 to 625 Da and LogP values—calculated using SRC's LogKow/KowWin Program (Meylan and Howard, 1995) —ranging from −0.49 to 4.09. Emulsions containing different coloured fluorochromes were mixed by combining the streams carrying the droplet having different fluorofers into a single stream containing all types of droplets. The stream carrying the collection of droplets then empties into a deep well on the device where the droplets can be stored in close proximity and monitored over time up to 24 hours. No cross contamination between the droplets is observed.

Example 9

Determining Mode of Inhibition and $K_i$ of PETG on β-Galactosidase

Using a microfluidic device as described in Example 1, we demonstrate that the mode of inhibition of the enzyme *E. coli* β-galactosidase (LacZ), by phenylethyl β-D-thiogalactopyranoside (PETG), is competitive, and we show how we can obtain the inhibition constant ($K_i$) of PETG. In the enzyme inhibition assay, the rate of catalysis is determined by using a non-fluorescent substrate for LacZ, fluorescein mono-β-D-galactoside (FMG), and measuring the appearance of the fluorescent product, fluorescein (excitation 488 nm, emission 514 nm). All components of the LacZ inhibition assay are dissolved in assay buffer (10 mM $MgCl_2$, 50 mM NaCl, 1 mM DTT, 100 µg/ml BSA, 10 mM Tris-HCl, pH 7.9.

Leading into each droplet forming module (FIG. 15) are two Teflon tubes leading from syringe pumps. The channels leading from each tube merge to create a single flow before entering the droplet forming module. The two syringes feeding into the first droplet forming module contain, (a) 50 µM PETG in assay buffer, and (b), assay buffer. The two syringes feeding into the second droplet forming module contain, (c) 100 nM LacZ in assay buffer and (d), assay buffer. The two syringes feeding into the third droplet forming module contain, (e) 5 mM FMG in assay buffer, and (f), assay buffer. The final concentration of each component in each droplet is independently controllable by adjusting relative flow rates of each component and buffer solution while maintaining a constant combined flow rate from both syringes.

The first droplet fusion mixes the inhibitor (PETG) with the enzyme (LacZ). After the combined droplet has spent two minutes in a delay line it is fused with a third droplet containing the fluorogenic enzyme substrate (FMG). Finally, after all the components are mixed the reaction is observed by measuring fluorescence of individual droplets or by integrating fluorescent light from droplets with the same concentration of each component during 10-second exposure time at multiple points in the second 10 min long delay line. Each fluorescence intensity value at different positions is proportional to the amount of product at different reaction times. Rate of product formation is linear during initial reaction time and initial rate (v) can be determined from linear fitting. Data from the repeated measurement at different concentration of FMG and PETG are expressed in a Lineweaver-Burk plot (1/v vs. 1/[S]; where [S]=substrate concentration). The same y-intercept values at different concentration of PETG show that the mode of PETG inhibition is competitive. In competitive inhibition, each slope divided by the y-intercept represents an apparent Michaelis-Menten constant that is a linear function of the concentration of inhibitor. The y-intercept in a graph of apparent Michaelis-Menten constant versus competitive inhibitor concentration gives the Michaelis-Menten constant, and the inverse of its slope multiplied by the y-intercept is $K_i$. Using the following conditions (in the final fused microcapsule), 30 nM LacZ, 0 to 13 µM PETG and 10 to 700 µM FMG the $K_M$ of FMG for LacZ can be determined to within 20% of the previously published value (118 µM; Huang, 1991), and the $K_i$ of PETG for LacZ can be determined to be within the range of the previously published value (0.98 µM; Huang, 1991).

Example 10

Synthesis of Secondary Compounds in Emulsion Microcapsules and Screening for PTP1B Inhibition in Microfluidic Systems Using a microfluidic device as described in Example 1, we describe how PTP1B inhibitors can be synthesised and screened using microcapsules in a microfluidic system.

All water-soluble reagents are dissolved in (25 mM HEPES, pH 7.4, 125 mM NaCl, 1 mM EDTA), a buffer compatible with PTP1B activity. A compound which is a primary amine is compartmentalised into microcapsules using the device. A second solution, of a compound which is an aldehyde is also compartmentalised into microcapsules using the device. The amines and aldehydes can either a) contain a difluoromethylene phosphonate moiety (FIG. 22, compounds A and B), or b) contain no difluoromethylene phosphonate moiety. Each microcapsule containing a primary amine is fused with a microcapsule containing an aldehyde. Microcapsules containing compounds with and without difluoromethylene phosphonate moieties can be formed by switching between injection with syringes containing amines or aldehydes with or without a difluoromethylene phosphonate moiety.

After microcapsule fusion the contents are rapidly mixed and the microcapsules pass down a delay line. This allows the amine and the aldehyde to react together by formation of a Schiff base to create a secondary compound and allows inhibitors to bind to PTP1B. Each microcapsules are then fused with a further microcapsule containing a solution of the target enzyme (human recombinant PTP1B, residues 1-322; Biomol Research Laboratories, Inc.) at 50 mU/ml, and the fluorogenic PTP1B substrate 6,8-difluoro-4-methylumbelliferyl phosphate (DiFMUP) (Molecular Probes). The fused microcapsules then run along a further delay line. Fluorescence of the microcapsules due to production of DiFMU (excitation/emission maxima 358/452 nm; blue fluorescence) is measured.

Predominantly, when the amine and aldehyde concentrations are low (<100 µM) inhibition of PTP1B activity is only observed in microcapsules containing both an amine with a difluoromethylene phosphonate moiety (compound A,) and an aldehyde with a difluoromethylene phosphonate moiety (compound B,). This because the Schiff base formed in these microcapsules (compound C,) contains bis-difluoromethylene phosphonate and is a much more potent PTP1B inhibitor than a molecule with a single difluoromethylene phosphonate moiety.

Predominantly, when the amine and aldehyde concentrations are high (>100 µM) inhibition of PTP1B activity is observed in microcapsules containing either an amine with a difluoromethylene phosphonate moiety (compound A, or an aldehyde with a difluoromethylene phosphonate moiety (compound B,), or both, but not in other microcapsules. This is because at higher concentrations molecules with either a single difluoromethylene phosphonate moiety or a bis-difluoromethylene phosphonate (compound C, FIG. 22) can inhibit PTP1B.

Example 11

Synthesis of a Library of 2304 Secondary Compounds in Emulsion Microcapsules and Screening of PTP1B Inhibition in Microfluidic Systems 96 aqueous mixtures are made in a buffer compatible with PTP1B activity (25 mM HEPES, pH 7.4, 125 mM NaCl, 10% glycerol, 1 mM EDTA) (Doman et al., 2002) and containing the target enzyme (human recombinant PTP1B, residues 1-322; Biomol Research Laboratories, Inc.) at a concentration of 5 mU/ml. The first 48 mixtures each contain a unique compound containing a primary amine. One of these compounds (compound A, FIG. 22) contains a difluoromethylene phosphonate moiety. The second 48 mixtures of microbeads each contain a unique compound containing an aldehyde. One of these compounds (compound B, FIG. 22) contains a difluoromethylene phosphonate moiety.

The 96 mixtures are distributed into 96 wells of a microtitre plate. Aliquots from each well of the plate are loaded sequentially into the microfluidic device described in Example 1 using thin tubes connected to the microfluidic device which are dipped into reservoirs containing the desired compounds, and capillary action is used to draw the desired compound from the reservoir into the microfluidic device. The mixtures are compartmentalised into microcapsules in the device.

Each microcapsule containing an amine is fused with a microdroplet containing an aldehyde and incubated for 10 min, at 37° C. in a delay line. The amine and the aldehyde react together by forming a Schiff base, resulting in the creation of a new molecule (an imine) in solution. The microcapsule is then fused with a further microcapsule containing the fluorogenic PTP1B substrate 6,8-difluoro-4-methylumbelliferyl phosphate (DiFMUP) (Molecular Probes), and incubated at 37° C. for 30 min. in a delay line. Inhibitors reduce the amount of non-fluorescent substrate (DiFMUP) converted to the dephosphorylated product (DiFMU; excitation/emission maxima 358/452 nm; blue fluorescence). Microcapsule fluorescence is then analysed.

Microcapsules containing a primary compound which is itself a PTP1B inhibitor, or which reacts with another primary compound to form a second inhibitor are identified as little substrate has been converted to product. When the compounds are present in the microcapsules at high concentration, the identified microcapsules where little substrate has been converted to product include those carrying compounds containing a difluoromethylene phosphonate moiety. When the compounds are present in the microcapsules at low concentration, the concentration of the compounds containing a difluoromethylene phosphonate moieties in the microcapsules is insufficient to efficiently inhibit PTP1B (see example 10). However, in microcapsules where two primary compounds have reacted to form an imine containing a bis-difluoromethylene phosphonate moiety, which is a highly potent PTP1B inhibitor (compound C, FIG. 22), this inhibits conversion of the PTP1B substrate to product and little fluorescence is observed.

Example 12

Synthesis of Secondary Compounds in Emulsion Microcapsules and Screening for

A set of 100 5.5 µm diameter polystyrene microbeads, bearing carboxylate functional groups on the surface and each with a unique optical signature (Luminex Corporation) as a result of incorporation of precise ratios of orange (585 nm), and red (>650 nm) fluorochromes (Fulton et al., 1997) are modified to convert the carboxylate functional groups to primary amines as in example 4, then derivatised with a phosphopeptide substrate for PTP1B, the undecapeptide EGFR$_{988-998}$(DADEpYLIPQQG; SEQ ID NO: 1) (Zhang et al., 1993), as in example 5. The first 50 sets of microbeads are reacted to convert a proportion of the surface carboxyl groups to aldehydes as in example 10. The second 50 sets of microbeads are left unreacted (i.e. with primary amines on the surface).

The first set of microbeads (set 1), are then reacted with a compound containing a difluoromethylene phosphonate moiety and a primary amine (compound A, FIG. 22) via reaction with the surface aldehyde groups to form a Schiff base. The second set of microbeads (set 2), with a distinct optical tag from the first set of beads, are reacted with a compound containing a difluoromethylene phosphonate moiety and an aldehyde (compound B, FIG. 22) via reaction of the aldehyde with the surface amine groups to form a Schiff base. The formation of Schiff bases is enhanced by reaction at alkaline pH (i.e. pH9-10). Microbeads coated with compounds at various densities are created.

The two sets of microbeads are separately suspended in a buffer compatible with PTP1B activity (25 mM HEPES, pH 7.4, 125 mM NaCl, 10% glycerol, 1 mM EDTA) (Doman et al., 2002). Each set of microbeads is compartmentalised into microcapsules in the device described in Example 1. The number of microbeads is varied such that, at one extreme, most microcapsules contain one or no beads, and at the other, the majority of microcapsules contain two or more microbeads. Each microcapsule containing a set 1 microbead is fused with a microcapsule containing a set 2 microbead and incubated for 10 min, at 37° C. in a delay line. The Schiff base is a relatively labile, reversible interaction, readily hydrolysed at neutral pH, resulting in release of compounds from the beads. In microcapsules containing a microbead from both set 1 and set 2, the compounds released from the microbeads can react with each other, forming a Schiff base and creating a new molecule in solution. This new molecule (FIG. 22, compound C) contains a bis-difluoromethylene phosphonate moiety and has significantly more potency as a PTP1B inhibitor than compounds with a single difluoromethylene phosphonate moiety (see FIG. 22). The microcapsule is then fused with a further microcapsule containing the target enzyme (human recombinant PTP1B, residues 1-322; Biomol Research Laboratories, Inc.) at a concentration of 5 mU/ml in 25 mM HEPES, pH 7.4, 125 mM NaCl, 10% glycerol, 1 mM EDTA, and incubated at 37° C. for 30 min. in a delay line. Inhibitors reduce the amount of substrate converted to product (dephosphorylated peptide). The microcapsules are collected, cooled to 4° C., and broken into 100 μM vanadate to stop the reaction (Harder et al., 1994). After labelling with an anti-substrate (anti-phosphotyrosine) antibody labelled with the green (530 nm) fluorochrome fluorescein isothiocyanate (mouse monoclonal $IgG_{2b}$ PY20 (Santa Cruz) according to the manufacturer's instructions, beads are analysed by 3-colour flow cytometry using a FACScan (Becton-Dickinson), FACScalibur (Becton-Dickinson) or MoFlo (Cytomation) flow cytometers to simultaneously determine the extent of inhibition and the compound on the beads. With low microbead numbers, most microcapsules contain only a single or no microbeads and PTP1B inhibition is only detected on beads coated with a high density of inhibitor, when the concentration of inhibitor released into solution in each microcapsule is sufficiently high for effective inhibition. In contrast, when the bead numbers are higher, many microbeads are detected where little substrate has been converted to product, even when the microbeads are coated with inhibitor at low density. This is due to the formation of a highly potent PTP1B inhibitor (FIG. 22, compound C) containing a bis-difluoromethylene phosphonate moiety in microcapsules containing a microbead each from set 1 and set 2.

Example 13

Synthesis of a Library of 2500 Secondary Compounds in Emulsion Microcapsules and Screening for PTP1B Inhibition Using Compounds Attached to Microbeads in Microfluidic Systems A set of 100 5.5 μm diameter polystyrene microbeads, bearing carboxylate functional groups on the surface and each with a unique optical signature (Luminex Corporation) as a result of incorporation of precise ratios of orange (585 nm), and red (>650 nm) fluorochromes (Fulton et al., 1997) are modified to convert the carboxylate functional groups to primary amines as in example 4, then derivatised with a phosphopeptide substrate for PTP1B, the undecapeptide $EGFR_{988-998}$ (DADEpYLIPQQG; SEQ ID NO: 1) (Zhang et al., 1993), as in example 5. The first 50 sets of microbeads are reacted to convert a proportion of the surface carboxyl groups to aldehydes as in example 10. The second 50 sets of microbeads are left unreacted (i.e. with primary amines on the surface).

The first 50 sets of microbeads are each reacted with a unique compound containing a primary amine via reaction with the surface aldehyde groups to form a Schiff base which links the compounds to the beads. One of these compounds (compound A, FIG. 22) contains a difluoromethylene phosphonate moiety. The second 50 sets of microbeads are each reacted with a unique compound containing an aldehyde via reaction with the surface amine groups to form a Schiff base which links the compounds to the beads. One of these compounds (compound B, FIG. 22) contains a difluoromethylene phosphonate moiety. The formation of Schiff bases is enhanced by reaction at alkaline pH (i.e. pH9-10).

The 50 sets of microbeads which were reacted with primary amines (amine microbeads) are pooled and suspended in a buffer compatible with PTP1B activity (25 mM HEPES, pH 7.4, 125 mM NaCl, 10% glycerol, 1 mM EDTA) (Doman et al., 2002). The 50 sets of microbeads which were reacted with aldehydes (aldehyde microbeads) are pooled and suspended in the same buffer. The amine microbeads and the aldehyde microbeads are compartmentalised into microcapsules in the device described in Example 1. The number of microbeads is set such that the majority of microdroplets contain a single microbead. Each microcapsule containing an amine microbead is fused with a microcapsule containing an aldehyde microbead and incubated for 10 min, at 37° C. in a delay line. The microcapsule is then fused with a further microcapsule containing the target enzyme (human recombinant PTP1B, residues 1-322; Biomol Research Laboratories, Inc.) at a concentration of 5 mU/ml in 25 mM HEPES, pH 7.4, 125 mM NaCl, 10% glycerol, 1 mM EDTA, and incubated at 37° C. for 30 min. in a delay line. The Schiff base is a relatively labile, reversible interaction, readily hydrolysed at neutral pH, resulting in release of compounds from the beads. In microcapsules containing a microbead from one of the first 50 sets and a microbead from one of the second 50 sets, the compounds released from the microbeads can react with each other, forming a Schiff base and creating a new molecule in solution. Inhibitors reduce the amount of substrate converted to product (dephosphorylated peptide). The microcapsules are collected, cooled to 4° C., and broken into 100 μM vanadate to stop the reaction (Harder et. al., 1994). After labelling with an anti-substrate (anti-phosphotyrosine) antibody labelled with the green (530 nm) fluorochrome fluorescein isothiocyanate (mouse monoclonal $IgG_{2b}$ PY20 (Santa Cruz) according to the manufacturer's instructions, beads are analysed by 3-colour flow cytometry using a FACScan (Becton-Dickinson), FACScalibur (Becton-Dickinson) or MoFlo (Cytomation) flow cytometers to simultaneously determine the extent of inhibition and the compound on the beads.

Beads which were coated with a primary compound which is itself a PTP1B inhibitor, or which reacts with another primary compound released from another co-compartmentalised bead to form a second inhibitor are identified as little substrate has been converted to product. The identified beads where as little substrate has been converted to product include those carrying compounds containing a difluoromethylene phosphonate moiety. When the microbeads are coated with compounds at low density the concentration of the released compounds containing a difluoromethylene phosphonate moieties in the microcapsules is insufficient to efficiently inhibit PTP1B (see example 12). However in microcapsules containing two microbeads, one from the first set of 50 beads and one from the second set of 50 beads, and where each microbead carries a molecule with a difluoromethylene phosphonate moiety, the released molecules can form a highly potent PTP1B inhibitor (compound C, FIG. 22) containing a bis-difluoromethylene phosphonate moiety in the microcapsules which inhibits conversion of the PTP1B substrate to product.

REFERENCES

Adang, A. E., and Hermkens, P. H. (2001). The contribution of combinatorial chemistry to lead generation: an interim analysis. Curr Med Chem 8, 985-998.

Anderson, J. E. (1993). Restriction endonucleases and modification methylases. Curr Op Struct Biol 3, 24-30.

Becher, P. (1957) *Emulsions: theory and practice*. Reinhold, New York.

Benita, S. (ed.). (1996) *Microencapsulation: methods and industrial applications*. Marcel Dekker, New York.

Bernath, K., Hai, M., Mastrobattista, E., Griffiths, A. D., Magdassi, S, and Tawfik, D. S. (2004) In vitro compartmentalization by double emulsions: sorting and gene enrichment by fluorescence activated cell sorting. *Anal Biochem*, 325, 151-157.

Bru, R. and Walde, P. (1991) Product inhibition of alpha-chymotrypsin in reverse micelles. *Eur J Biochem*, 199, 95-103.

Bru, R. and Walde, P. (1993) Catalytic activity of elastase in reverse micelles. *Biochem Mol Biol Int*, 31, 685-692.

Burbaum, J. (1998). Miniaturization technologies in HTS: how fast, how small, how soon? Drug Discov Today 3, 313-322.

Calvert, P. (2001) Inkjet printing for materials and devices. *Chem. Mater.,* 13, 3299-3305.

Chakrabarti, A. C., Breaker, R. R., Joyce, G. F. and Deamer, D. W. (1994) Production of RNA by a polymerase protein encapsulated within phospholipid vesicles. *J Mol Evol,* 39, 555-559.

Chang, T. M. (1987) Recycling of NAD(P) by multienzyme systems immobilized by microencapsulation in artificial cells. *Methods Enzymol,* 136, 67-82.

Chang, T. M. S. (1992) Recent advances in artificial cells based on microencapsulation. In Donbrow, M. (ed.), *Microcapsules and nanoparticles in medicine and pharmacy*. CRC Press, Boca Raton, Fla., pp. 323-339.

Creagh, A. L., Prausnitz, J. M. and Blanch, H. W. (1993) Structural and catalytic properties of enzymes in reverse micelles. *Enzyme Microb Technol,* 15, 383-392.

Curran, D. P. (1998) Strategy-level separations in organic synthesis: from planning to practice. *Angew Chem Int Ed,* 37, 1174-1196.

Czarnik, A. W. (1997). Encoding methods for combinatorial chemistry. Curr Opin Chem Biol 1, 60-66.

Davis, S. S., and Walker, I. M. (1987). Multiple emulsions as targetable delivery systems. Methods in Enzymology 149, 51-64.

de Gans, B.-J., Duineveld, P. C. and Schubert, U. S. (2004) Inkjet printing of polymers: state of the art and future developments. *Advanced materials,* 16, 203-213.

Dickinson, E. (1994) Emulsions and droplet size control. In Wedlock, D.J. (ed.), *Controlled particle, droplet and bubble formation*. Butterworth-Heinemann, Oxford, pp. 191-257.

Doi, N., and Yanagawa, H. (1999). STABLE: protein-DNA fusion system for screening of combinatorial protein libraries in vitro. FEBS Lett 457, 227-230.

Doman, T. N., McGovern, S. L., Witherbee, B. J., Kasten, T. P., Kurumbail, R., Stallings, W. C., Connolly, D. T. and Shoichet, B. K. (2002) Molecular docking and high-throughput screening for novel inhibitors of protein tyrosine phosphatase-1B. *J Med Chem,* 45, 2213-2221.

Finch, C. A. (1993) Encapsulation and controlled release. *Spec. Publ.-R. Soc. Chem.,* 138, 35.

Fornusek & Vetvicka, Crit Rev Ther Drug Carrier Syst. 1986; 2(2):137-74

Fu, A. Y., Chou, H. P., Spence, C., Arnold, F. H. and Quake, S. R. (2002) An integrated microfabricated cell sorter. *Anal Chem,* 74, 2451-2457.

Fulton, R. J., McDade, R. L., Smith, P. L., Kienker, L. J. and Kettman, J. R., Jr. (1997) Advanced multiplexed analysis with the FlowMetrix system. *Clin Chem,* 43, 1749-1756.

Ghadessy, F. J., Ong, J. L. and Holliger, P. (2001) Directed evolution of polymerase function by compartmentalized self-replication. *Proc Natl Acad Sci USA,* 98, 4552-4557.

Gordon, K., and Balasubramanian, S. (1999). Solid phase chemistry—designer linkers for combinatorial chemistry. J Chem Technol Biotechnol 74, 835-851.

Griffiths, A. D., Williams, S. C.; Hartley, O., Tomlinson, I. M., Waterhouse, P., Crosby, W. L., Kontermann, R. E., Jones, P. T., Low, N. M., Allison, T. J., and et al. (1994). Isolation of high affinity human antibodies directly from large synthetic repertoires. Embo J 13, 3245-3260.

Griffiths, A. D. and Tawfik, D. S. (2003) Directed evolution of an extremely fast phosphotriesterase by in vitro compartmentalization. *Embo J,* 22, 24-35.

Guixe et al., Ligand-induced conformational transitions in *Escherichia coli* phosphofructokinase 2: evidence for an allosteric site for MgATP2-. Biochemistry. 1998 Sep. 22; 37(38):13269-75.

Haber, J., Maslakiewicz, P., Rodakiewicz, N. J. and Walde, P. (1993) Activity and spectroscopic properties of bovine liver catalase in sodium bis(2-ethylhexyl)sulfosuccinate/isooctane reverse micelles. *Eur J Biochem,* 217, 567-573.

Han, M., Gao, X., Su, J. Z., and Nie, S. (2001). Quantum-dot-tagged microbeads for multiplexed optical coding of biomolecules. Nat Biotechnol 19, 631-635.

Han, M., Gao, X., Su, J. Z. and Nie, S. (2001) Quantum-dot-tagged microbeads for multiplexed optical coding of biomolecules. *Nat Biotechnol,* 19, 631-635.

Handen, J. S. (Summer 2002). High-throughput screening—challenges for the future. Drug Discov World, 47-50.

Harder, K. W., Owen, P., Wong, L. K., Aebersold, R., Clark-Lewis, I., and Jirik, F. R. (1994). Characterization and kinetic analysis of the intracellular domain of human protein tyrosine phosphatase beta (HPTP beta) using synthetic phosphopeptides. Biochem J 298 (Pt 2), 395-401.

Heim R, Tsien R y. Engineering green fluorescent protein for improved brightness, longer wavelengths and fluorescence resonance energy transfer. Curr Biol. 1996 Feb. 1; 6(2):178-82.

Hergenrother, P. J., Depew, K. P., and Schreiber, S. L. (2000). Small-molecule microarrays: covalent attachment and screening of alcohol-containing small molecules on glass slides. J Am Chem Soc 122, 7849-7850.

Hermanson, G. T. (1996) *Bioconjugate techniques*. Academic Press, San Diego.

Hildebrand, J. H. and Cochran, D. F. R. (1949) *J. Am. Chem. Soc.,* 71, 22.

Hochuli, E., Dobeli, H., and Schacher, A. (1987). New metal chelate adsorbent selective for proteins and peptides containing neighbouring histidine residues. J Chromatogr 411, 177-184.

Holmes, C. P., and Jones, D. G. (1995). Reagents for combinatorial organic synthesis: development of a new o-nitrobenzyl photolabile linker for solid phase synthesis. J Org Chem 60, 2318-2319.

Huang, Z. J., Kinetic assay of fluorescein mono-beta-D-galactoside hydrolysis by beta-galactosidase: a front-face measurement for strongly absorbing fluorogenic substrates (1991). Biochemistry. 30, 8530-4.

Hudlicky, M. (1992) *Chemistry of Organic Fluorine Compounds*. Ellis Horwood, New York.

Johannsson, A. (1991). Heterogeneous enzyme immunoassays. In Principles and practice of immunoassays, C. P. Price, and D. J. Newman, eds. (New York, Stockton Press), pp. 295-325.

Johannsson, A., and Bates, D. L. (1988). Amplification by second enzymes. In ELISA and other solid phase immunoassays, D. M. Kemeny, and S. J. Challacombe, eds. (Chichester, John Wiley), pp. 85-106.

Johnson, T. O., Ermolieff, J., and Jirousek, M. R. (2002). Protein tyrosine phosphatase 1B inhibitors for diabetes. Nature Reviews Drug Discovery 1, 696-709.

Keij et al., Cytometry. 1995 Mar. 1; 19(3):209-16

Kerker, Cytometry. 1983 July; 4(1):1-10

Klug, A. (1995). Gene regulatory proteins and their interaction with DNA. Ann N Y Acad Sci 758, 143-160.

Klug, A., and Schwabe, J. W. (1995). Protein motifs 5. Zinc fingers. Faseb J 9, 597-604.

Krafft, M. P., Chittofrati, A. and Riess, J. G. (2003) Emulsions and microemulsions with a fluorocarbon phase. *Curr. Op. Colloid Interface Sci.*, 8, 251-258.

Kumar, A., Kumar, A. and Katiyar, S. S. (1989) Activity and kinetic characteristics of glutathione reductase in vitro in reverse micellar waterpool. *Biochim Biophys Acta*, 996, 1-6.

Lee, Y.-F., Tawfik D. S., and Griffiths, A. D. (2002). Investigating the target recognition of DNA cytosine-5 methyltransferase HhaI by library selection using in vitro compartmentalisation (IVC). Nucleic Acids Res 30, 4937-4944.

Lim, F. (ed.). (1984) *Biomedical applications of microencapsulation*. CRC Press, Boca Raton, Fla.

Lim, F. and Sun, A. M. (1980) Microencapsulated islets as bioartificial endocrine pancreas. *Science*, 210, 908-910.

Link, D. R., Anna, S. L., Weitz, D. A. and Stone, H. A. (2004) Geometrically mediated breakup of drops in microfluidic devices. *Phys. Rev. Letts.*, 92, 054503.

Lipinski, C. A., Lombardo, F., Dominy, B. W. and Feeney, P. J. (2001) Experimental and computational approaches to estimate solubility and permeability in drug discovery and development settings. *Adv Drug Deliv Rev*, 46, 3-26.

Lissant, K. J. (ed.). (1974) *Emulsions and emulsion technology*. Marcel Dekker, New York.

Lissant, K. J. (ed.). (1984) *Emulsions and emulsion technology*. Marcel Dekker, New York.

Lowe, K. C. (2002) Perfluorochemical respiratory gas carriers: benefits to cell culture systems. *J. Fluorine Chem.*, 118, 19-26.

Luisi, P. L. and B., S.-H. (1987) Activity and conformation of enzymes in reverse micellar solutions. *Methods Enzymol*, 136, 188-216.

Lyne, P. D. (2002). Structure-based virtual screening: an overview. Drug Discov Today 7, 1047-1055.

Mackenzie and Pinder, Dev Biol Stand. 1986; 64:181-93.

Mahajan N P, Linder K, Berry G, Gordon G W, Heim R, Herman B. Bcl-2 and Bax interactions in mitochondria probed with green fluorescent protein and fluorescence resonance energy transfer. Nat. Biotechnol. 1998 June; 16(6):547-52.

Mao, Q. and Walde, P. (1991) Substrate effects on the enzymatic activity of alpha-chymotrypsin in reverse micelles. *Biochem Biophys Res Commun*, 178, 1105-1112.

Mao, Q., Walde, P. and Luisi, P. L. (1992) Kinetic behaviour of alpha-chymotrypsin in reverse micelles. A stopped-flow study. *Eur J Biochem*, 208, 165-170.

Masui and Kuramitsu, Probing of DNA-binding sites of *Escherichia coli* RecA protein utilizing 1-anilinonaphthalene-8-sulfonic acid. Biochemistry. 1998 Sep. 1; 37 (35): 12133-43

McDonald, J. C. and Whitesides, G. M. (2002) Poly(dimethylsiloxane) as a material for fabricating microfluidic devices. *Acc Chem Res*, 35, 491-499.

Menger, F. M. and Yamada, K. (1979) *J. Am. Chem. Soc.*, 101, 6731-6734.

Meylan, W. M. and Howard, P. H. (1995) Atom/fragment contribution method for estimating octanol-water partition coefficients. *J Pharm Sci*, 84, 83-92.

Miyawaki A, Llopis J, Heim R, McCaffery J M, Adams J A, Ikura M, Tsien R y. Fluorescent indicators for Ca2+ based on green fluorescent proteins and calmodulin. Nature. 1997 Aug. 28; 388(6645):882-7.

Mize, P. D., Hoke, R. A., Linn, C. P., Reardon, J. E., and Schulte, T. H. (1989). Dual-enzyme cascade—an amplified method for the detection of alkaline phosphatase. Anal Biochem 179, 229-235.

Montigiani, S., Neri, G., Neri, P., and Neri, D. (1996). Alanine substitutions in calmodulin-binding peptides result in unexpected affinity enhancement. J Mol Biol 258, 6-13.

New, R. R. C. (ed.). (1990) *Liposomes: a practical approach*. Oxford University Press, Oxford.

Norman, Med. Phys. 1980 November-December; 7(6):609-15.

Oberholzer, T., Albrizio, M. and Luisi, P. L. (1995) Polymerase chain reaction in liposomes. *Chem Biol*, 2, 677-682.

Oberholzer, T., Wick, R., Luisi, P. L. and Biebricher, C. K. (1995) Enzymatic RNA replication in self-reproducing vesicles: an approach to a minimal cell. *Biochem Biophys Res Commun*, 207, 250-257.

Obukowicz, M. G., Turner, M. A., Wong, E. Y. and Tacon, W. C. (1988) Secretion and export of IGF-1 in *Escherichia coli* strain JM101. *Mol Gen Genet*, 215, 19-25.

Perelson, A. S., and Oster, G. F. (1979). Theoretical studies of clonal selection: minimal antibody repertoire size and reliability of self-non-self discrimination. J Theor Biol 81, 645-670.

Perez, G. M., Sanchez, F. A. and Garcia, C. F. (1992) Application of active-phase plot to the kinetic analysis of lipoxygenase in reverse micelles. *Biochem J*.

Pirrung, M. C., and Huang, C. Y. (1996). A general method for the spatially defined immobilization of biomolecules on glass surfaces using "caged" biotin. Bioconjug Chem 7, 317-321.

Qi and Grabowski, Acid beta-glucosidase: intrinsic fluorescence and conformational changes induced by phospholipids and saposin C. Biochemistry. 1998 Aug. 18; 37(33): 11544-54

Ramstrom, O., and Lehn, J. M. (2002). Drug discovery by dynamic combinatorial libraries. Nat Rev Drug Discov 1, 26-36.

Riess, J. G. (2002) Fluorous micro- and nanophases with a biomedical perspective. *Tetrahedron,* 58, 4113-4131.

Rolland, J Immunol Methods. 1985 Jan. 21; 76(1):1-10

Sadtler, V. M., Krafft, M. P. and Riess, J. G. (1996) Achieving stable, reverse water-in-fluorocarbon emulsions. *Angew. Chem. Int. Ed. Engl.,* 35, 1976-1978.

Sambrook, J., and Russell, D. W., eds. (2001). Molecular cloning: a laboratory manual (New York, Cold Spring Harbor Laboratory Press).

Savage, M. D., Mattson, G., Desai, S., Nielander, G. W., Morgensen, S., and Conklin, E. J. (1994). Avidin-biotin chemistry: a handbook, 2 edn (Rockford, Pierce Chemical Company).

Schick, M. J. (1966) *Nonionic surfactants.* Marcel Dekker, New York.

Scott, R. L. (1948) *J. Am. Chem. Soc.,* 70, 4090.

Sepp, A., Tawfik, D. S., and Griffiths, A. D. (2002). Microbead display by in vitro compartmentalisation: selection for binding using flow cytometry. FEBS Letters 532, 455-458.

Shapiro, H. M. (1995). Practical Flow Cytometry, 3 edn (New York, Wiley-Liss).

Sherman, P. (1968) *Emulsion science.* Academic Press, London.

Song, H. and Ismagilov, R. F. (2003) Millisecond kinetics on a microfluidic chip using nanoliters of reagents. *J Am Chem Soc,* 125, 14613-14619.

Song, H., Tice, J. D. and Ismagilov, R. F. (2003) A microfluidic system for controlling reaction networks in time. *Angew. Chem. Int. Ed. Engl.,* 42, 767-772.

Stofko, H. R., Carr, D. W., and Scott, J. D. (1992). A single step purification for recombinant proteins. Characterization of a microtubule associated protein (MAP 2) fragment which associates with the type II cAMP-dependent protein kinase. Febs Lett 302, 274278.

Studer, A., Hadida, S., Ferritto, R., Kim, S. Y., Jeger, P., Wipf, P. and Curran, D. P. (1997) Fluorous synthesis: a fluorous-phase strategy for improving separation efficiency in organic synthesis. *Science,* 275, 823-826.

Sun, A. M., Vasek, I. and Tai, I. (1992) Microencapsulation of living cells and tissues. In Donbrow, M. (ed.), *Microencapsulation and nanoparticles in medicine and pharmacy.* CRC Press, Boca Raton, Fla., pp. 315-322.

Sundberg, S. A., Barrett, R. W., Pirrung, M., Lu, A. L., Kiangsoontra, B., and Holmes, C. P. (1995). Spatially-addressable immobilisation of macromolecules on solid supports. J Am Chem Soc 117, 12050-12057.

Tawfik, D. S., and Griffiths, A. D. (1998). Man-made cell-like compartments for molecular evolution. Nat Biotechnol 16, 652-656.

Thorsen, T., R. W., R., Arnold, F. H. and Quake, S. R. (2001) Dynamic pattern formation in a vesicle-generating microfluidic device. *Phys. Rev. Letts.,* 86, 41634166.

Tripet, B., Yu, L., Bautista, D. L., Wong, W. Y., Win, R. T., and Hodges, R. S. (1996). Engineering a de novo-designed coiled-coil heterodimerization domain off the rapid detection, purification and characterization of recombinantly expressed peptides and proteins. Protein Eng 9, 1029-1042.

Umbanhowar, P. B., Prasad, V. and Weitz, D. A. (2000) Monodisperse emulsions generated via drop break off in a coflowing steam. *Langmuir,* 16, 347-351.

van Hal, D. A., Bouwstra, J. A. and Junginger, H. E. (1996) Nonionic surfactant vesicles containing estradiol for topical application. In Benita, S. (ed.), *Microencapsulation: methods and industrial applications.* Marcel Dekker, New York, pp. 329-347.

Voss E W Jr. Kinetic measurements of molecular interactions by spectrofluorometry. J Mol Recognit. 1993 June; 6(2):51-8

Walde, P., Goto, A., Monnard, P.-A., Wessicken, M. and Luisi, P. L. (1994) Oparin's reactions revisited: enzymatic synthesis of poly(adenylic acid) in micelles and self-reproducing vesicles. *J. Am. Chem. Soc.,* 116, 7541-7547.

Walde, P., Han, D. and Luisi, P. L. (1993) Spectroscopic and kinetic studies of lipases solubilized in reverse micelles, *Biochemistry,* 32, 4029-4034.

Walde, P., Peng, Q., Fadnavis, N. W., Battistel, E. and Luisi, P. L. (1988) Structure and activity of trypsin in reverse micelles. *Eur J Biochem,* 173, 401-409.

Whateley, T. L. (1996) Microcapsules: preparation by interfacial polymerisation and interfacial complexation and their applications. In Benita, S. (ed.), *Microencapsulation: methods and industrial applications.* Marcel Dekker, New York, pp. 349-375.

Wick, R. and Luisi, P. L. (1996) Enzyme-containing liposomes can endogenously produce membrane-constituting lipids. *Chem Biol,* 3, 277-285.

Zhang, Z. Y., Thieme-Sefler, A. M., Maclean, D., McNamara, D. J., Dobrusin, E. M., Sawyer, T. K., and Dixon, J. E. (1993). Substrate specificity of the protein tyrosine phosphatases. Proc Natl Acad Sci USA 90, 4446-4450.

All publications mentioned in the above specification, and references cited in said publications, are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for preparing secondary compounds comprising the steps of:
   (a) attaching a first set of primary compounds to one or more microbeads in a first aqueous fluid;
   (b) attaching a second set of primary compounds to one or more microbeads in a second aqueous fluid, wherein the second set of primary compounds is different from the first set of primary compounds;
   (c) forming a plurality of first water-in-fluorocarbon oil microcapsules by partitioning the first aqueous fluid with an immiscible fluorocarbon oil comprising a fluorinated surfactant, as the first aqueous fluid is flowing through a microfluidic channel, wherein the first aqueous fluid of each first water-in-fluorocarbon oil microcapsule comprises one or more first sets of primary compounds attached to one or more microbeads;
   (d) forming a plurality of second water-in-fluorocarbon oil microcapsules by partitioning the second aqueous fluid with the immiscible fluorocarbon oil comprising a fluorinated surfactant, as the second aqueous fluid is flowing through a microfluidic channel, wherein each aqueous fluid portion of the second water-in-fluorocarbon oil microcapsule comprises a second set of primary compounds attached to one or more microbeads;
   (e) merging the plurality of first water-in-fluorocarbon oil microcapsules with the plurality of second water-in-fluorocarbon oil microcapsules in presence of an applied electric field to form a plurality of merged water-in-fluorocarbon oil microcapsules in the microfluidic channel, wherein the immiscible fluorocarbon oil in the plurality of first water-in-fluorocarbon oil microcapsules and the plurality of second water-in-fluorocarbon oil microcapsules comprises a fluorinated surfactant and the aqueous fluid portion of each merged water-in-fluorocarbon oil microcapsule comprises a first set of primary compounds attached to one or more microbeads and a second set of primary compounds attached to one or more microbeads;
   (f) releasing, in the merged water-in-fluorocarbon oil microcapsules, the first set of primary compounds from the one or more microbeads and the second set of primary compounds from the one or more microbeads;
   (g) forming secondary compounds in the merged water-in-fluorocarbon oil microcapsules by chemical reactions between the released first set of primary compounds and the released second set of primary compounds, wherein the secondary compounds are present in the aqueous fluid portion of each of the plurality of merged water-in-fluorocarbon oil microcapsules;
   (h) fusing each merged water-in-fluorocarbon oil microcapsule with a third water-in-fluorocarbon oil microcapsule containing a target enzyme to form second merged water-in-fluorocarbon oil microcapsules containing the secondary compounds and the target enzyme, wherein one or more of steps (c) through (h) are performed under microfluidic control; and
   (i) determining subsets of the first set of primary compounds or the second set of primary compounds which react to form secondary compounds that bind to or modulate the activity of the target enzyme.

2. The method according to claim 1, further comprising: sorting the merged water-in-fluorocarbon oil microcapsules based upon identification of the secondary compounds that bind to or modulate the activity of the target.

3. The method of claim 1, wherein the first set of primary compounds and/or the second set of primary compounds are nucleic acids.

4. The method of claim 3, wherein each first water-in-fluorocarbon oil microcapsule comprises a single nucleic acid from each of the first set of primary compounds and the second set of primary compounds.

5. The method of claim 3, wherein said chemical reaction is a nucleic acid polymerization reaction.

6. The method of claim 1, wherein each of the first water-in-fluorocarbon oil microcapsules further comprises a cell.

7. The method of claim 6, wherein the target enzyme is associated with the cell.

8. The method of claim 7, wherein the target enzyme is in the cell.

9. The method of claim 1, further comprising merging each of the second merged water-in-fluorocarbon oil microcapsules containing the secondary compounds and the target enzyme with a fourth water-in-fluorocarbon oil microcapsule containing a fluorogenic substrate for the target enzyme.

10. The method of claim 1, wherein either the first set of primary compounds or the second set of primary compounds comprises a fluorogenic substrate for the target enzyme.

* * * * *

SEQUENCE LISTING

```
<160> NUMBER OF SEQ ID NOS: 1

<210> SEQ ID NO 1
<211> LENGTH: 11
<212> TYPE: PRT
<213> ORGANISM: Homo sapiens

<400> SEQUENCE: 1

Asp Ala Asp Glu Tyr Leu Ile Pro Gln Gln Gly
1               5                   10
```